(12) United States Patent
Fink et al.

(10) Patent No.: US 10,519,187 B2
(45) Date of Patent: Dec. 31, 2019

(54) CYCLIC DINUCLEOTIDES AS ANTICANCER AGENTS

(71) Applicant: BRISTOL-MYERS SQUIBB COMPANY, Princeton, NJ (US)

(72) Inventors: Brian E. Fink, Yardley, PA (US); Dharmpal S. Dodd, Monmouth Junction, NJ (US); Steven J. Walker, Portage, MI (US); Libing Chen, Newtown, PA (US); Yufen Zhao, Pennington, NJ (US); Zheming Ruan, Dayton, NJ (US); Lan-Ying Qin, Plainsboro, NJ (US); Peter Kinam Park, New York, NY (US); Muthoni G. Kamau, Lawrenceville, NJ (US); Lalgudi S. Harikrishnan, Skillman, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/272,172

(22) Filed: Feb. 11, 2019

(65) Prior Publication Data

US 2019/0248828 A1 Aug. 15, 2019

Related U.S. Application Data

(60) Provisional application No. 62/629,956, filed on Feb. 13, 2018.

(51) Int. Cl.
| | | |
|---|---|---|
| *C07H 19/213* | (2006.01) | |
| *A61P 35/00* | (2006.01) | |
| *C07K 16/28* | (2006.01) | |

(52) U.S. Cl.
CPC ............ *C07H 19/213* (2013.01); *A61P 35/00* (2018.01); *C07K 16/2896* (2013.01)

(58) Field of Classification Search
None
See application file for complete search history.

(56) References Cited

FOREIGN PATENT DOCUMENTS

| WO | WO2017027645 A1 | 2/2017 |
| WO | WO2017123669 A1 | 7/2017 |
| WO | 2019023459 | * 1/2019 |
| WO | WO2019023459 A1 | 1/2019 |
| WO | WO2019046496 A1 | 3/2019 |
| WO | WO2019046500 A1 | 3/2019 |
| WO | WO2019092660 A1 | 5/2019 |

* cited by examiner

*Primary Examiner* — Karl J Puttlitz
(74) *Attorney, Agent, or Firm* — Elliott Korsen

(57) ABSTRACT

The present invention is directed to compounds of the formulae I, II and III as shown below

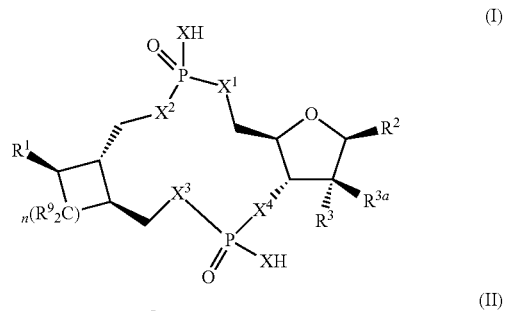

(I)

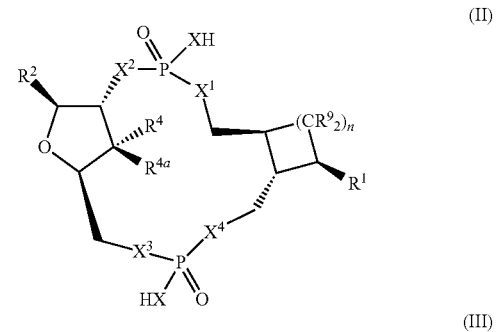

(II)

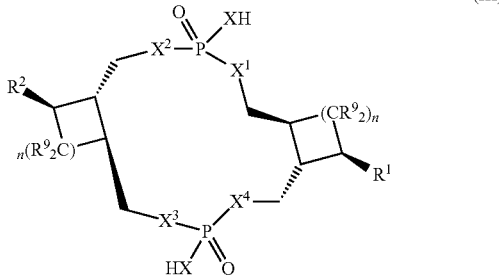

(III)

wherein all substituents are defined herein, as well as pharmaceutically acceptable compositions comprising compounds of the invention and methods of using said compositions in the treatment of various disorders.

70 Claims, No Drawings

Specification includes a Sequence Listing.

SEQUENCE LISTING

```
<160> NUMBER OF SEQ ID NOS: 2

<210> SEQ ID NO 1
<211> LENGTH: 210
<212> TYPE: PRT
<213> ORGANISM: Artificial Sequence
<220> FEATURE:
<223> OTHER INFORMATION: Homosapien

<400> SEQUENCE: 1

Met Gly Ser Ser His His His His His His Ser Ser Gly Glu Thr Val
1               5                   10                  15

Arg Phe Gln Gly His Met Ser Val Ala His Gly Leu Ala Trp Ser Tyr
            20                  25                  30
```

Tyr Ile Gly Tyr Leu Arg Leu Ile Leu Pro Glu Leu Gln Ala Arg Ile
            35                  40                  45

Arg Thr Tyr Asn Gln His Tyr Asn Asn Leu Leu Arg Gly Ala Val Ser
 50                  55                  60

Gln Arg Leu Tyr Ile Leu Pro Leu Asp Cys Gly Val Pro Asp Asn
 65                  70                  75                  80

Leu Ser Met Ala Asp Pro Asn Ile Arg Phe Leu Asp Lys Leu Pro Gln
                85                  90                  95

Gln Thr Gly Asp Arg Ala Gly Ile Lys Asp Arg Val Tyr Ser Asn Ser
                100                 105                 110

Ile Tyr Glu Leu Leu Glu Asn Gly Gln Arg Ala Gly Thr Cys Val Leu
                115                 120                 125

Glu Tyr Ala Thr Pro Leu Gln Thr Leu Phe Ala Met Ser Gln Tyr Ser
 130                 135                 140

Gln Ala Gly Phe Ser Arg Glu Asp Arg Leu Glu Gln Ala Lys Leu Phe
145                 150                 155                 160

Cys Arg Thr Leu Glu Asp Ile Leu Ala Asp Ala Pro Glu Ser Gln Asn
                165                 170                 175

Asn Cys Arg Leu Ile Ala Tyr Gln Glu Pro Ala Asp Asp Ser Ser Phe
                180                 185                 190

Ser Leu Ser Gln Glu Val Leu Arg His Leu Arg Gln Glu Glu Lys Glu
                195                 200                 205

Glu Val
    210

<210> SEQ ID NO 2
<211> LENGTH: 210
<212> TYPE: PRT
<213> ORGANISM: Artificial Sequence
<220> FEATURE:
<223> OTHER INFORMATION: Homosapien

<400> SEQUENCE: 2

Met Gly Ser Ser His His His His His His Ser Ser Gly Glu Thr Val
 1               5                   10                  15

Arg Phe Gln Gly His Met Ser Val Ala His Gly Leu Ala Trp Ser Tyr
                20                  25                  30

Tyr Ile Gly Tyr Leu Arg Leu Ile Leu Pro Glu Leu Gln Ala Arg Ile
            35                  40                  45

Arg Thr Tyr Asn Gln His Tyr Asn Asn Leu Leu Arg Gly Ala Val Ser
 50                  55                  60

Gln Arg Leu Tyr Ile Leu Pro Leu Asp Cys Gly Val Pro Asp Asn
 65                  70                  75                  80

Leu Ser Met Ala Asp Pro Asn Ile Arg Phe Leu Asp Lys Leu Pro Gln
                85                  90                  95

Gln Thr Ala Asp Arg Ala Gly Ile Lys Asp Arg Val Tyr Ser Asn Ser
                100                 105                 110

Ile Tyr Glu Leu Leu Glu Asn Gly Gln Arg Ala Gly Thr Cys Val Leu
                115                 120                 125

Glu Tyr Ala Thr Pro Leu Gln Thr Leu Phe Ala Met Ser Gln Tyr Ser
 130                 135                 140

Gln Ala Gly Phe Ser Arg Glu Asp Arg Leu Glu Gln Ala Lys Leu Phe
145                 150                 155                 160

Cys Gln Thr Leu Glu Asp Ile Leu Ala Asp Ala Pro Glu Ser Gln Asn
                165                 170                 175

-continued

Asn Cys Arg Leu Ile Ala Tyr Gln Glu Pro Ala Asp Asp Ser Ser Phe
            180                 185                 190

Ser Leu Ser Gln Glu Val Leu Arg His Leu Arg Gln Glu Glu Lys Glu
        195                 200                 205

Glu Val
    210

CYCLIC DINUCLEOTIDES AS ANTICANCER AGENTS

CROSS-REFERENCE TO RELATED APPLICATIONS

This application claims the benefit of U.S. Provisional Application No. 62/629,956, filed Feb. 13, 2018, the disclosure of which is incorporated herein by reference in its entirety.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

Immunotherapy is a rapidly expanding area of medical treatment in which a patient's immune system is deliberately activated, suppressed or otherwise modulated for a positive therapeutic effect. Immunotherapy agents include such things as cells, antigens, antibodies, nucleic acids, proteins, peptides, naturally occurring ligands and synthetically prepared molecules. Cytokines are small glycoprotein molecules known for their role in causing immune response through complex signaling networks. Cytokines have been explored as immunotherapy agents but their direct administration is hampered by many factors including their short half-life in blood which can only be compensated with frequent and often high doses. One highly promising approach is cytokine induction in which the patient is treated with an immunomodulatory agent that triggers the production of one or more therapeutically beneficial cytokines in their body.

One agent in the production of cytokines is the adaptor protein STING (STimulator of INterferon Genes; also known as MPYS, TMEM173, MITA and ERIS). STING is an intracellular receptor situated on the endoplasmic reticulum. The binding to STING by an agonist activates a signaling pathway culminating in the induction of Type I IFNs, which are secreted and protect the secreting and nearby cells. STING can be activated by two different pathways, each involving a different type of cyclic dinucleotide ("CDN") agonist. In the first pathway, the agonist is an exogenous CDN used by bacterial pathogens as a second messenger (Burdette et al. 2013). In the second pathway the enzyme cyclic GMP-AMP synthase (cGAS) detects cytosolic DNA and, in response, synthesizes a CDN that functions as an endogenous STING agonist (Ablasser et al. 2013; Gao et al. 2013; Sun et al. 2013).

Activation of STING results in up-regulation of IRF3 and NF-κB pathways leading to induction of Interferon-β and other cytokines. STING is crucial for responses to cytosolic DNA of pathogen or host origin.

Two exogenous bacterial STING agonist CDNs are 3'3'-cGAMP and c-GMP. The endogenous STING agonist CDN made by cGAS is 2'3'-cGAMP. The bacterial CDNs are characterized by two 3'5' phosphodiester bridges, while the cGAS-produced CDN is characterized by one 2'5' and one 3'5' phosphodiester bridge. As a shorthand, the former CDNs are referred to as 3'3' CDNs and the latter as 2'3' CDNs. For historical reasons, 3'3' CDNs also are referred to as the "canonical" form and 2'3' CDNs are referred to as the "non-canonical" form.

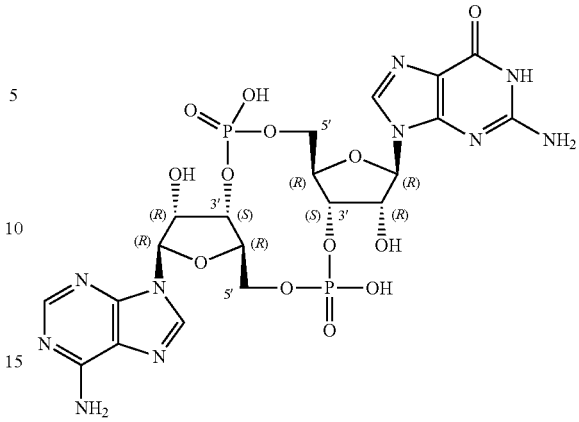

3'3'-cGAMP

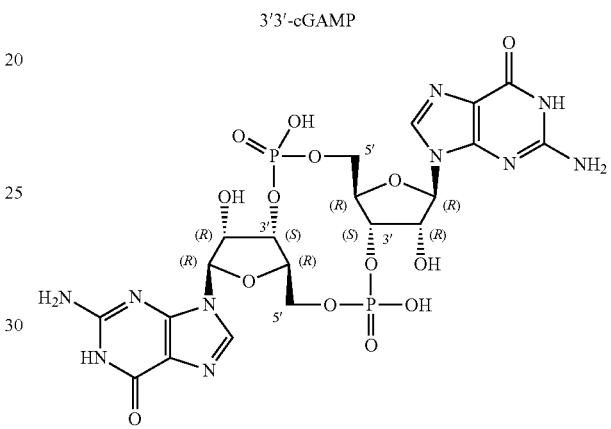

c-di-GMP

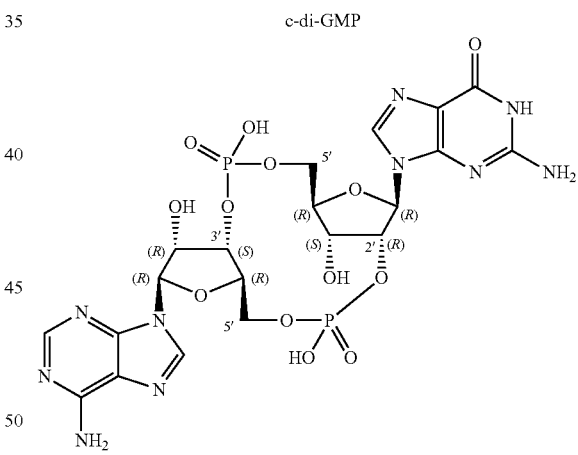

2'3'-cGAMP

In addition to protecting an organism against pathogen infection, STING activation has also been reported to be beneficial in the treatment of inflammatory diseases and, in an area of particular current interest, cancer. Administration of a synthetic CDN in combination with the cancer vaccine STINGVAX demonstrated enhanced antitumor efficacy in multiple therapeutic models (Fu et al. 2015). Administration of STING agonists alone has been reported to show potent antitumor immune efficacy in a mouse model (Corrales et al. 2015a). For reviews on the role of STING in infection, inflammation, and/or cancer, see Ahn et al. 2015; Corrales et al. 2015b and 2016; and Barber 2015.

The present invention, therefore, provides novel cyclic dinucleotides which may be useful for the treatment of cancer.

SUMMARY OF THE INVENTION

There are provided compounds of formulae (I), (II) and (III)

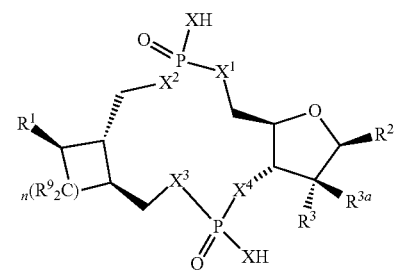
(I)

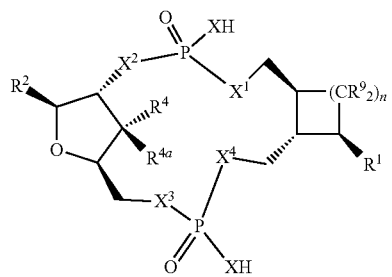
(II)

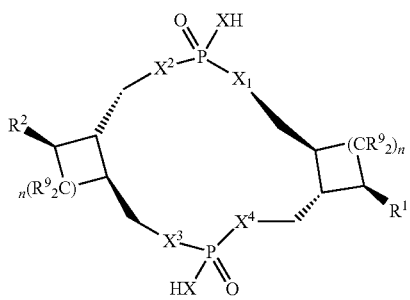
(III)

wherein all substituents are defined herein.

In another aspect, there is provided a pharmaceutical composition comprising a compound of the invention or a pharmaceutically acceptable salt thereof and one or more pharmaceutically acceptable carriers, diluents or excipients.

In another aspect, there is provided a method of treating cancer which comprises administering to a subject in need thereof a therapeutically effective amount of an activator of STING (of Formula I).

DETAILED DESCRIPTION OF THE INVENTION

The following are aspects and embodiments of the present invention, as well as additional aspects and embodiments that can be within the scope of those shown. The aspects of the invention are not limited to those described below.

In a first aspect, there is disclosed a compound of formula I

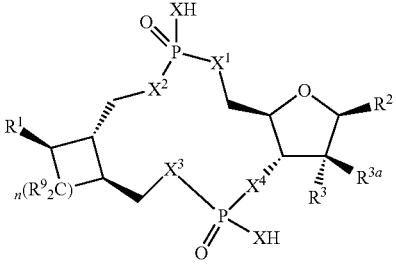
(I)

wherein
  X is independently O or S;
  $X^1$, $X^2$, $X^3$ and $X^4$ are each independently O or NH;
  $R^1$ and $R^2$ are each independently

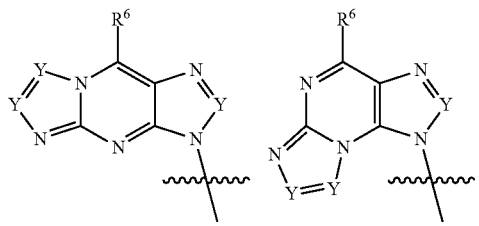

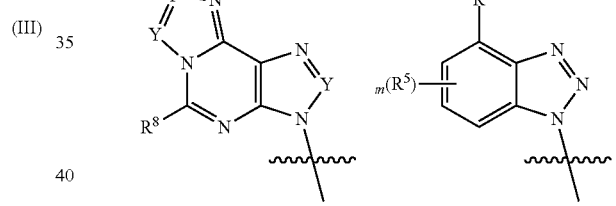

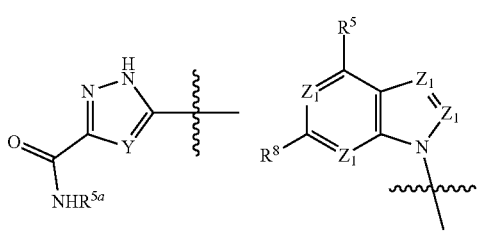

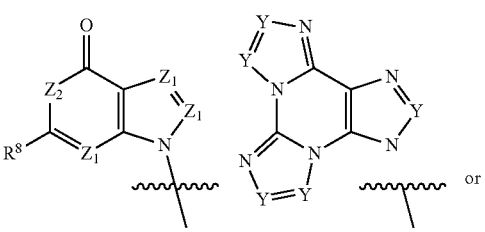 or

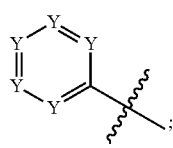 ;

with the proviso that one of $R^1$ and $R^2$ must be

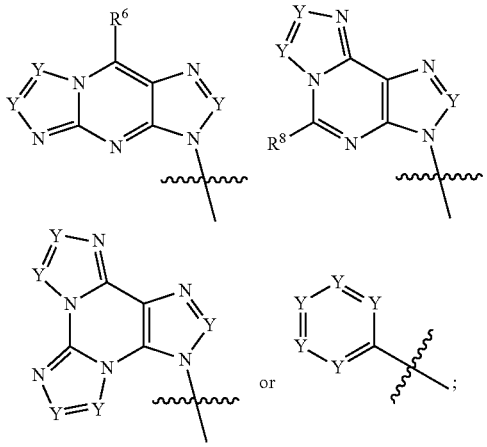

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
or two $R^5$ groups may be taken together to form a 5-6 membered carbocyclic or heterocyclic group;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

Additional aspects of the invention include compounds according to formula (I) wherein
$R^1$ is

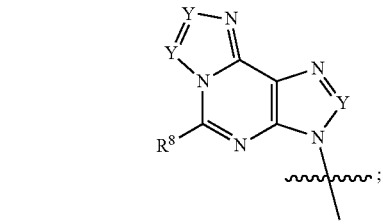

and
$R^2$ is

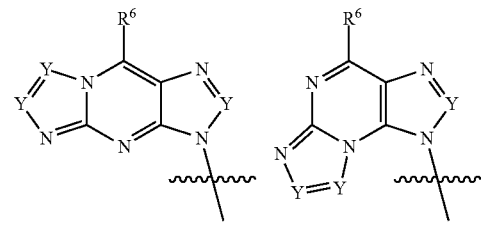

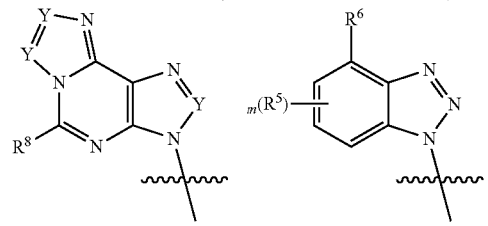

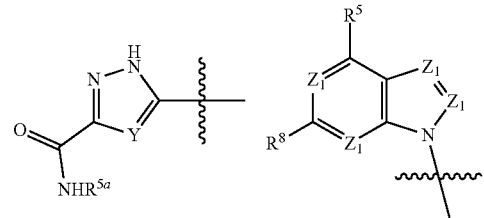

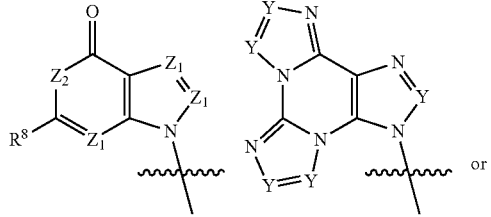

$R^1$ is

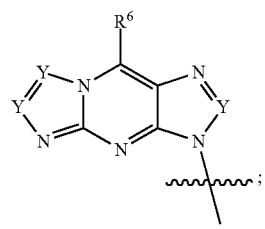

and

R² is
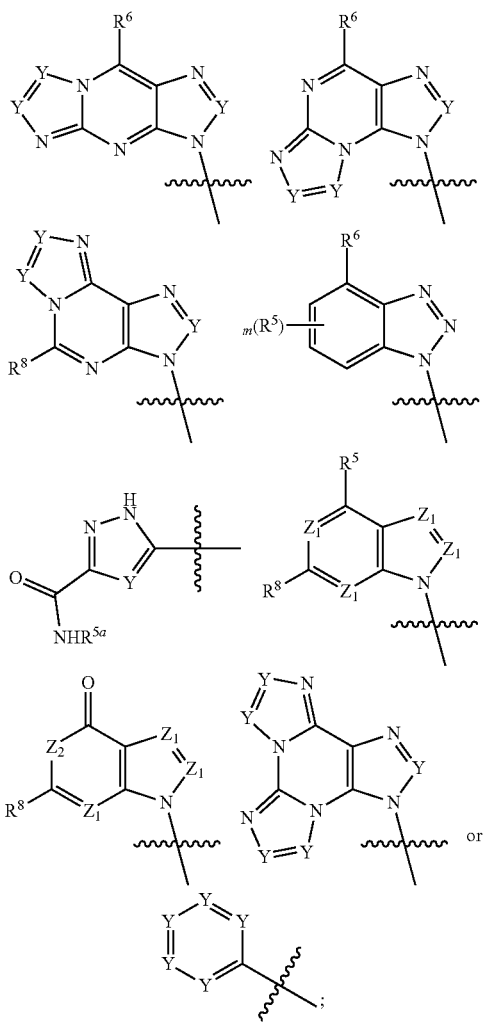
R¹ is
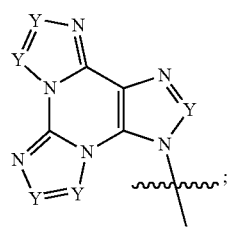
and
R² is
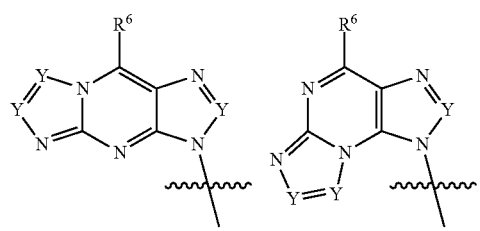
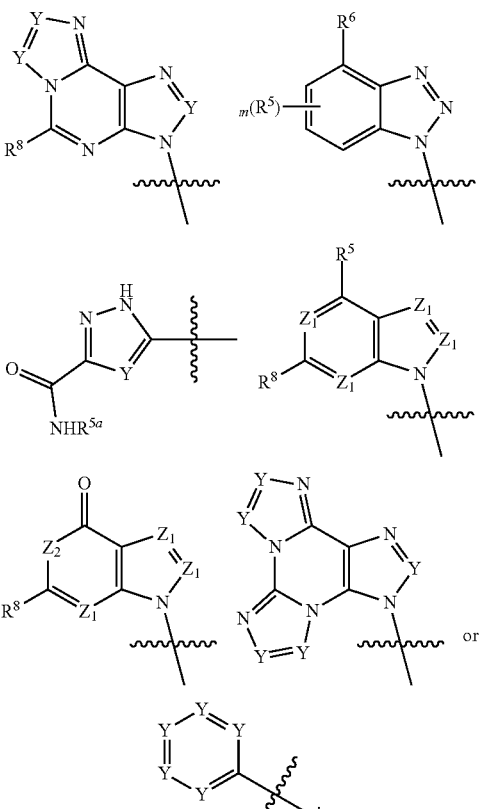
R¹ is
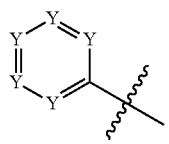
and
R² is
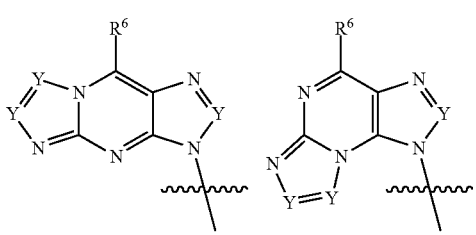
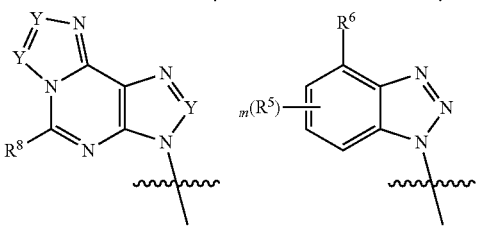

-continued
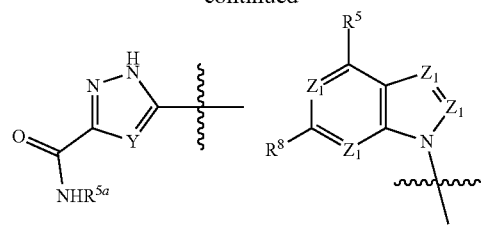
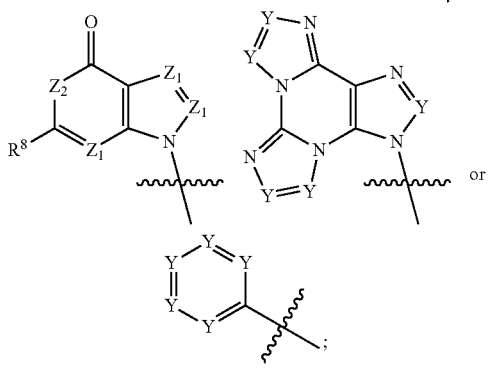
R[1] is
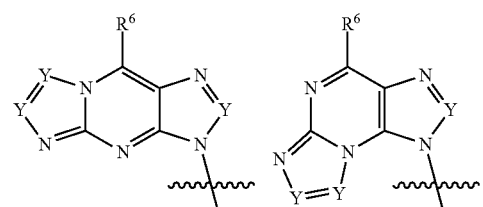
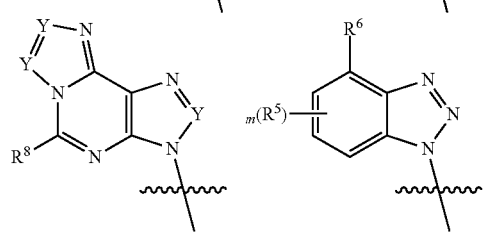
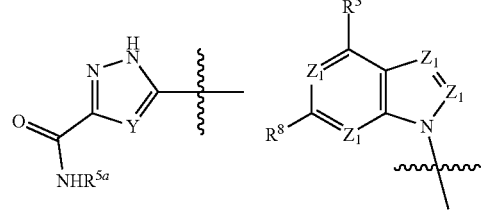
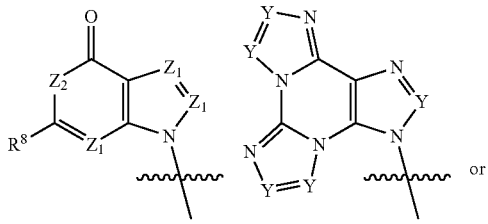
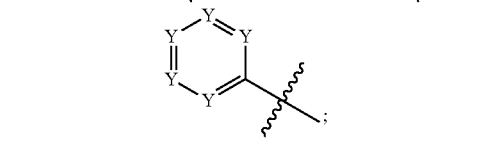
and
R[2] is
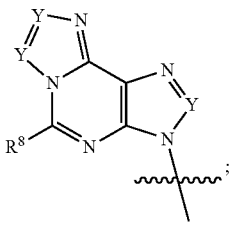
R[1] is
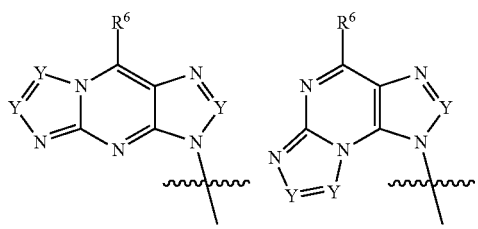
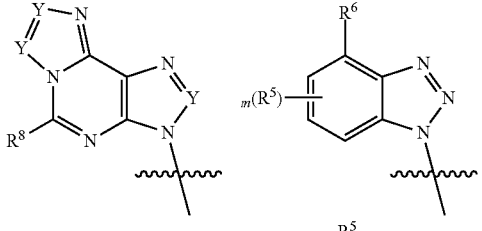
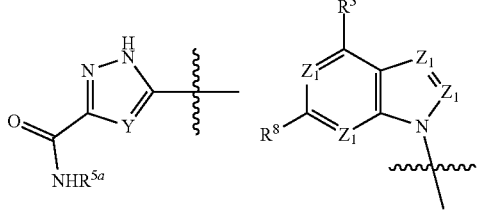
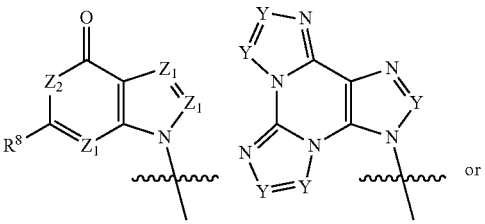
and
R[2] is
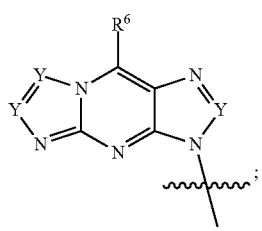

R¹ is
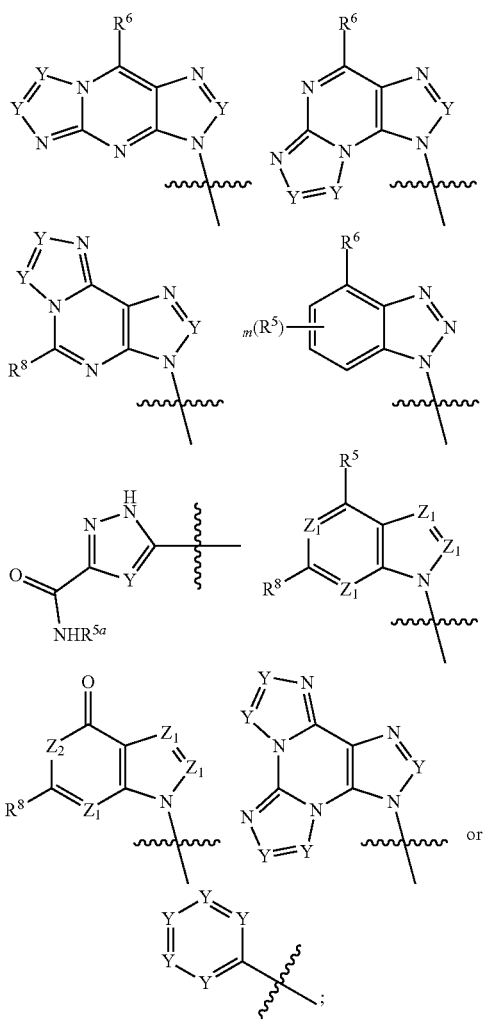
and
R² is
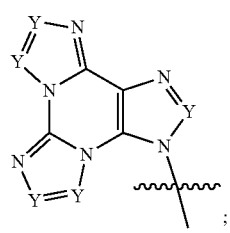
R¹ is
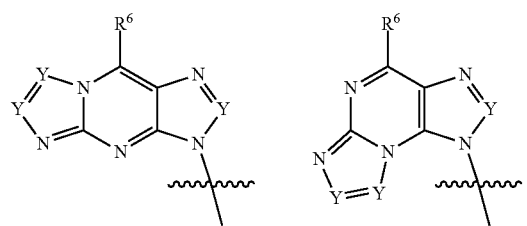
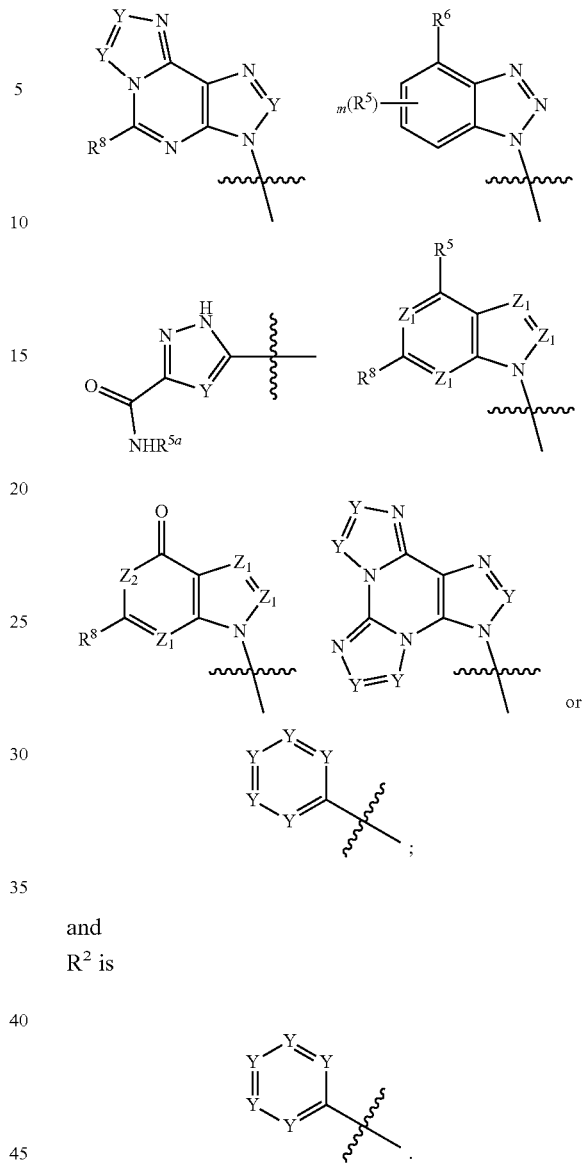
and
R² is
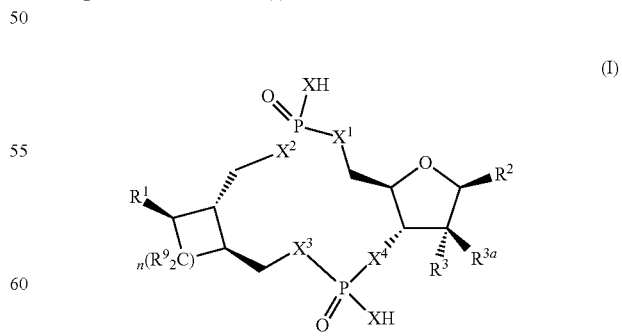
In another aspect of the invention, there is provided a compound of formula (I)
wherein
X is S;
X¹, X², X³ and X⁴ are each independently O or NH;

$R^1$ and $R^2$ are independently

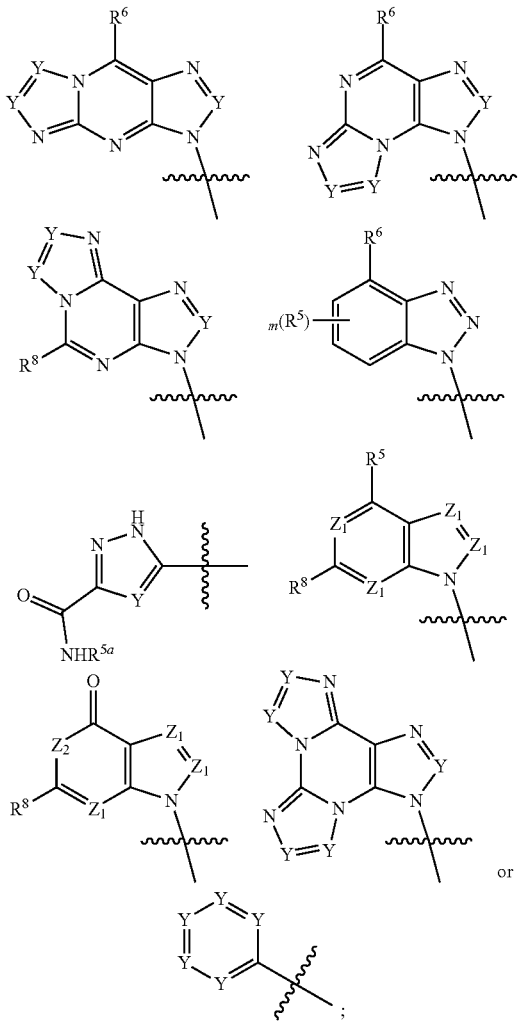

with the proviso that one of $R^1$ and $R^2$ must be

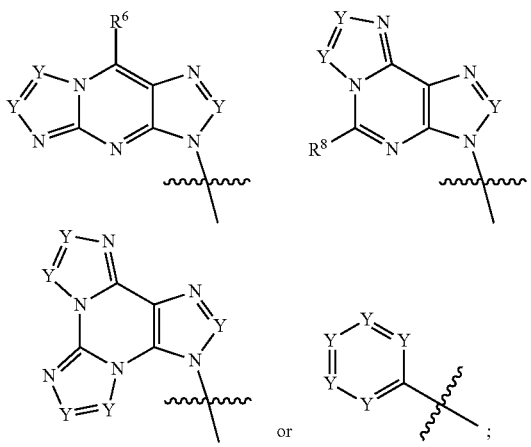

$Z_1$ is N or $CR^a$;
$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a C=CH$_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of formula (I)

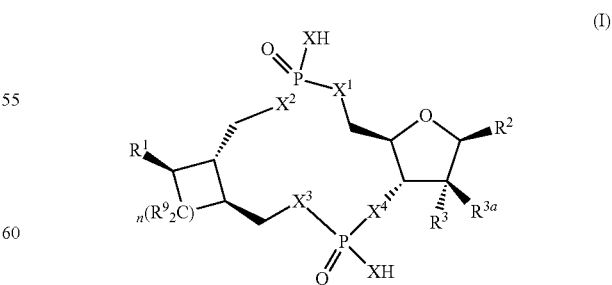

(I)

wherein

X is O;

$X^1$, $X^2$, $X^3$ and $X^4$ are each independently O or NH;

$R^1$ and $R^2$ are independently

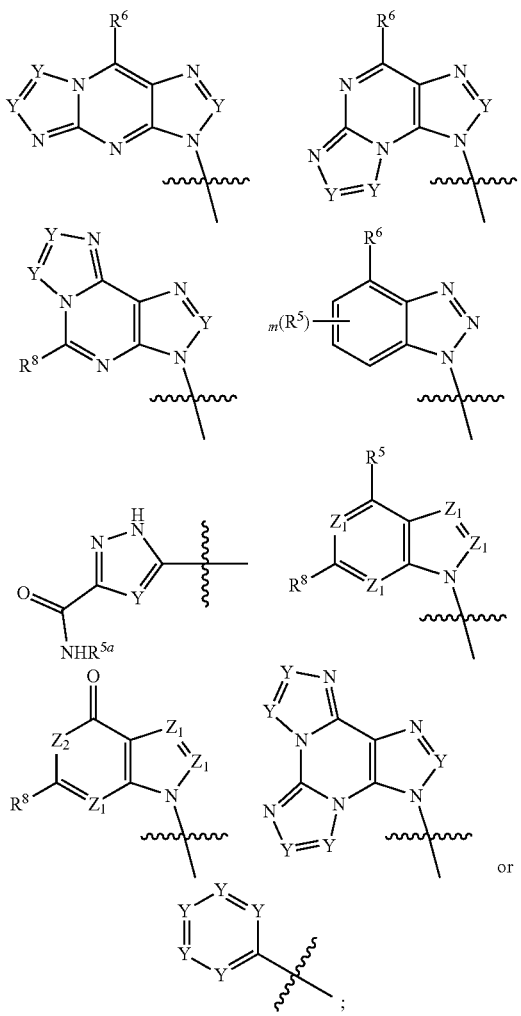

with the proviso that one of $R^1$ and $R^2$ must be

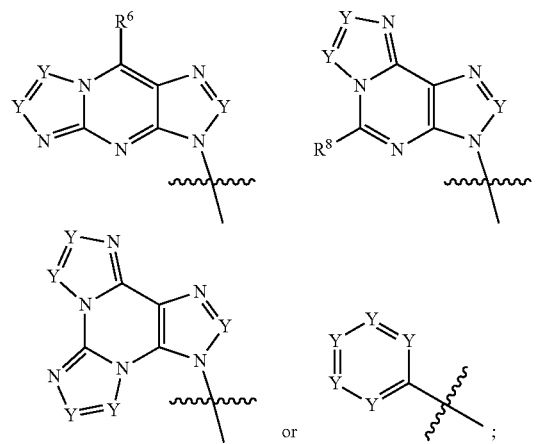

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of formula (I)

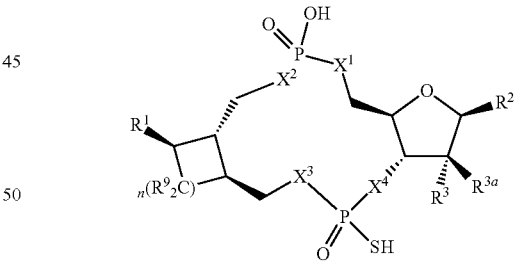

wherein
$X^1$, $X^2$, $X^3$ and $X^4$ are each independently O or NH;
$R^1$ and $R^2$ are independently

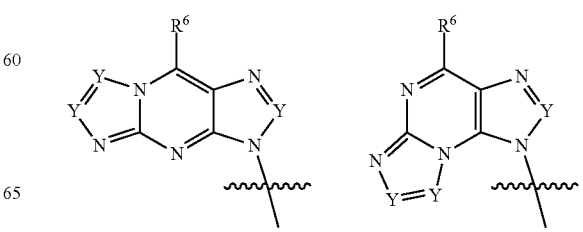

-continued

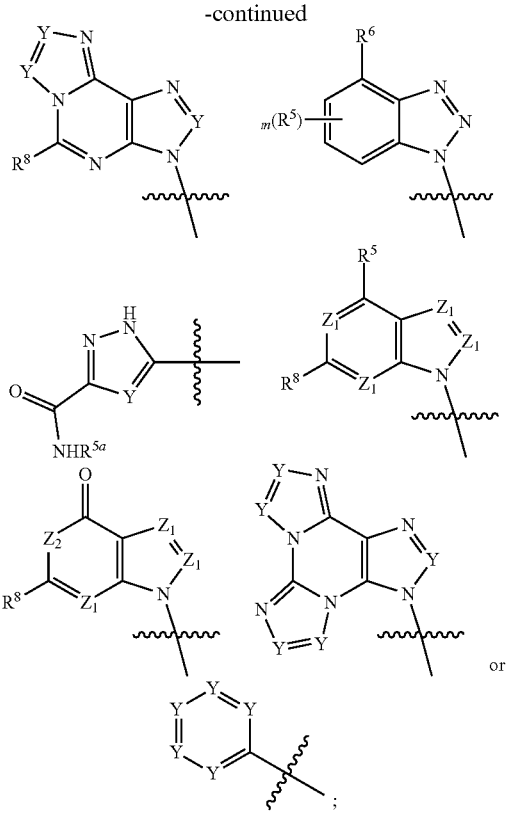

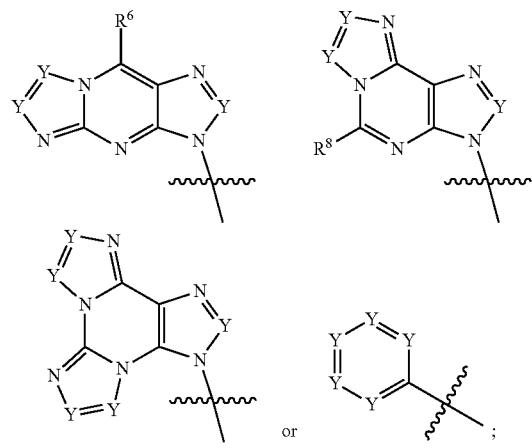

with the proviso that one of $R^1$ and $R^2$ must be

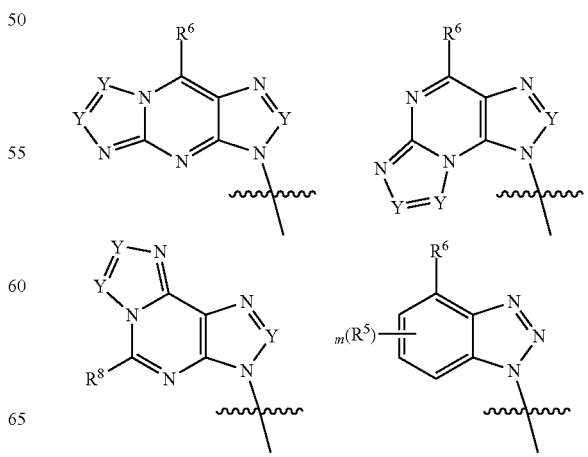

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of formula (I)

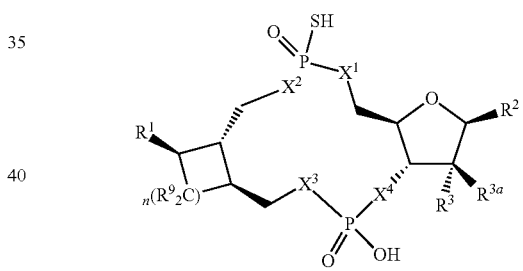

wherein
$X^1$, $X^2$, $X^3$ and $X^4$ are each independently O or NH;
$R^1$ and $R^2$ are independently -continued

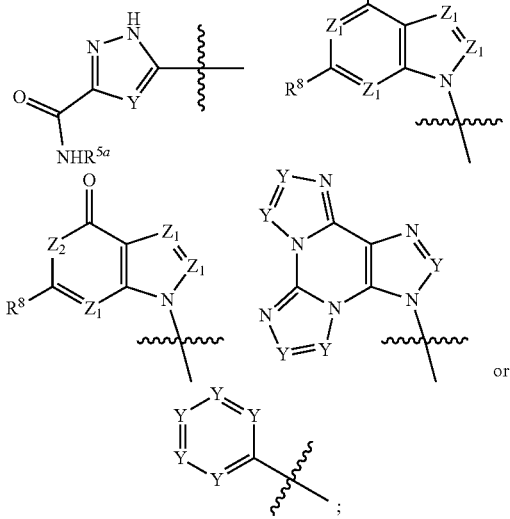

with the proviso that one of $R^1$ and $R^2$ must be

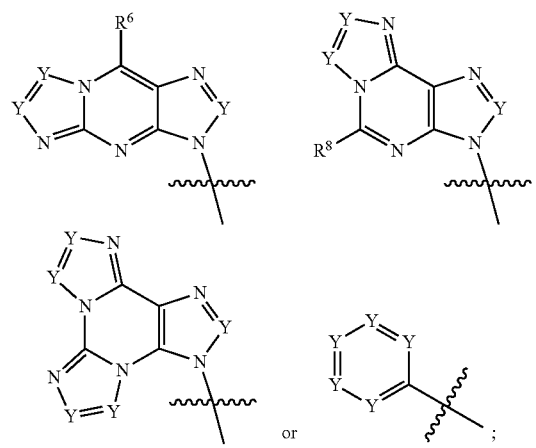

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of the formula

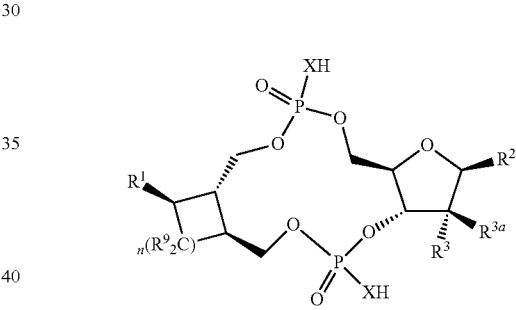

wherein
X is independently O or S;
$R^1$ and $R^2$ are independently

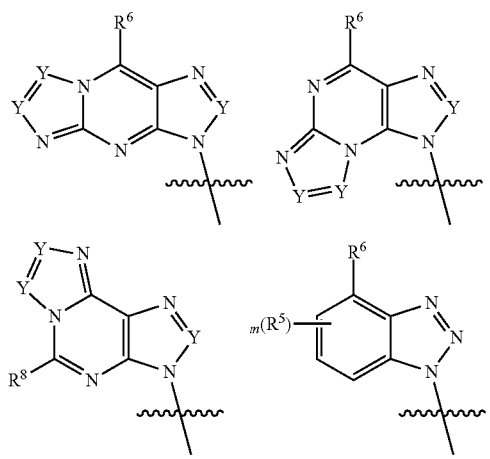

-continued

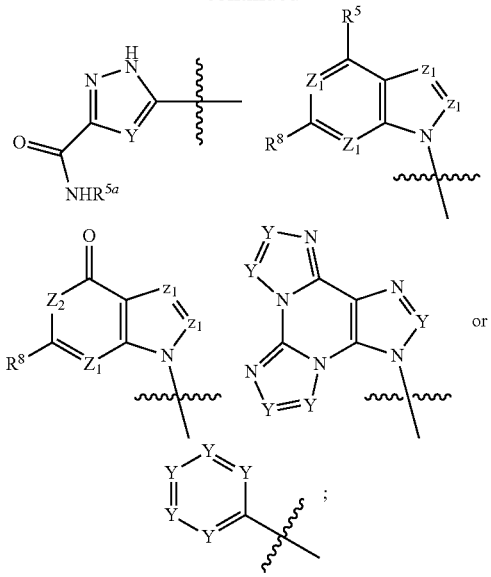

with the proviso that one of $R^1$ and $R^2$ must be

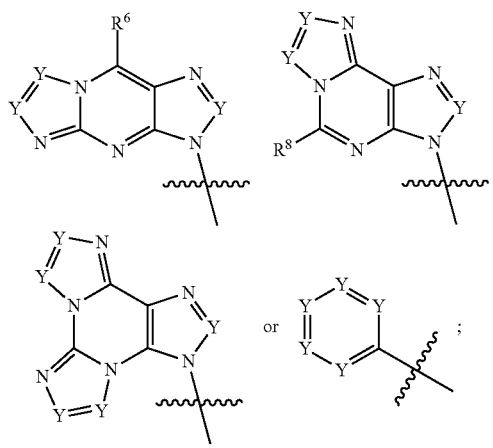

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of the formula

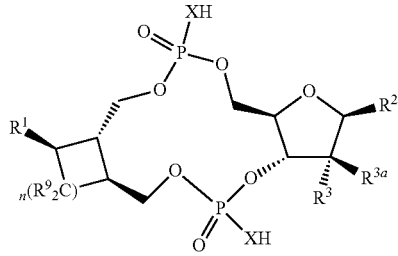

wherein
X is S;
$R^1$ and $R^2$ are independently

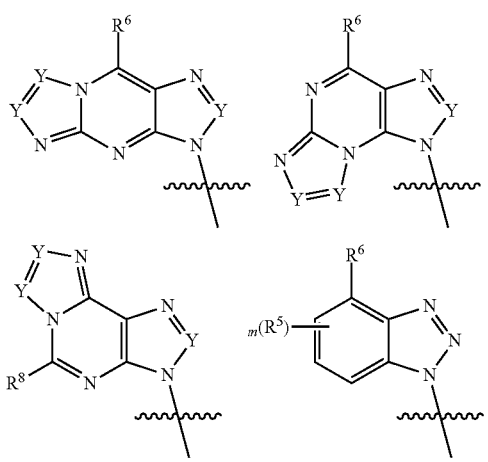

-continued

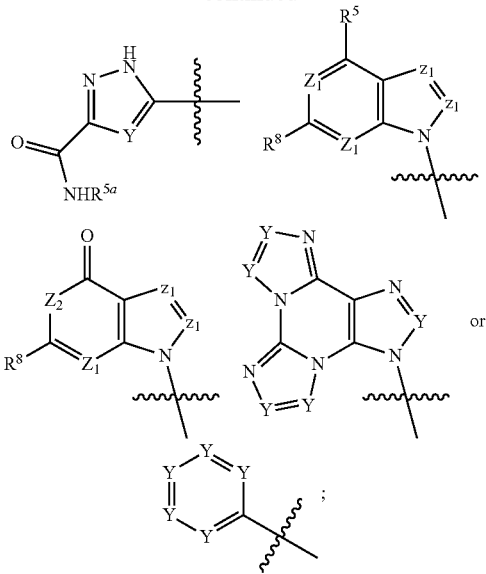

with the proviso that one of $R^1$ and $R^2$ must be

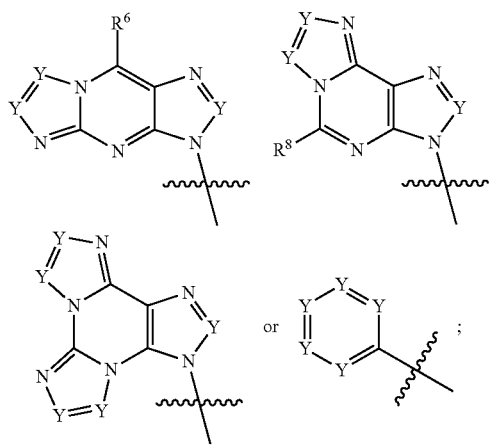

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of the formula

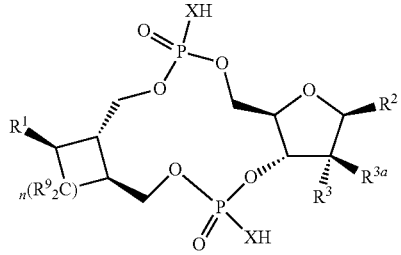

wherein

X is O;

$R^1$ and $R^2$ are independently

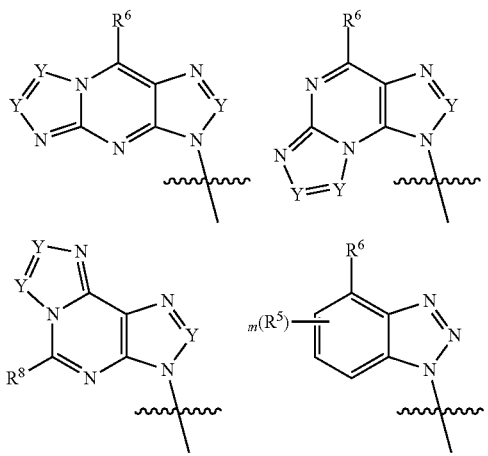

-continued

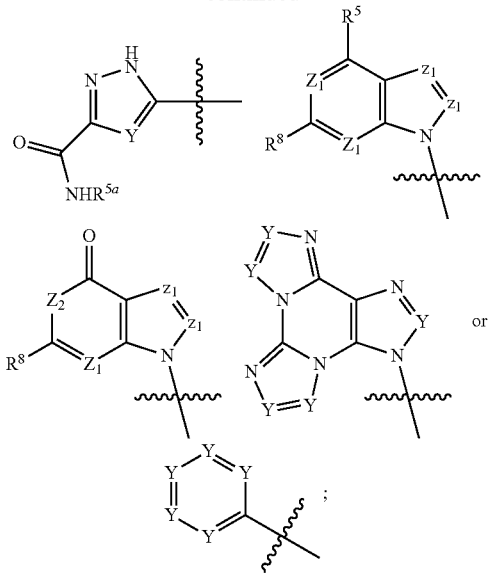

with the proviso that one of $R^1$ and $R^2$ must be

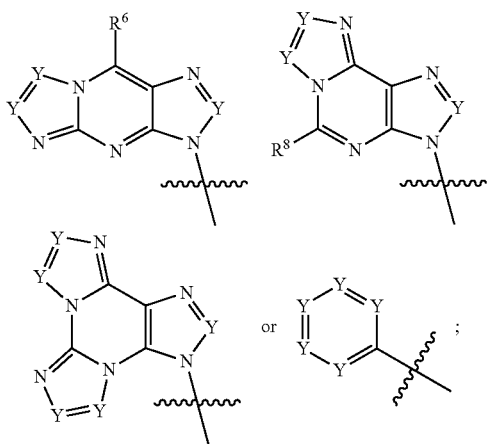

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of the formula

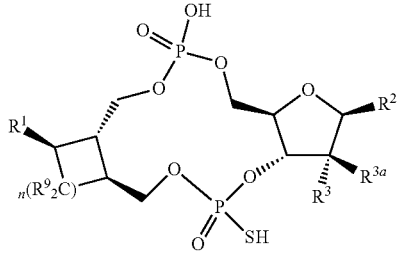

wherein
$R^1$ and $R^2$ are independently

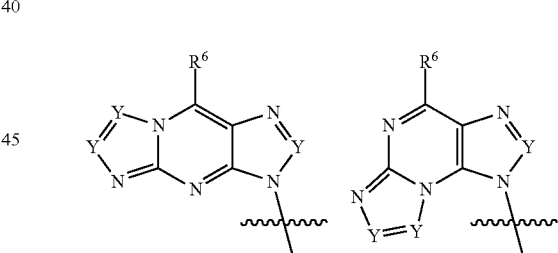

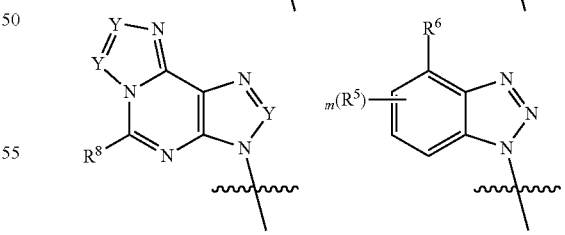

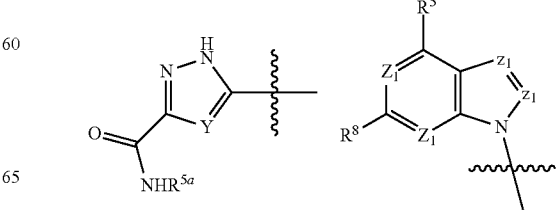

-continued

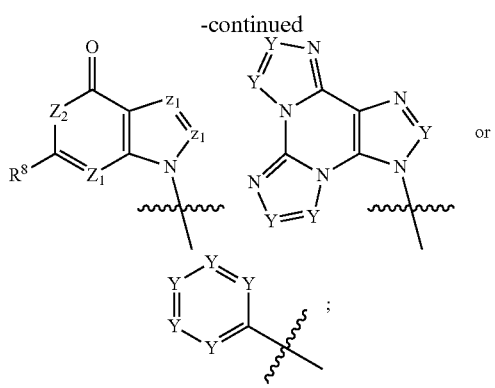

with the proviso that one of $R^1$ and $R^2$ must be

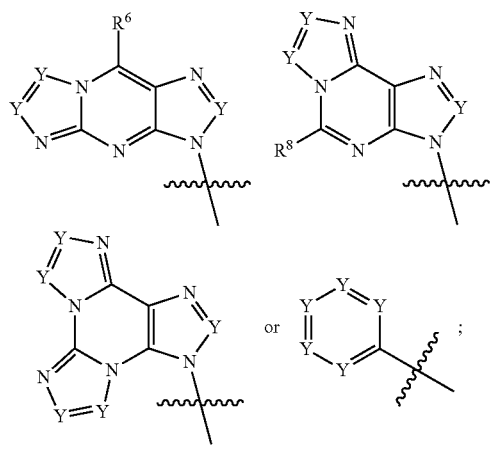

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of the formula

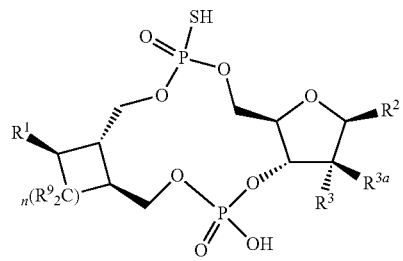

wherein
$R^1$ and $R^2$ are independently

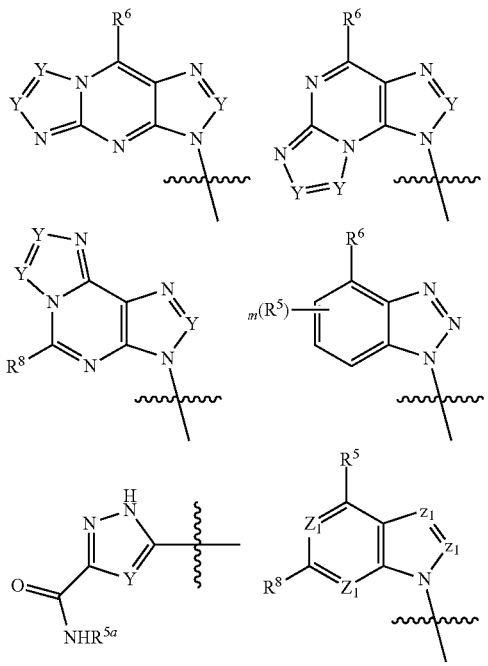

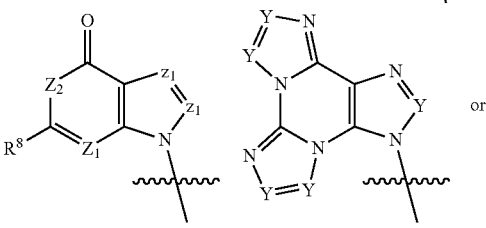

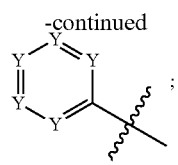

with the proviso that one of $R^1$ and $R^2$ must be

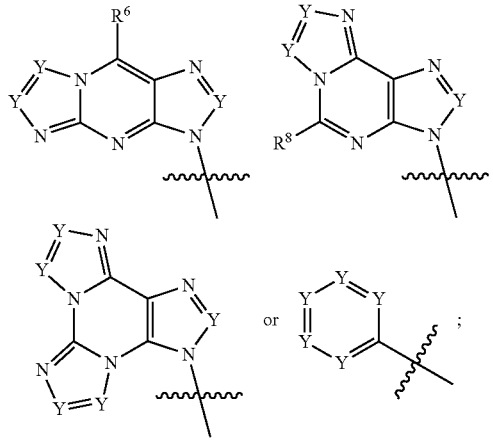

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —$OC(O)R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of the formula

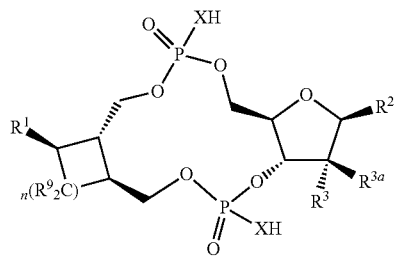

wherein

X is independently O or S;

$R^1$ and $R^2$ are independently

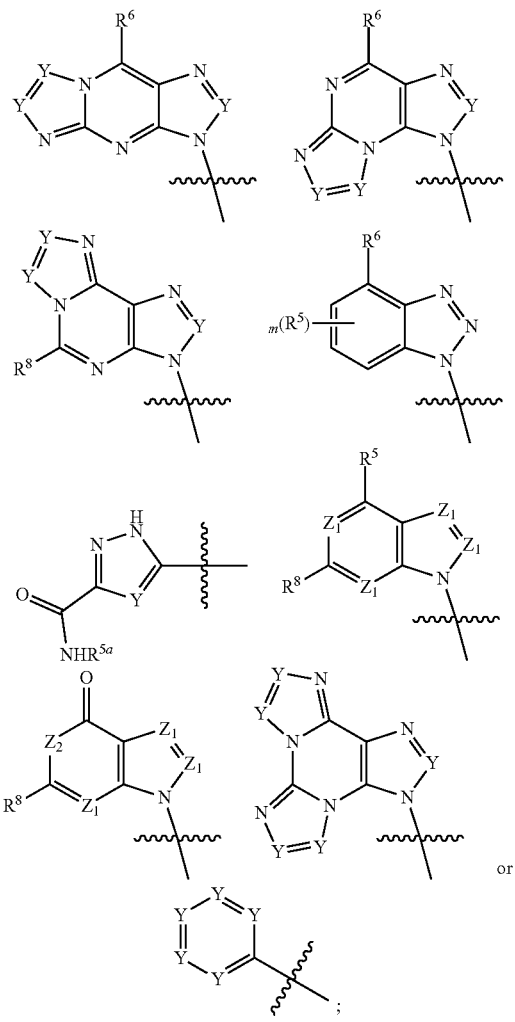

with the proviso that one of $R^1$ and $R^2$ must be

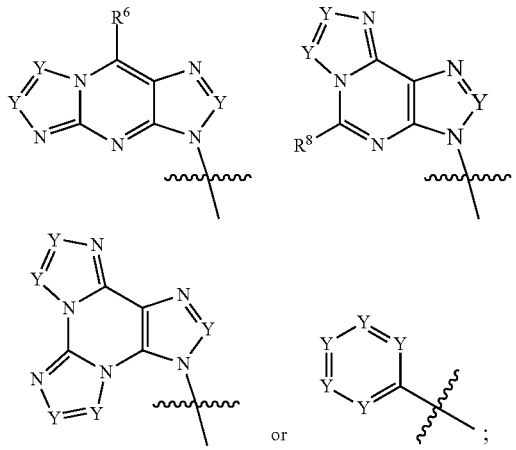

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is F;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of the formula

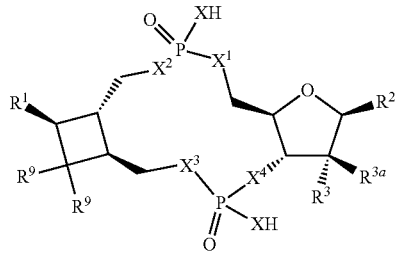

wherein

X is independently O or S;

$X^1$, $X^2$, $X^3$ and $X^4$ are each independently O or NH;

$R^1$ and $R^2$ are independently

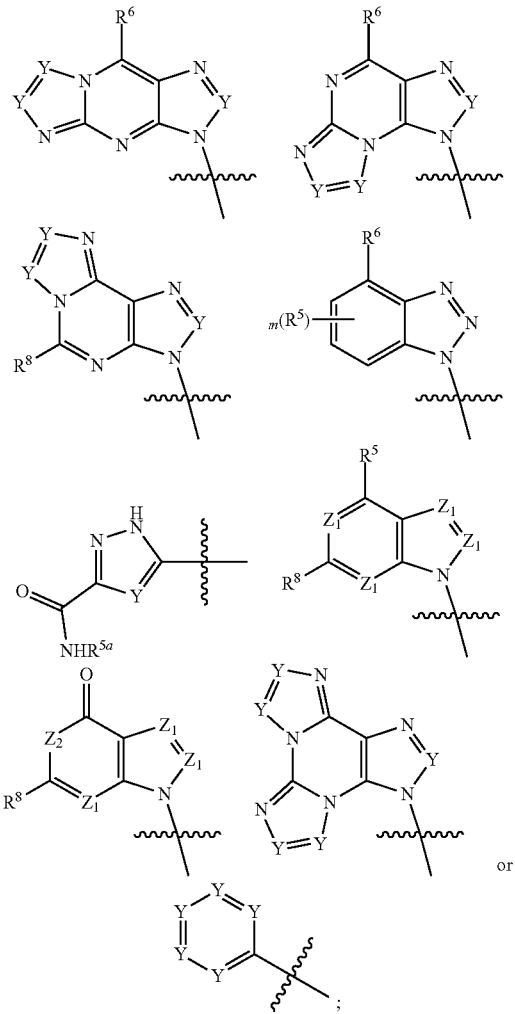

with the proviso that one of $R^1$ and $R^2$ must be

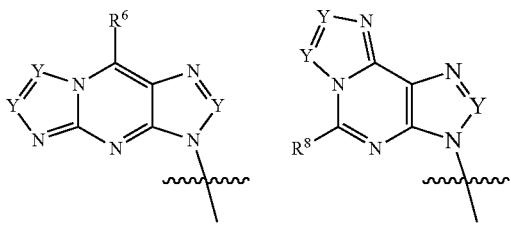

-continued

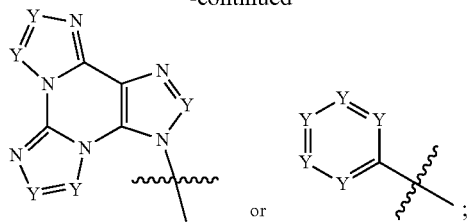

or $Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=CH$_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

In another aspect of the invention, there is provided a compound of the formula

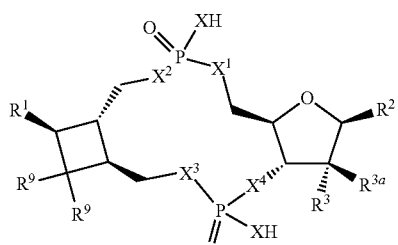

wherein
X is S;
$X^1$, $X^2$, $X^3$ and $X^4$ are each independently O or NH;
$R^1$ and $R^2$ are independently

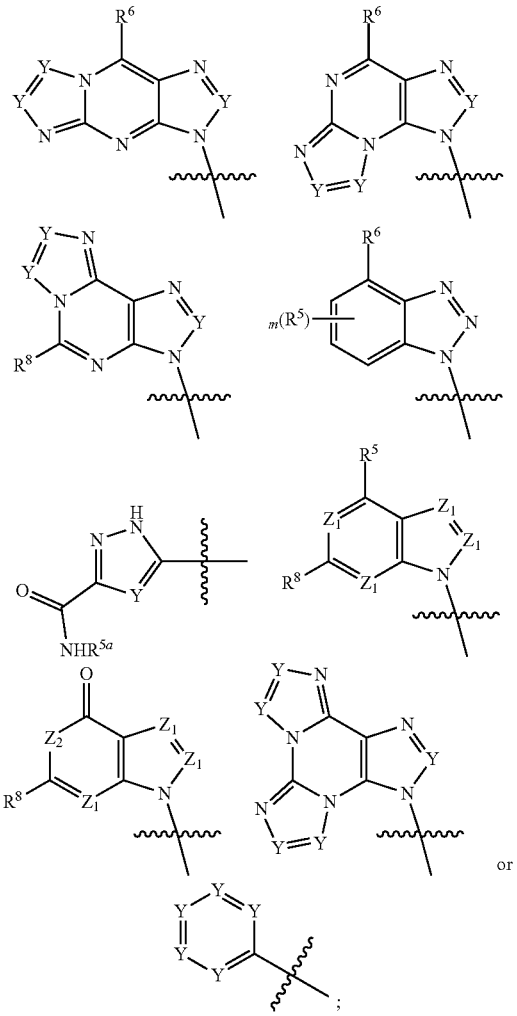

with the proviso that one of $R^1$ and $R^2$ must be

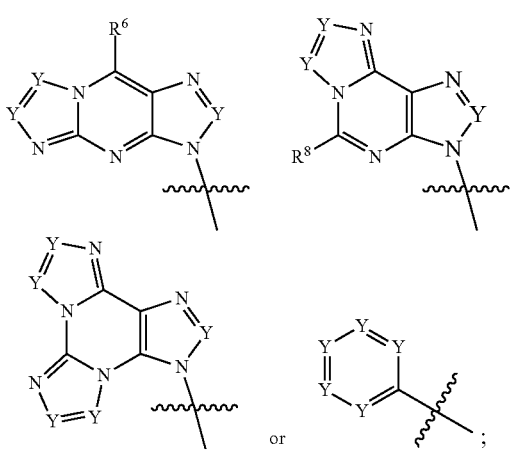

$Z_1$ is N or $CR^a$;
$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, $-NR^{a1}R^{a1}$ or $OR^{a1}$;

$R^{3a}$ is H, $CH_3$, halogen, $-NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

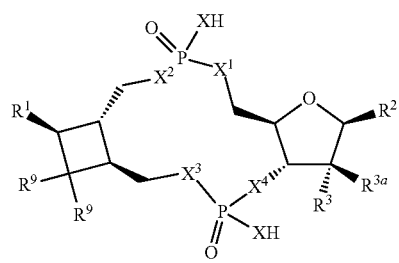

wherein

X is O;

$X^1$, $X^2$, $X^3$ and $X^4$ are each independently O or NH;

$R^1$ and $R^2$ are independently

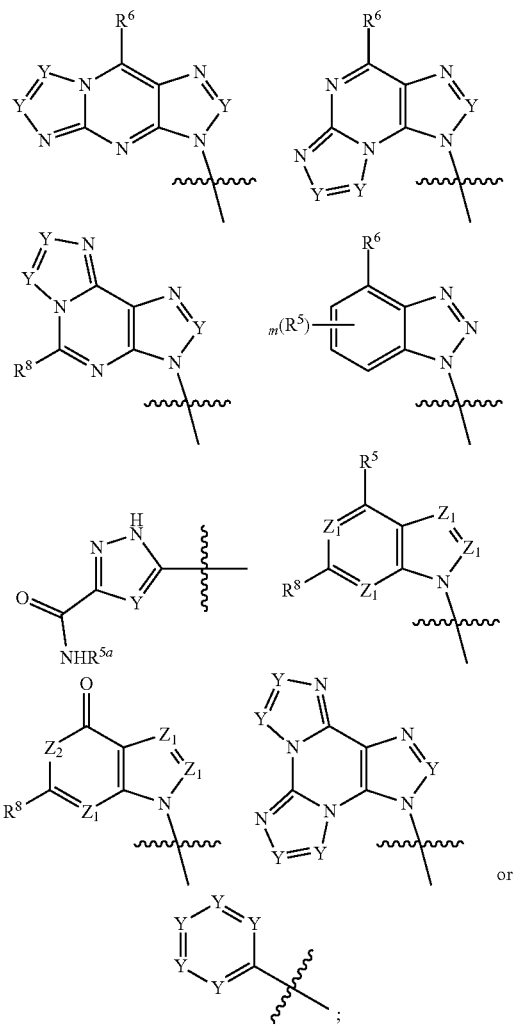

with the proviso that one of $R^1$ and $R^2$ must be

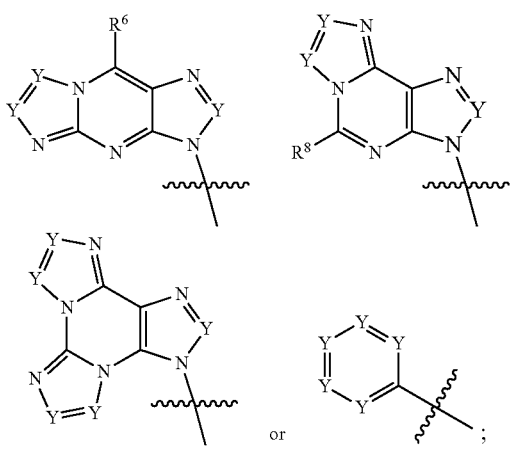

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, $-NR^{a1}R^{a1}$ or $OR^{a1}$;

$R^{3a}$ is H, $CH_3$, halogen, $-NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

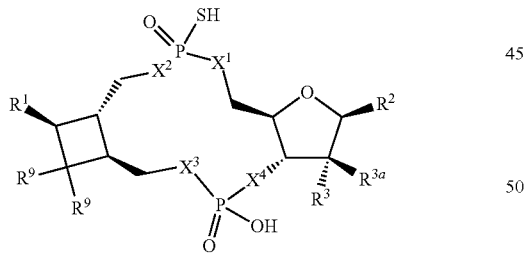

wherein $X^1$, $X^2$, $X^3$ and $X^4$ are each independently O or NH;

$R^1$ and $R^2$ are each independently

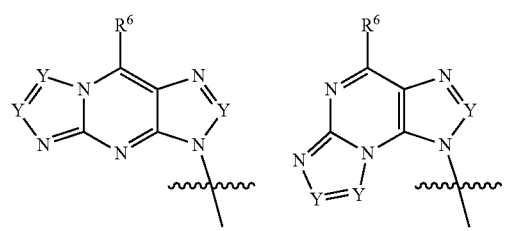

-continued

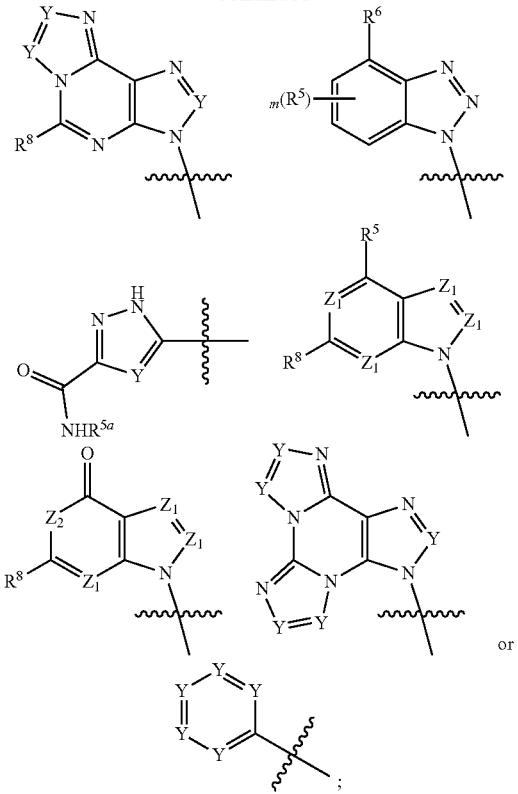

with the proviso that one of $R^1$ and $R^2$ must be

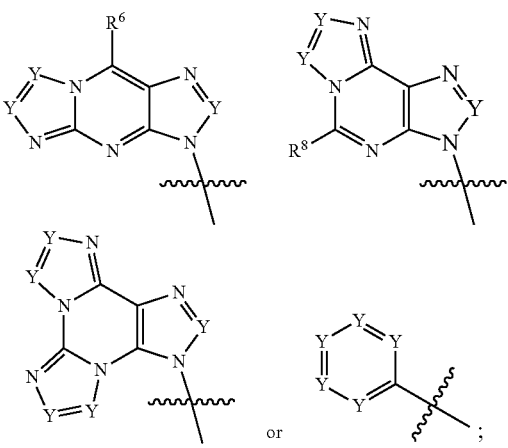

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

R³ is H, CH₃, halogen, —NR^{a1}R^{a1} or OR^{a1};
R^{3a} is H, CH₃, halogen, —NR^{a1}R^{a1} or OR^{a1}; or
R³ and R^{3a} may be taken together to form a 3-4 membered carbocycle; or
R³ and R^{3a} may be taken together to form a C=CH₂ substituent;
R⁵ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R^{5a} is H or C₁₋₃ alkyl;
R⁶ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R⁸ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R⁹ is H, halogen or methyl;
Y is CR^a or N;
m is 0, 1, 2 or 3;
or a pharmaceutically acceptable salt, tautomer or stereoisomer thereof.

In another aspect of the invention, there is provided a compound of the formula

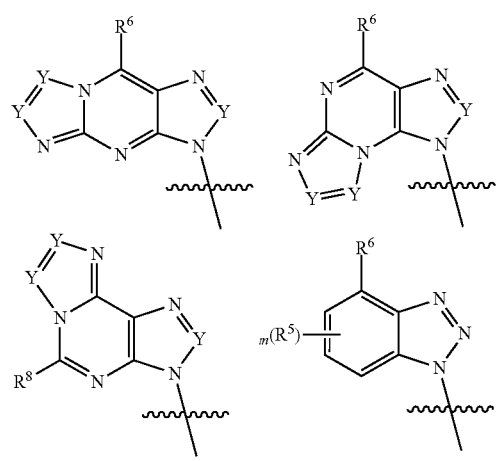

wherein
X¹, X², X³ and X⁴ are each independently O or NH;
R¹ and R² are each independently

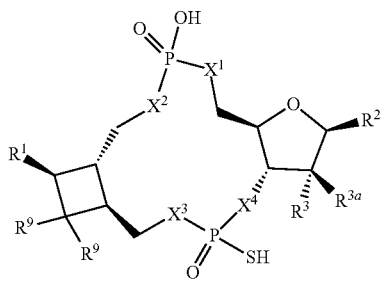

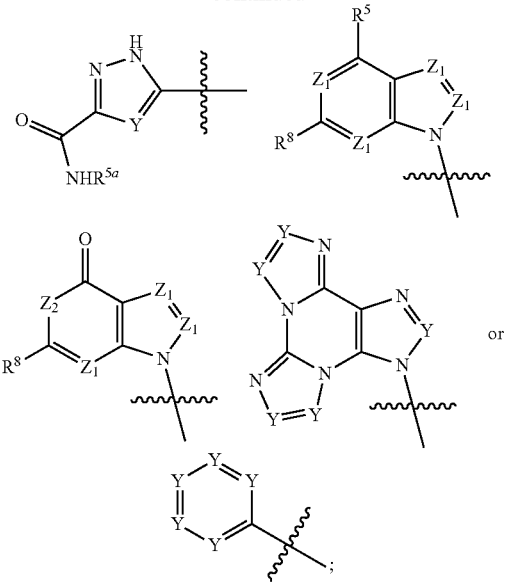

with the proviso that one of R¹ and R² must be

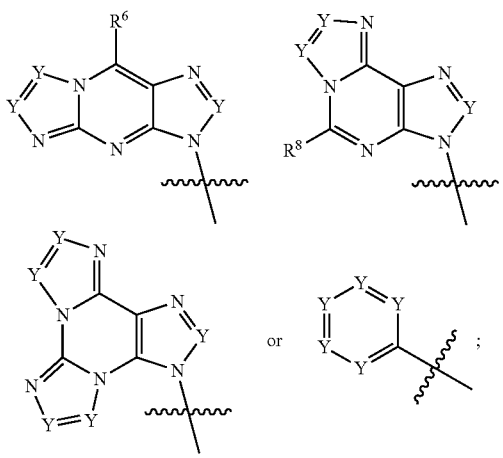

Z₁ is N or CR^a;
Z₂ is NR^b;
R^a is H, halogen, C₁₋₆ alkyl substituted with 0-6 R⁵, C₃₋₆ cycloalkyl substituted with 0-6 R⁵, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R^b is H, C₁₋₆ alkyl substituted with 0-6 R⁵, C₃₋₆ cycloalkyl substituted with 0-6 R⁵, —C(O)R^{a1}, —C(O)NR^{a1}R^{a1}, —S(O)₂R^{a1} or S(O)₂NR^{a1}R^{a1};
R^{a1} is H, C₁₋₃ alkyl or C₃₋₆ cycloalkyl;
R³ is H, CH₃, halogen, —NR^{a1}R^{a1} or OR^{a1};
R^{3a} is H, CH₃, halogen, —NR^{a1}R^{a1} or OR^{a1}; or
R³ and R^{3a} may be taken together to form a 3-4 membered carbocycle; or
R³ and R^{3a} may be taken together to form a C=CH₂ substituent;
R⁵ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)

$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

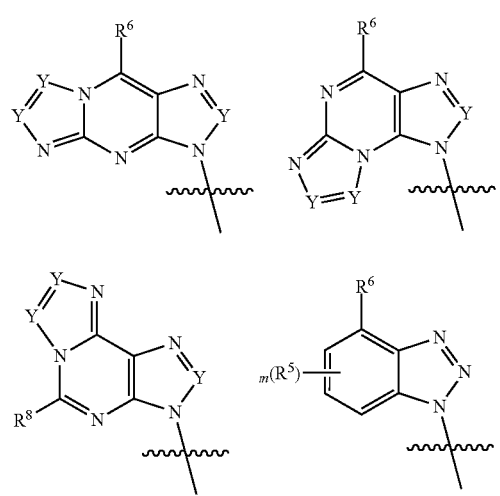

wherein

X is independently O or S;

$R^1$ and $R^2$ are each independently

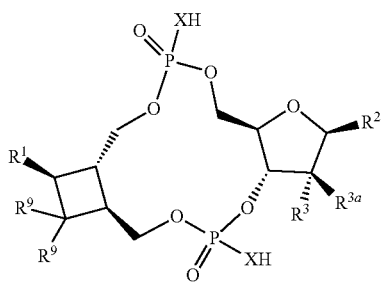

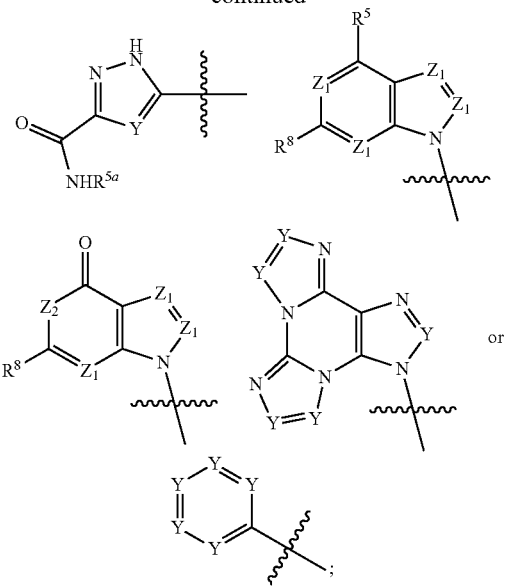

with the proviso that one of $R^1$ and $R^2$ must be

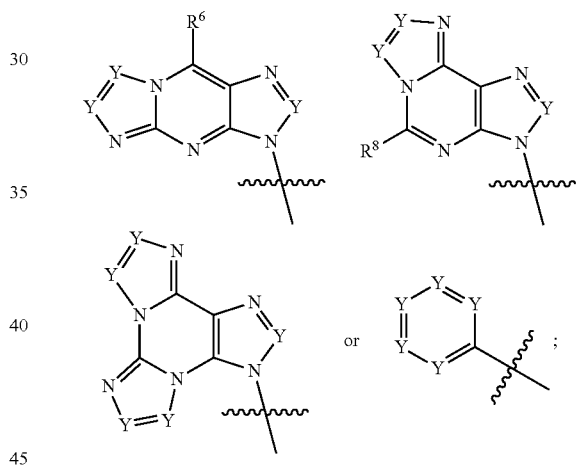

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

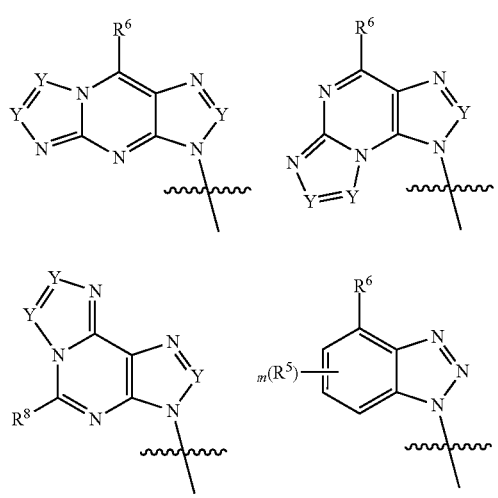

wherein

X is S;

$R^1$ and $R^2$ are each independently

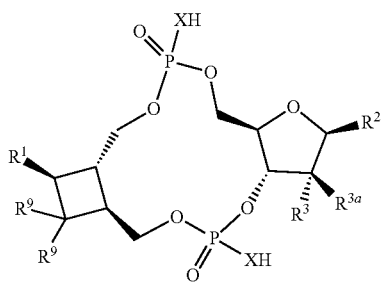

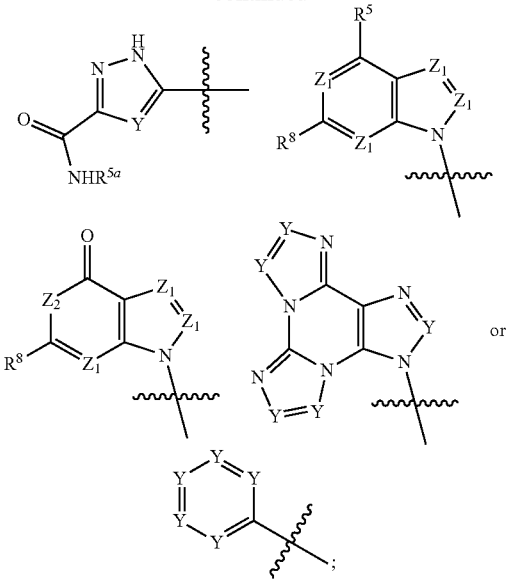

with the proviso that one of $R^1$ and $R^2$ must be

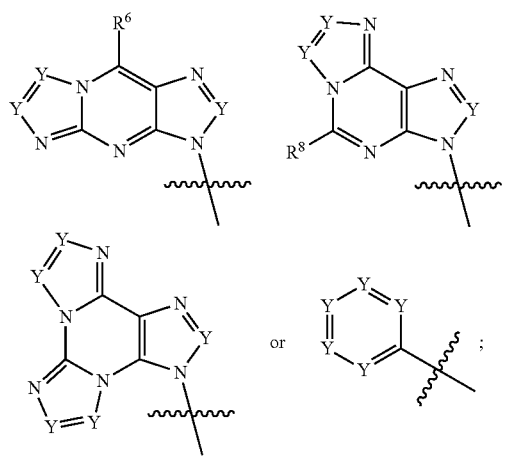

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

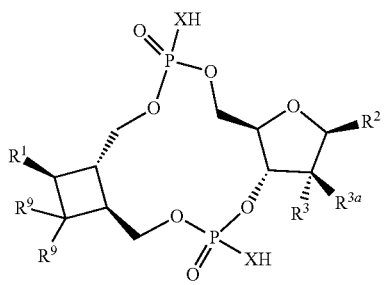

wherein

X is O;

$R^1$ and $R^2$ are each independently

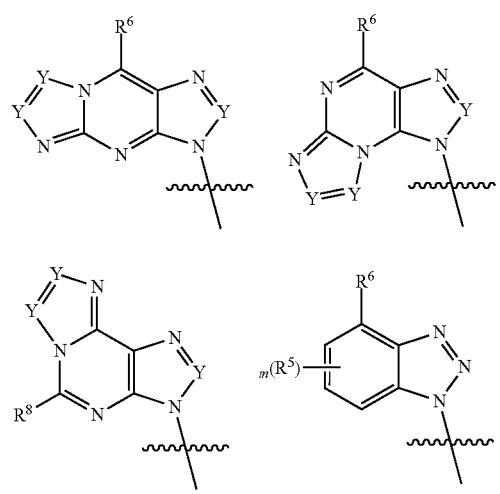

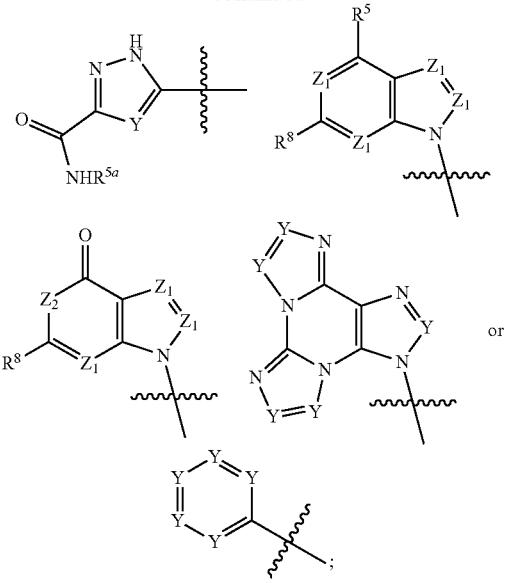

with the proviso that one of $R^1$ and $R^2$ must be

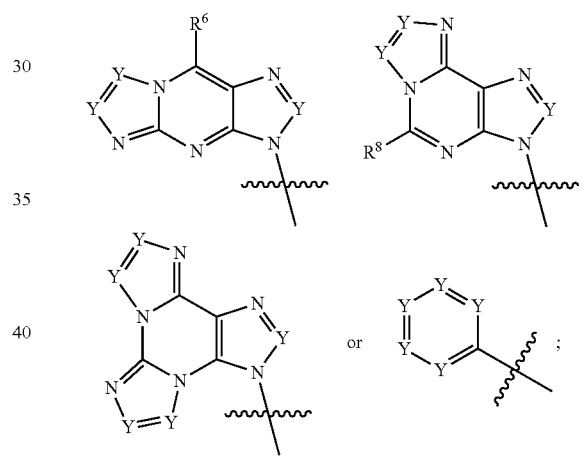

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

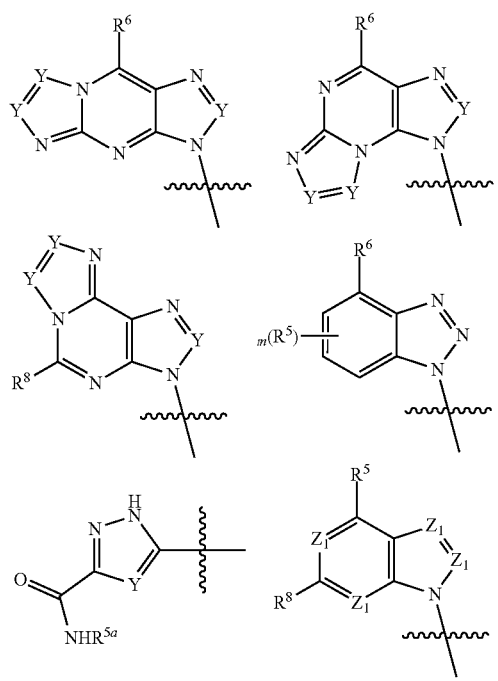

wherein
$R^1$ and $R^2$ are each independently

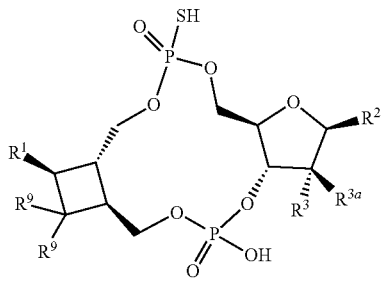

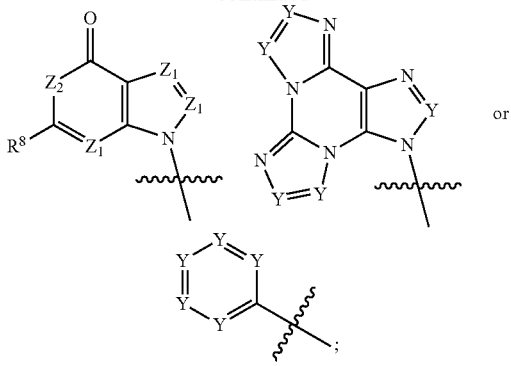

with the proviso that one of $R^1$ and $R^2$ must be

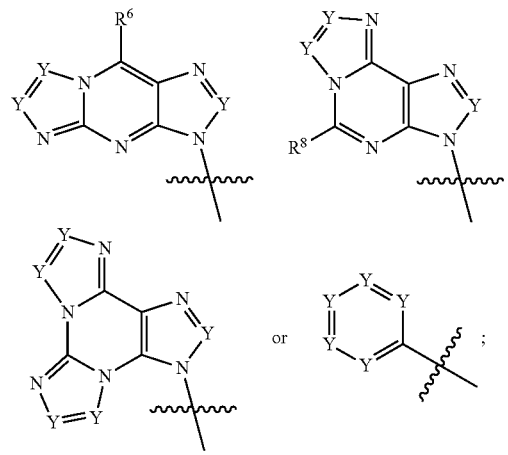

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

In another aspect of the invention, there is provided a compound of the formula

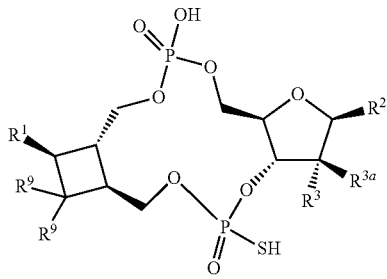

wherein

R$^1$ and R$^2$ are each independently

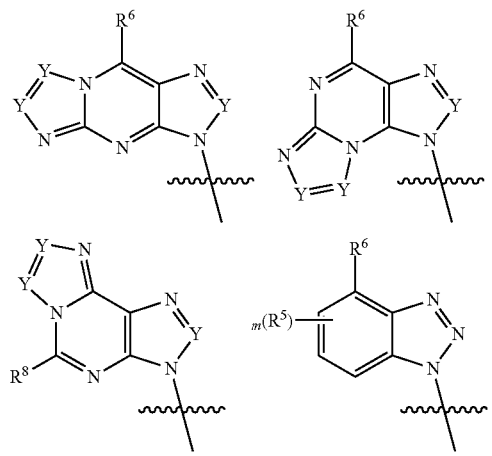

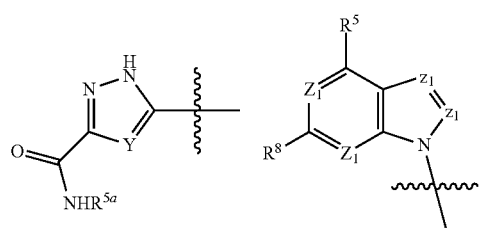

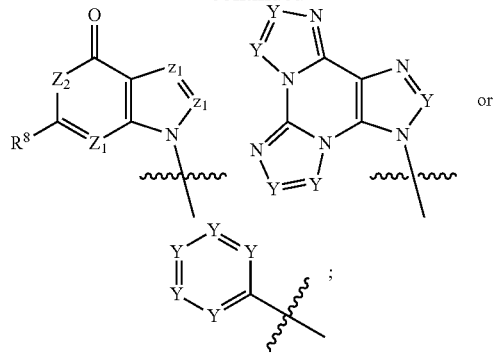

with the proviso that one of R$^1$ and R$^2$ must be

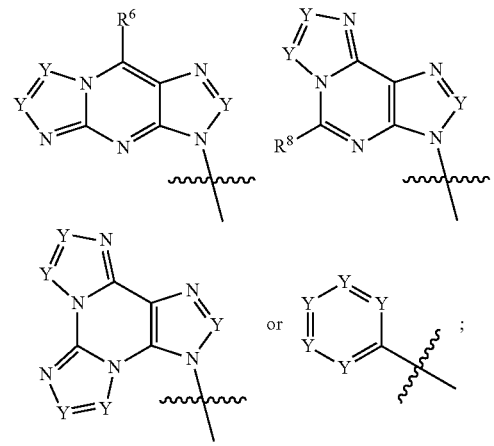

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^3$ is H, CH$_3$, halogen, —NR$^{a1}$R$^{a1}$ or OR$^{a1}$;

R$^{3a}$ is H, CH$_3$, halogen, —NR$^{a1}$R$^{a1}$ or OR$^{a1}$; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

In another aspect of the invention, there is provided a compound of the formula

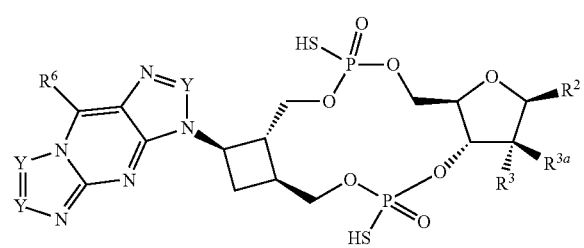

or a pharmaceutically acceptable salt, tautomer or stereoisomer thereof.

In another aspect of the invention, there is provided a compound of the formula

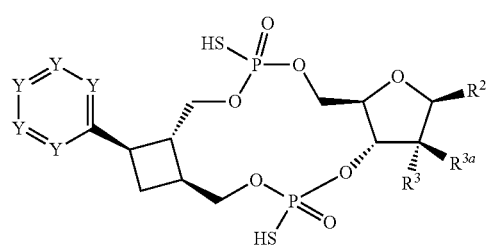

or a pharmaceutically acceptable salt, tautomer or stereoisomer thereof.

In another aspect of the invention, there is provided a compound of the formula

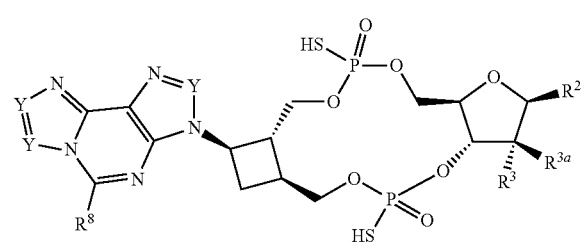

or a pharmaceutically acceptable salt, tautomer or stereoisomer thereof.

In another aspect of the invention, there is provided a compound of the formula

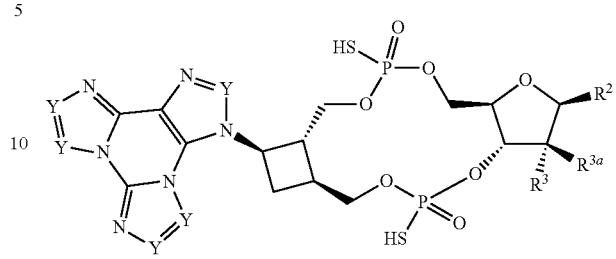

or a pharmaceutically acceptable salt, tautomer or stereoisomer thereof.

In another aspect of the invention, there is provided a compound of the formula

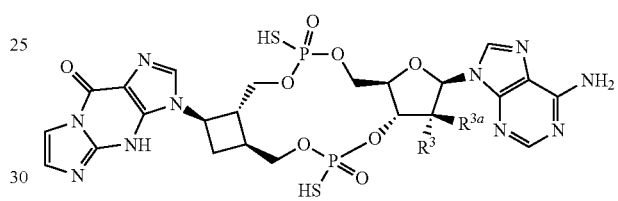

or a pharmaceutically acceptable salt, tautomer or stereoisomer thereof.

In another aspect of the invention, there is provided a compound of the formula

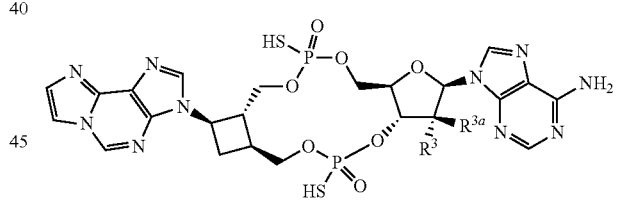

or a pharmaceutically acceptable salt, tautomer or stereoisomer thereof.

In another aspect of the invention, there is provided a compound of the formula

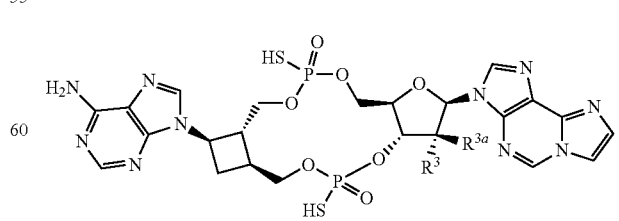

or a pharmaceutically acceptable salt, tautomer or stereoisomer thereof.

In another aspect of the invention, there is provided a compound of the formula
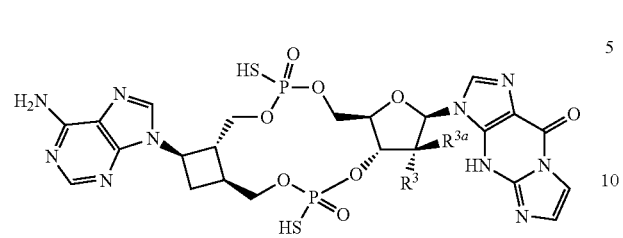
or a pharmaceutically acceptable salt, tautomer or stereoisomer thereof.
In another aspect of the invention, there is provided a compound of the formula

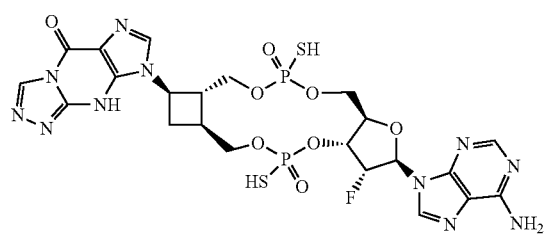
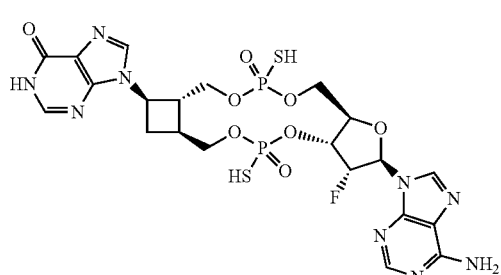
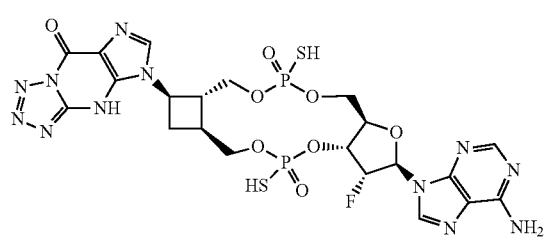
In another aspect of the invention, there is provided a pharmaceutically acceptable salt of a compound of the formula
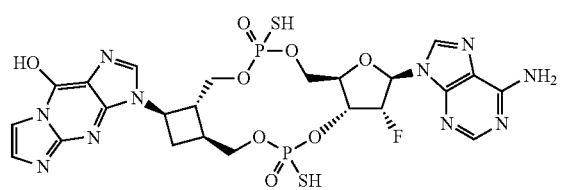
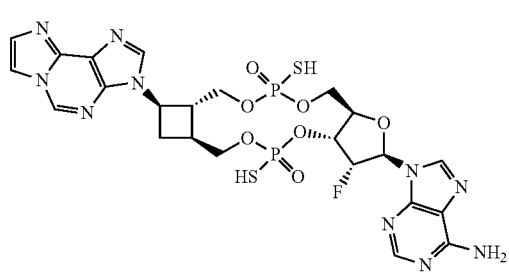
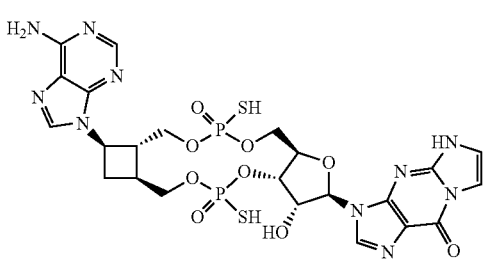
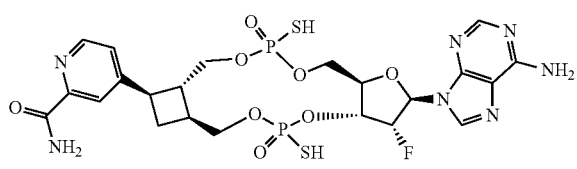
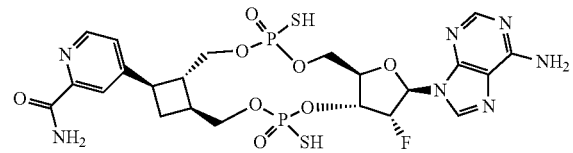
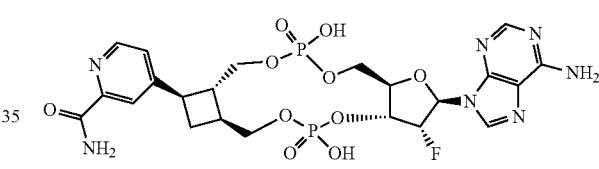
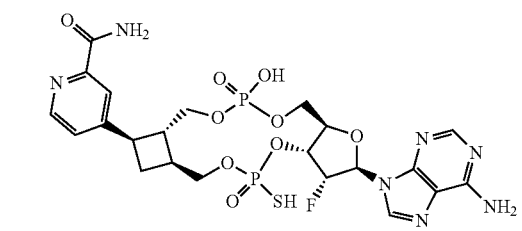
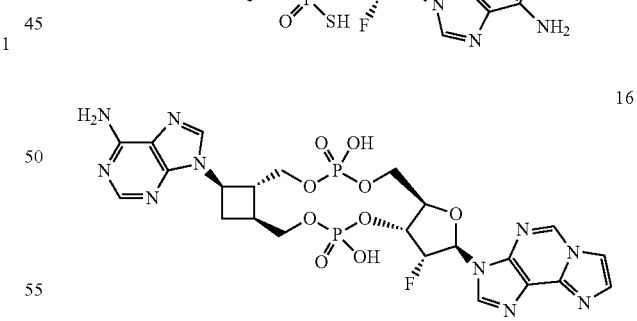
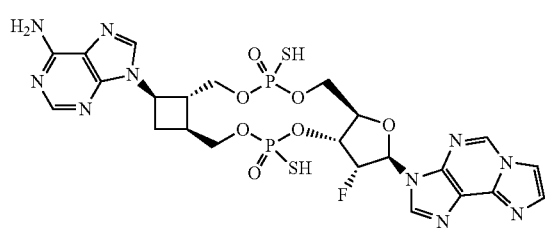

-continued

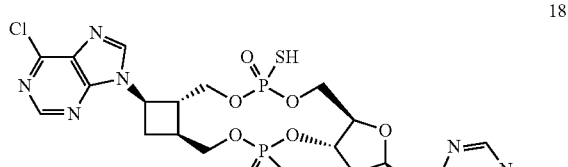
18

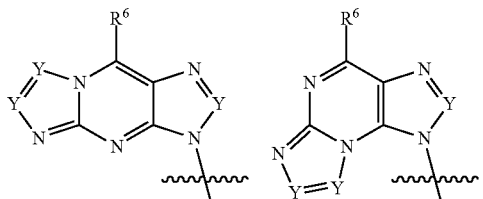
19

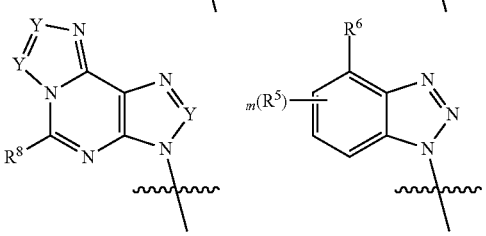
20

21

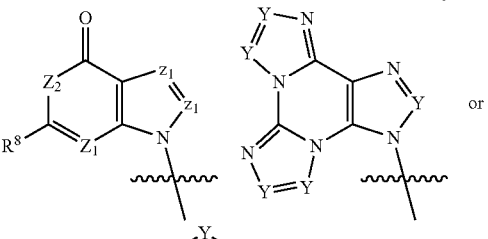
22

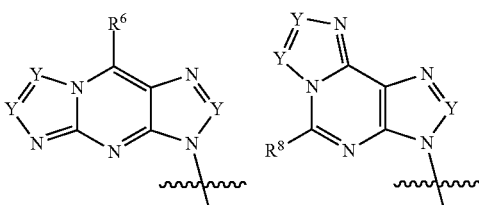
23

In another aspect of the invention, there is provided a compound of formula II (II)

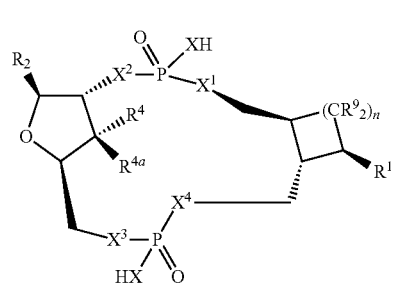

wherein
X is independently O or S;
$X^1$, $X^2$, $X^3$ and $X^4$ are each independently O or NH;
$R^1$ and $R^2$ are each independently

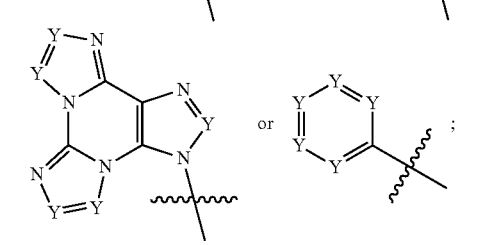

with the proviso that one of $R^1$ and $R^2$ must be $Z_1$ is N or $CR^a$;
$Z_2$ is $NR^b$;
$R^b$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC (O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^4$ is H, CH$_3$, halogen, —NR$^{a1}$R$^{a1}$ or OR$^{a1}$;

R$^{4a}$ is H, CH$_3$, halogen, —NR$^{a1}$R$^{a1}$ or OR$^{a1}$; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

or two R$^5$ groups may be taken together to form a 5-6 membered carbocyclic or heterocyclic group;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

n is 0 or 1;

or a pharmaceutically acceptable salt, tautomer or stereoisomer thereof.

Additional aspects of the invention include compounds according to formula (II) wherein R$^1$ is

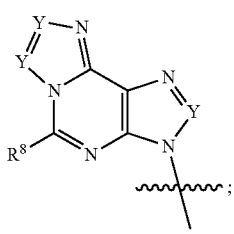

and

R$^2$ is

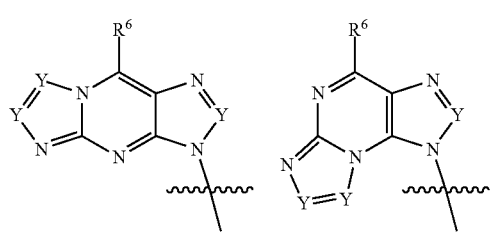

-continued

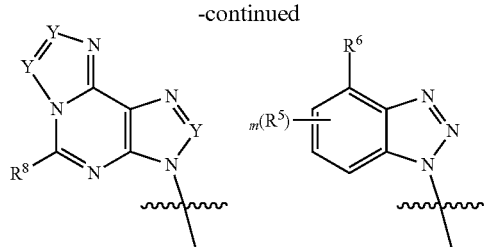

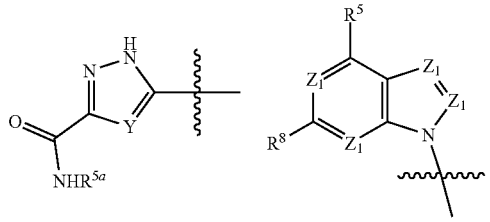

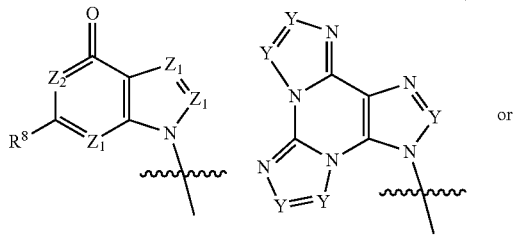

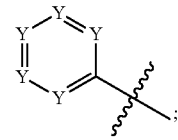

R$^1$ is

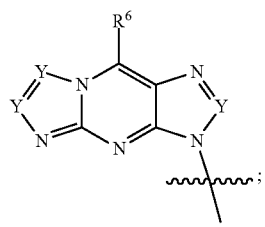

and

R$^2$ is

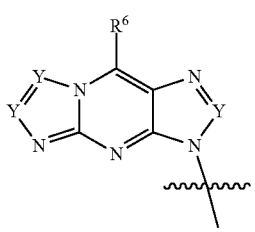 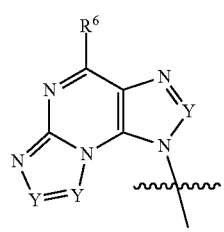

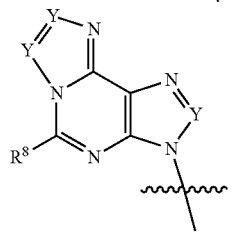 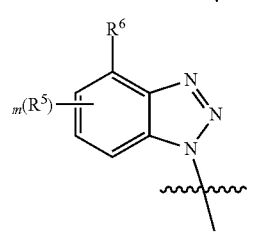

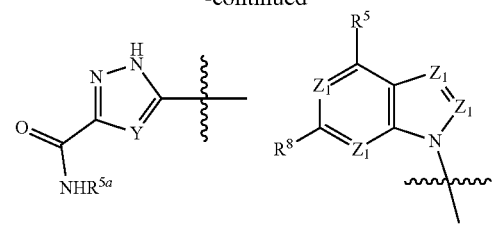
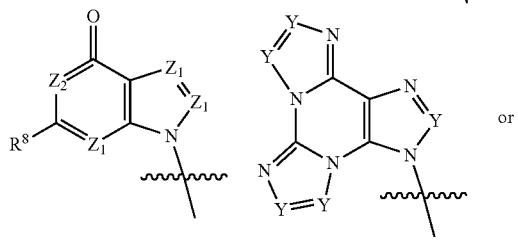
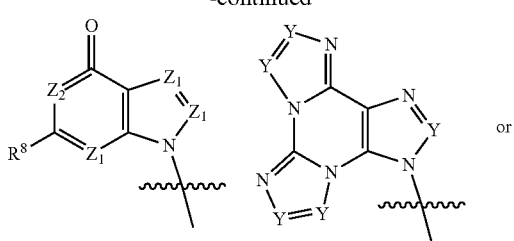
or
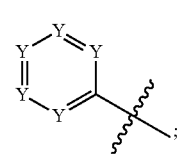
;
R¹ is
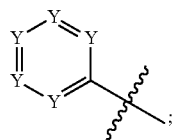
;
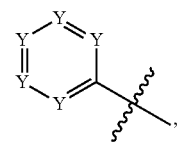
,
and
R² is
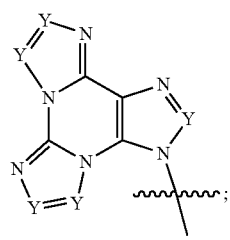
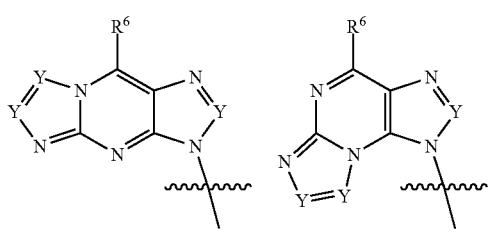
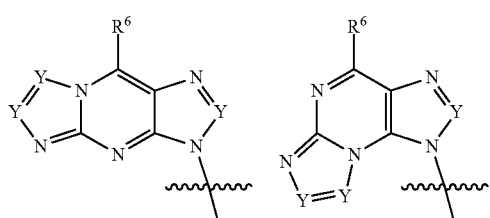
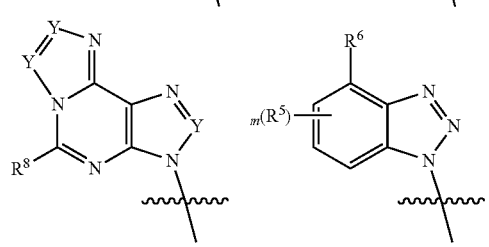
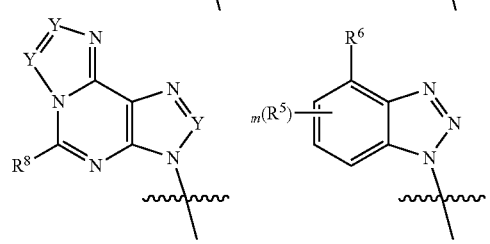
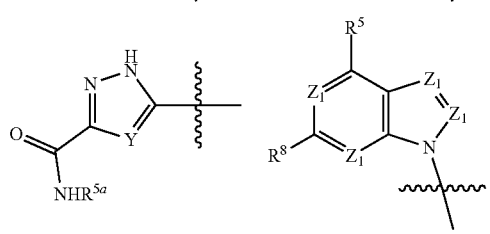
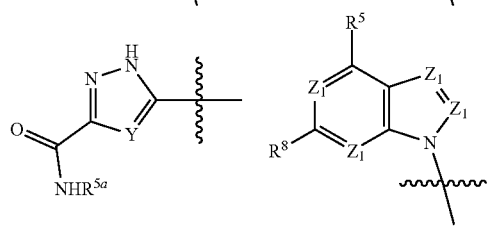
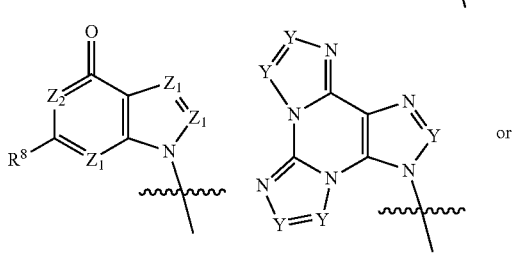
or -continued
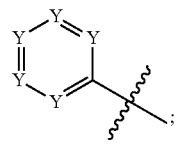
R¹ is
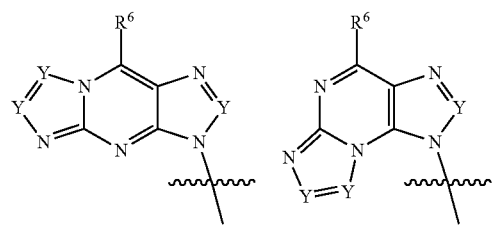
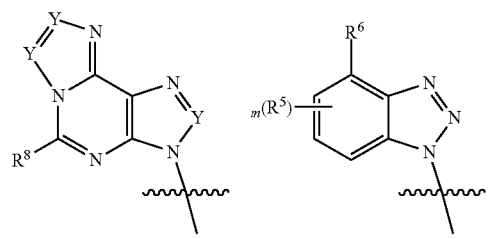
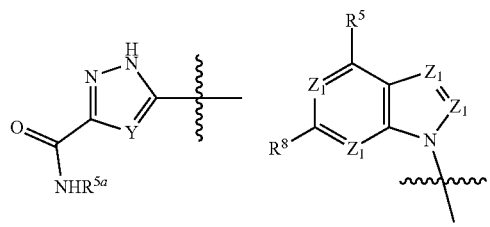
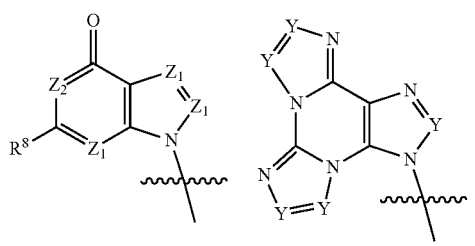
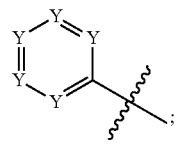
and
R² is
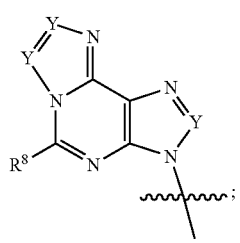
R¹ is
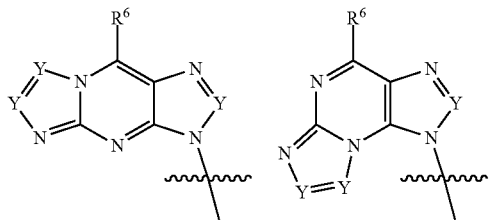
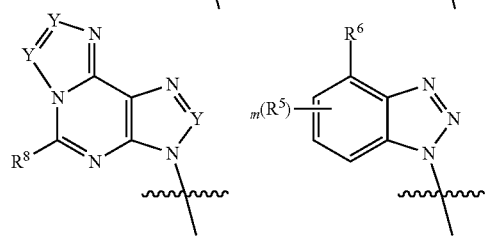
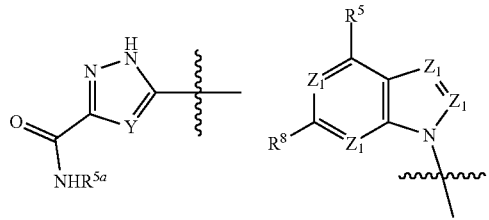
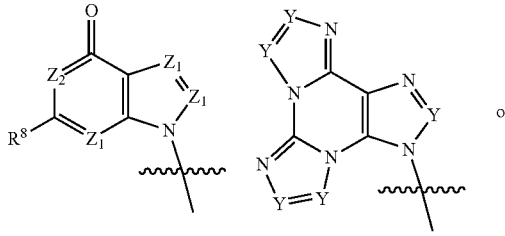
or
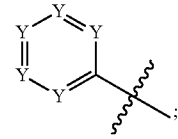
and
R² is
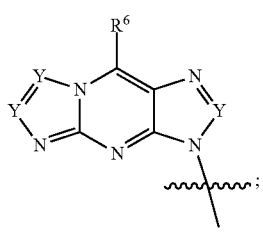
R¹ is
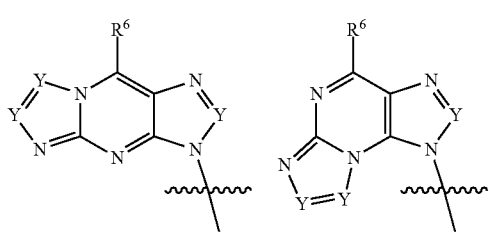

-continued
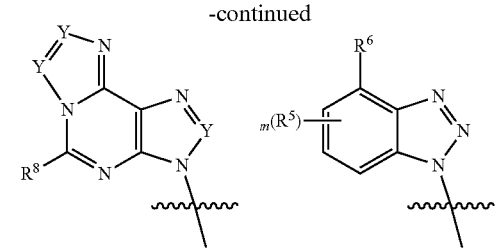
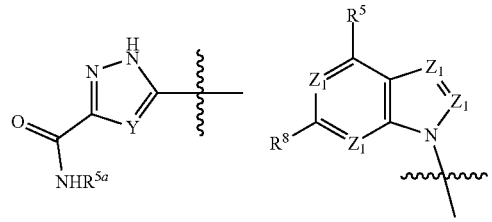
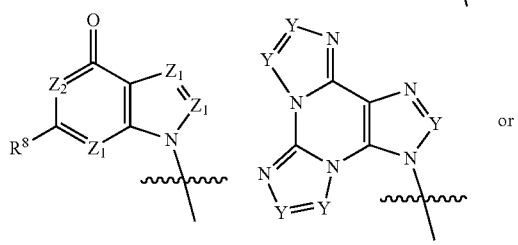
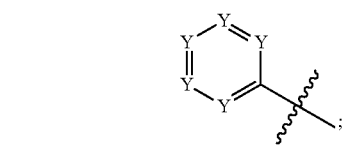
and
R² is
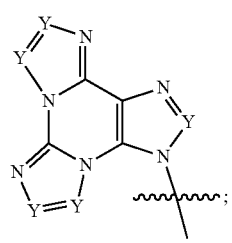
R¹ is
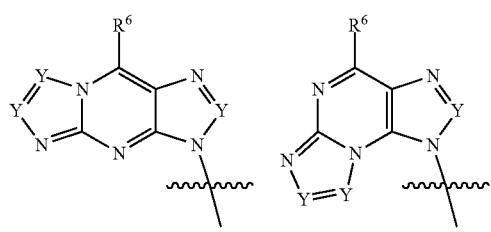
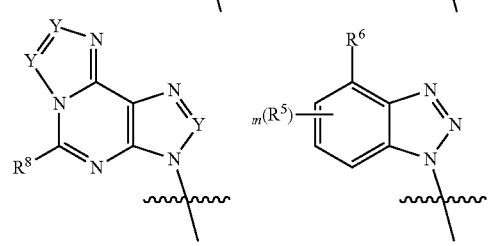
-continued
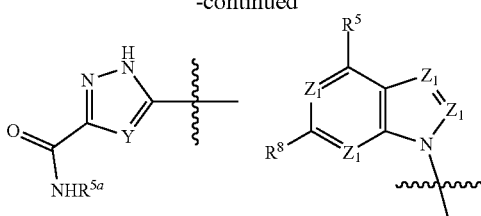
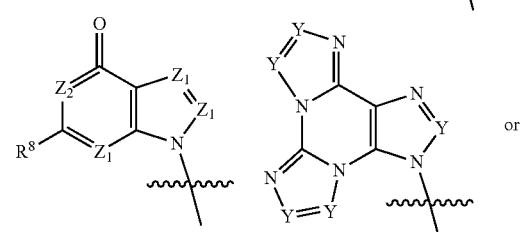
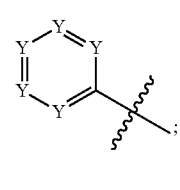
and
R² is
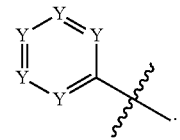
In another aspect of the invention, there is provided a compound of formula II
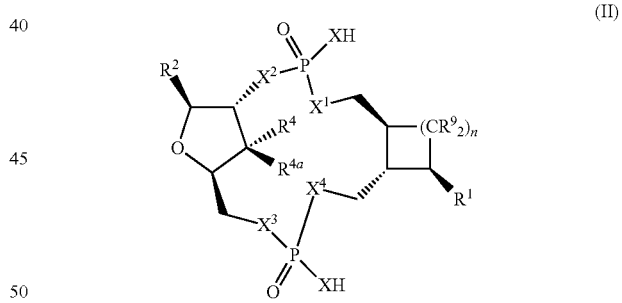
(II)
wherein
X is S;
$X^1$, $X^2$, $X^3$ and $X^4$ are each independently O or NH;
$R^1$ and $R^2$ are each independently
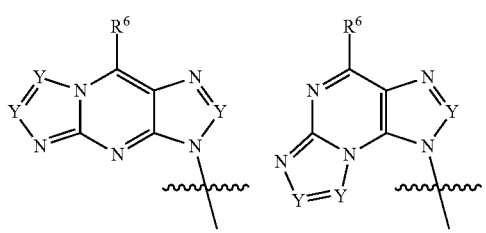
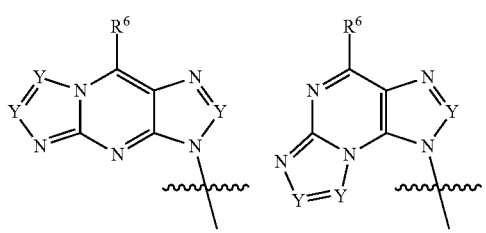

-continued

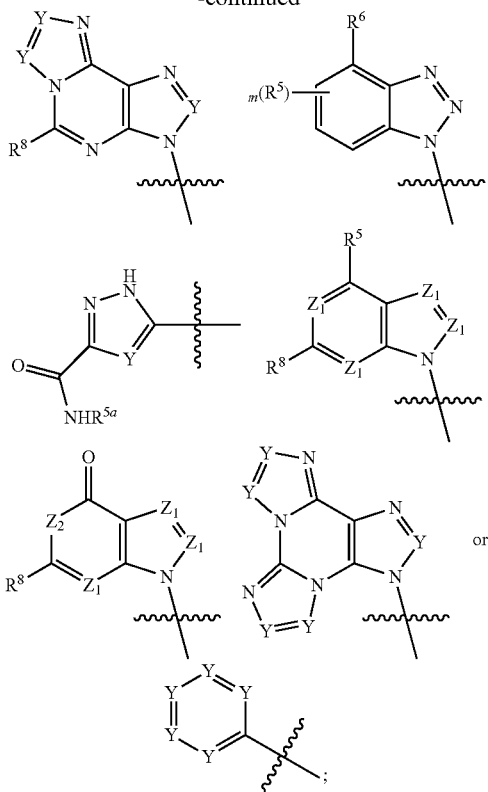

with the proviso that one of $R^1$ and $R^2$ must be

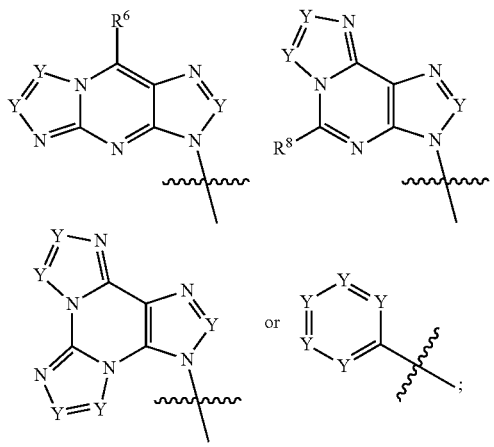

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of formula II

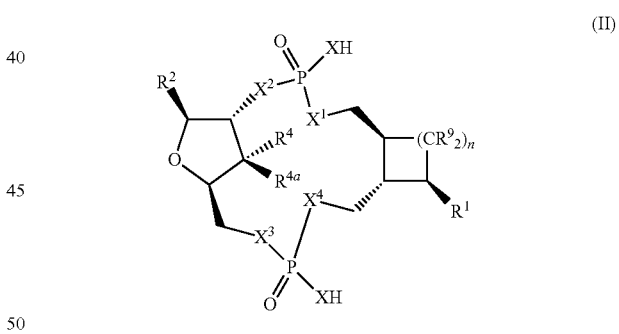

(II)

wherein
X is O;
$X^1$, $X^2$, $X^3$ and $X^4$ are each independently O or NH;
$R^1$ and $R^2$ are each independently

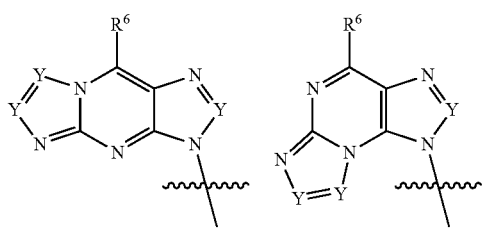

-continued

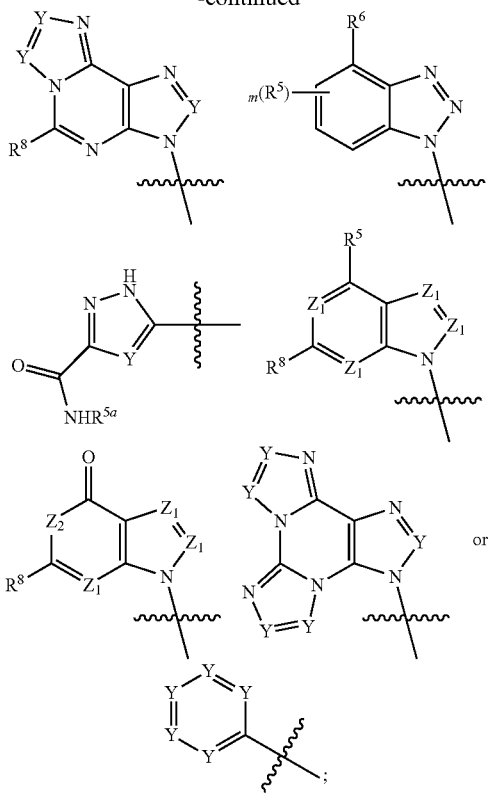

with the proviso that one of $R^1$ and $R^2$ must be

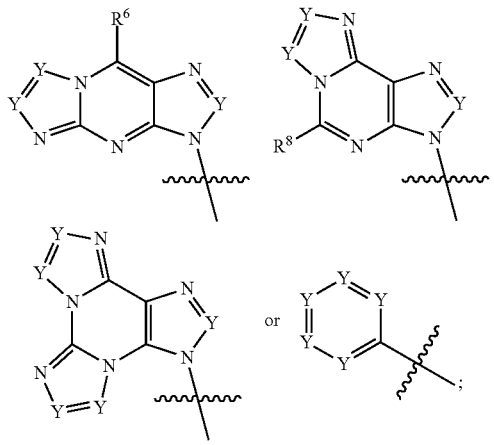

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of formula II

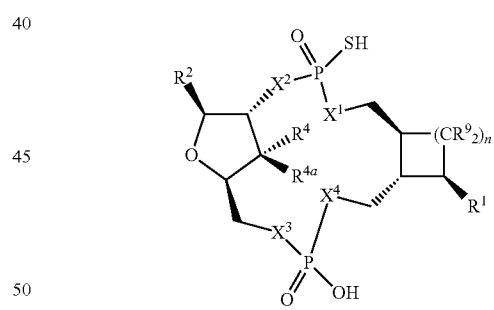

wherein
$X^1$, $X^2$, $X^3$ and $X^4$ are each independently O or NH;
$R^1$ and $R^2$ are each independently

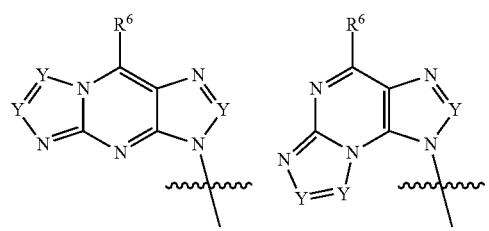

-continued

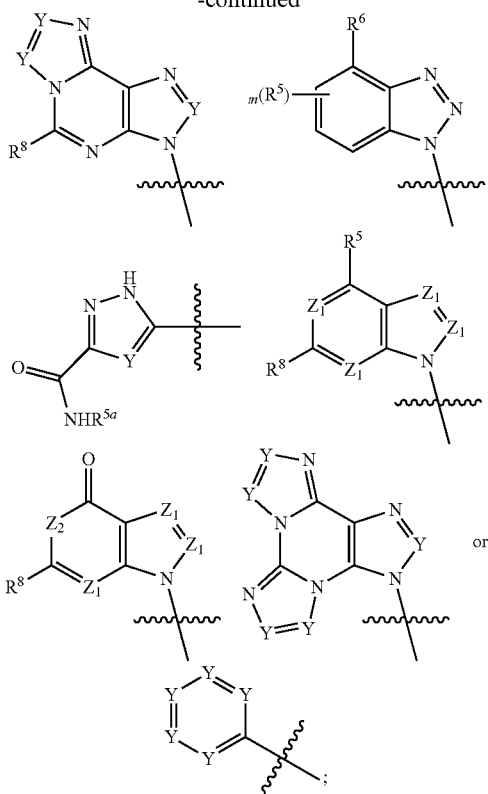

with the proviso that one of $R^1$ and $R^2$ must be

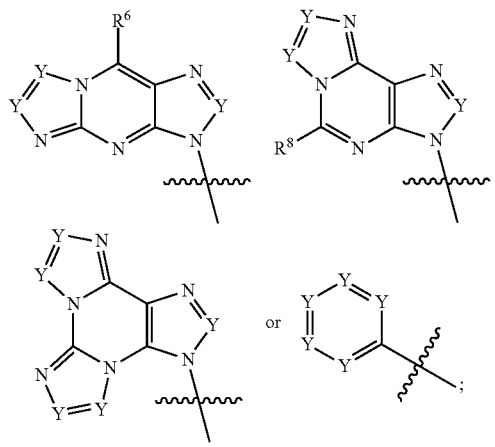

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of formula II

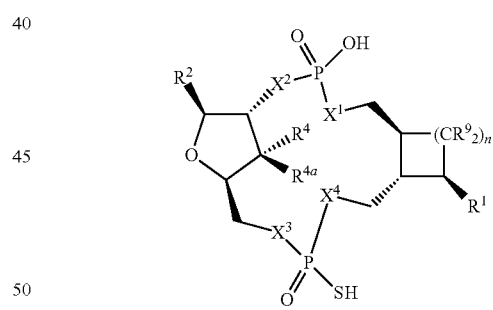

wherein
$X^1$, $X^2$, $X^3$ and $X^4$ are each independently O or NH;
$R^1$ and $R^2$ are each independently

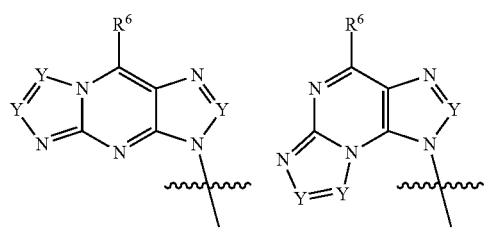

73

-continued

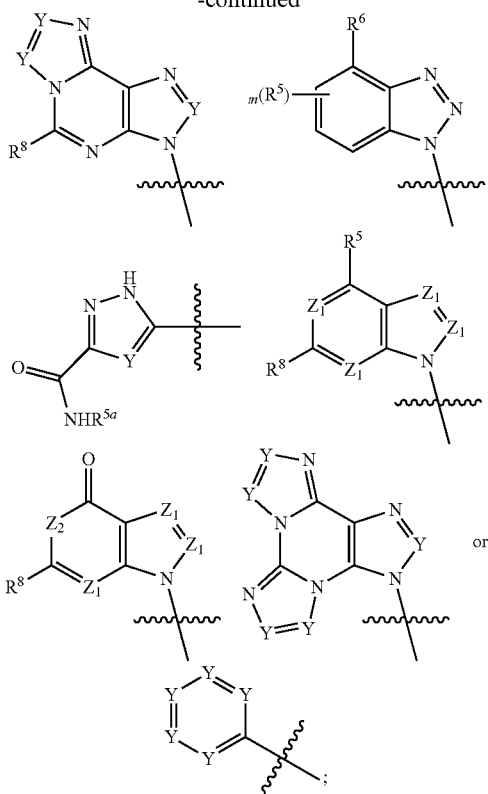

with the proviso that one of $R^1$ and $R^2$ must be

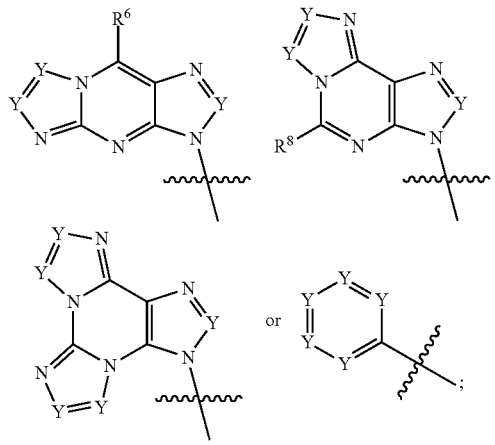

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

74

$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of the formula

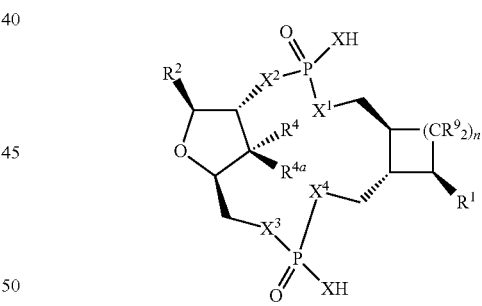

wherein
X is independently O or S;
$R^1$ and $R^2$ are each independently

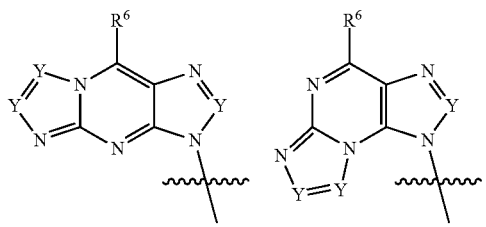

-continued

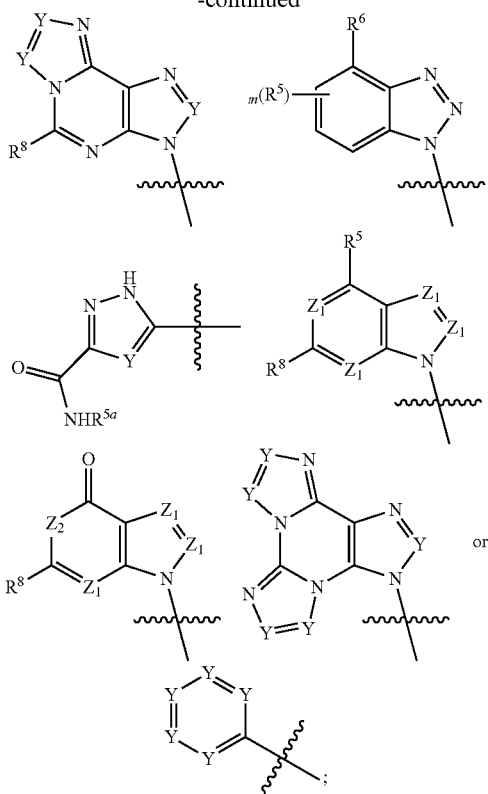

with the proviso that one of $R^1$ and $R^2$ must be

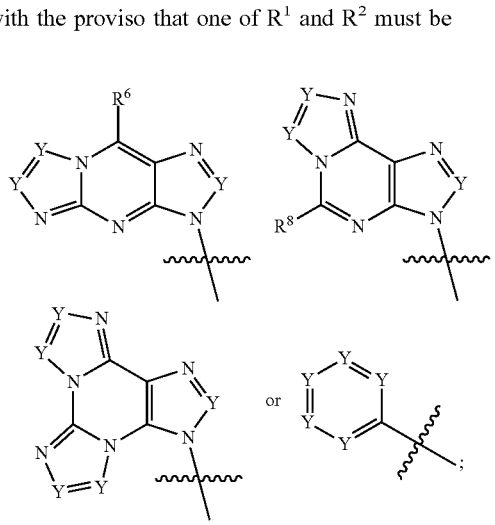

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of the formula

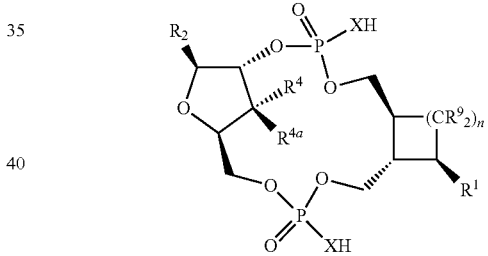

wherein
X is S;
$R^1$ and $R^2$ are each independently

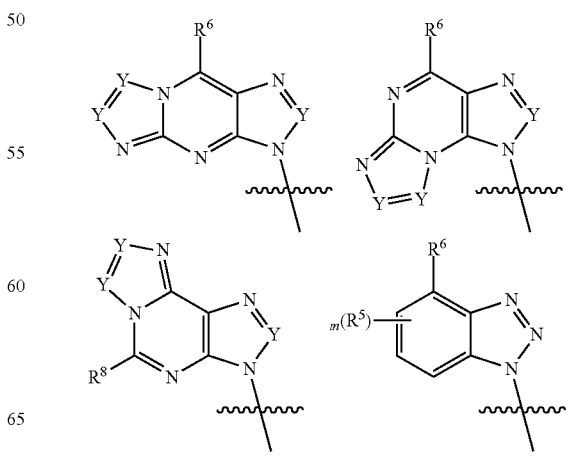

-continued

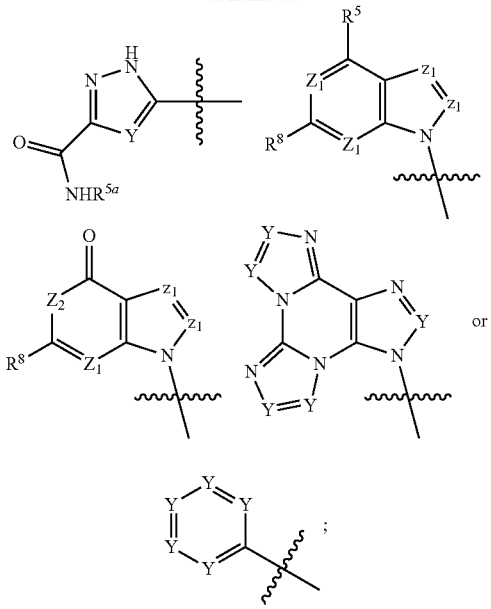

with the proviso that one of $R^1$ and $R^2$ must be

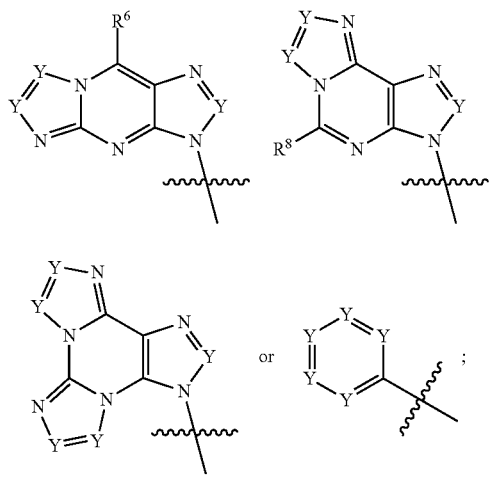

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

In another aspect of the invention, there is provided a compound of the formula

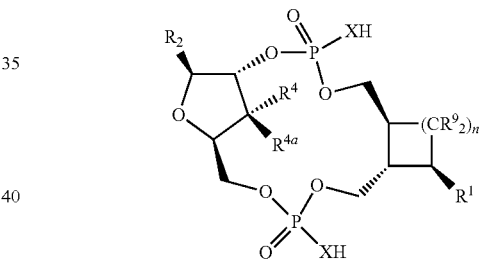

wherein
X is O;
$R^1$ and $R^2$ are each independently

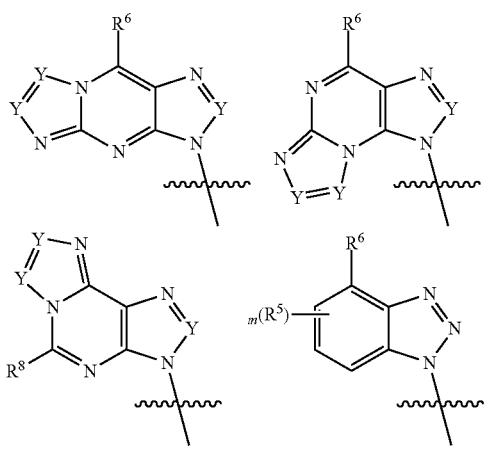

-continued

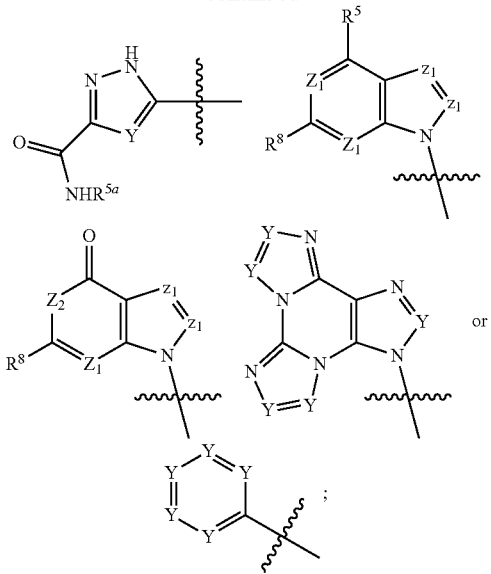

with the proviso that one of $R^1$ and $R^2$ must be

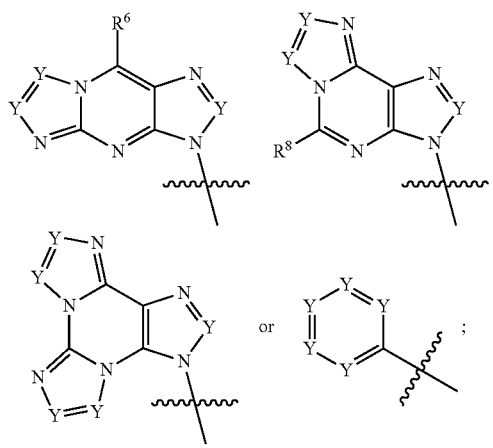

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of the formula

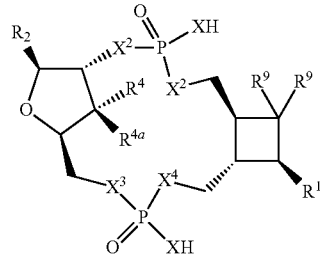

wherein

X is independently O or S;

$X^1$, $X^2$, $X^3$ and $X^4$ are each independently O or NH;

$R^1$ and $R^2$ are each independently

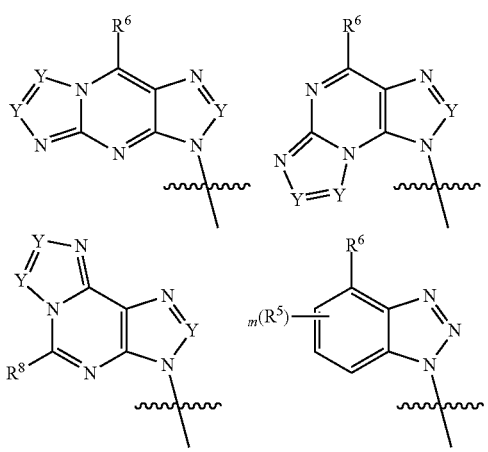

-continued

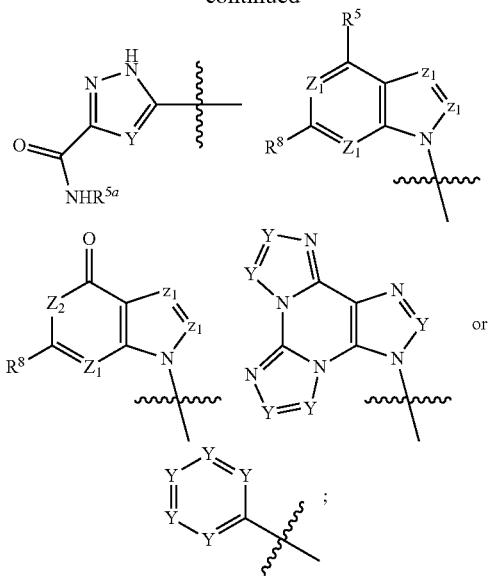

with the proviso that one of $R^1$ and $R^2$ must be

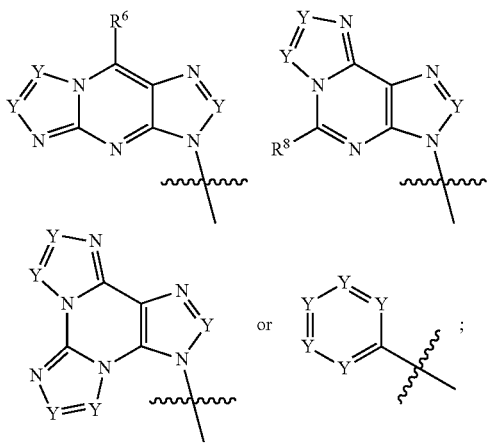

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

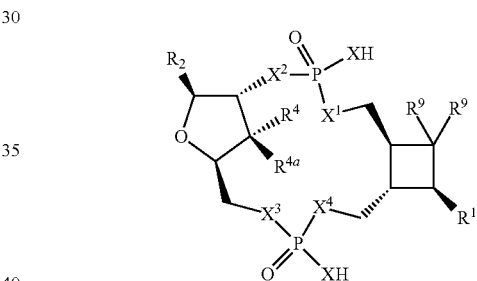

wherein

X is S;

$X^1$, $X^2$, $X^3$ and $X^4$ are each independently O or NH;

$R^1$ and $R^2$ are each independently

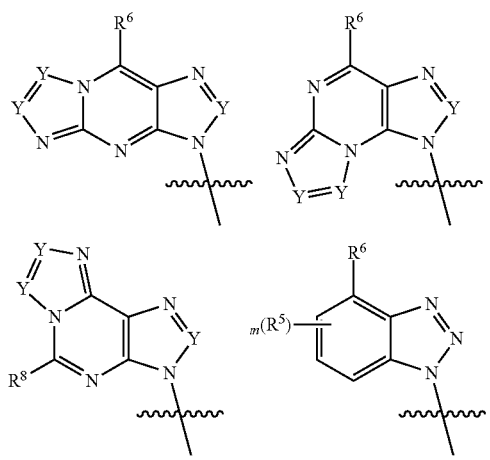

-continued

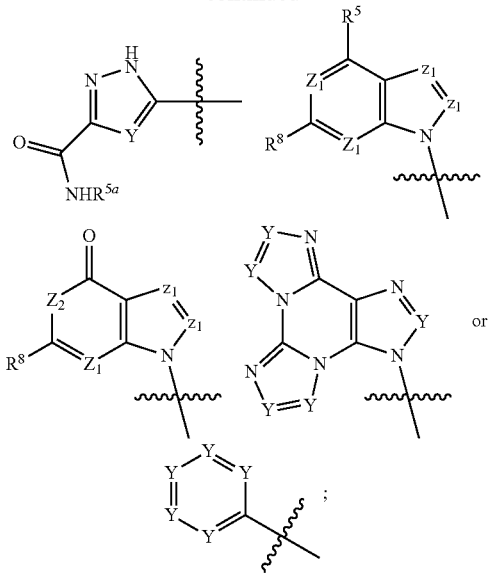

with the proviso that one of R¹ and R² must be

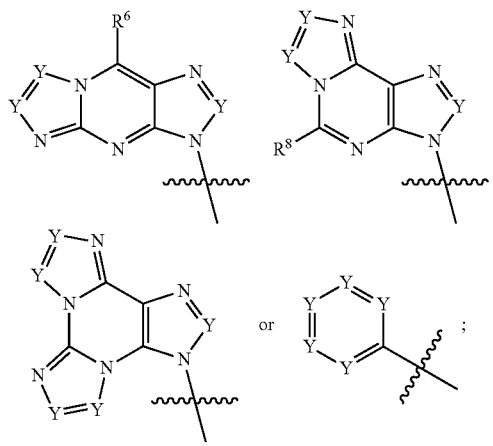

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, $-NR^{a1}R^{a1}$ or $OR^{a1}$;

$R^{4a}$ is H, $CH_3$, halogen, $-NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

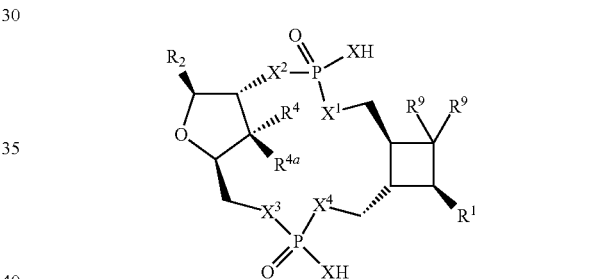

wherein

X is O;

$X^1$, $X^2$, $X^3$ and $X^4$ are each independently O or NH;

$R^1$ and $R^2$ are each independently

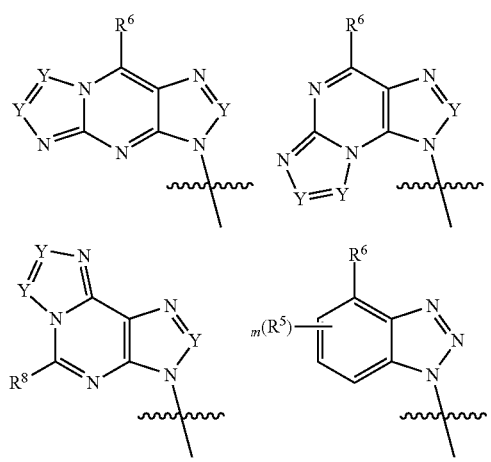

-continued

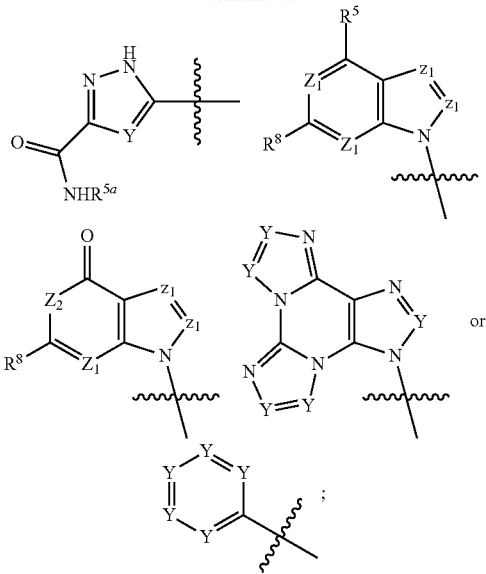

with the proviso that one of $R^1$ and R must be

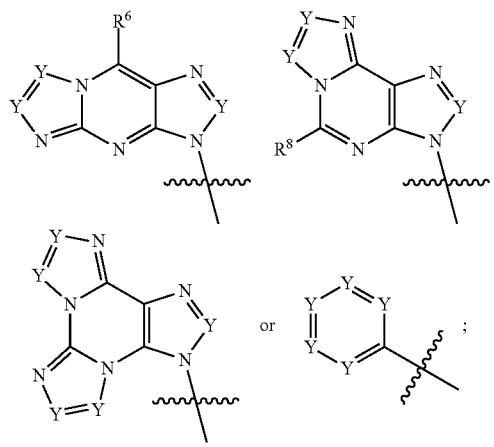

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, $-NR^{a1}R^{a1}$ or $OR^{a1}$;

$R^{4a}$ is H, $CH_3$, halogen, $-NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

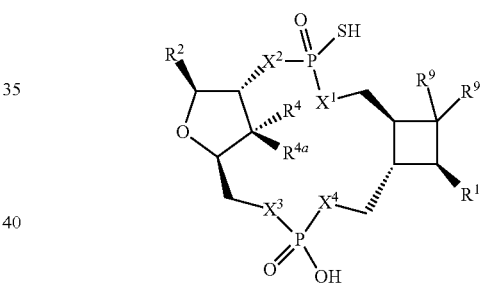

wherein $X^1$, $X^2$, $X^3$ and $X^4$ are each independently O or NH;

$R^1$ and $R^2$ are each independently

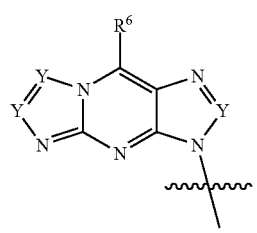 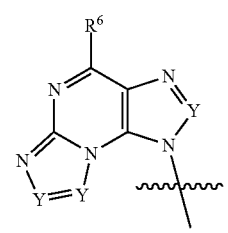

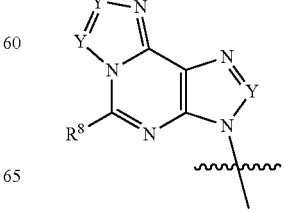 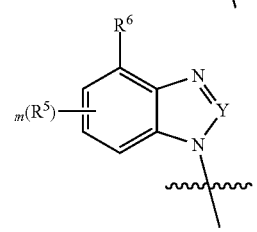

-continued

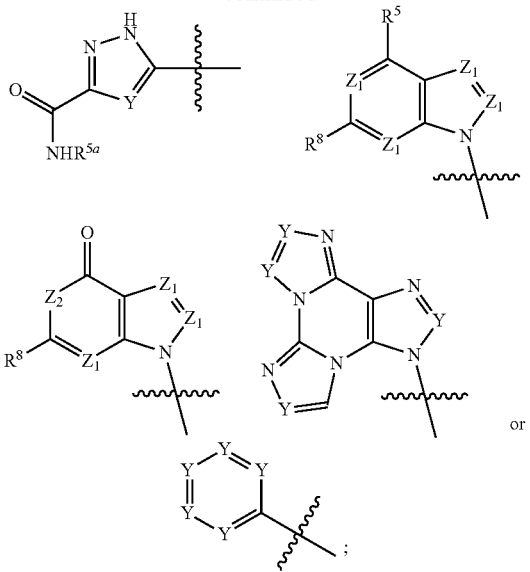

with the proviso that one of $R^1$ and $R^2$ must be

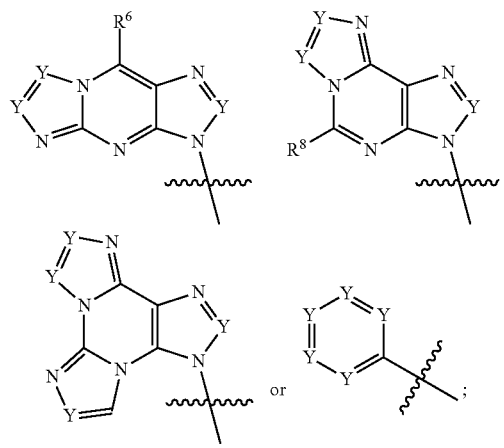

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

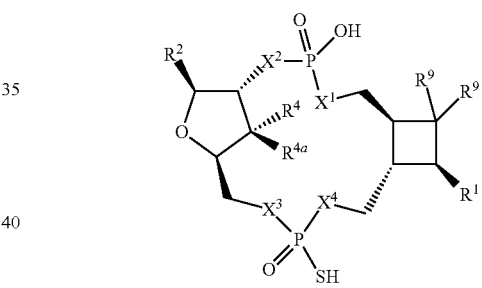

wherein $X^1$, $X^2$, $X^3$ and $X^4$ are each independently O or NH;

$R^1$ and $R^2$ are each independently

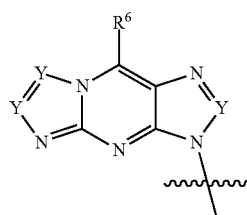 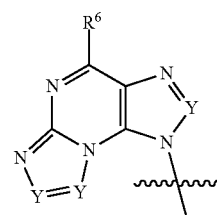

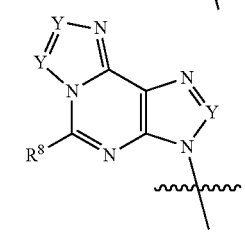 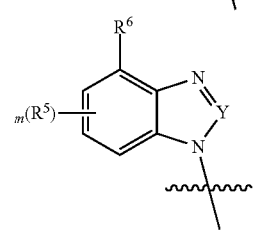

-continued

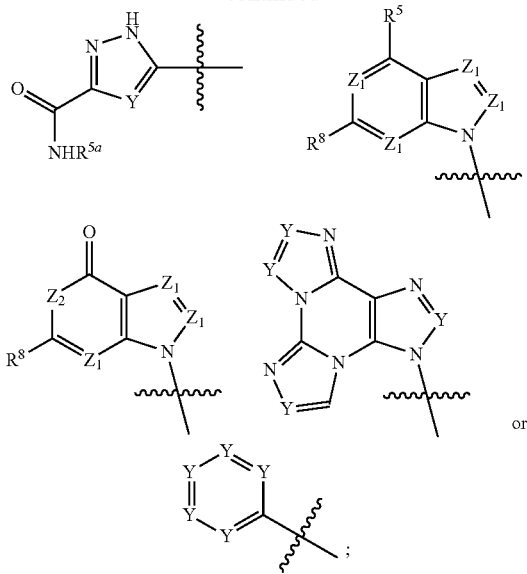

with the proviso that one of $R^1$ and $R^2$ must be

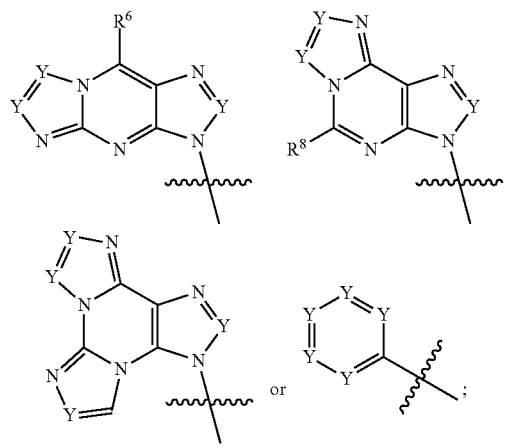

$Z_1$ is N or $CR^a$;

$Z_2$ is $NR^b$;

$R^b$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a C═$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

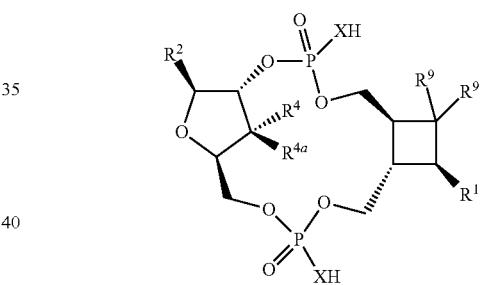

wherein

X is independently O or S;

$R^1$ and $R^2$ are each independently

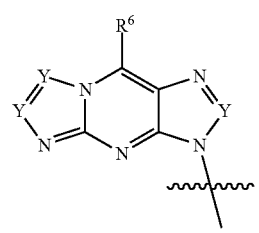 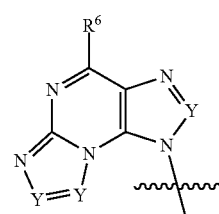

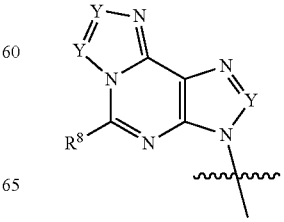 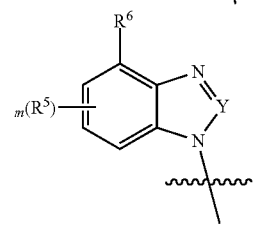

-continued

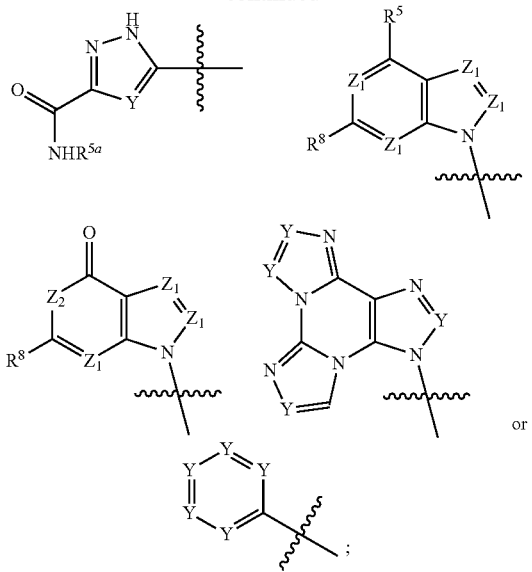

with the proviso that one of $R^1$ and $R^2$ must be

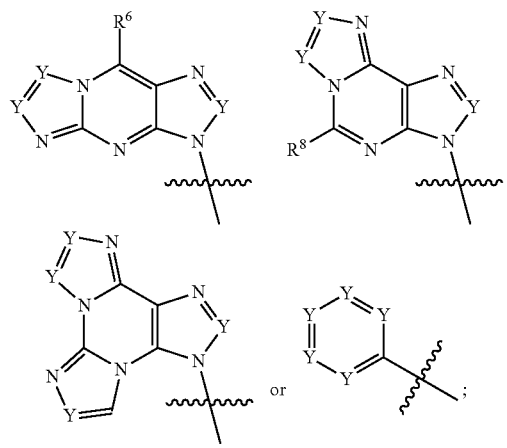

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

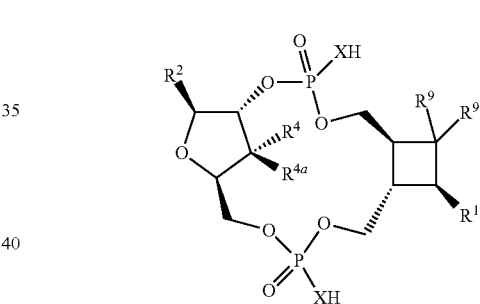

wherein

X is S;

$R^1$ and $R^2$ are each independently

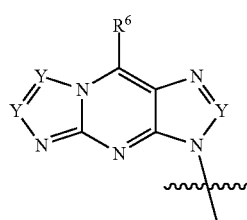 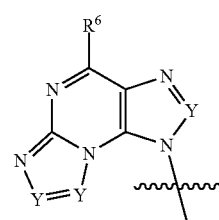

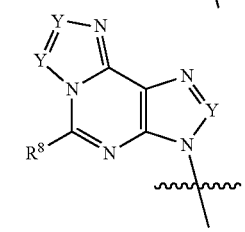 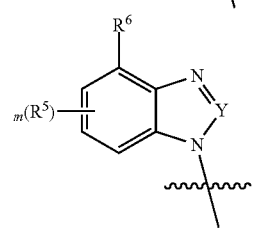

-continued

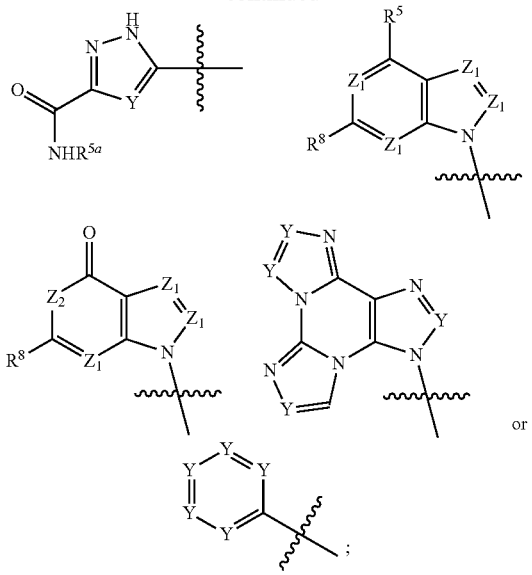

with the proviso that one of $R^1$ and $R^2$ must be

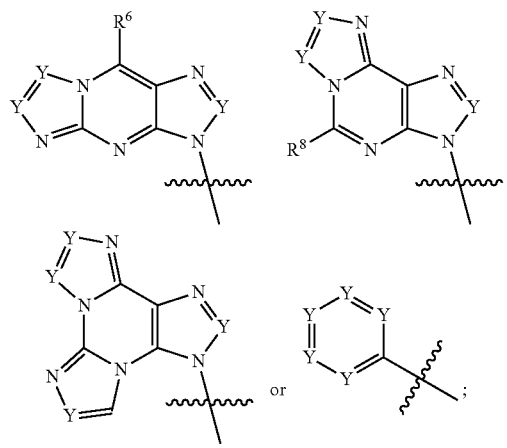

$Z_1$ is N or $CR^a$;

$Z_2$ is $NR^b$;

$R^a$ is H, halogen, that alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —NR$^{a1}R^{a1}$, —NR$^{a1}$C(O)$R^{a1}$, —NR$^{a1}$COOR$^{a1}$, —NR$^{a1}$C(O)$NR^{a1}R^{a1}$, —NR$^{a1}$S(O)$_2R^{a1}$, —NR$^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^4$ is H, $CH_3$, halogen, —NR$^{a1}R^{a1}$ or OR$^{a1}$;

$R^{4a}$ is H, $CH_3$, halogen, —NR$^{a1}R^{a1}$ or OR$^{a1}$; or $R^4$ and $R^{4a}$ may be taken together to form a 3-4 membered carbocycle; or $R^4$ and $R^{4a}$ may be taken together to form a C=CH$_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —NR$^{a1}R^{a1}$, —NR$^{a1}$C(O)$R^{a1}$, —NR$^{a1}$COOR$^{a1}$, —NR$^{a1}$C(O)$NR^{a1}R^{a1}$, —NR$^{a1}$S(O)$_2R^{a1}$, —NR$^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —NR$^{a1}R^{a1}$, —NR$^{a1}$C(O)$R^{a1}$, —NR$^{a1}$COOR$^{a1}$, —NR$^{a1}$C(O)$NR^{a1}R^{a1}$, —NR$^{a1}$S(O)$_2R^{a1}$, —NR$^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COOR$^{a1}$, —OC(O)$R^{a1}$, —OC(O)$NR^{a1}R^{a1}$, —NR$^{a1}R^{a1}$, —NR$^{a1}$C(O)$R^{a1}$, —NR$^{a1}$COOR$^{a1}$, —NR$^{a1}$C(O)$NR^{a1}R^{a1}$, —NR$^{a1}$S(O)$_2R^{a1}$, —NR$^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

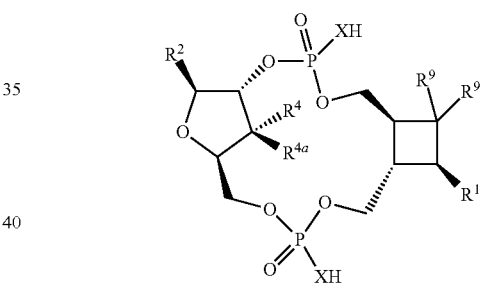

wherein

X is O;

$R^1$ and $R^2$ are each independently

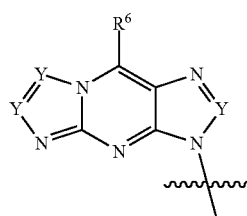 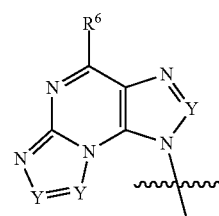

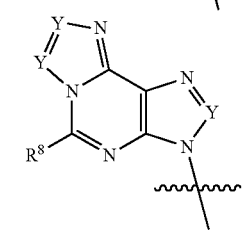 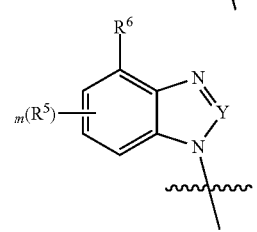

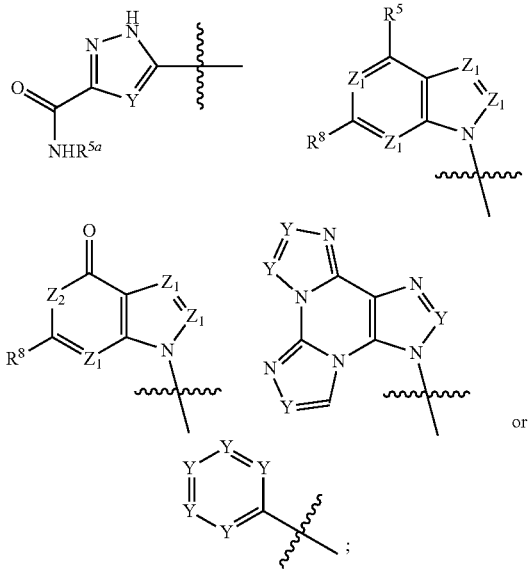

with the proviso that one of $R^1$ and $R^2$ must be

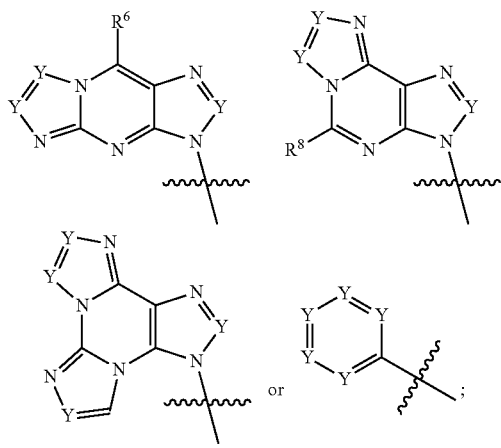

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

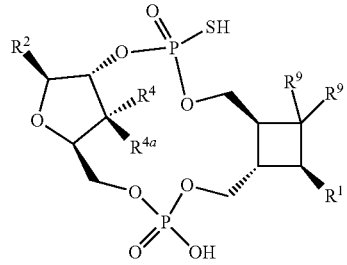

wherein
$R^1$ and $R^2$ are each independently

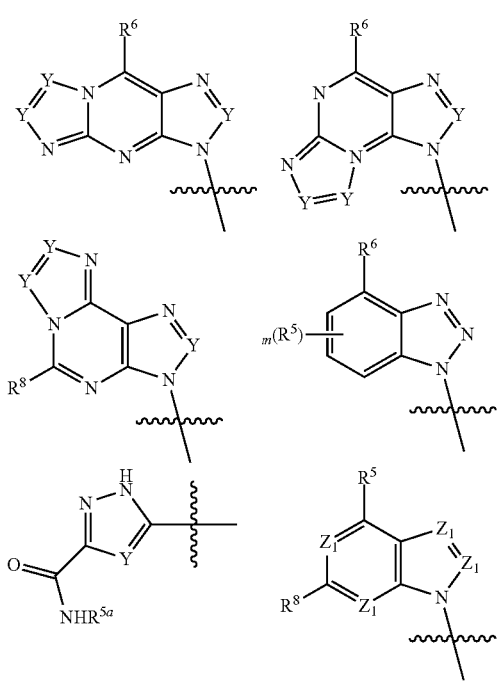

-continued

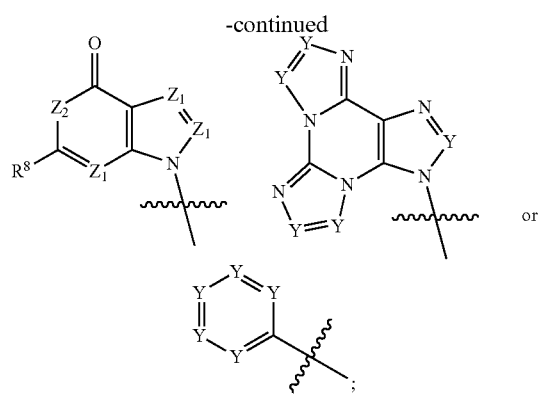

with the proviso that one of $R^1$ and $R^2$ must be

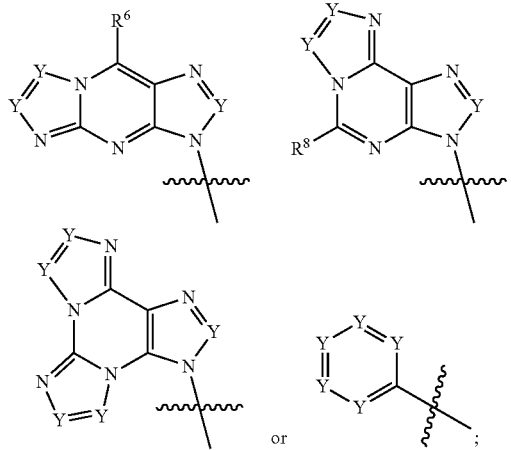

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;
$R^{a1}$ is H, $C_{1-3}$ alkyl or $C_{3-6}$ cycloalkyl;
$R^4$ is H, $CH_3$, halogen, $-NR^{a1}R^{a1}$ or $OR^{a1}$;
$R^{4a}$ is H, $CH_3$, halogen, $-NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

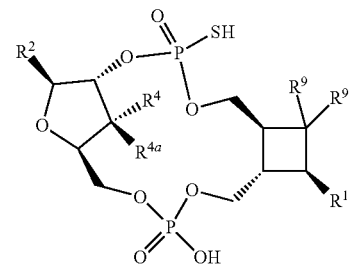

wherein $R^1$ and $R^2$ are each independently

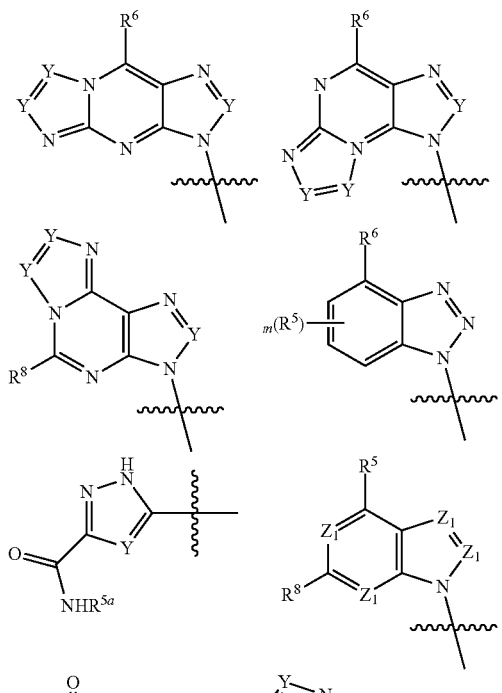

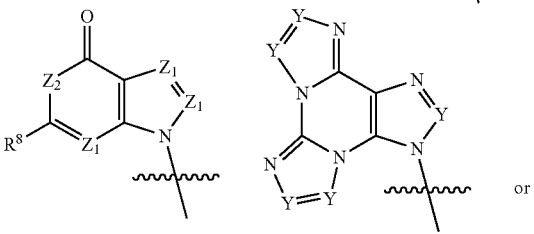

-continued

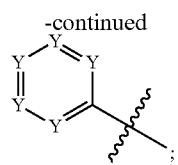

with the proviso that one of $R^1$ and $R^2$ must be

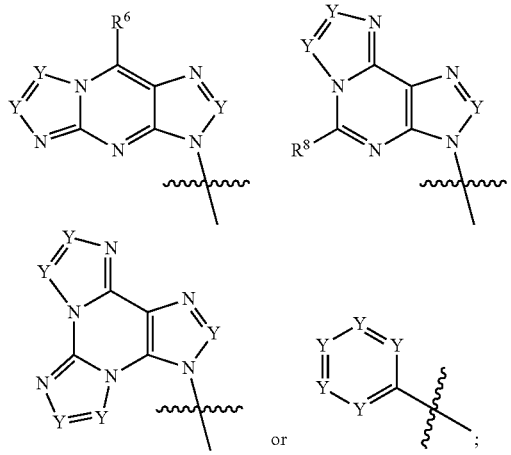

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

In another aspect of the invention, there is provided a compound of the formula

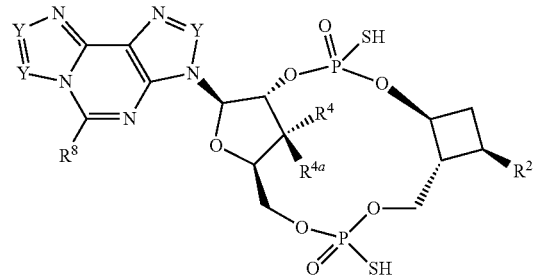

or a pharmaceutically acceptable salt, tautomer or stereoisomer thereof.

In another aspect of the invention, there is provided a compound of the formula

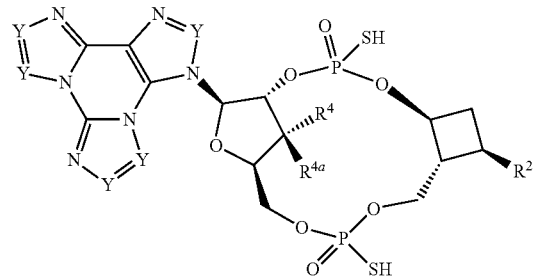

or a pharmaceutically acceptable salt, tautomer or stereoisomer thereof.

In another aspect of the invention, there is provided a compound of the formula

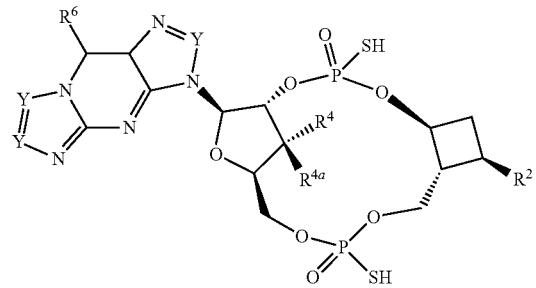

or a pharmaceutically acceptable salt, tautomer or stereoisomer thereof.

In another aspect of the invention, there is provided a compound of the formula

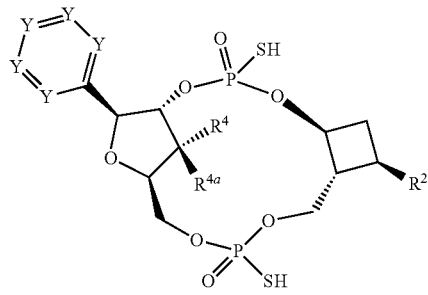

or a pharmaceutically acceptable salt, tautomer or stereoisomer thereof.

In another aspect of the invention, there is provided a compound of the formula
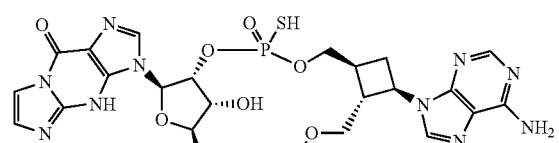
2
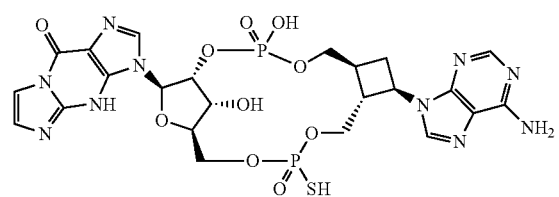
4
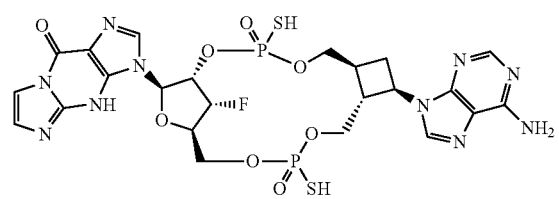
6
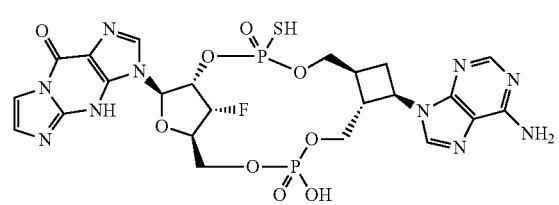
7
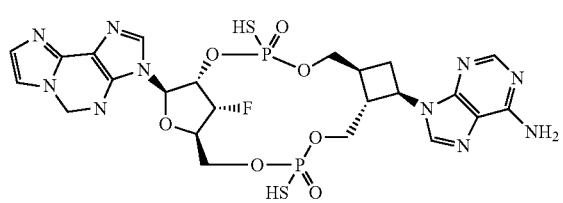
8
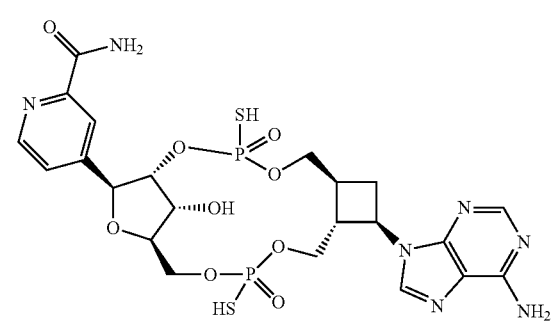
20
In another aspect of the invention, there is provided a pharmaceutically acceptable salt of a compound of the formula
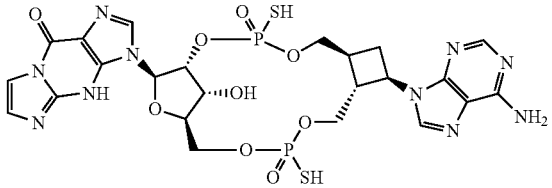
2
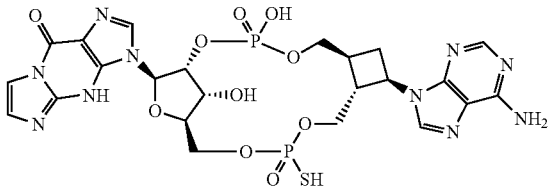
4
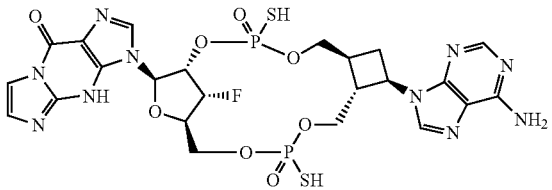
6
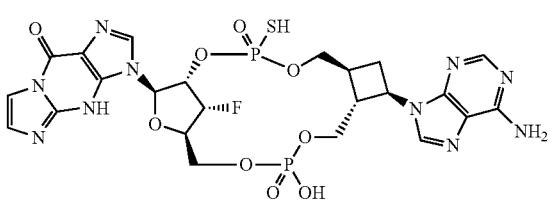
7
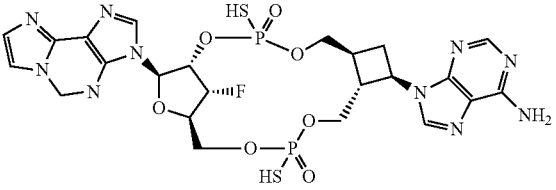
8
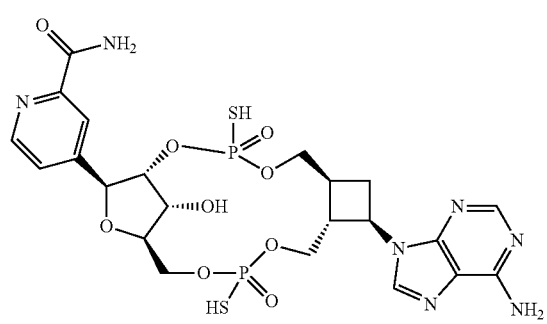
20
In another aspect of the invention, there is provided a compound of formula III

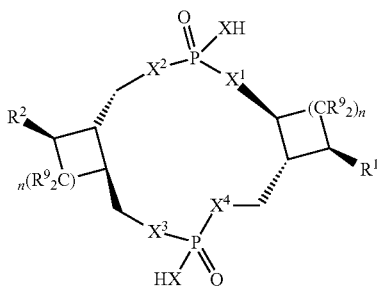

wherein

X is independently O or S;

$X^1$, $X^2$, $X^3$ and $X^4$ are each independently O or NH;

$R^1$ and $R^2$ are each independently

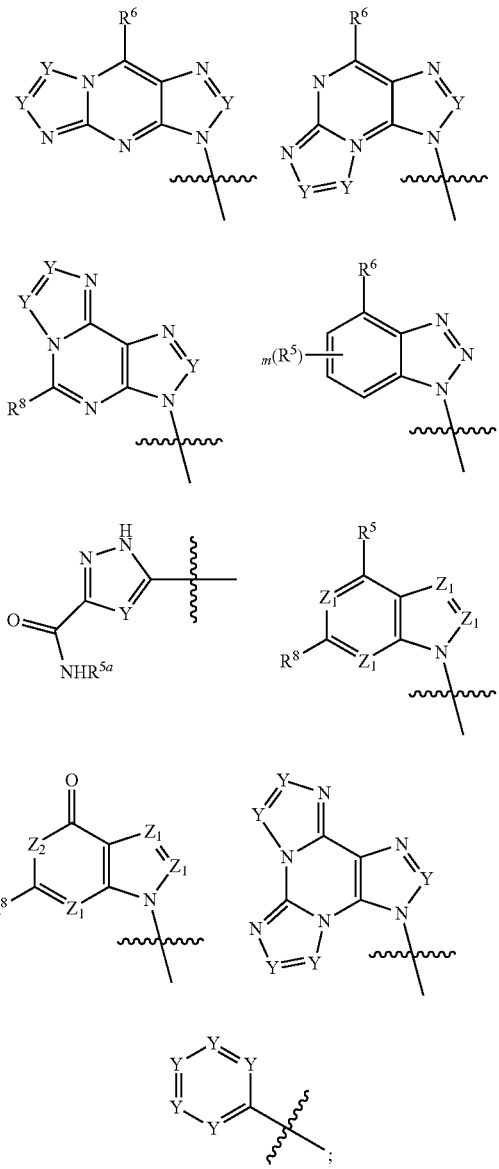

with the proviso that one of $R^1$ and $R^2$ must be

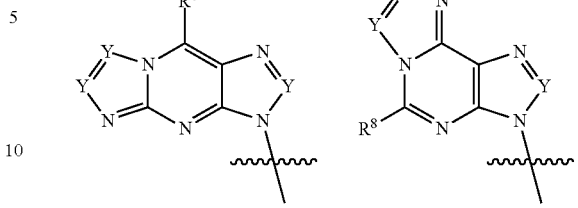

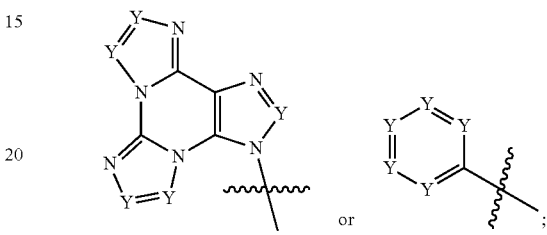

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

or two $R^5$ groups may be taken together to form a 5-6 membered carbocyclic or heterocyclic group;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

Additional aspects of the invention include compounds according to formula (III) wherein
R$^1$ is
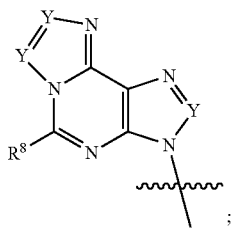
and
R$^2$ is
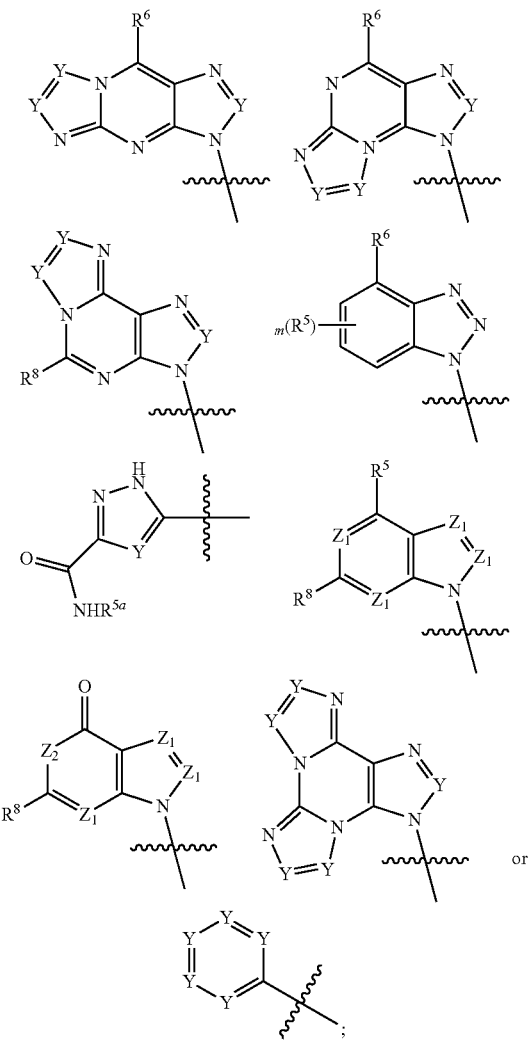
or
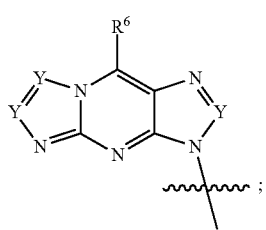
and
R$^2$ is
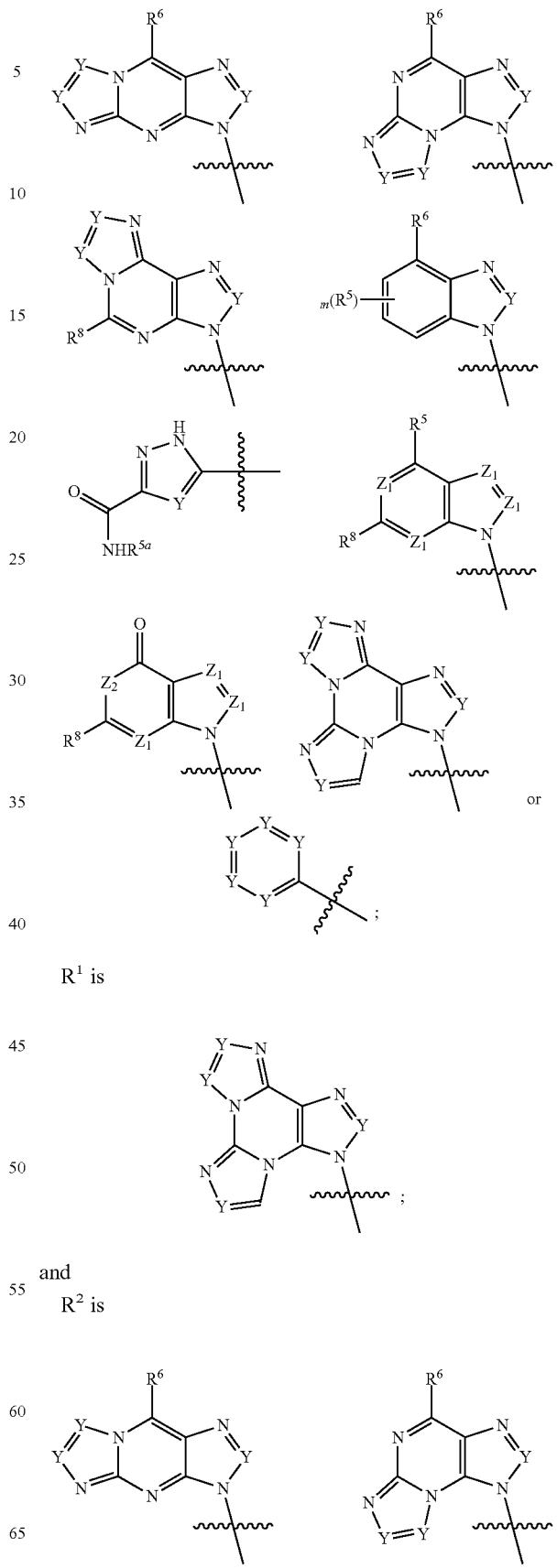
R$^1$ is
and
R$^2$ is R¹ is and
R² is R² is
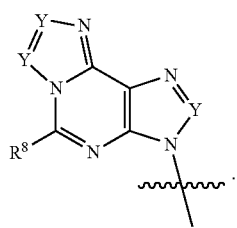
R¹ is
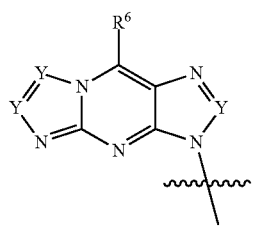
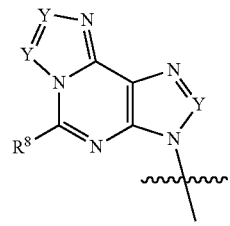
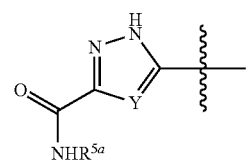
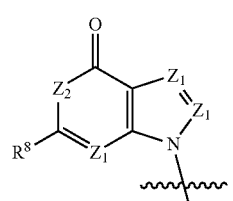 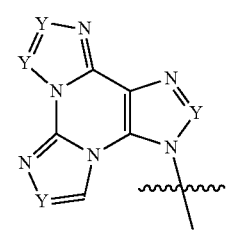
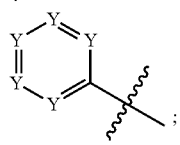
and
R² is
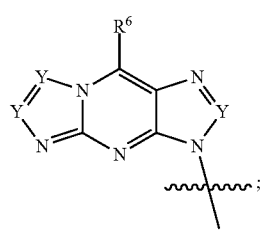
R¹ is
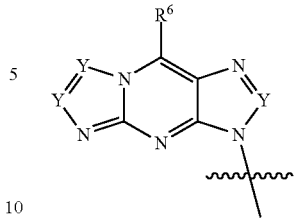
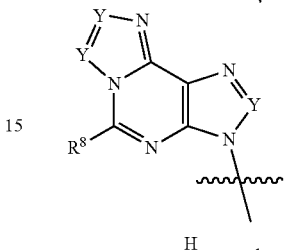
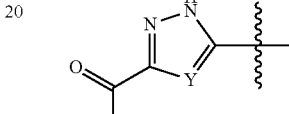
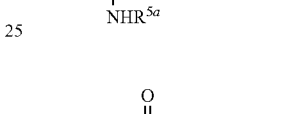
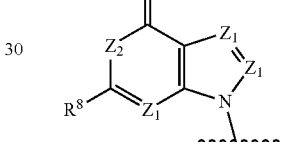
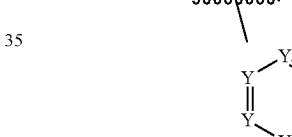
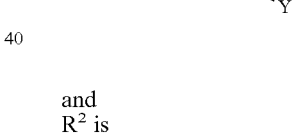
 or
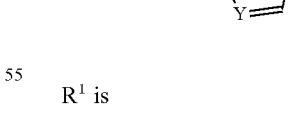
and
R² is
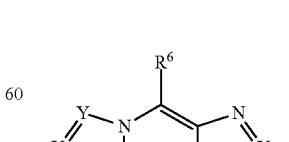
R¹ is
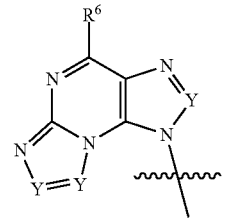 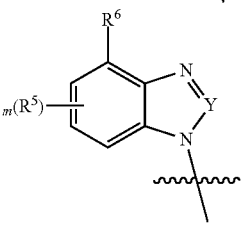
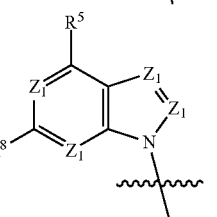
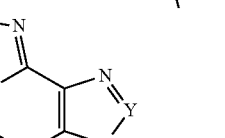
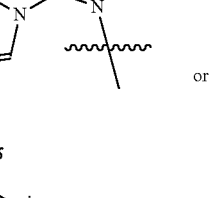
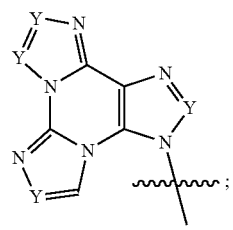
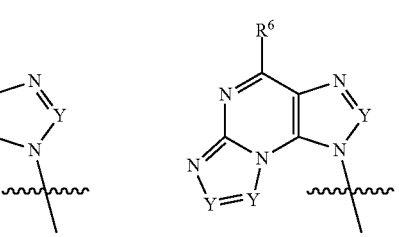

111
-continued
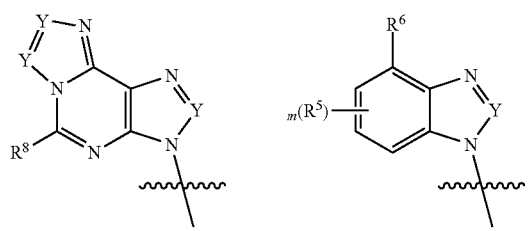
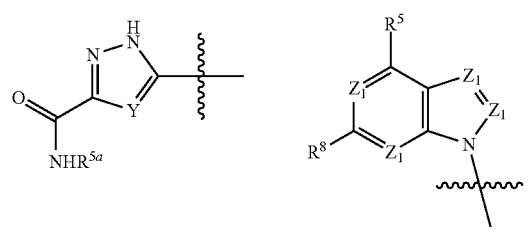
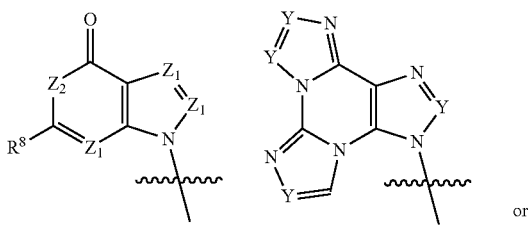
and
R² is
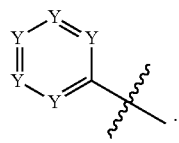
.
In another aspect of the invention, there is provided a compound of formula III
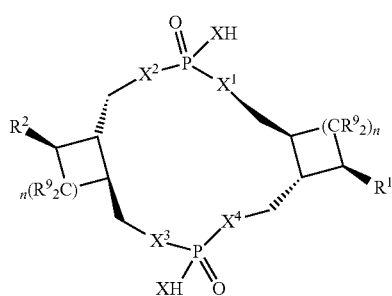
(III)
wherein
X is S;
X¹, X², X³ and X⁴ are each independently O or NH;
112
R¹ and R² are independently
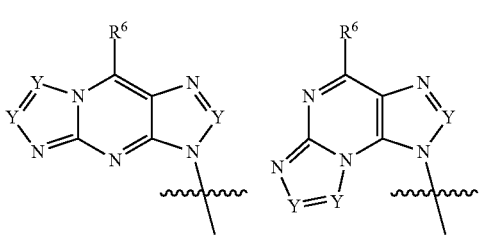
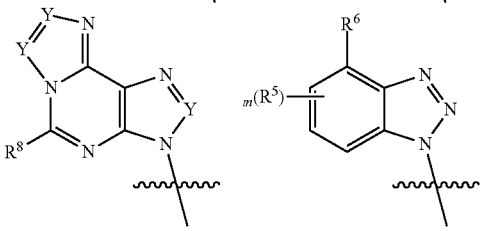
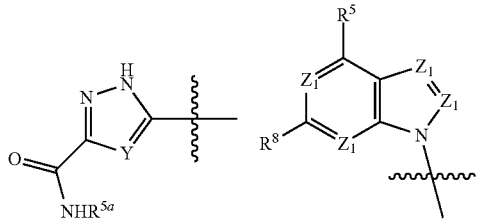
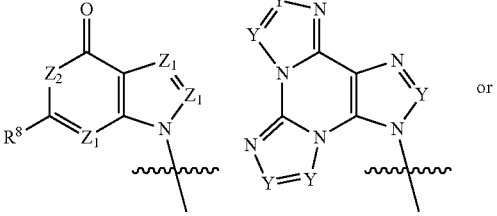
with the proviso that one of R¹ and R² must be
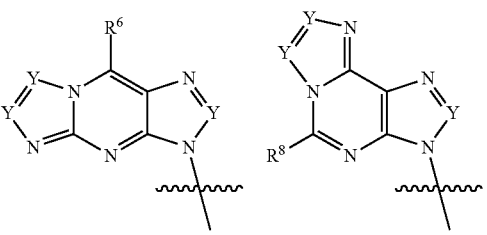
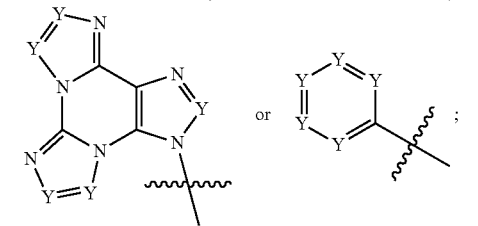
$Z_1$ is N or $CR^a$;
$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{am}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of formula III

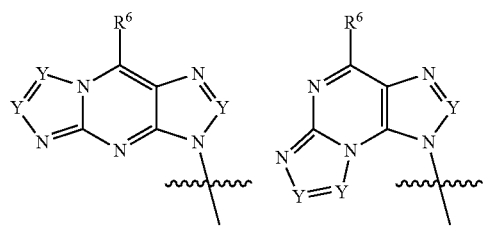

(III)

wherein

X is O;

$X^1$, $X^2$, $X^3$ and $X^4$ are each independently O or NH;

$R^1$ and $R^2$ are independently

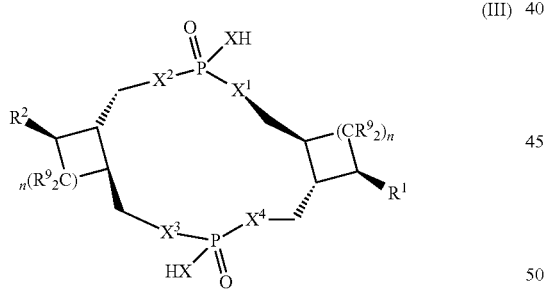

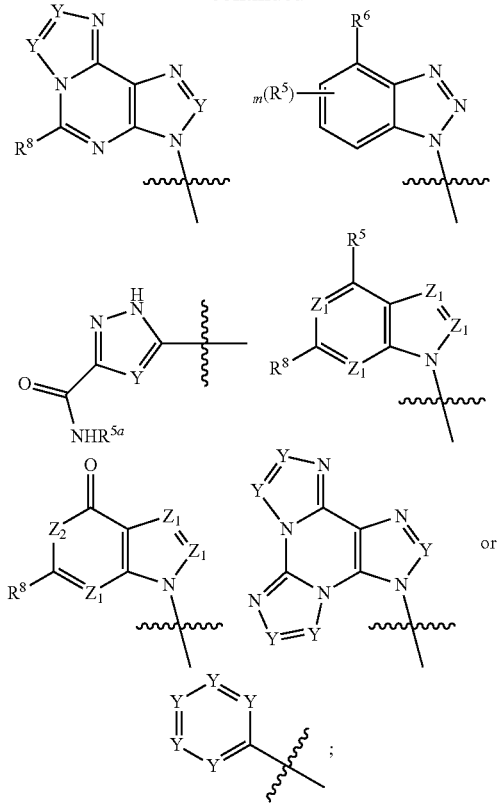

with the proviso that one of $R^1$ and $R^2$ must be

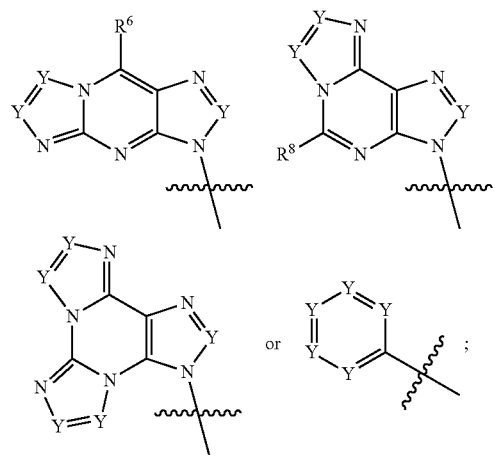

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$; $R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

In another aspect of the invention, there is provided a compound of the formula

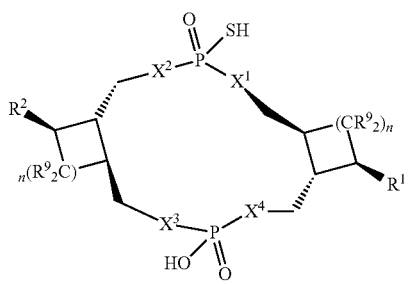

wherein $X^1$, $X^2$, $X^3$ and $X^4$ are each independently O or NH;

$R^1$ and $R^2$ are independently

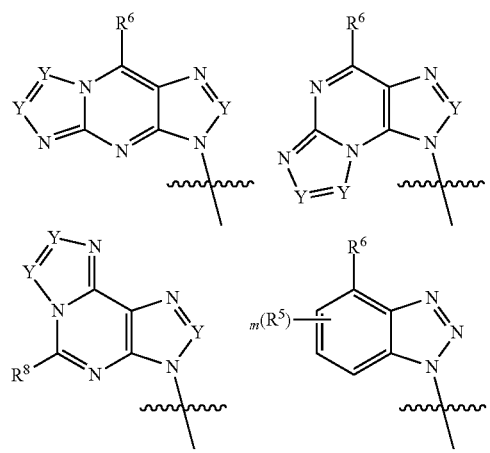

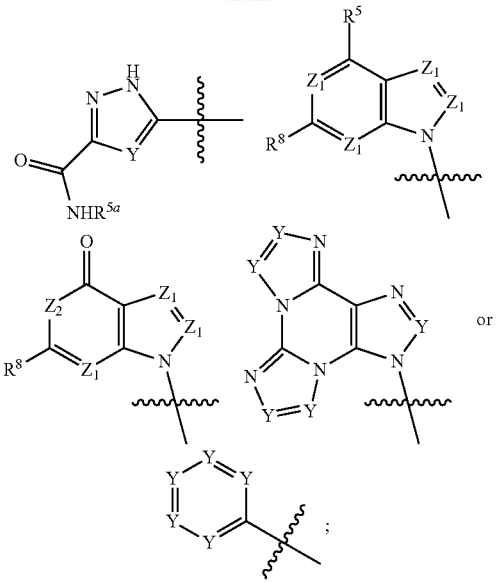

with the proviso that one of $R^1$ and $R^2$ must be

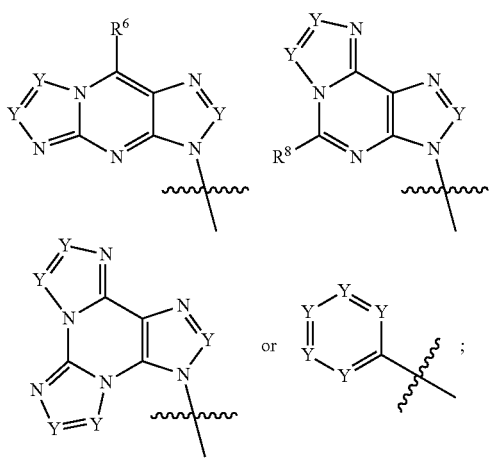

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$; $R^{5a}$ is H or $C_{1-3}$ alkyl;

$R^{5a}$ is H or $C_{1-3}$ alkyl or $C_{3-6}$ cycloalkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)$ NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

n is 0 or 1;

or a pharmaceutically acceptable salt, tautomer or stereoisomer thereof.

In another aspect of the invention, there is provided a compound of the formula

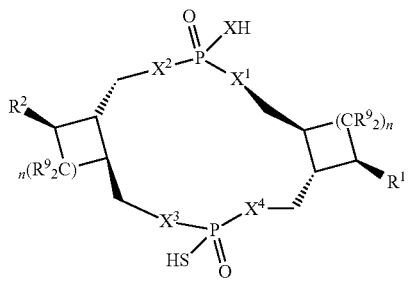

wherein

X$^1$, X$^2$, X$^3$ and X$^4$ are each independently O or NH;

R$^1$ and R$^2$ are each independently

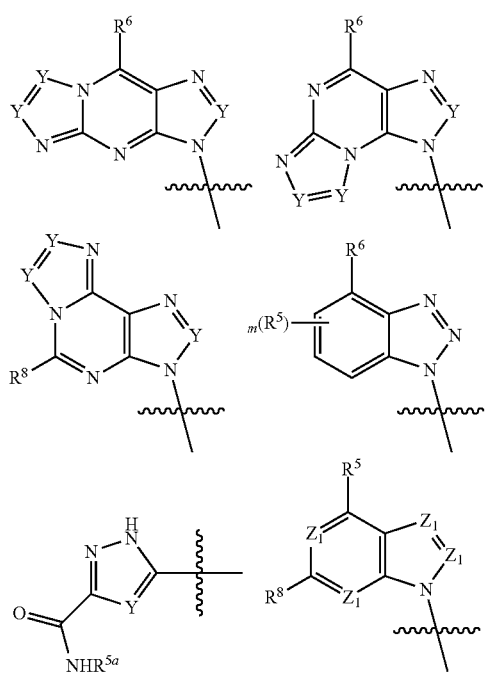

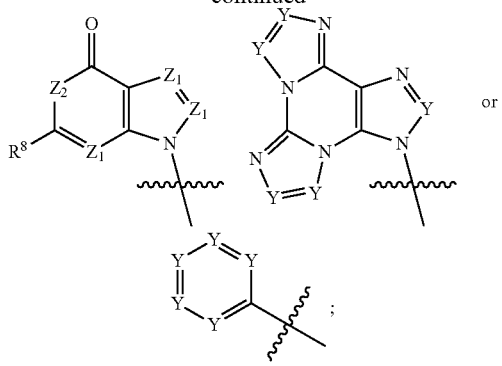

with the proviso that one of R$^1$ and R$^2$ must be

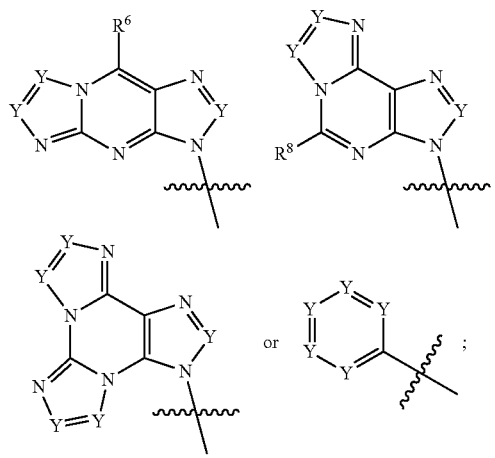

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

n is 0 or 1;

or a pharmaceutically acceptable salt, tautomer or stereoisomer thereof.

In another aspect of the invention, there is provided a compound of the formula

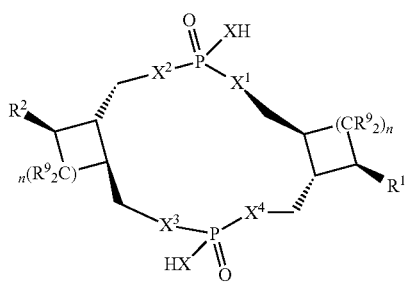

wherein

X is independently O or S;

R$^1$ and R$^2$ are each independently

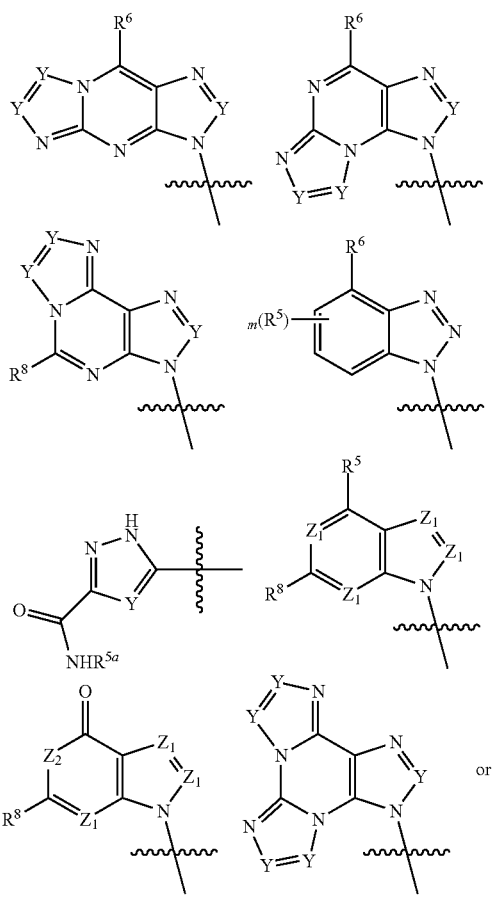

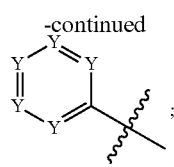

with the proviso that one of R$^1$ and R$^2$ must be

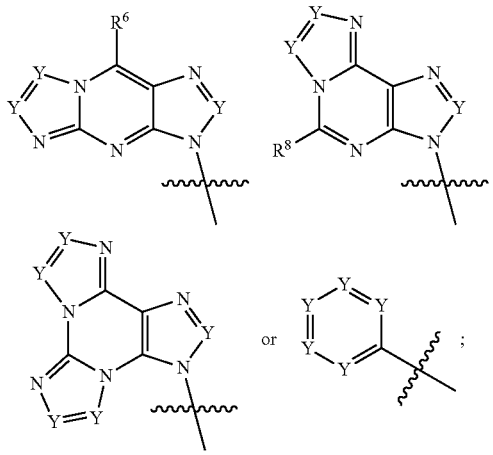

$Z_1$ is N or CR$^a$;

$Z_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

n is 0 or 1;

or a pharmaceutically acceptable salt, tautomer or stereoisomer thereof.

In another aspect of the invention, there is provided a compound of the formula

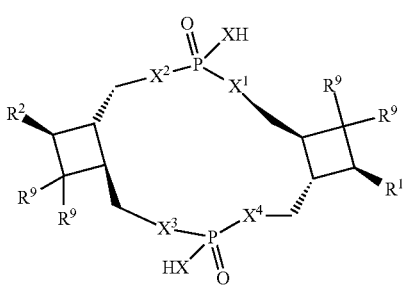

wherein

X is independently O or S;

$X^1$, $X^2$, $X^3$ and $X^4$ are each independently O or NH;

$R^1$ and $R^2$ are independently

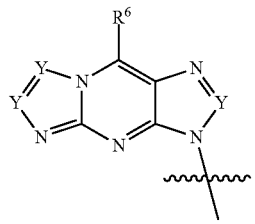 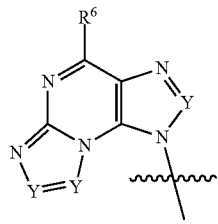

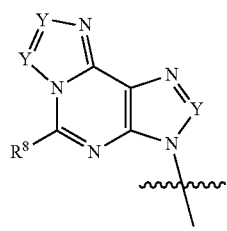 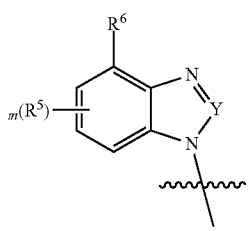

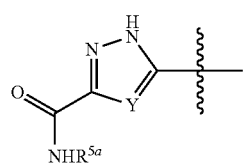 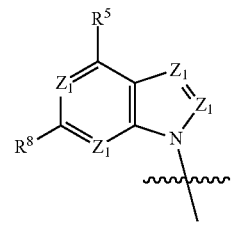

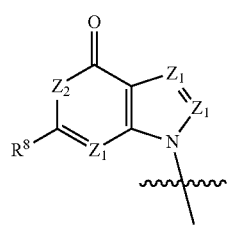 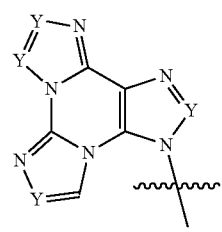 or

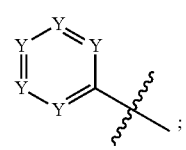 ;

with the proviso that one of $R^1$ and $R^2$ must be

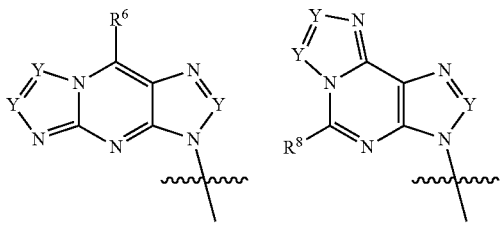

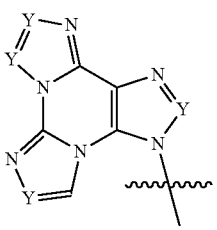 or 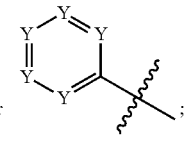 ;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

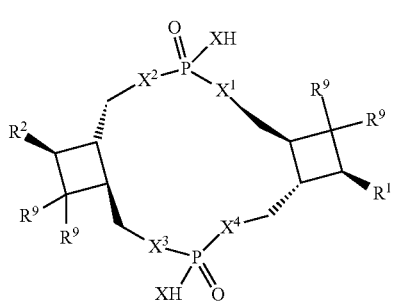

wherein
X is S;
$X^1$, $X^2$, $X^3$ and $X^4$ are each independently O or NH;
$R^1$ and $R^2$ are independently

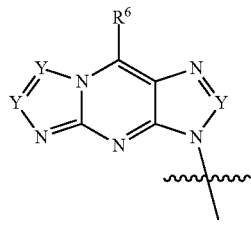 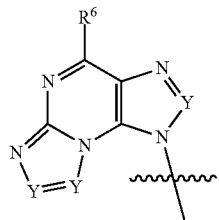

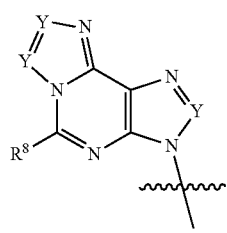 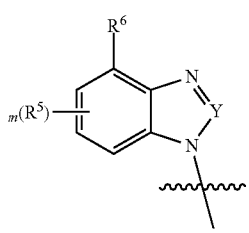

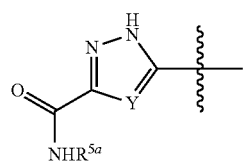 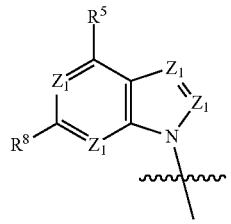

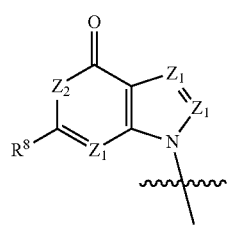 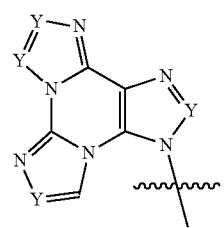 or

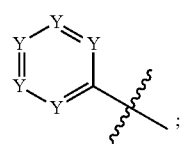 ;

with the proviso that one of $R^1$ and $R^2$ must be

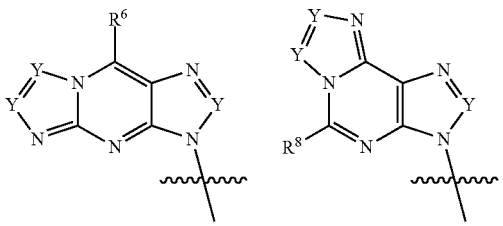

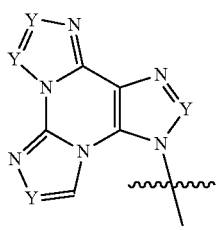 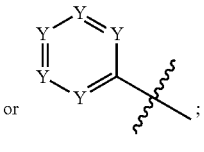 or ;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

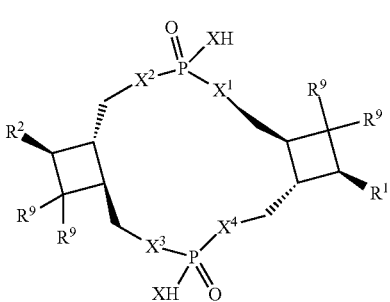

wherein
X is O;
$X^1$, $X^2$, $X^3$ and $X^4$ are each independently O or NH;
$R^1$ and $R^2$ are independently

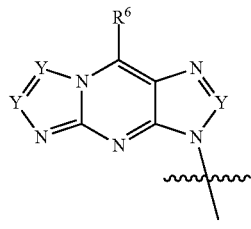 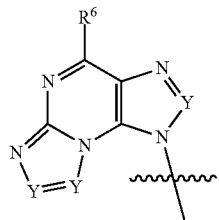

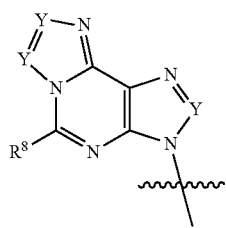 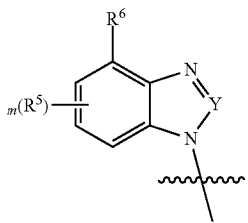

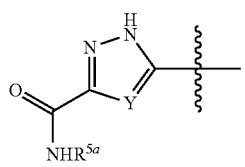 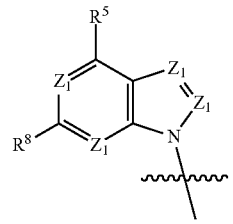

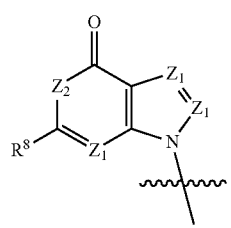 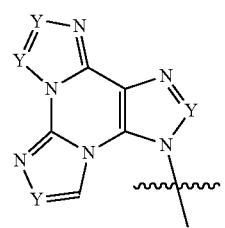 or

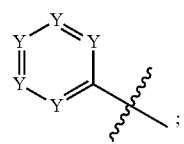;

with the proviso that one of $R^1$ and $R^2$ must be

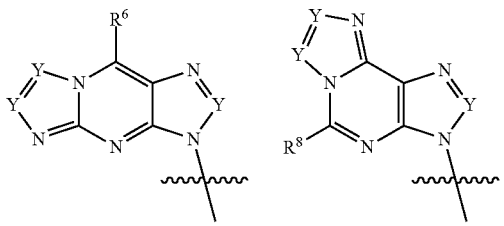

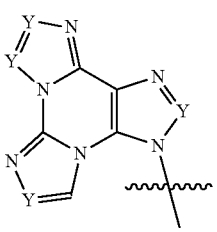 or 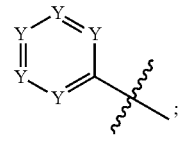;

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

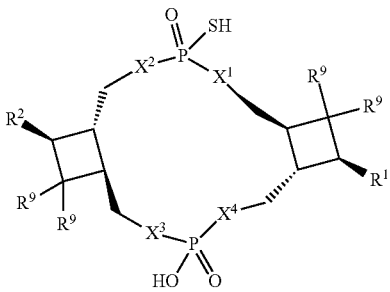

wherein
$X^1$, $X^2$, $X^3$ and $X^4$ are each independently O or NH;
$R^1$ and $R^2$ are independently

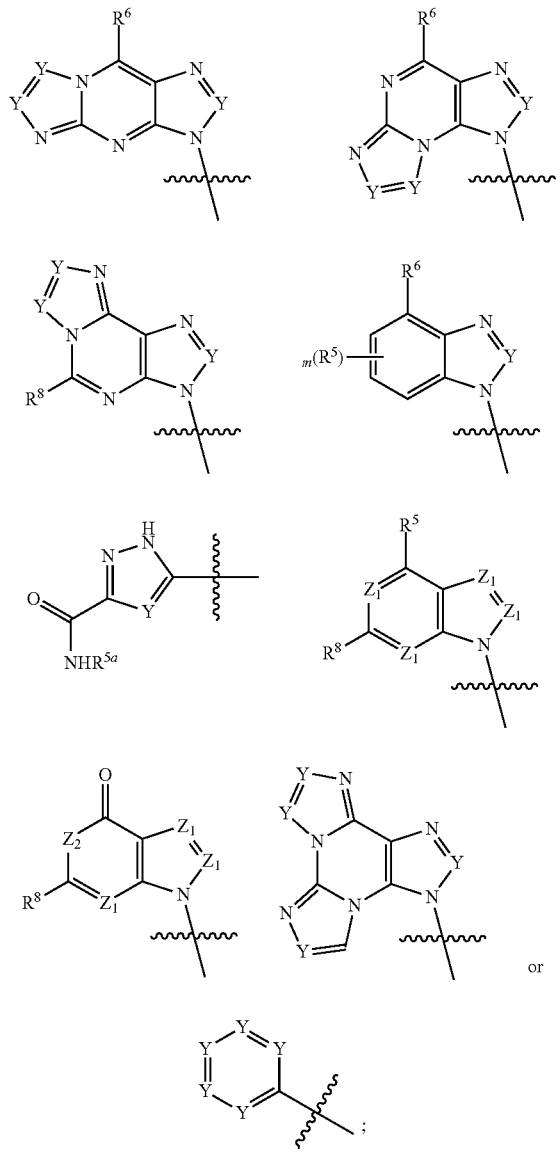

with the proviso that one of $R^1$ and $R^2$ must be

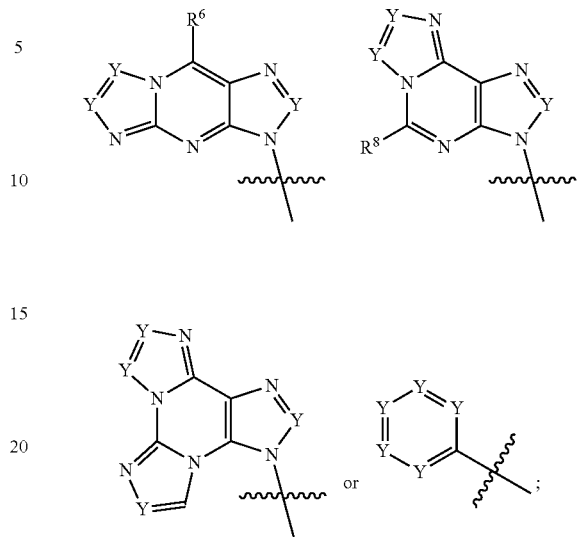

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

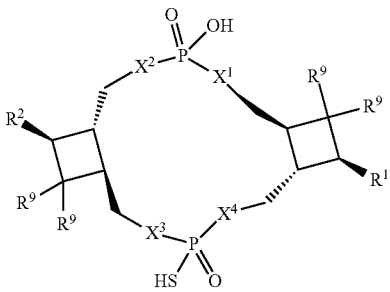

wherein
$X^1$, $X^2$, $X^3$ and $X^4$ are each independently O or NH;
$R^1$ and $R^2$ are each independently

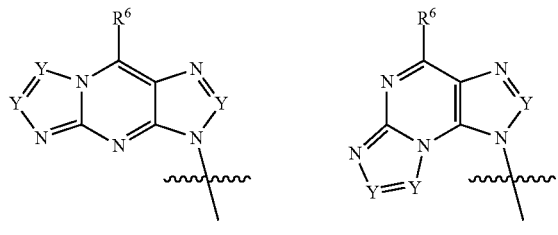

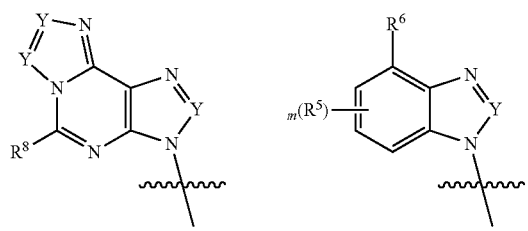

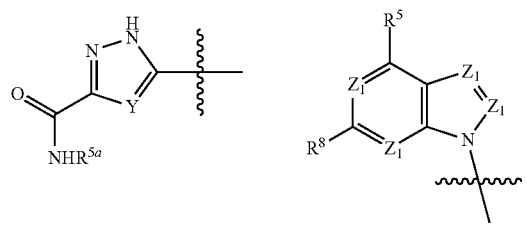

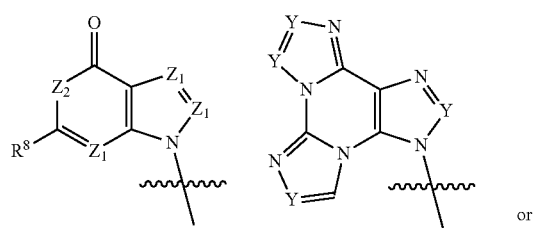

or

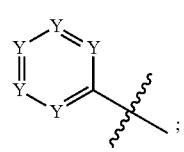

with the proviso that one of $R^1$ and $R^2$ must be

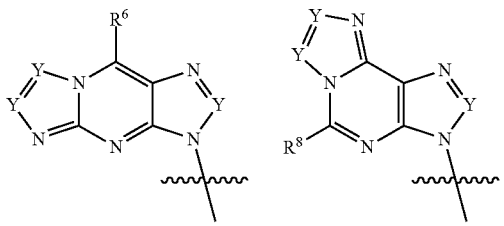

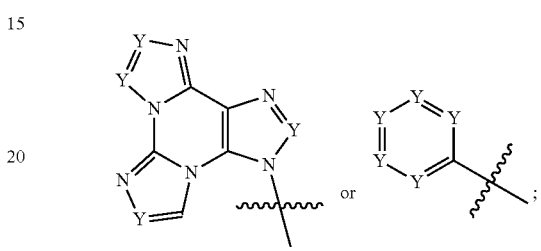

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

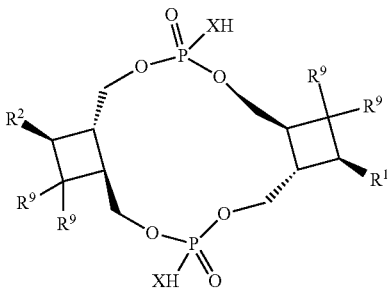

wherein

X is independently O or S;

$R^1$ and $R^2$ are each independently

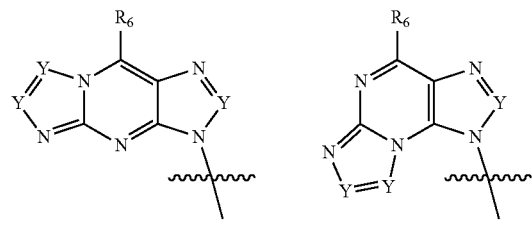

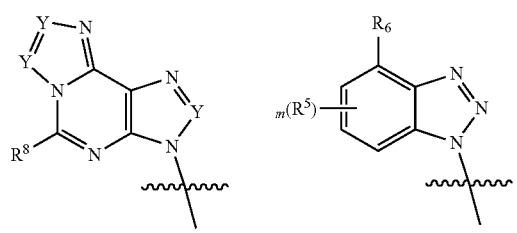

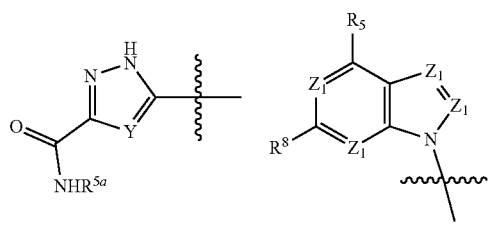

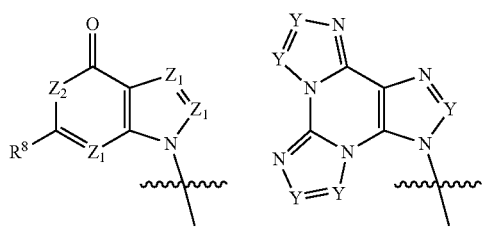

or

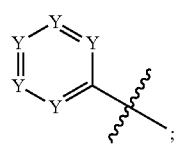

with the proviso that one of $R^1$ and $R^2$ must be

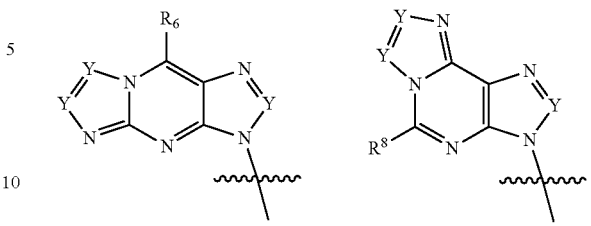

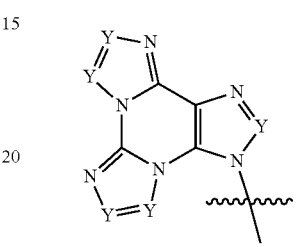

or ;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

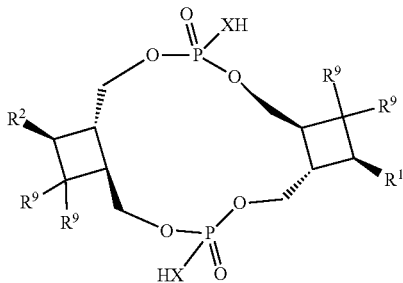

wherein

X is S;

R¹ and R² are independently

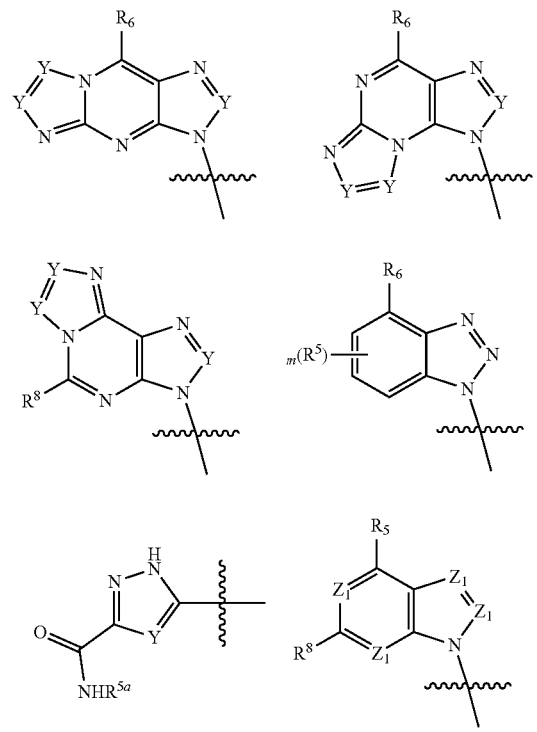

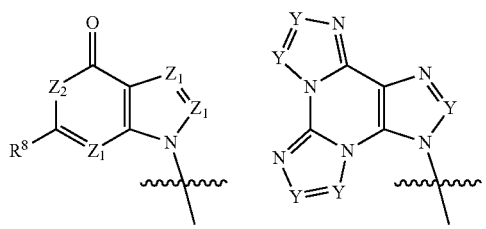

or

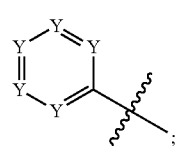

with the proviso that one of $R^1$ and $R^2$ must be

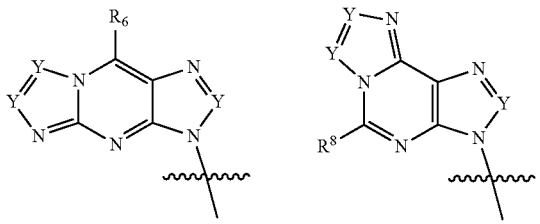

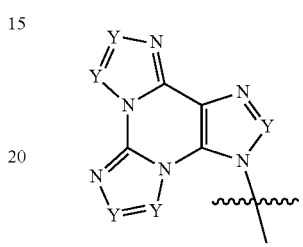

or ;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

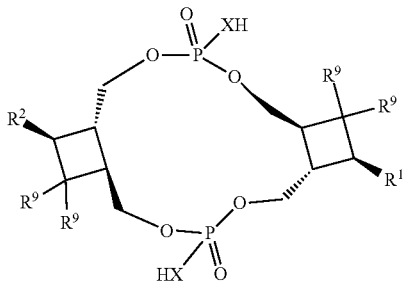

wherein
X is O;
R¹ and R² are independently

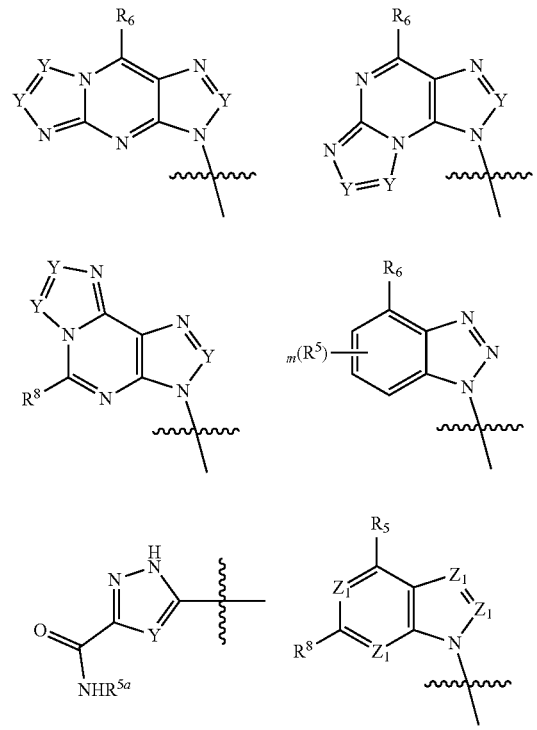

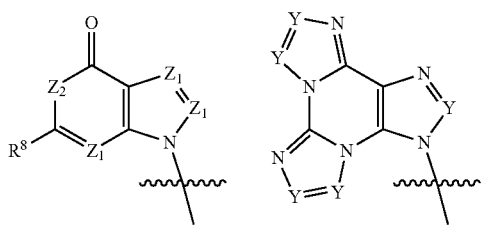

or

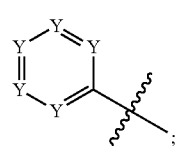

with the proviso that one of R¹ and R² must be

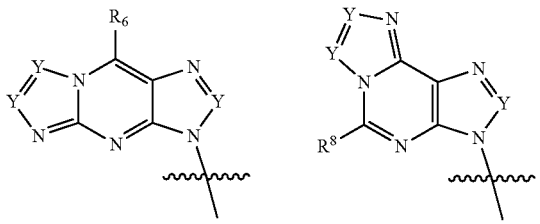

or

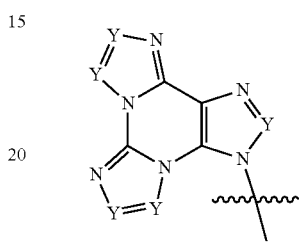

;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

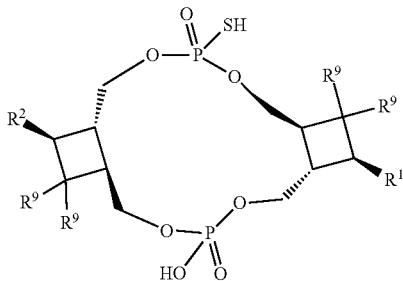

wherein
R¹ and R² are independently

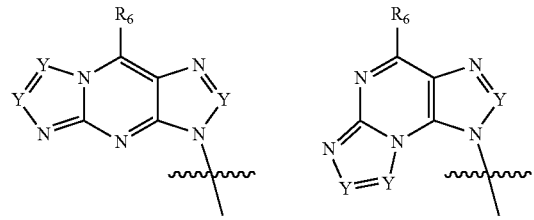

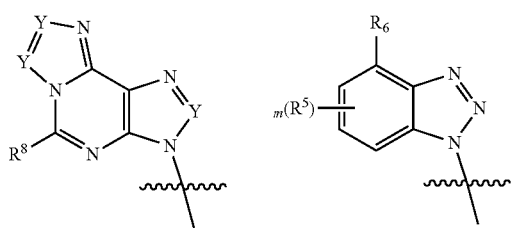

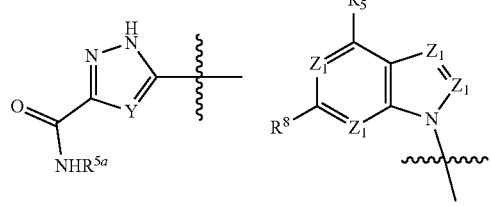

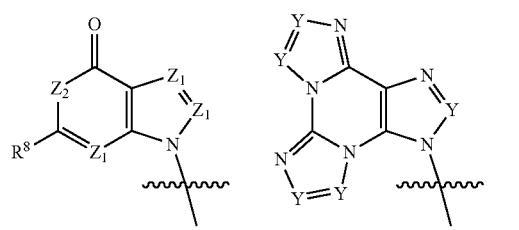

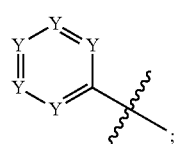

with the proviso that one of $R^1$ and $R^2$ must be

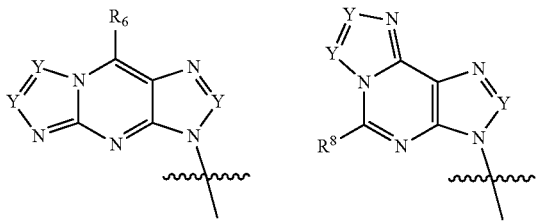

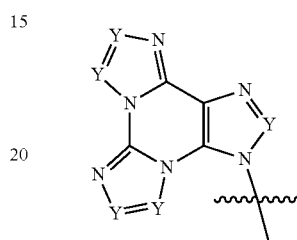 or 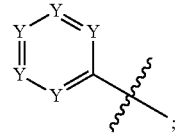;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

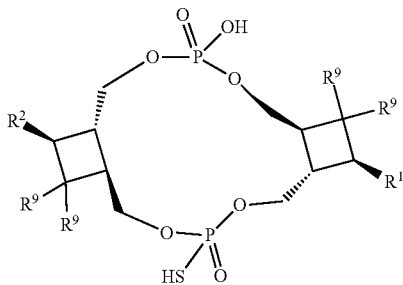

wherein
R¹ and R² are each independently

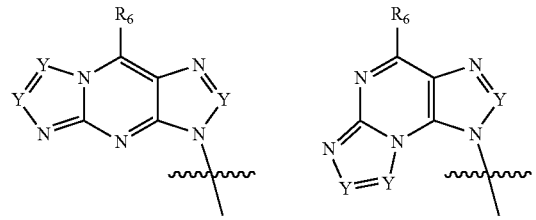

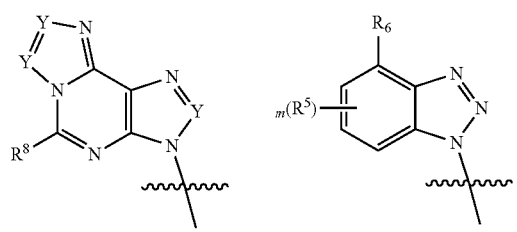

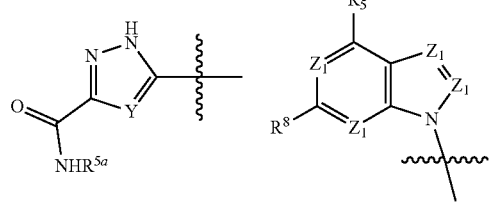

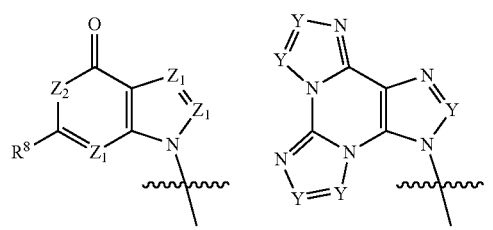

or

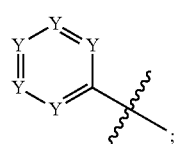

with the proviso that one of $R^1$ and $R^2$ must be

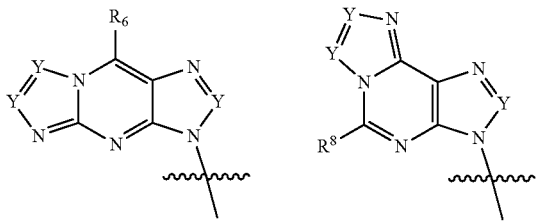

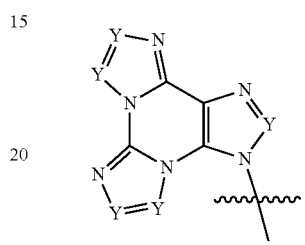 or 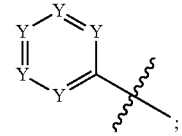;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

In another aspect of the invention, there is provided a compound of the formula

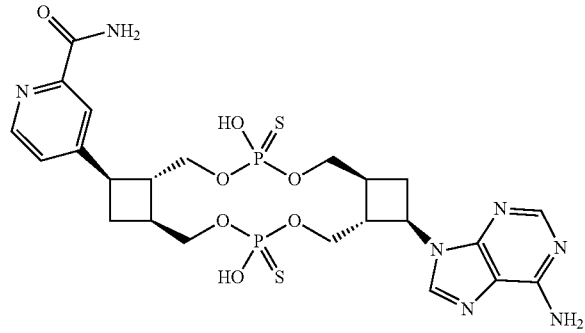

In another aspect of the invention, there is provided a pharmaceutically acceptable salt of a compound of the formula

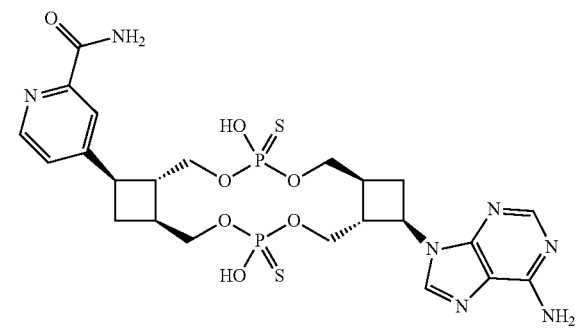

In another aspect, there is provided a compound selected from the exemplified examples or a pharmaceutically acceptable salt, tautomer or stereoisomer thereof.

(1R,6S,8R,9R,15R,17R,18R)-17-(6-amino-9H-purin-9-yl)-18-fluoro-8-{9-hydroxy-3H-imidazo[1,2-a]purin-3-yl}-3,12-disulfanyl-2,4,11,13,16-pentaoxa-3λ$^5$,12λ$^5$-diphosphatricyclo[13.3.0.0$^{6,9}$]octadecane-3,12-dione, (1R,6S,8R,9R,15R,17R,18R)-8-(6-amino-9H-purin-9-yl)-18-hydroxy-17-{9-oxo-3H,4H,9H-imidazo[1,2-a]purin-3-yl}-3,12-disulfanyl-2,4,11,13,16-pentaoxa-3λ$^5$,12λ$^5$-diphosphatricyclo[13.2.1.0$^{6,9}$]octadecane-3,12-dione, (1R,6S,8R,9R,15R,17R,18R)-17-(6-amino-9H-purin-9-yl)-18-fluoro-8-{3H-imidazo[2,1-f]purin-3-yl}-3,12-disulfanyl-2,4,11,13,16-pentaoxa-3λ$^5$,12λ$^5$-diphosphatricyclo[13.3.0.0$^{6,9}$]octadecane-3,12dione, (1R,6S,8R,9R,15R,17R,18R)-8-(6-amino-9H-purin-9-yl)-3,18-dihydroxy-17-{9-oxo-3H,4H,9H-imidazo[1,2-a]purin-3-yl}-12-sulfanyl-2,4,11,13,16-pentaoxa-3λ$^5$,12λ$^5$-diphosphatricyclo[13.2.1.0$^{6,9}$]octadecane-3,12-dione, (1S,6S,8R,9R,15R,17R,18R)-8-(6-amino-9H-purin-9-yl)-18-hydroxy-17-{9-oxo-3H,5H,9H-imidazo[1,2-a]purin-3-yl}-3,12-disulfanyl-2,4,11,13,16-pentaoxa-3λ$^5$,12λ$^5$-diphosphatricyclo[13.3.0.0$^{6,9}$]octadecane-3,12-dione, (1S,6S,8R,9R,15R,17R,18R)-8-(6-amino-9H-purin-9-yl)-18-fluoro-17-{9-oxo-3H,4H,9H-imidazo[1,2-a]purin-3-yl}-3,12-disulfanyl-2,4,11,13,16-pentaoxa-3λ$^5$,12λ$^5$-diphosphatricyclo[13.2.1.0$^{6,9}$]octadecane-3,12-dione, (1S,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ$^5$,12λ$^5$-diphosphatricyclo[13.2.1.0$^{6,9}$]octadecane-3,12-dione, (1S,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ$^5$,12λ$^5$-diphosphatricyclo[13.2.1.0$^{6,9}$]octadecane-3,12-dione, 4-[(1R,6S,8R,9S,15R,17R,18R)-17-(6-amino-9H-purin-9-yl)-18-fluoro-3,12-dioxo-3,12-disulfanyl-2,4,11,13,16-pentaoxa-3λ$^5$,12λ$^5$-diphosphatricyclo[13.3.0.0$^{6,9}$]octadecan-8-yl]pyridine-2-carboxamide, 4-[(1R,6S,8R,9S,15R,17R,18S)-17-(6-amino-9H-purin-9-yl)-18-fluoro-3,12-dioxo-3,12-disulfanyl-2,4,11,13,16-pentaoxa-3λ$^5$,12λ$^5$-diphosphatricyclo[13.3.0.0$^{6,9}$]octadecan-8-yl]pyridine-2-carboxamide, 4-[(1R,6S,8R,9S,15R,17R,18R)-17-(6-amino-9H-purin-9-yl)-18-fluoro-3,12-dihydroxy-3,12-dioxo-2,4,11,13,16-pentaoxa-3λ$^5$,12λ$^5$-diphosphatricyclo[13.3.0.0$^{6,9}$]octadecan-8-yl]pyridine-2-carboxamide, 4-[(1R,6S,8R,9S,15R,17R,18R)-17-(6-amino-9H-purin-9-yl)-18-fluoro-12-hydroxy-3,12-dioxo-3-sulfanyl-2,4,11,13,16-pentaoxa-3λ$^5$,12λ$^5$-diphosphatricyclo[13.3.0.0$^{6,9}$]octadecan-8-yl]pyridine-2-carboxamide, 4-[(1S,7S,8R,10S,16R,17R)-17-(6-amino-9H-purin-9-yl)-4,13-dioxo-4,13-disulfanyl-3,5,12,14-tetraoxa-4λ$^5$,13λ$^5$-diphosphatricyclo[14.2.0.0$^{7,10}$]octadecan-8-yl]pyridine-2-carboxamide, (1R,6S,8R,9R,15R,17R,18R)-8-(6-amino-9H-purin-9-yl)-18-fluoro-3,12-dihydroxy-17-{3H-imidazo[2,1-f]purin-3-yl}-2,4,11,13,16-pentaoxa-3λ$^5$,12λ$^5$-diphosphatricyclo[13.3.0.0$^{6,9}$]octadecane-3,12-dione, (1R,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ$^5$,12λ$^5$-diphosphatricyclo[13.3.0.0$^{6,9}$]octadecane-3,12-dione, (1R,6S,8R,9R,15R,17R,18R)-8-(6-chloro-9H-purin-9-yl)-18-fluoro-17-{3H-imidazo[2,1-f]purin-3-yl}-3,12-disulfanyl-2,4,11,13,16-pentaoxa-3λ$^5$,12λ$^5$-diphosphatricyclo[13.3.0.0$^{6,9}$]octadecane-3,12-dione, 4-[(1R,6S,8R,9S,15R,17R,18R)-18-fluoro-17-{3H-imidazo[2,1-f]purin-3-yl}-3,12-dioxo-3,12-disulfanyl-2,4,11,13,16-pentaoxa-3λ$^5$,12λ$^5$-diphosphatricyclo[13.3.0.0$^{6,9}$]octadecan-8-yl]pyridine-2-carboxamide, 4-[(1R,6S,8R,9R,15R,17S,18R)-8-(6-amino-9H-purin-9-yl)-18-hydroxy-3,12-dioxo-3,12-disulfanyl-2,4,11,13,16-pentaoxa-3λ$^5$,12λ$^5$-diphosphatricyclo[13.2.1.0$^{6,9}$]octadecan-17-yl]pyridine-2-carboxamide, (1R,6S,8R,9R,15R,17R,18R)-17-(6-amino-9H-purin-9-yl)-18-fluoro-8-{5-oxo-5H,8H,9H-[1,2,4]triazolo[4,3-a]purin-8-yl})-3,12-disulfanyl-2,4,11,13,16-pentaoxa-3λ$^5$,12λ$^5$-diphosphatricyclo[13.3.0.0$^{6,9}$]octadecane-3,12-dione, (1R,6S,8R,9R,15R,17R,18R)-17-(6-amino-9H-purin-9-yl)-18-fluoro-8-(6-oxo-6,9-dihydro-1H-purin-9-yl)-3,12-disulfanyl-2,4,11,13,16-pentaoxa-3λ$^5$,12λ$^5$-diphosphatricyclo[13.3.0.0$^{6,9}$]octadecane-3,12-dione, (1R,6S,8R,9R,15R,17R,18R)-17-(6-amino-9H-purin-9-yl)-18-fluoro-8-{8-oxo-4H,5H,8H-[1,2,3,4]tetrazolo[1,5-a]purin-5-yl})-3,12-disulfanyl-2,4,11,13,16-pentaoxa-3λ$^5$,12λ$^5$-diphosphatricyclo[13.3.0.0$^{6,9}$]octadecane-3,12-dione, or a pharmaceutically acceptable salt, tautomer or stereoisomer thereof.

In another aspect, there is provided a compound selected from any subset list of compounds within the scope of any of the above aspects.

In another aspect, there is provided a compound of the formula
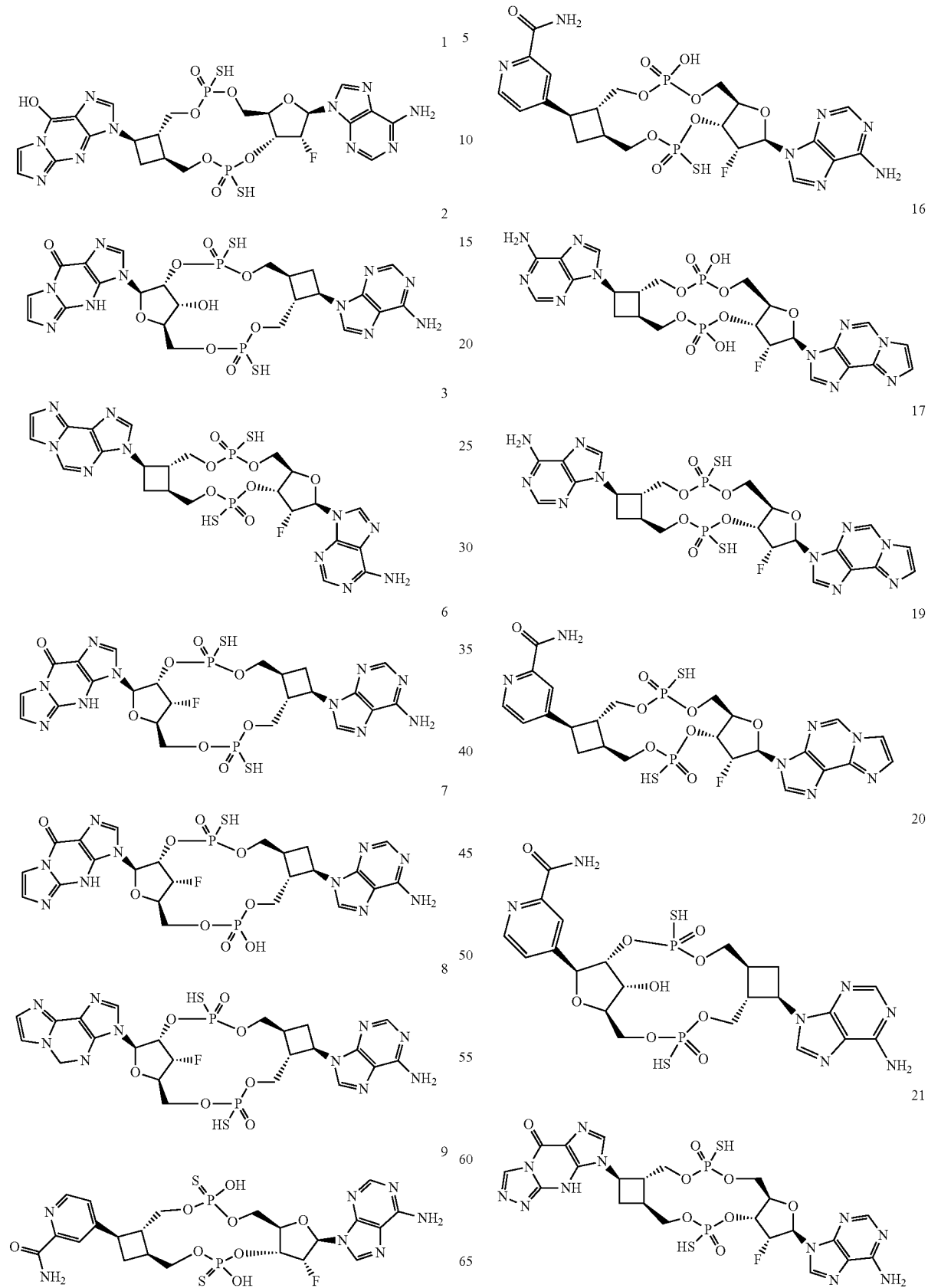

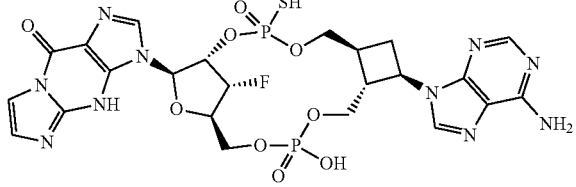
7
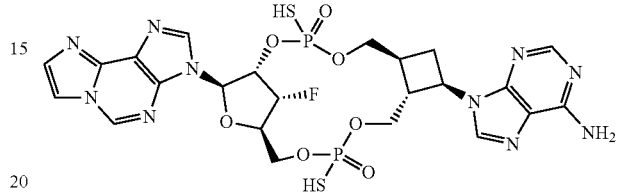
8
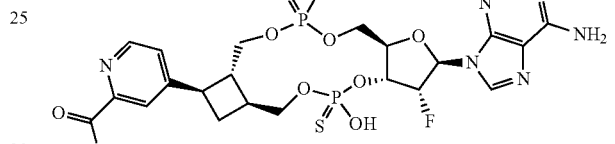
9
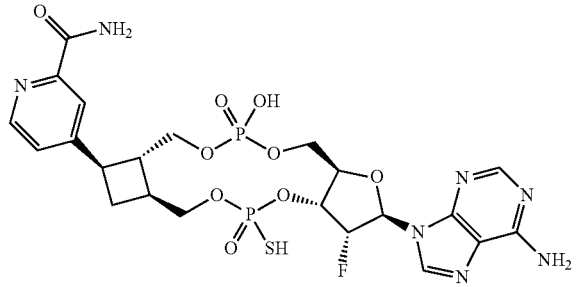
13
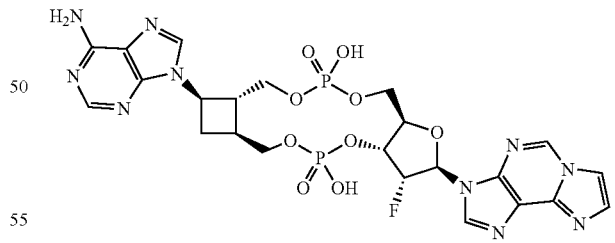
16
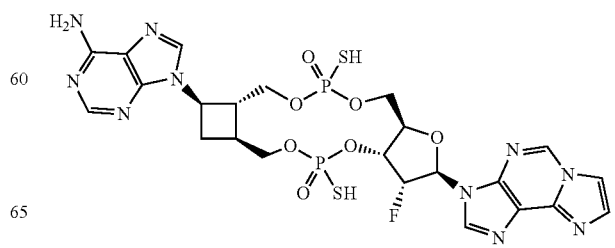
17
In another aspect, there is provided a pharmaceutically acceptable salt of a compound of the formula
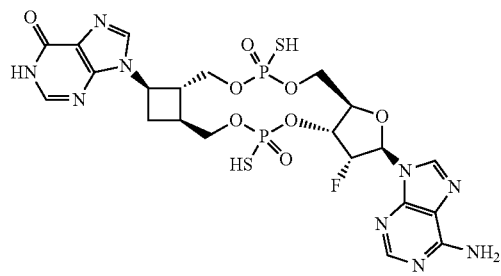
1
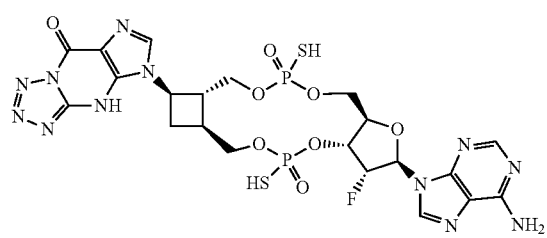
2
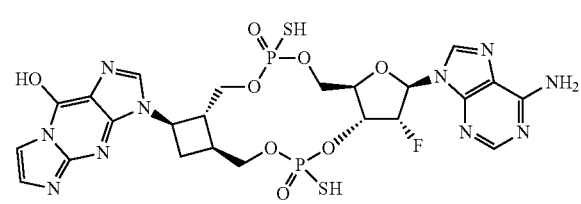
3
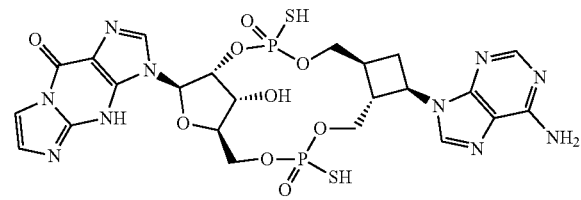
6
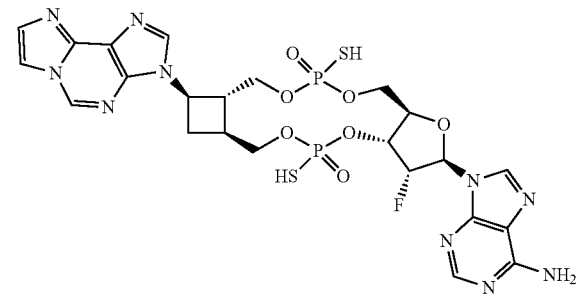
22
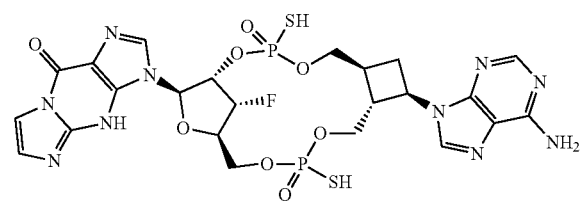
23

147
-continued
19
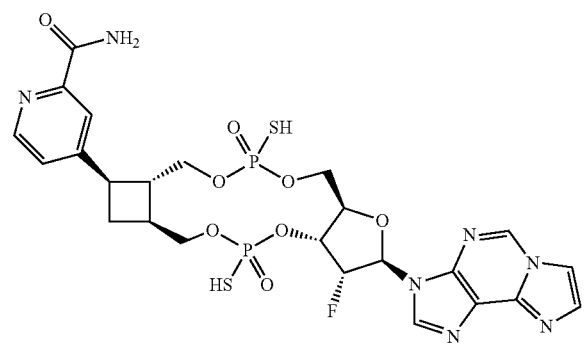
20
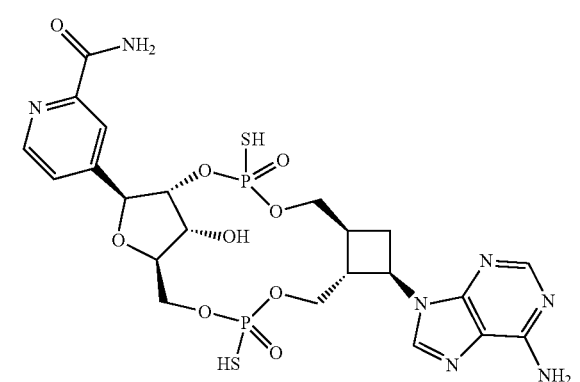
21
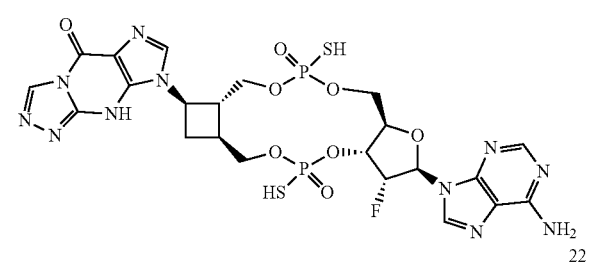
22
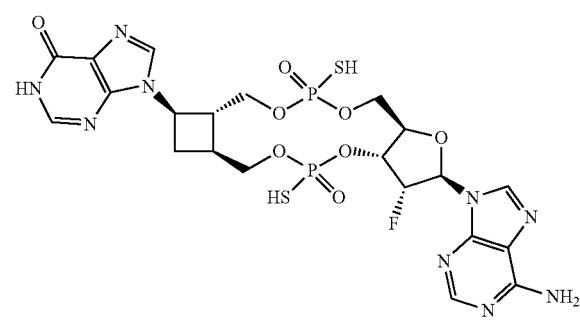
23
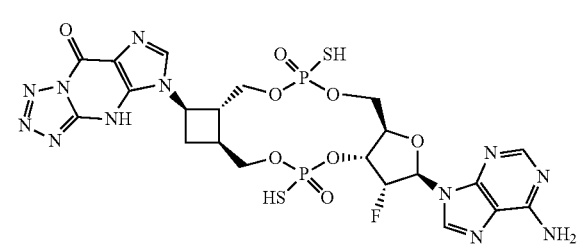
In another aspect, there is provided a compound of the formula
148
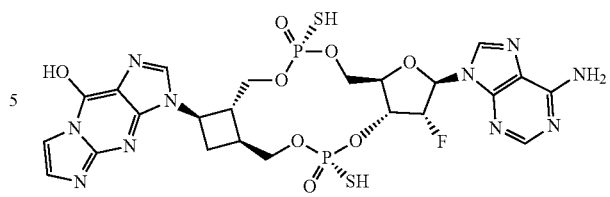
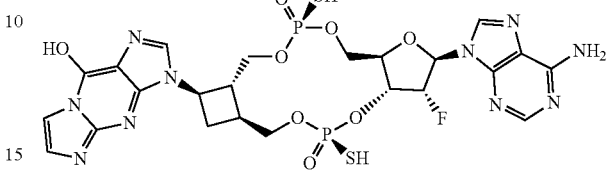
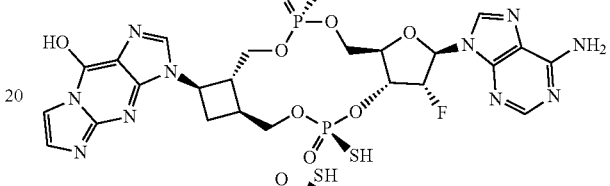
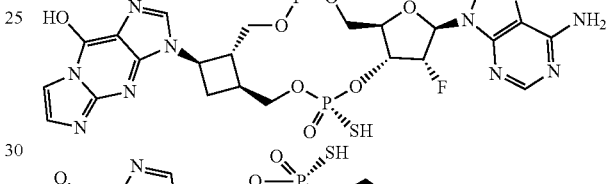

149
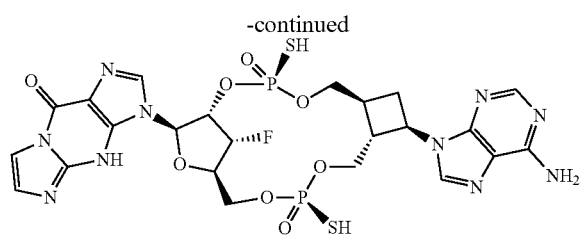
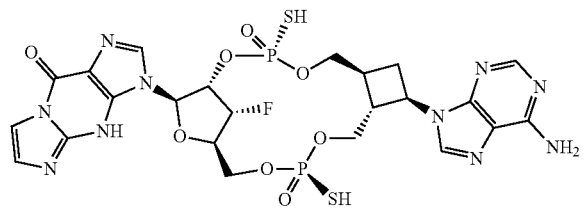
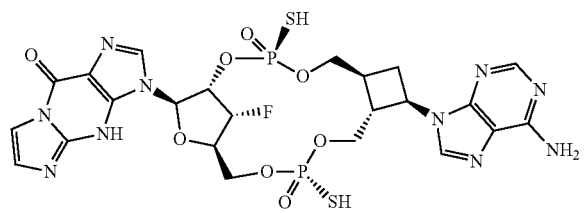
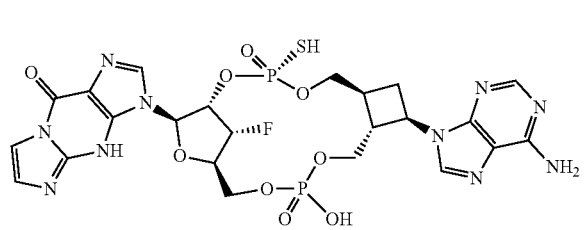
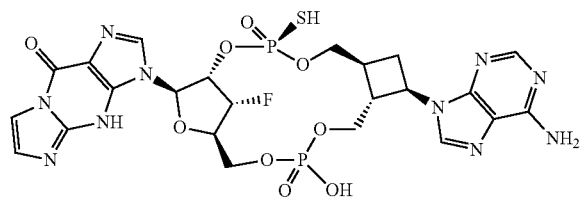
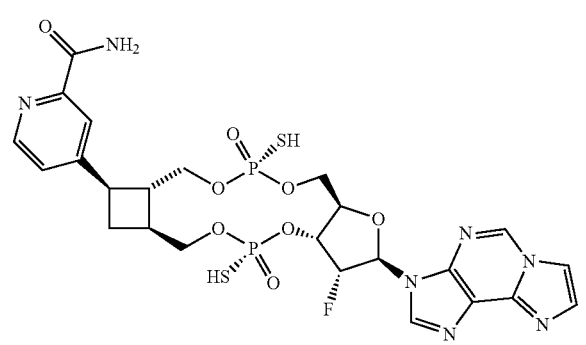
150
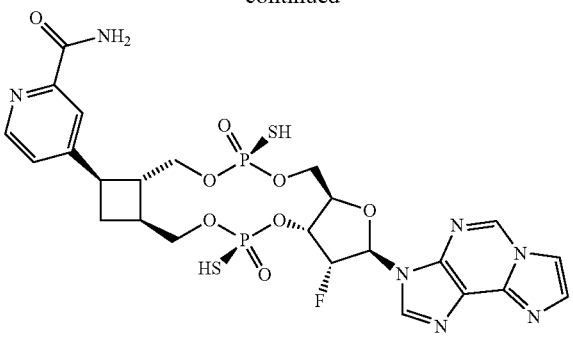
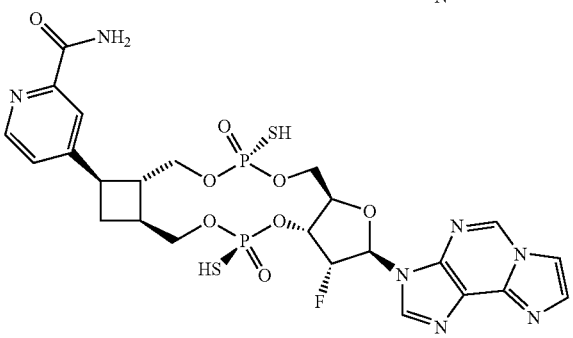
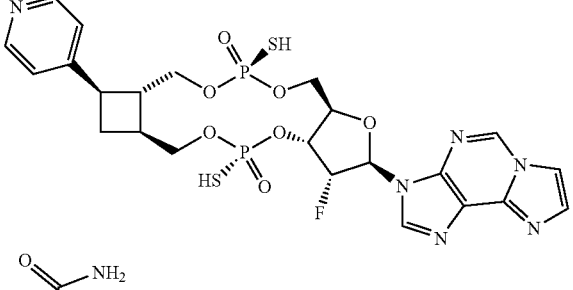
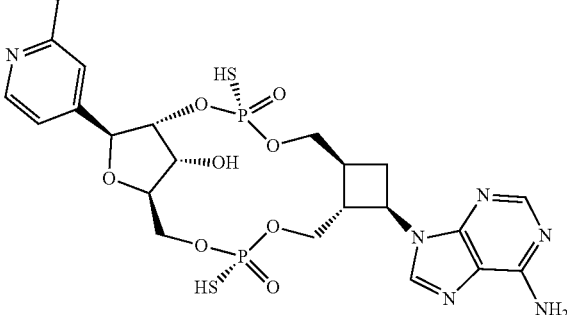
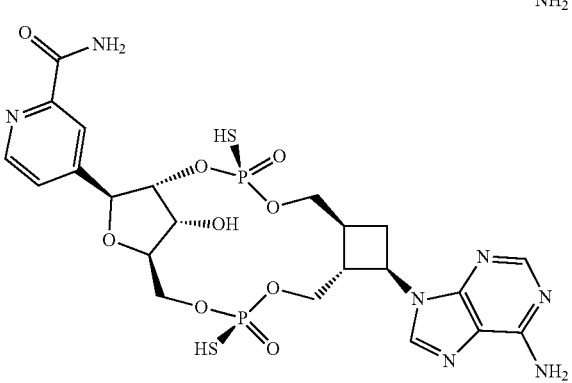

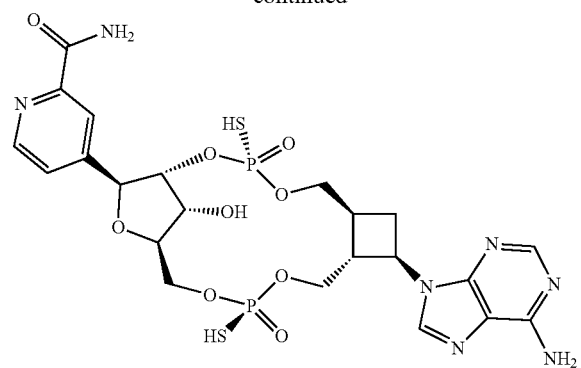
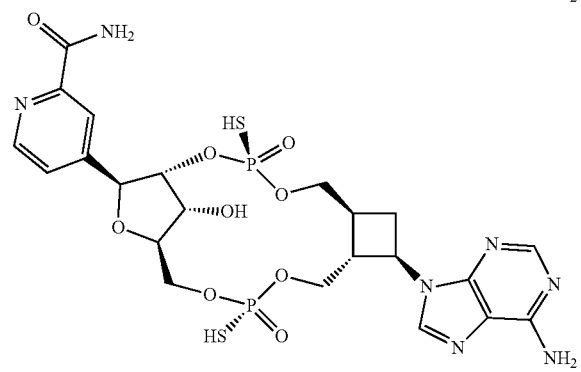
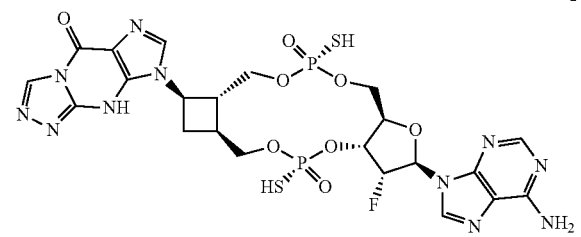
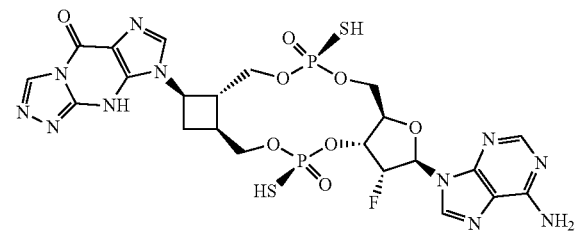
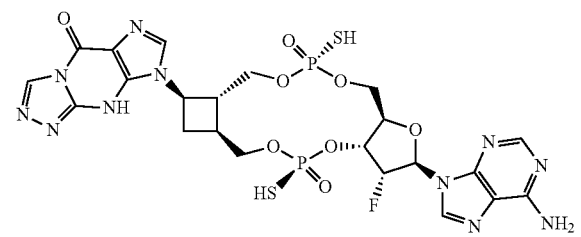
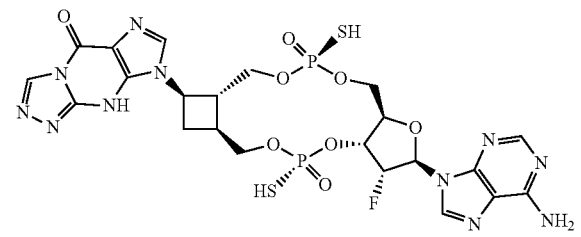
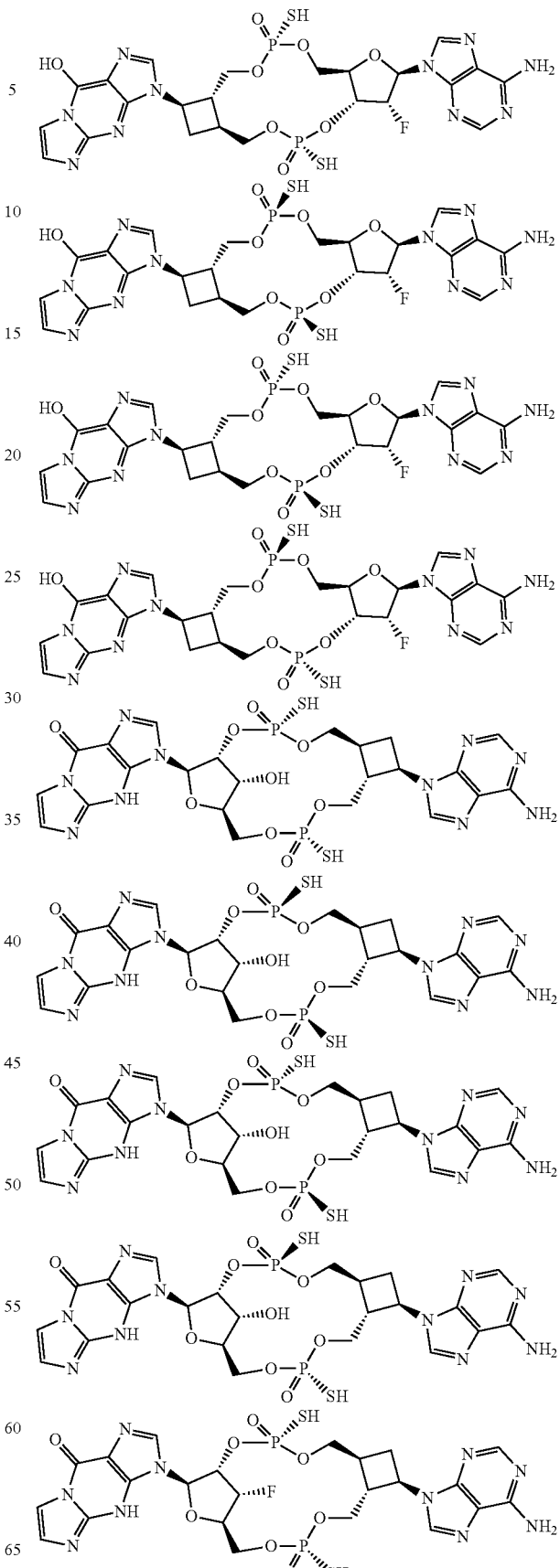
In another aspect, there is provided a pharmaceutically acceptable salt of a compound of the formula

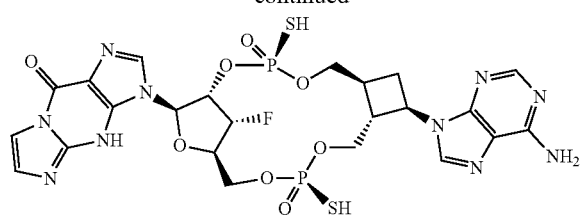
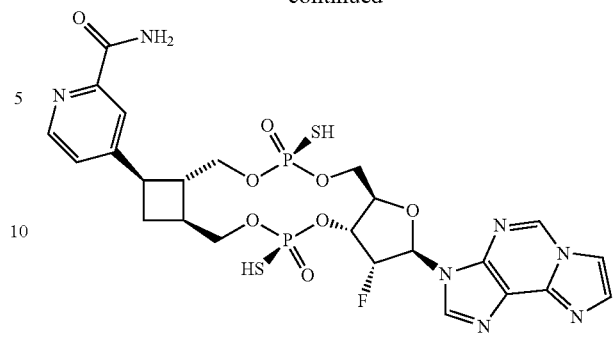
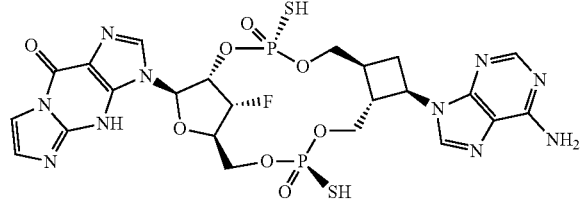
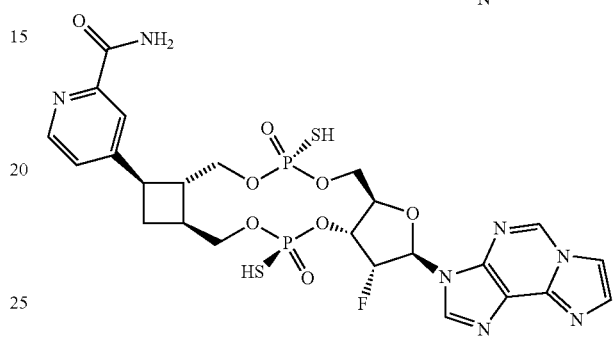
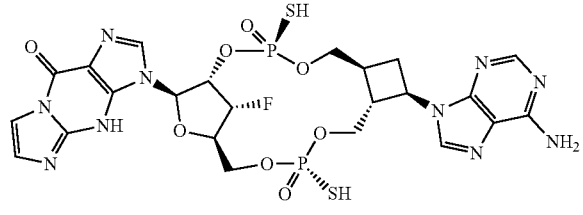
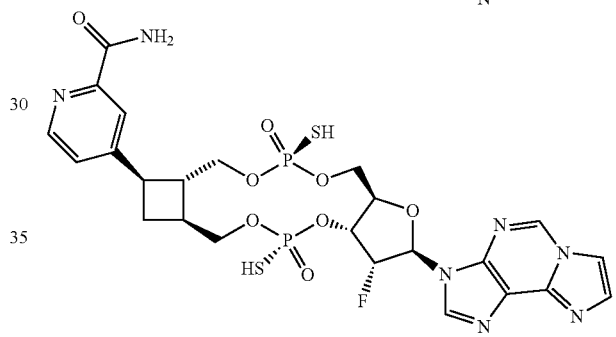
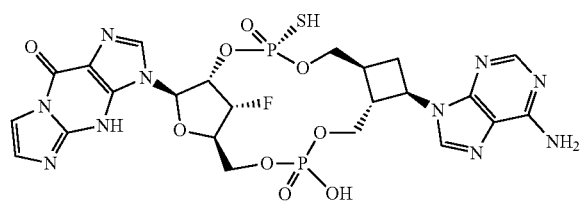
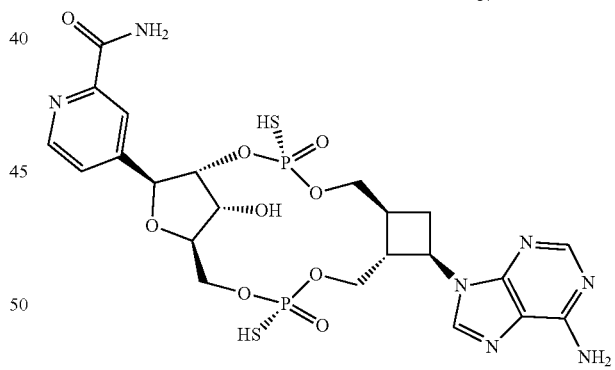
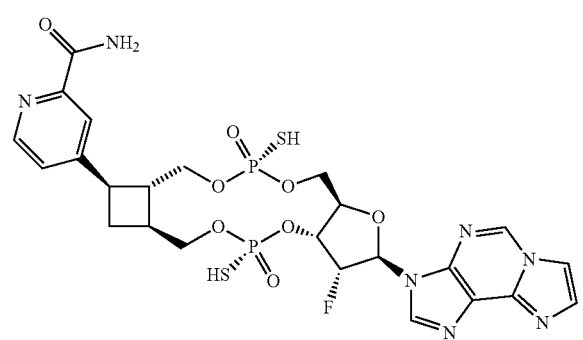
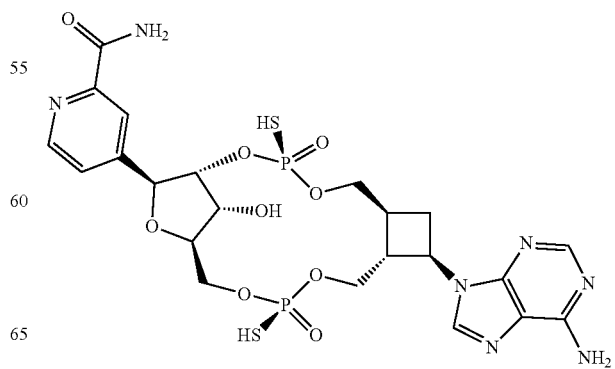

-continued

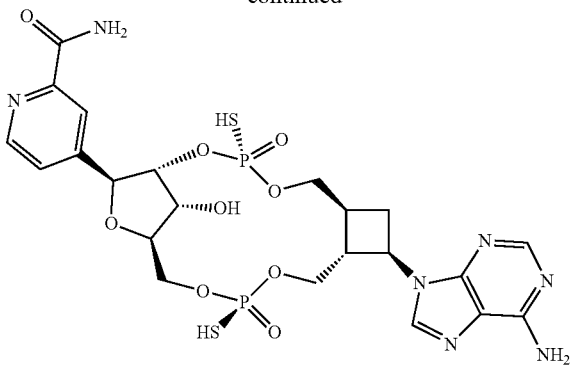

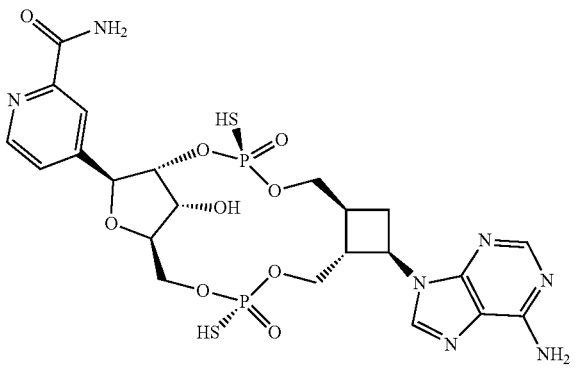

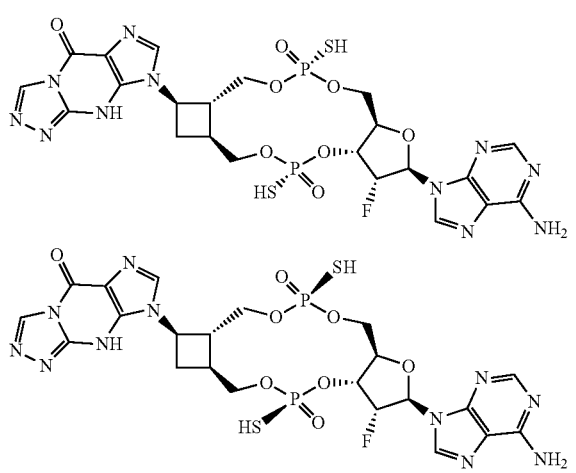

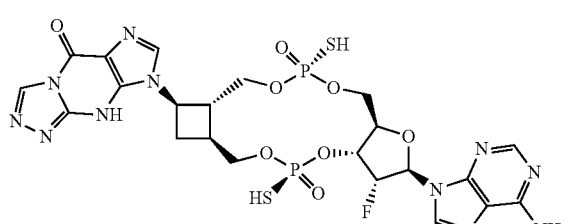

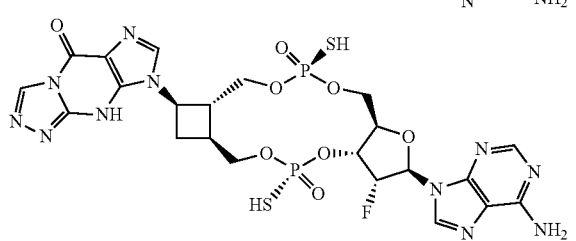

Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The cyclic dinucleotides of the invention induce Type I interferons and/or pro-inflammatory cytokines in vitro in human cells, animal cells and human blood. The cytokine-inducting activity of these CDNs requires the presence of STING, as confirmed by in vitro experiments in human or animal cells.

The CDNs of the invention are agonists of the receptor STING.

The term "agonist" refers to any substance that activates a biologic receptor in vitro or in vivo to provoke a physiological response.

"STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein that in humans is encoded by the gene TMEM173. Activation of STING by cyclic dinucleotides (CDN) leads to activation of the IRF3 and NF-κB pathways and consequently, to induction of Type I interferons and of pro-inflammatory cytokines, respectively.

Another object of the present invention is the cyclic dinucleotides of Formula (I), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the cyclic dinucleotide of Formula (I) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the cyclic dinucleotides of the present invention can be used for cytokine induction immunotherapy of immunosuppressed individuals.

In this example, a cyclic dinucleotide of Formula (I) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof a cyclic dinucleotide of Formula (I) or a pharmaceutically acceptable salt or prodrug thereof.

In another embodiment, the cyclic dinucleotides of the present invention can be used for cytokine induction immunotherapy in combination with chemotherapy. In this example, a cyclic dinucleotide of Formula (I) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof: a chemotherapeutic agent; and a cyclic dinucleotide of Formula (I) or a pharmaceutically acceptable salt or prodrug thereof.

Another object of the present invention is the cyclic dinucleotides of Formula (I) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof a cyclic dinucleotide of Formula (I) or a pharmaceutically acceptable salt or prodrug thereof.

Another object of the present invention is the cyclic dinucleotides of Formula (I) for use in the treatment of a pathology that may be alleviated by the induction of an immune response via the STING pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s)

of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224 In one aspect, In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO006/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

Additionally, the phosphorothioate group can be drawn as either

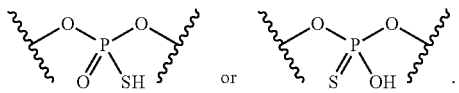 [SMILES: *OP(=O)(S)O* ; *OP(O)(=S)O*]

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, CF$_3$, CF$_2$CF$_3$, CN, halogen, haloalkyl, NO$_2$, sulfone, sulfoxide, ester, sulfonamide, carboxamide, alkoxy, alkoxyether, alkenyl, alkynyl, OH, C(O)alkyl, CO$_2$H, phenyl, heteroaryl, —O-phenyl, and —O— heteroaryl. Preferred examples of EWG include, but are not limited to, CF$_3$, CF$_2$CF$_3$, CN, halogen, SO$_2$(C$_{1-4}$ alkyl), CONH(C$_{1-4}$ alkyl), CON(C$_{1-4}$ alkyl)$_2$, and heteroaryl. More preferred examples of EWG include, but are not limited to, CF$_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, CD3 denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);
c) Bundgaard, H., *Adv. Drug Deliv. Rev.*, 8:1-38 (1992);
d) Bundgaard, H. et al., *J. Pharm. Sci.*, 77:285 (1988);
e) Kakeya, N. et al., *Chem. Pharm. Bull.*, 32:692 (1984); and
f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2007).

Compounds of Formula (I) may be prepared by reference to the methods illustrated in the following Scheme. As shown therein, the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

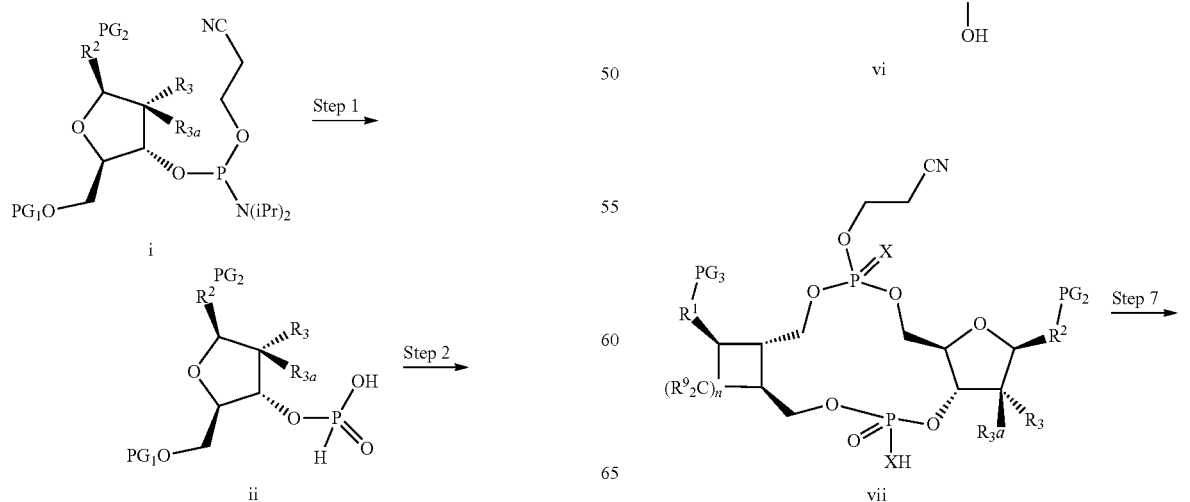

-continued

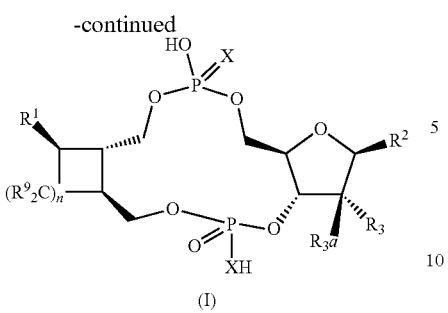

(I)

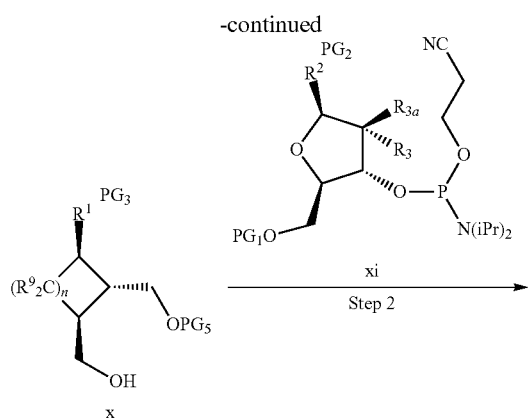

One method for preparation of examples of the present disclosure is described in Scheme 1. The method starts from an appropriately substituted cycloalkyl or ribo-nucleoside (i), wherein the nucleobase ($R^1$ or $R^2$) is appropriately protected ($PG_2$ or $PG_3$), such as with a benzoyl group, and the 5'-hydroxy group is appropriately protected ($PG_1$), such as with a DMTr ether, and the 3'-position is a phosphoramidite functionality. In step 1, treatment with appropriate reagents, such as pyridine trifluoroacetate followed by butylamine, affords the H-phosphonate (ii). Subsequent removal of the 5'-OH protecting group in step 2, under acidic conditions ($PG_1$=DMTr) affords compounds of formula iii. The resulting compound of formula iii may be reacted with a fully protected phosphoramidite (iv) in step 3 followed by oxidation with, for example, t-butylhydroperoxide (X=O) or sulfurization with, for example DDTT (X=S), to provide compounds of formula v. Removal of the protecting group from v in step 4, under appropriate conditions (for example triethylamine trihydrofluoride when $PG_4$=TBS) provides compounds of formula vi. Treatment of compounds vi with an appropriate cyclization reagent in step 5, such as DMOCP followed by oxidation with, for example, t-butylhydroperoxide (X=O) or sulfurization with, for example DDTT (X=S) in step 6 affords compounds of formula vii. Compounds of formula vii may be treated with an appropriate reagent to remove the remaining protecting groups of the nucleobase, for example $NH_4OH/MeOH$ ($PG_2$ and $PG_3$=benzoyl) to afford compounds of formula (I).

An additional method for preparation of examples of the present disclosure is described in Scheme 2.

Scheme 2

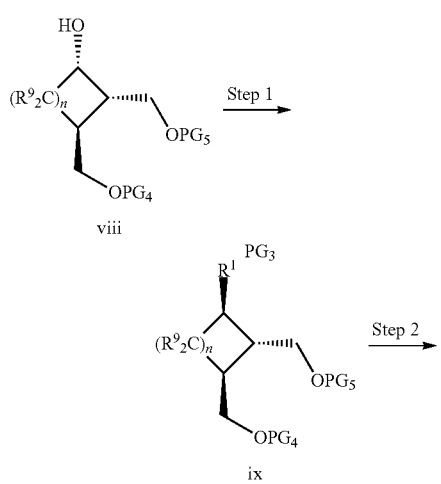

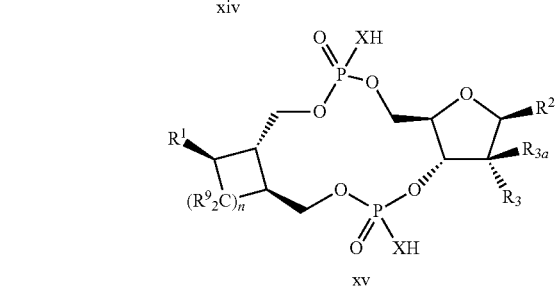
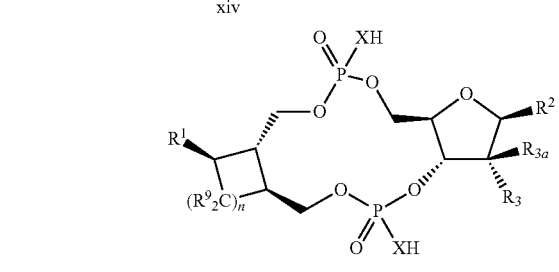
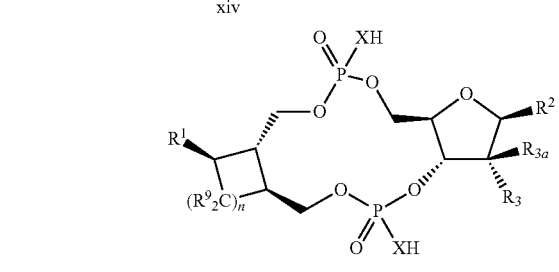
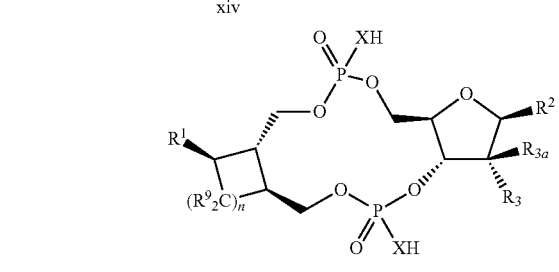
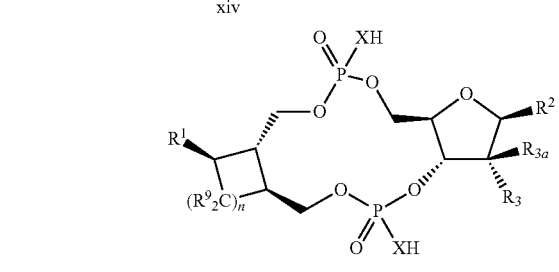
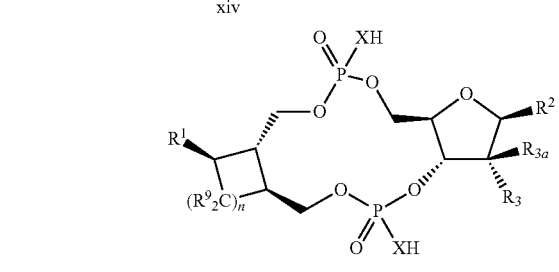
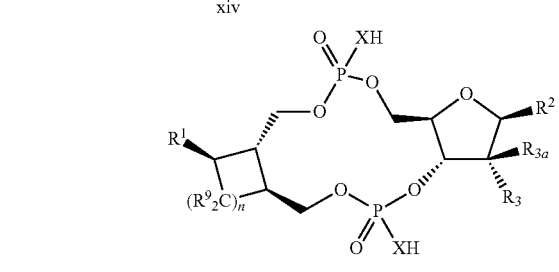

Compounds of formula ix may be prepared from an appropriately protected compound of formula viii through a number of ways known to those skilled in the art. For example, treatment of viii (where $PG_5$=Trityl and $PG_4$=Ac) with an appropriate heterocyclic compound under Mitsunobu conditions provides compounds of formula ix. Selective removal of one protecting group, for example where $PG_4$=Ac, may be accomplished under a number of conditions, for example by treatment with ammonia or MeMgCl, to afford compounds of formula x. Coupling of compounds of formula x with an appropriately protected phosphoramidite (xi) followed by oxidation with, for example, t-butylhydroperoxide (X=O) or sulfurization with, for example DDTT (X=S) provides compounds of formula xii. Subsequent removal of protecting groups (for example PG₅=Trityl or TBS, PG₁=DMTr) under a variety of conditions known to one skilled in the art (for example with TFA) provides compounds of formula xiii. Macrocyclization of compounds of formula xiii may be accomplished in a number of ways known to those skilled in the art. For example, treatment with diphenyl phosphite, followed by oxidation with, for example, t-butylhydroperoxide (X=O) or sulfurization with, for example DDTT (X=S) provides compounds of formula xiv. Removal of all remaining protecting group provides compounds of general formula xv.

An additional method for preparation of examples of the present disclosure is described in Scheme 3.

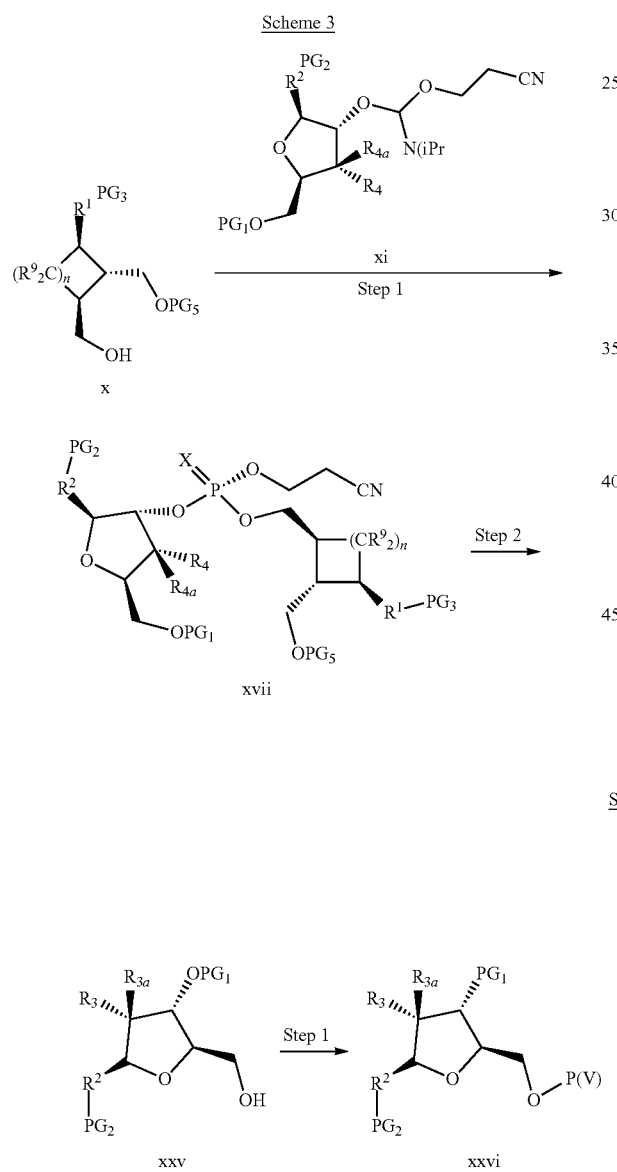

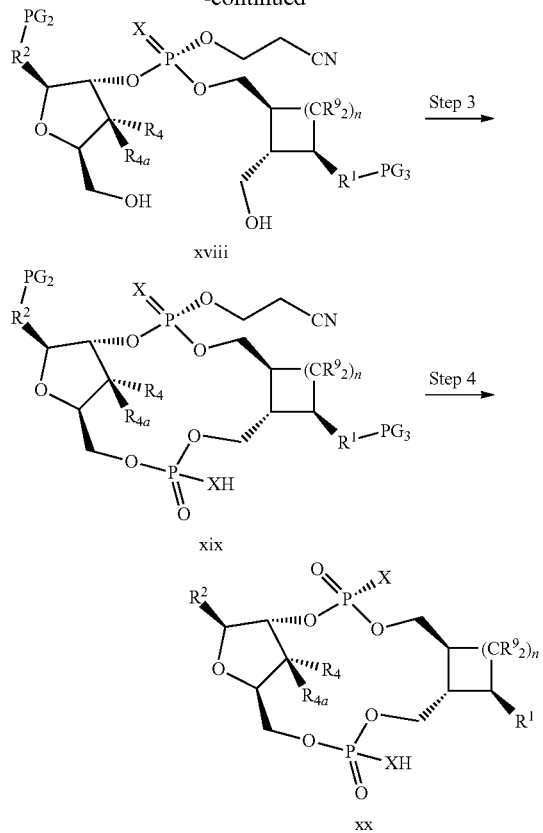

The reaction of compounds of formula x may also be carried out with phosphoramidites of formula xvi, followed by oxidation with, for example, t-butylhydroperoxide (X=O) or sulfurization with, for example DDTT (X=S) to afford compounds of general formula xvii. Subsequent removal of protecting groups (for example PG₅=Trityl or TBS, PG₁=DMTr) under a variety of conditions know to one skilled in the art (for example with TFA) provides compounds of formula xviii. Macrocyclization of compounds of formula xviii may be accomplished in a number of ways known to those skilled in the art. For example, treatment with diphenyl phosphite, followed by oxidation with, for example, t-butylhydroperoxide (X=O) or sulfurization with, for example DDTT (X=S) provides compounds of formula xix. Removal of all remaining protecting group provides compounds of general formula xx.

Alternatively, an additional method for the preparation of examples of the present disclosure is described in Scheme 4.

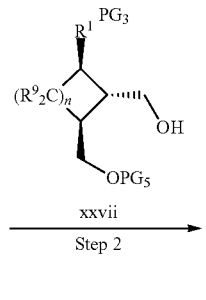

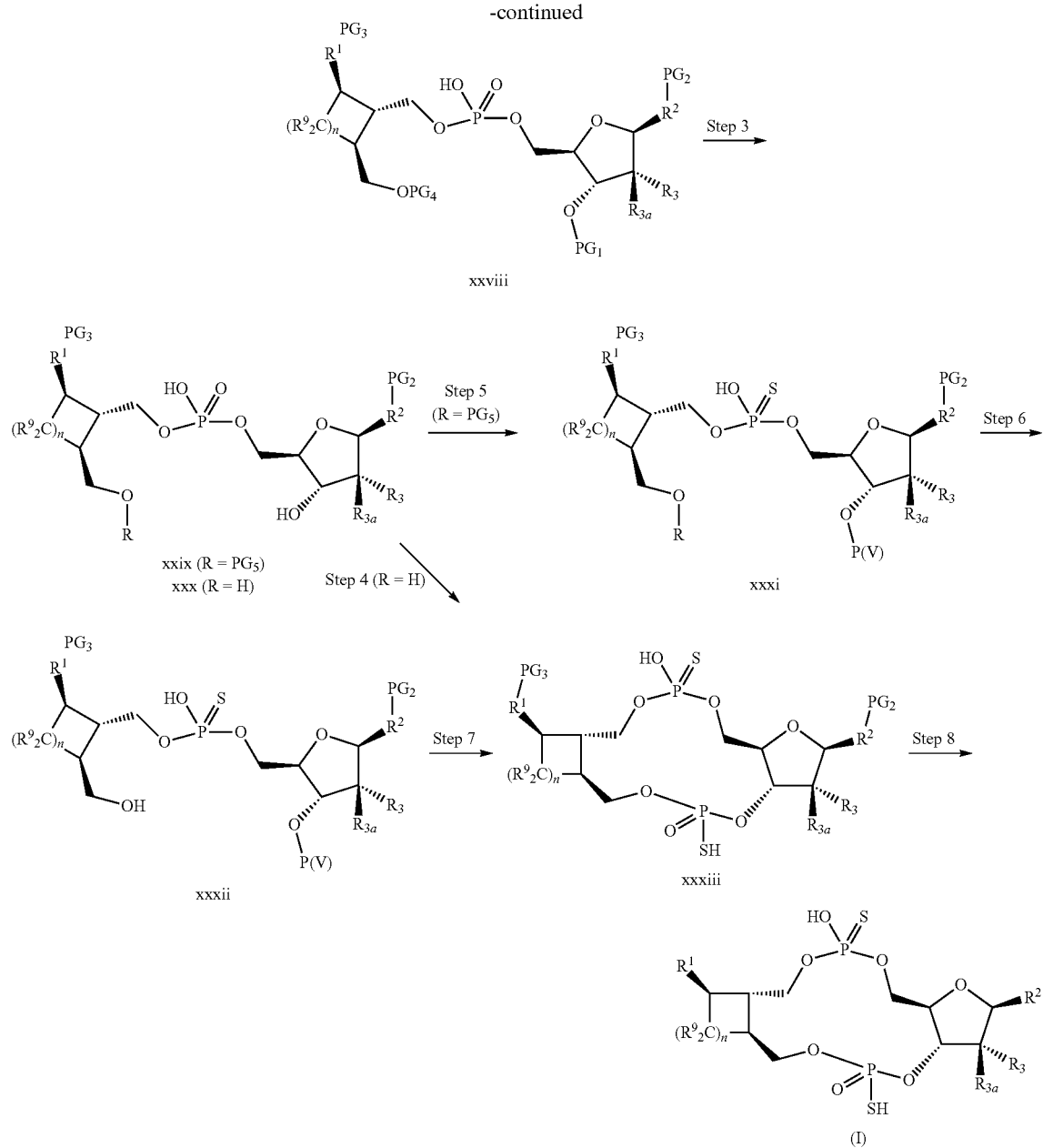

The method starts from an appropriately substituted natural or modified nucleoside (xxv), wherein the nucleobase ($R^2$) is appropriately protected (PG=protecting group), such as with a benzoyl group. In Step 1, treatment of xxv with an appropriate organophosphorus (V) reagent, for example one of those listed in Table 1, in an appropriate solvent (such as acetonitrile or dimethylformamide), with an appropriate base (for example DBU) affords compounds of formula xxvi. Treatment with an appropriately protected alcohol (for example xxvii) in Step 2, in an appropriate solvent (for example acetonitrile or dimethylformamide) in the presence of a base (for example DBU) affords compounds of formula xxviii. In Step 3, one or both protecting groups ($PG_1$ and $PG_5$) may be removed under conditions known to one skilled in the art to afford alcohol (xxix) or a diol (xxx). Compounds of formula xxx may be treated with an appropriate organophosphorus (V) reagent, for example one of those listed in Table 1, in an appropriate solvent (such as acetonitrile or dimethylformamide), with an appropriate base (for example DBU) to afford compounds of formula xxxiii. Alternatively, one may treat compounds of formula xxix with an appropriate organophosphorus (V) reagent, for example one of those listed in Table 1, in an appropriate solvent (such as acetonitrile of dimethylformamide), with an appropriate base (for example DBU) to afford compounds of formula xxxi. In Step 6, the protecting group ($R=PG_5$) may be removed to afford the alcohol xxxii. Treatment of xxxii, in Step 7, with an appropriate base (for example DBU) affords compounds of formula xxxiii. Removal of the remaining protecting groups, if necessary, affords compounds of formula (I).

An additional method for the preparation of examples of the present disclosure is described in Scheme 5.

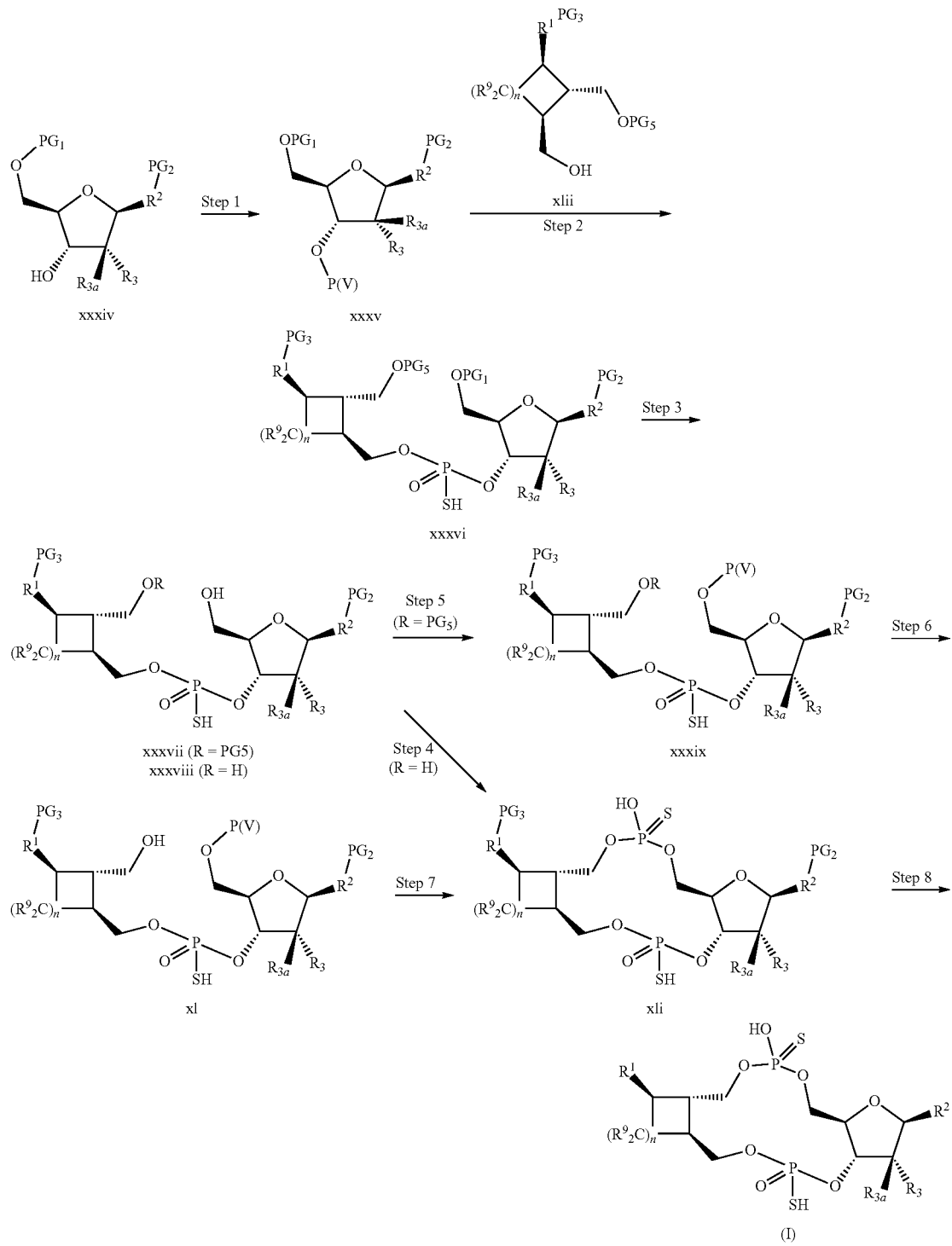

Scheme 5

The method starts from an appropriately substituted natural or modified nucleoside (xxxiv), wherein the nucleobase ($R^2$) is appropriately protected (PG=protecting group), such as with a benzoyl group. In Step 1, treatment of xxxiv with an appropriate organophosphorus (V) reagent, for example one of those listed in Table 1, in an appropriate solvent (such as acetonitrile or dimethylformamide), with an appropriate base (for example DBU) affords compounds of formula xxxv. Treatment with an appropriately protected alcohol (for example xlii) in Step 2, in an appropriate solvent (for example acetonitrile or dimethylformamide) in the presence of a base (for example DBU) affords compounds of formula xxxvi. In Step 3, one or both protecting groups ($PG_1$ and $PG_5$) may be removed under conditions known to one skilled in the art to afford alcohol (xxxvii) or a diol (xxxviii). Compounds of formula xxxviii may be treated with an appropriate organophosphorus (V) reagent, for example one of those listed in Table 1, in an appropriate solvent (such as acetonitrile or dimethylformamide), with an appropriate base (for example DBU) to afford compounds of formula xli. Alternatively, one may treat compounds of formula xxxvii with an appropriate organophosphorus (V) reagent, for example one of those listed in Table 1, in an appropriate solvent (such as acetonitrile of dimethylformamide), with an appropriate base (for example DBU) to afford compounds of formula xxxix. In Step 6, the protecting group (R=PG$_5$) may be removed to afford the alcohol xl. Treatment of xl, in Step 7, with an appropriate base (for example DBU) affords compounds of formula xli. Removal of the remaining protecting groups, if necessary, affords compounds of formula (I).

An additional method for preparation of examples of the present disclosure is described in Scheme 6.

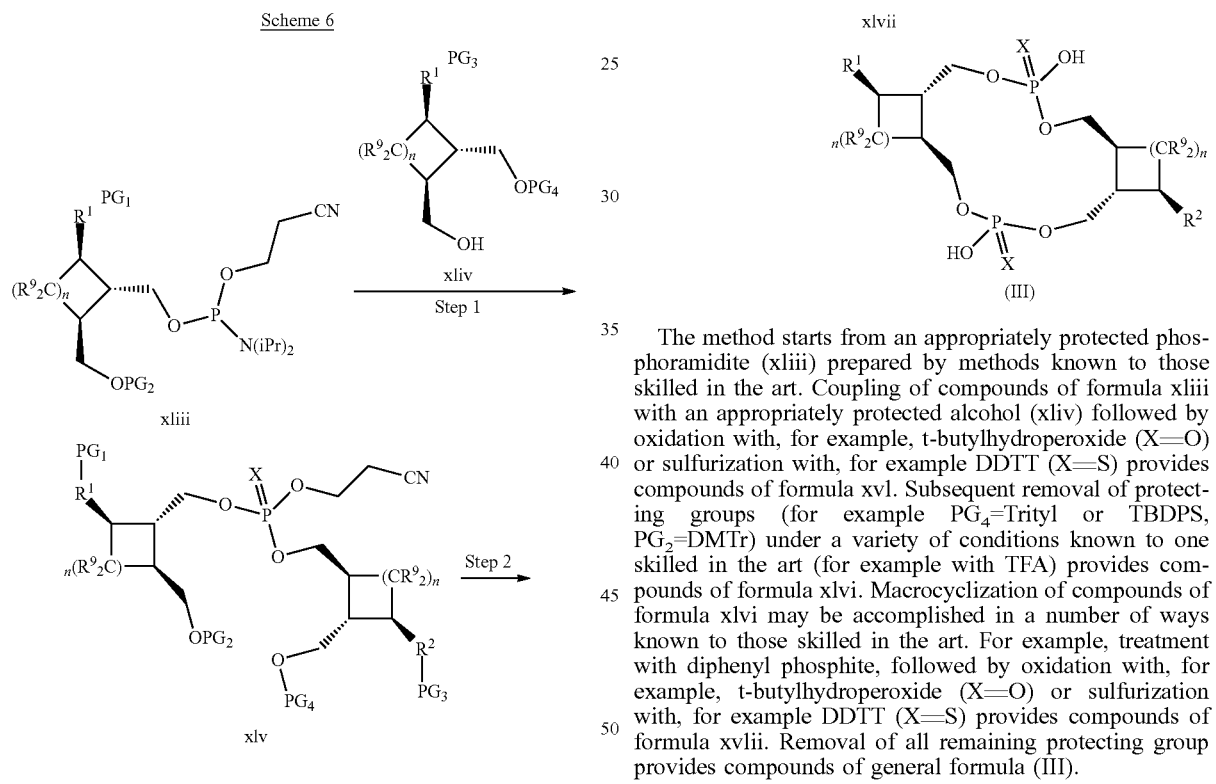

The method starts from an appropriately protected phosphoramidite (xliii) prepared by methods known to those skilled in the art. Coupling of compounds of formula xliii with an appropriately protected alcohol (xliv) followed by oxidation with, for example, t-butylhydroperoxide (X=O) or sulfurization with, for example DDTT (X=S) provides compounds of formula xvl. Subsequent removal of protecting groups (for example PG$_4$=Trityl or TBDPS, PG$_2$=DMTr) under a variety of conditions known to one skilled in the art (for example with TFA) provides compounds of formula xlvi. Macrocyclization of compounds of formula xlvi may be accomplished in a number of ways known to those skilled in the art. For example, treatment with diphenyl phosphite, followed by oxidation with, for example, t-butylhydroperoxide (X=O) or sulfurization with, for example DDTT (X=S) provides compounds of formula xvlii. Removal of all remaining protecting group provides compounds of general formula (III).

TABLE 1

Organophosphorus Reagents and Corresponding —P(V) groups

| Organophosphorus (V) Reagent | —P(V) |
|---|---|
| Reagent-1 | |

TABLE 1-continued

Organophosphorus Reagents and Corresponding —P(V) groups

| Organophosphorus (V) Reagent | —P(V) |
|---|---|
| Reagent-2 | |
| Reagent-3 | |
| Reagent-4 | |

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Abbreviations

The following abbreviations may be used in the example section below and elsewhere herein:

| Abbreviation | Full Name |
|---|---|
| Ac | acetyl |
| ACN | acetonitrile |
| aq. | aqueous |
| DBU | 1,8-Diazabicyclo[5.4.0]undec-7-ene |
| DCM | dichloromethane |
| DDTT | ((dimethylamino-methylidene)amino)-3H-1,2,4-dithiazoline-3-thione |
| DIAD | diisopropyl azodicarboxylate |
| DMSO | dimethylsulfoxide |
| DMOCP | 2-chloro-5,5-dimethyl-1,3,2-dioxaphosphorinane 2-oxide |
| DMTr | 4,4'-dimethoxytrityl |
| EtOAc | ethyl acetate |

| Abbreviation | Full Name |
|---|---|
| $Et_3N$ or TEA | triethylamine |
| EtOH | ethanol |
| HPLC | high-performance liquid chromatography |
| iPr | isopropyl |
| MeOH | methanol |
| RT | room temperature |
| satd. or sat'd | saturated |
| TBS | tButyldimethylsilyl |
| THF | tetrhydrofuran |
| TFA | Trifluoroacetic acid |
| Tr or Trt | Trityl |
| $t_R$ | retention time |

Preparation of Phosphorus (V) Reagents

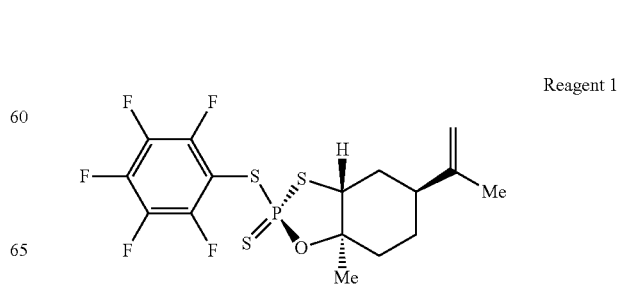

Reagent 1

Reagent 2

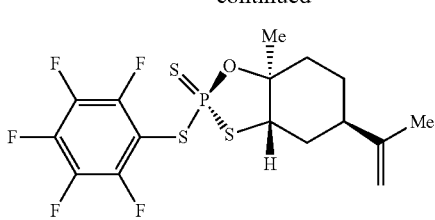

Reagent 3

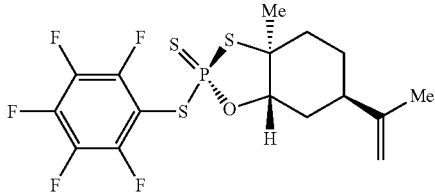

Reagent 4

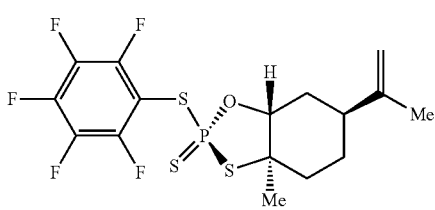

The phosphorus (V) reagents (Reagents 1-4) used in the preparation of Examples of this invention were prepared according to the procedures provided in U.S. Ser. No. 62/657,551 filed Apr. 13, 2018, U.S. Ser. No. 62/656,8098 filed May 7, 2018, U.S. Ser. No. 62/697,896 filed Jul. 13, 2018 and U.S. Ser. No. 62/729,314 filed Sep. 10, 2018.

Examples 1-1, 1-2, 1-3 and 1-4

(1R,6S,8R,9R,15R,17R,18R)-17-(6-amino-9H-purin-9-yl)-18-fluoro-8-{9-hydroxy-3H-imidazo[1,2-a]purin-3-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione

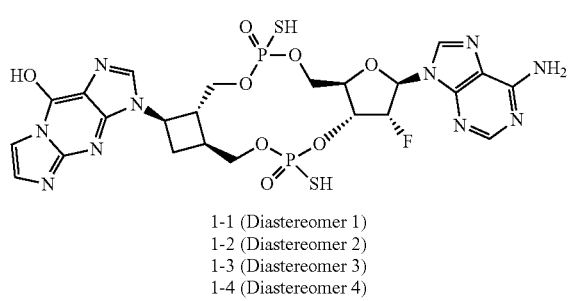 [SMILES: Nc1ncnc2c1ncn2[C@@H]1O[C@@H]2COP(=O)(S)OC[C@@H]3[C@@H](COP(=O)(S)O[C@H]2[C@H]1F)C[C@H]3n1cnc2c(O)n3ccnc3nc21]

1-1 (Diastereomer 1)
1-2 (Diastereomer 2)
1-3 (Diastereomer 3)
1-4 (Diastereomer 4)

Preparation of Intermediate 1A:

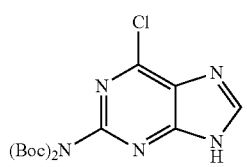

1A

To a slurry containing 6-chloro-9H-purin-2-amine (4.24 g, 25.0 mmol) in THF (200 mL) was added DMAP (0.31 g, 2.50 mmol) followed by the addition of BOC-anhydride (17.41 mL, 75 mmol). The reaction was stirred overnight and then concentrated to dryness. The crude material was dissolved in ethylacetate (200 mL) and washed with 1 N HCl, and sat. aq. NaCl solution. The organic layer was dried (Na$_2$SO$_4$), filtered and concentrated. The crude material was dissolved in MeOH (100 mL) and sat. aq. NaHCO$_3$ and was heated at 50° C. for 1 h. The resulting mixture was concentrated to remove organics and the aqueous layer was extracted with DCM (3×100 mL). The combined organic layers were dried (Na$_2$SO$_4$), filtered and concentrated. The residue was re-dissolved in THF (50 mL), adsorbed onto a small amount of celite (10 g) and purified on an ISCO silica gel chromatography system (120 g ISCO silica gel column) with a MeOH/DCM/(0%-10%) over a 30 min gradient to give 1A (3 g, 8.11 mmol, 32.4% yield).

Preparation of Intermediate 1B:

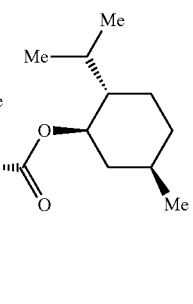

1B

To a −78° C. solution of bis((1R,2S,5R)-2-isopropyl-5-methylcyclohexyl) fumarate (5 g, 12.7 mmol) in toluene (64 mL) was added diethylaluminium chloride (25 mL, 25 mmoL) dropwise, under nitrogen. The reaction was stirred at −78° C. for 10 min, then 1,1-dimethoxyethene (1.3 mL, 14 mmol) was added and the reaction was stirred for an additional 10 min. The reaction was quenched with dropwise addition of 1 mL methanol and 1 mL of 15% aqueous sodium hydroxide. Methanol (2.5 mL) was added and the mixture was stirred for 10 min. To the mixture was added 1 g of magnesium sulfate and the mixture was stirred at room temperature for 30 min. The suspension was filtered through a pad of Celite and the filtrate was concentrated in vacuo to give the crude. The crude material was purified by flash chromatography over 120 g of silica gel (20 min gradient, with 0-10% ethyl acetate in hexanes) and was then recrystallized from 95:5 methanol:water to give 1B (5.6 g, 91%) as a white solid. $^1$H NMR (400 MHz, CHLOROFORM-d) δ 4.85-4.66 (m, 2H), 3.56-3.49 (m, 1H), 3.36-3.28 (m, 3H), 3.16 (s, 3H), 2.61 (dd, J=11.9, 10.7 Hz, 1H), 2.22-2.15 (m, 1H), 2.11-1.96 (m, 2H), 1.93-1.80 (m, 1H), 1.75-1.65 (m, 3H), 1.62-1.34 (m, 8H), 1.12-0.84 (m, 18H), 0.80-0.75 (m, 6H).

Preparation of Intermediate 1C:

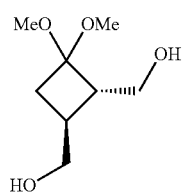

1C

To a 0° C. solution of 1B (17 g, 35.4 mmol) in THF (88 mL) was added LAH (2.01 g, 53.0 mmol). The reaction was slowly warmed to room temperature, then heated at 55° C.

for 5 h, followed by stirring at room temperature for 16 h. The solution was cooled to 0° C., quenched with 5 mL water, 5 mL 15% aq NaOH, slowly warmed to room temperature and stirred for 10 min. Water (20 mL) was added, and the mixture was stirred at room temperature for 10 min. To this mixture was added 10 g MgSO$_4$, and stirring continued for 10 min. It was then filtered through a pad of Celite and the filtrate was concentrated in vacuo. The resulting material was dissolved in 200 mL of hexanes and extracted with water (3×150 mL). The combined aqueous extracts were saturated with ammonium sulfate. The aqueous phase was extracted (3×125 mL) with ethyl acetate, and the combined organic layers were dried (sodium sulfate), filtered and concentrated in vacuo to give 1C (3.74 g, 60%) as a clear, colorless oil. $^1$H NMR (400 MHz, CHLOROFORM-d) δ 3.84-3.71 (m, 3H), 3.56 (dd, J=10.4, 8.3 Hz, 1H), 3.21 (d, J=2.2 Hz, 6H), 2.49-2.24 (m, 2H), 2.23-1.95 (m, 2H), 1.72 (ddd, J=12.4, 7.6, 1.0 Hz, 2H).

Preparation of Intermediate 1D:

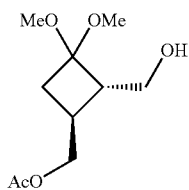

1D

To a solution of 1C (24 g, 136 mmol) in toluene (1362 ml) at room temperature was added vinyl acetate (129 g, 1498 mmol). Then, lipase from porcine pancreas (36 g, 136 mmol) was added in one portion and the resulting light suspension was stirred at room temperature for 21.6 h. The mixture was then filtered through Celite and the filter cake was rinsed with EtOAc. The combined filtrates were then evaporated in vacuo and the residue was purified by column chromatography using a 330 g ISCO column eluting with 0-100% ethyl acetate in hexane to afford 1D (30 g, 137 mmol, 101% yield) as an oil that was used as is in the next reaction $^1$H NMR (400 MHz, CHLOROFORM-d) δ 4.27-3.99 (m, 2H), 3.88-3.61 (m, 2H), 3.33-3.05 (m, 6H), 2.46-2.32 (m, 2H), 2.32-2.17 (m, 1H), 2.12-2.00 (m, 3H), 1.88-1.73 (m, 1H).

Preparation of Intermediate 1E:

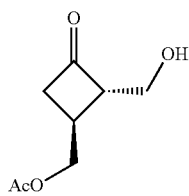

1E

Tosic acid (1.307 g, 6.87 mmol) was added in one portion to a solution of 1D (30 g, 137 mmol) in acetone (500 mL) at room temperature. The reaction was allowed to stir at room temperature for 3 hrs at which point the reaction was complete. Et$_3$N (1.916 ml, 13.75 mmol) was added and the mixture was evaporated in vacuo. The residue was then purified on an ISCO system using a hexane/ethyl acetate gradient—product eluted with neat ethyl acetate. The fractions containing product were then combined and evaporated. During evaporation, no heat was applied and 1E (22 g, 93%) was obtained as an oil. $^1$H NMR (400 MHz, CHLOROFORM-d) δ 4.44-4.22 (m, 2H), 4.02-3.88 (m, 1H), 3.85-3.69 (m, 1H), 3.41-3.25 (m, 1H), 3.17-3.02 (m, 1H), 2.97-2.85 (m, 1H), 2.85-2.66 (m, 1H), 2.20-2.09 (m, 3H), 1.86-1.72 (m, 1H).

Preparation of Intermediate 1F:

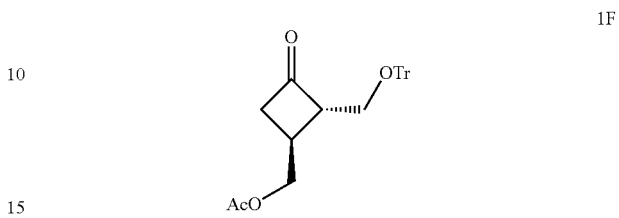

1F

A solution 1E (23.67 g, 137 mmol) in anhydrous DCM (916 mL) at room temperature under a nitrogen atmosphere was treated with Et$_3$N (30.7 mL, 220 mmol) followed by DMAP (1.680 g, 13.75 mmol). (Chloromethanetriyl)tribenzene (49.8 g, 179 mmol) was then added in one portion and the resulting mixture was allowed to stir at room temperature under a nitrogen atmosphere overnight. The reaction was quenched by the addition of saturated sodium bicarbonate solution (200 mL). The aqueous layer was then extracted with an additional portion of DCM (100 mL) and the combined organics were then dried (MgSO$_4$) and evaporated in vacuo. The resulting oil was then purified on a 330 g ISCO column eluting with 0-40% ethyl acetate in hexane to afford 1F (31.83 g, 77 mmol, 55.9% yield) as a white solid. $^1$H NMR (400 MHz, CHLOROFORM-d) δ 7.57-7.39 (m, 6H), 7.39-7.18 (m, 9H), 4.41-4.21 (m, 2H), 3.57-3.42 (m, 1H), 3.34-3.24 (m, 1H), 3.24-3.11 (m, 2H), 2.95-2.78 (m, 2H), 2.07-1.93 (m, 3H).

Preparation of Intermediate 1G

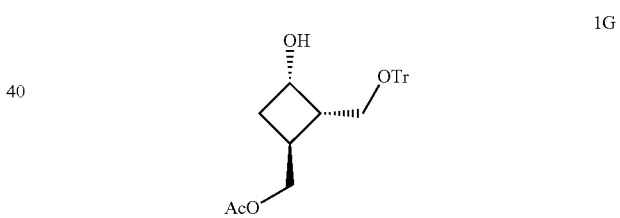

1G

LS-Selectride (36.2 mL, 36.2 mmol) was added dropwise via a pressure equalizing funnel to a stirred solution of 1F (12 g, 29.0 mmol) at −78° C. under a nitrogen atmosphere. The addition took a total of 30 min to complete. The reaction was then allowed to stir at −78° C. for 40 min. The reaction was quenched by the slow addition of sat. aq. sodium bicarbonate solution (85 mL) and the cold bath was then removed and replaced with an ice-water bath. When the internal temp. had reached 0° C., hydrogen peroxide (59.1 mL, 579 mmol) was added dropwise via glass pipette. The resulting mixture was allowed to stir at room temperature for ~4 h before diluting with water and extracting with ethyl acetate (3×). The combined organic layers were then washed with sat. sodium bicarbonate solution, dried (MgSO$_4$) and evaporated in vacuo. This crude material was purified by column chromatography on an ISCO system eluting with a 0-40% ethyl acetate/hexane gradient. Fractions were collected and evaporated to give 1G (7.75 g, 18.61 mmol, 64.3% yield). $^1$H NMR (400 MHz, CHLOROFORM-d) δ 7.60-7.42 (m, 6H), 7.42-7.18 (m, 10H), 4.61-4.40 (m, 1H), 4.13-4.02 (m, 2H), 3.47-3.27 (m, 2H), 2.71-2.65 (m, 1H), 2.65-2.44 (m, 2H), 2.20-2.11 (m, 2H), 2.11-2.02 (m, 3H).

Preparation of Intermediate 1H:

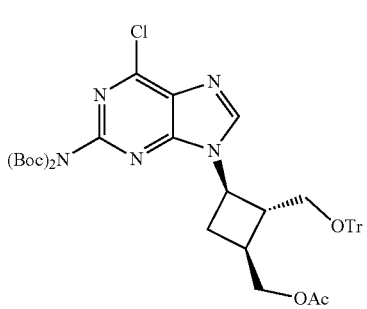

A solution containing triphenylphosphine (732 mg, 2.79 mmol) in a mixture of THF (12 mL)/toluene (6 mL) was cooled in a ice bath and treated dropwise with DIAD (0.525 mL, 2.70 mmol), resulting in a cream colored slurry. To this slurry was added a solution containing 1G (750 mg, 1.801 mmol) and 1A (999 mg, 2.70 mmol) in THF (5 mL). The ice bath was removed and the reaction was stirred at 35° C. for 20 h. The reaction was cooled to room temperature and concentrated to dryness. The crude product was dissolved in a small amount of DCM and charged onto an 80 g ISCO silica gel column and purified using the Teledyne ISCO system, eluting over a 20 min gradient with 0%-100% EtOAc/DCM/to give 1H (900 mg, 1.171 mmol, 65.1% yield). m/z (768, M+H).

Preparation of Intermediate 1I:

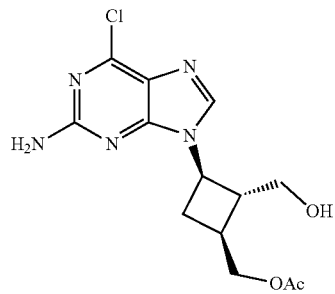

To a solution of 1H (900 mg, 1.171 mmol) in DCM (10 mL) was added triethylsilane (1.871 mL, 11.71 mmol) followed by the addition of TFA (0.902 mL, 11.71 mmol). The reaction was stirred for 30 min. Additional TFA (0.45 mL) was added and the reaction was allowed to stir for an additional 30 min. The reaction was then diluted with additional DCM (50 mL) and quenched with ammonium hydroxide (~5 mL) and shaken in a separatory funnel and the organic layer isolated and the aqueous layer extracted with additional DCM (2×10 mL). The organic extracts were combined, washed with pH 7 buffer, dried ($Na_2SO_4$), filtered and concentrated. The crude product was dissolved in a small amount of DCM and charged onto a 12 g ISCO silica gel column and purified using the Teledyne ISCO system, eluting over a 10 min gradient with 0%-10% MeOH/DCM to give 1I (275 mg, 0.844 mmol, 72.1% yield). m/z (326, M+H).

Preparation of Intermediate 1J:

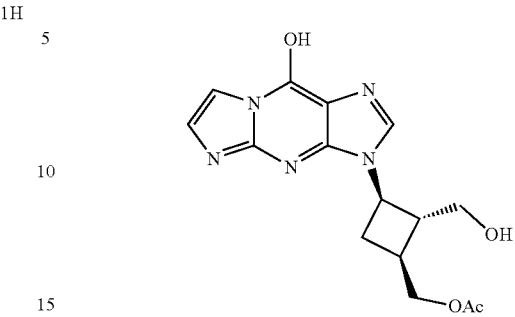

To a suspension of 1I (275 mg, 0.844 mmol) in ethanol (5 mL) was added sodium acetate/acetic acid buffer pH 4.5 (4.22 mL, 4.22 mmol) followed by the addition of an ethanolic/water solution of bromoacetaldehyde (3 mL, 3.75 mmol). The reaction was heated at 45° C. for 22 h. The reaction was then cooled 0° C. in an ice bath and neutralized using solid ammonium bicarbonate. The resulting solids were filtered, washed with water and dried. The solid was redissolved in DCM/MeOH (5 mL), adsorbed onto a small amount of Celite (2 g) and purified on an ISCO silica gel chromatography system using a 4 g ISCO silica gel column with MeOH/DCM (0%-10%) over a 10 min gradient to give desired 1J (135 mg, 0.407 mmol, 48.3% yield). m/z (332, M+H).

Preparation of Intermediate 1K:

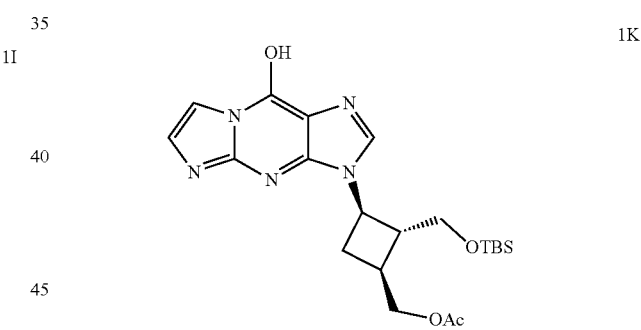

To a solution containing imidazole (216 mg, 3.17 mmol) in DMF (1 mL) was added TBS-Cl (199 mg, 1.320 mmol) and the mixture was stirred for 20 min. A solution containing 1J (175 mg, 0.528 mmol) was added to the solution of TBSCl/imidazole and allowed to stir for 20 h. An additional amount of imidazole (50 mg) and TBSCl (25 mg) were added and the reaction was heated at 50° C. for 1 h. The reaction was then cooled to room temperature, diluted with ethylacetate (50 mL) and washed with water (2×20 mL), aqueous 10% LiCl solution (2×10 mL) and sat. aq. NaCl solution (10 mL). The aqueous washes were combined and back extracted with additional ethyl acetate (50 mL), then washed with sat. aq. NaCl solution. The organic layers were combined, dried ($Na_2SO_4$), filtered and concentrated. The crude product was dissolved in a small amount of DCM and charged onto a 12 g ISCO silica gel column and purified using the Teledyne ISCO system, eluting over a 10 min gradient with 0%-5% MeOH/DCM to give 1K (220 mg, 0.494 mmol, 93% yield). m/z (446, M+H).

Preparation of Intermediate 1L:

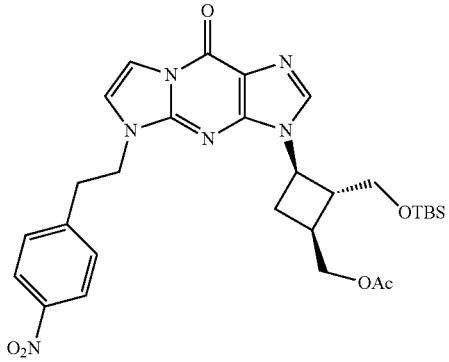

To a 0° C. solution containing 1K (210 mg, 0.471 mmol), 2-(4-nitrophenyl)ethan-1-ol (158 mg, 0.943 mmol) and triphenylphosphine (253 mg, 0.966 mmol) in dioxane (5 mL) was added DIAD (0.183 mL, 0.943 mmol) The reaction was stirred at room temperature for 20 h and then concentrated to a thick oil. The residue was re-dissolved in DCM (1 mL), adsorbed onto a small amount of Celite (1 g) and purified on the ISCO silica gel chromatography system using a 12 g ISCO silica gel column with MeOH/DCM (0%-10%) over a 10 min gradient to give the desired 1L (180 mg, 0.303 mmol, 64.2% yield). m/z (595, M+H).

Preparation of Intermediate 1M:

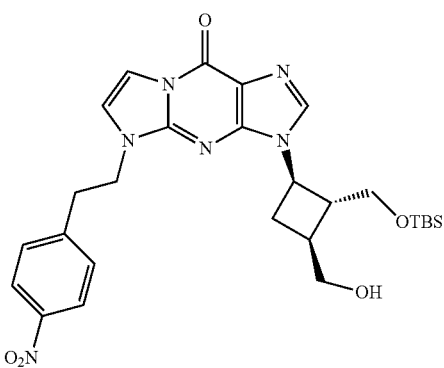

Intermediate 1L (265 mg, 0.446 mmol) was dissolved in a methanolic solution of ammonia (7 N in MeOH) (5 mL, 35.0 mmol), sealed in a vial and heated at 35° C. for 2 h. The reaction was then concentrated and the crude product was dissolved in a small amount of DCM and charged onto 4 g ISCO silica gel column and purified using the Teledyne ISCO system, eluting over a 10 min gradient with 0%-5% MeOH/DCM to give 1M (180 mg, 0.326 mmol, 73.1% yield), m/z (553, M+H).

Preparation of Intermediate 1N:

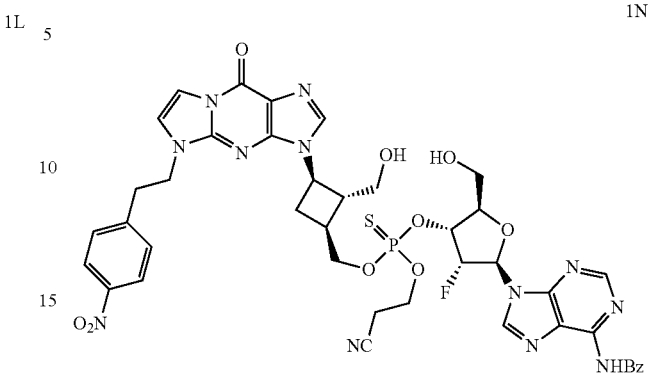

A solution containing tetrazole (25.10 mg, 0.358 mmol) and (2R,3R,4R,5R)-5-(6-benzamido-9H-purin-9-yl)-2-((bis(4-methoxyphenyl)(phenyl)methoxy)methyl)-4-fluorotetrahydrofuran-3-yl 2-cyanoethyl diisopropylphosphoramidite (Sigma-Aldrich, 285 mg, 0.326 mmol) in acetonitrile (5 mL) was concentrated to dryness on the rotary evaporator (2×5 mL) and then re-suspended in acetonitrile (5 mL) and left under a nitrogen atmosphere. In a separate flask was suspended 1M (180 mg, 0.326 mmol) and dry acetonitrile (5 mL) was added and this was concentrated to dryness on the rotoary evaporator (2×5 mL). This material was re-suspended in acetonitrile (2 mL) and then added to the stirring solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl 2-cyanoethyl diisopropylphosphoramidite via syringe. The reaction was evacuated and purged with nitrogen gas and then sealed. The reaction was allowed to stir for 1 h at room temperature. The reaction was then heated at 50° C. for 20 h, cooled to room temperature and treated with (E)-N,N-dimethyl-N'-(3-thioxo-3H-1,2,4-dithiazol-5-yl)formimidamide (100 mg, 0.489 mmol). The reaction was stirred for 1 h and then concentrated. The crude product was dissolved in a small amount of DCM and charged onto a 40 g ISCO silica gel column and purified using the Teledyne ISCO system, eluting over a 20 min gradient with 0%-5% MeOH/DCM. The fractions containing the desired compound were concentrated and the crude material was dissolved in DCM (5 mL) and triethylsilane (550 uL) was added followed by the addition of TFA (125 uL). The reaction was concentrated to dryness and then resuspended in ACN (4 mL) and triethylamine trihydrofluoride was added (550 uL). The reaction was heated at 35° C. for 30 min. The reaction mixture was then loaded onto an ISCO 150 g Gold C-18 RediSep Rf column that had been pre-equilibrated with mobile Phase A: 5:95 acetonitrile:water (0.01 M ammonium acetate); Mobile Phase B: 95:5 acetonitrile:water (0.01 M ammonium acetate); The compound was eluted using gradient: 0% B for 2 column volumes to 100% B over 20 columns to give compound 1N (200 mg, 0.212 mmol, 65.1% yield), m/z (943, M+H).

Preparation of Intermediate 1O:

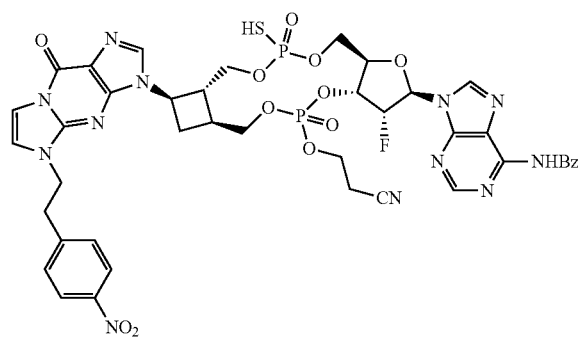

Intermediate 1N (200 mg, 0.212 mmol) was dissolved in pyridine (10 mL) and concentrated to dryness. The procedure was repeated one more time with pyridine (10 mL) and the resulting residue was suspended in dry pyridine (30 mL) under a nitrogen atmosphere and treated in small portions (~0.2 mL) every 10 min with diphenyl phosphite (0.081 mL, 0.424 mmol) that was dissolved in pyridine (10 mL). The reaction was then treated with DDTT (109 mg, 0.530 mmol) and stirred for 10 h. The reaction was concentrated to dryness, resuspended in acetonitrile (5 mL) and adsorbed to Celite (2 g) and purified on reverse phase ISCO C-18 Gold column that had been equilibrated with mobile Phase A: 5:95 acetonitrile:water with 0.01 M ammonium acetate; Mobile Phase B: 95:5 acetonitrile:water with 0.01 M ammonium acetate; Gradient: 0% B for 2 column volumes to 100% B over 20 columns to give 1O (150 mg, 0.147 mmol, 69.3% yield), M+H (1021, M+H) as mixture of four diastereomers.

Examples 1-1, 1-2, 1-3 and 1-4

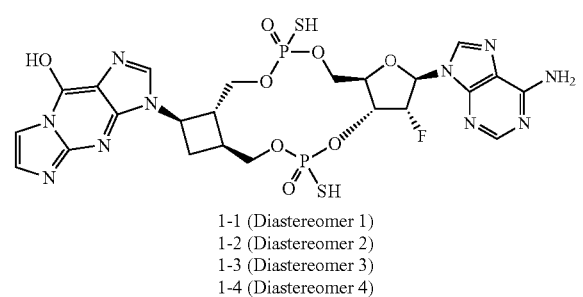 [SMILES: Nc1ncnc2c1ncn2[C@@H]1O[C@@H]2COP(=O)(S)OC[C@@H]3[C@@H](COP(=O)(S)O[C@H]2[C@H]1F)C[C@H]3n1cnc2c(O)n3ccnc3nc21]

1-1 (Diastereomer 1)
1-2 (Diastereomer 2)
1-3 (Diastereomer 3)
1-4 (Diastereomer 4)

Intermediate 1O (185 mg, 0.181 mmol) was suspended in 7 N ammonia in MeOH (5 mL, 35.0 mmol), sealed in a vial and stirred overnight. The reaction was then concentrated to dryness. The crude material was dissolved in pyridine (1 mL) and DBU (225 μL, 1.493 mmol) was added and the reaction was heated at 35° C. for 3 h. The reaction was then concentrated and the residue was suspended in water (1 mL) and brought to pH ~8 with ammonium acetate/acetic acid buffer (pH 4.5) and purified on reverse phase ISCO C-18 Gold column that had been equilibrated with using mobile Phase A: 5:95 acetonitrile:water with 0.01 M ammonium acetate; Mobile Phase B: 95:5 acetonitrile:water with 0.01 M ammonium acetate; Gradient: 0% B for 2 column volumes to 100% B over 20 columns to give a mixture of four diastereomers. The combined four isomers were dissolved in water (2 mL) and purified using preparative reverse phase HPLC with the following conditions to afford four diastereomers: Column: Xselect CSH C18 Column, 3.5 μm, 3.0×150 mm; Mobile Phase A: 20 mM triethyl ammonium acetate (pH 6.5); Mobile Phase B: 80:20 ACN:20 mM triethyl ammonium acetate (pH 6.5); Gradient: 10%-12% B over 9 minutes, then 12-23% B over 5 min, then 23%-95% B over one minute; Flow: 20 mL/min. Fractions containing the desired product were combined and dried via centrifugal evaporation.

Example 1-1

5 mg. Retention Time: 0.39 min. (Column: ACQUITY UPLC® BEH C18 1.7 μm; Mobile Phase A: water with 0.05% TFA; Mobile Phase B: acetonitrile with 0.05% TFA; Gradient: 2% B to 98% B over 1 min, then 98% B to 2% B over 0.5 min; Flow: 0.8 mL/min; Detection: MS and UV (220 nm)). Observed Mass: 715.2 (M+H). $^1$H NMR (400 MHz, METHANOL-$d_4$) δ 8.98-8.91 (m, 1H), 8.26-8.19 (m, 1H), 8.17-8.09 (m, 1H), 7.67-7.60 (m, 1H), 7.34-7.27 (m, 1H), 6.44-6.36 (m, 1H), 5.56-5.38 (m, 1H), 5.35-5.19 (m, 1H), 4.84-4.72 (m, 1H), 4.56-4.49 (m, 1H), 4.48-4.35 (m, 2H), 4.32-4.16 (m, 2H), 4.13-3.97 (m, 2H), 3.28-3.20 (m, 1H), 2.69-2.56 (m, 1H), 2.56-2.38 (m, 2H)

Example 1-2

5 mg. Retention Time: 0.41 min. (Column: ACQUITY UPLC® BEH C18 1.7 μm; Mobile Phase A: water with 0.05% TFA; Mobile Phase B: acetonitrile with 0.05% TFA; Gradient: 2% B to 98% B over 1 min, then 98% B to 2% B over 0.5 min; Flow: 0.8 mL/min; Detection: MS and UV (220 nm)). Observed Mass: 715.1 (M+H). $^1$H NMR (400 MHz, METHANOL-$d_4$) δ 8.94-8.90 (m, 1H), 8.20-8.16 (m, 1H), 8.06-8.01 (m, 1H), 7.56-7.51 (m, 1H), 7.16 (br d, J=1.5 Hz, 1H), 6.40-6.32 (m, 1H), 5.49-5.32 (m, 1H), 5.18-5.06 (m, 1H), 4.74-4.65 (m, 1H), 4.57-4.42 (m, 3H), 4.26-4.18 (m, 2H), 4.15-3.98 (m, 2H), 3.51-3.40 (m, 1H), 2.84-2.73 (m, 1H), 2.58-2.39 (m, 2H).

Example 1-3

10 mg. Retention Time: 0.42 min. (Column: ACQUITY UPLC® BEH C18 1.7 μm; Mobile Phase A: water with 0.05% TFA; Mobile Phase B: acetonitrile with 0.05% TFA; Gradient: 2% B to 98% B over 1 min, then 98% B to 2% B over 0.5 min; Flow: 0.8 mL/min; Detection: MS and UV (220 nm)). Observed Mass: 715.0 (M+H$^1$H NMR (400 MHz, METHANOL-$d_4$) δ 8.61-8.59 (m, 1H), 8.23-8.21 (m, 1H), 8.09-8.06 (m, 1H), 7.65-7.61 (m, 1H), 7.32-7.29 (m, 1H), 6.41-6.35 (m, 1H), 5.64-5.48 (m, 1H), 5.35-5.21 (m, 1H), 4.83-4.73 (m, 1H), 4.57-4.49 (m, 1H), 4.47-4.33 (m, 2H), 4.30-4.19 (m, 2H), 4.18-4.05 (m, 2H), 3.25-3.16 (m, 1H), 2.64-2.44 (m, 3H).

Example 1-4

10 mg. Retention Time: 0.46 min. (Column: ACQUITY UPLC® BEH C18 1.7 μm; Mobile Phase A: water with 0.05% TFA; Mobile Phase B: acetonitrile with 0.05% TFA; Gradient: 2% B to 98% B over 1 min, then 98% B to 2% B over 0.5 min; Flow: 0.8 mL/min; Detection: MS and UV (220 nm)). Observed Mass: 715.1 (M+H).). $^1$H NMR (400 MHz, METHANOL-$d_4$) δ 8.61-8.59 (m, 1H), 8.23-8.21 (m, 1H), 8.09-8.06 (m, 1H), 7.65-7.61 (m, 1H), 7.32-7.29 (m, 1H), 6.41-6.35 (m, 1H), 5.64-5.48 (m, 1H), 5.35-5.21 (m, 1H), 4.83-4.73 (m, 1H), 4.57-4.49 (m, 1H), 4.47-4.33 (m, 2H), 4.30-4.19 (m, 2H), 4.18-4.05 (m, 2H), 3.25-3.16 (m, 1H), 2.64-2.44 (m, 3H).

Example 2-1, 2-2, and 2-3

(1R,6S,8R,9R,15R,17R,18R)-8-(6-amino-9H-purin-9-yl)-18-hydroxy-17-{9-oxo-3H,4H,9H-imidazo[1,2-a]purin-3-yl}-3,12-disulfanyl-2,4,11,13,16-pentaoxa-3λ⁵,12λ⁵-diphosphatricyclo[13.2.1.0⁶,⁹]octadecane-3,12-dione

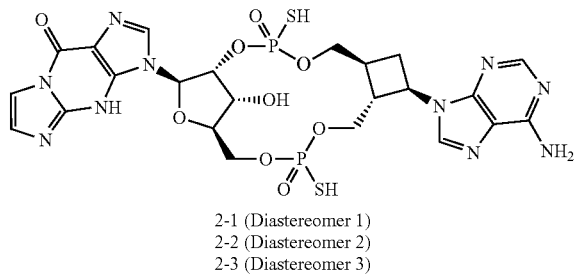 [SMILES: Nc1ncnc2c1ncn2[C@@H]1C[C@@H]2COP(=O)(S)O[C@@H]3[C@H](O)[C@@H](COP(=O)(S)OC[C@H]21)O[C@H]3n1cnc2c(=O)n3ccnc3[nH]c21]

2-1 (Diastereomer 1)
2-2 (Diastereomer 2)
2-3 (Diastereomer 3)

Preparation of Intermediate 2A:

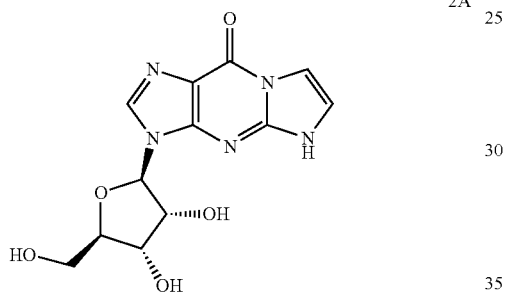

2A

To a solution containing (2R,3R,4S,5R)-2-(2-amino-6-chloro-9H-purin-9-yl)-5-(hydroxymethyl)tetrahydrofuran-3,4-diol (10 g, 33.1 mmol) in AcOH/NH₄OAc buffer (pH 4.5) (100 mL) and EtOH (100 mL) was added 2-bromoacetaldehyde (80 mL, 104 mmol). The reaction was heated for 48 h at 37° C. The filtrate was then neutralized to pH ~7 with solid ammonium bicarbonate and the resulting solid was collected by filtration and the solid was rinsed with acetonitrile. The filtrate was concentrated to ~½ volume on a rotary evaporator and then treated with acetonitrile (~100 mL) and a second crop of product was collected and rinsed with additional acetonitrile to give 2A (5 g, 16.27 mmol, 49.1% yield), m/z (308, M+H). ¹H NMR (400 MHz, DMSO-d₆) δ 8.15 (m, 1H), 7.63 (m, 1H), 7.42 (d, J=2.5 Hz, 1H), 5.83 (d, J=5.8 Hz, 1H), 5.42 (br d, J=5.8 Hz, 1H), 5.21-5.07 (m, 2H), 4.50 (q, J=5.3 Hz, 1H), 4.14 (br d, J=3.9 Hz, 1H), 3.92 (q, J=3.8 Hz, 1H), 3.73-3.62 (m, 1H), 3.60-3.49 (m, 1H).

Preparation of Intermediate 2B:

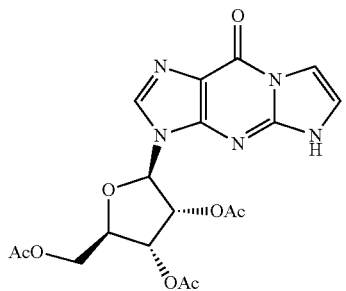

2B

A solution containing 2A (4.5 g, 14.65 mmol) was dissolved in pyridine (50 mL) and the slurry was azeotrophed on the rotary evaportor to dryness and then re-dissolved in pyridine (50 mL) and treated dropwise with acetic anhydride (13.82 mL, 146 mmol). The reaction was stirred for 20 h and then treated with MeOH (10 mL) and concentrated. The material was taken up in DCM (100 mL) and washed with 1.5 N K₂HPO₄ aq. solution (1×50 mL), dried (Na₂SO₄), filtered and concentrated. The crude product was dissolved in a small amount of DCM and charged to a 40 g ISCO silica gel column and purified using a Teledyne ISCO system, eluting over a 15 min gradient with 1%-10% DCM (0.1% TEA)/MeOH to give 2B (3.1 g, 7.15 mmol, 48.8% yield), m/z (434, M+H). ¹H NMR (400 MHz, DMSO-d₆) δ 12.58-12.53 (m, 1H), 8.15 (s, 1H), 7.65 (t, J=2.2 Hz, 1H), 7.47 (t, J=2.5 Hz, 1H), 6.14 (d, J=5.9 Hz, 1H), 5.92 (t, J=6.0 Hz, 1H), 5.54 (dd, J=5.9, 4.4 Hz, 1H), 4.46-4.26 (m, 3H), 2.16-2.11 (m, 3H), 2.04 (d, J=2.4 Hz, 6H)

Preparation of Intermediate 2C:

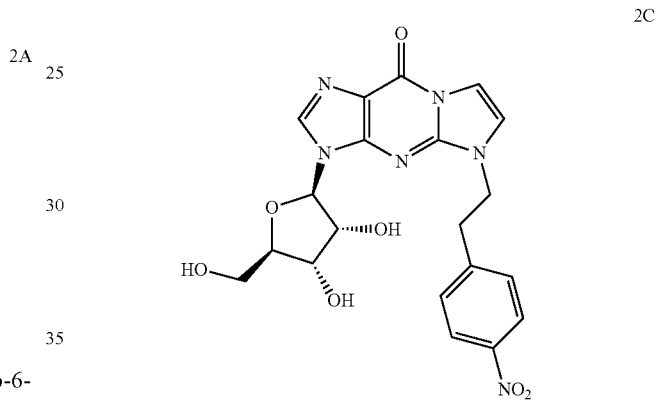

2C

To a solution containing 2B (2.5 g, 5.77 mmol), 2-(4-nitrophenyl)ethan-1-ol (1.543 g, 9.23 mmol) and triphenylphosphine (2.270 g, 8.65 mmol) in THF (50 mL) was added dropwise, DIAD (1.682 mL, 8.65 mmol). The reaction was stirred at room temperature for 20 h and then concentrated in vacuo. The crude product was dissolved in a small amount of DCM and charged to a 80 g ISCO silica gel column and purified using a Teledyne ISCO system, eluting over a 30 min gradient with 5%-100% DCM/EtOAc to give (2R,3R,4R,5R)-2-(acetoxymethyl)-5-(5-(4-nitrophenethyl)-9-oxo-5,9-dihydro-3H-imidazo[1,2-a]purin-3-yl)tetrahydrofuran-3,4-diyl diacetate, m/z (583, M+H). The crude (2R,3R,4R,5R)-2-(acetoxymethyl)-5-(5-(4-nitrophenethyl)-9-oxo-5,9-dihydro-3H-imidazo[1,2-a]purin-3-yl)tetrahydrofuran-3,4-diyl diacetate was re-dissolved in 7 N ammonia in MeOH (50 mL) and stirred for 20 h. The reaction was then concentrated to ~½ volume and treated with diethylether ~50 mL. The resulting solid was collected by filtration and rinsed with diethylether and dried to give 2C (2.5 g, 5.48 mmol, 95% yield), m/z (457, M+H). ¹H NMR (400 MHz, DMSO-d₆) δ 8.16-8.10 (m, 3H), 7.66-7.63 (m, 1H), 7.53-7.48 (m, 1H), 7.46-7.43 (m, 1H), 5.86-5.82 (m, 1H), 5.44-5.39 (m, 1H), 5.24-5.20 (m, 1H), 5.06-5.01 (m, 1H), 4.63-4.56 (m, 1H), 4.45-4.39 (m, 2H), 4.22-4.17 (m, 1H), 3.98-3.93 (m, 1H), 3.72-3.65 (m, 1H), 3.63-3.55 (m, 1H), 3.33-3.27 (m, 2H)

Preparation of Intermediate 2D:

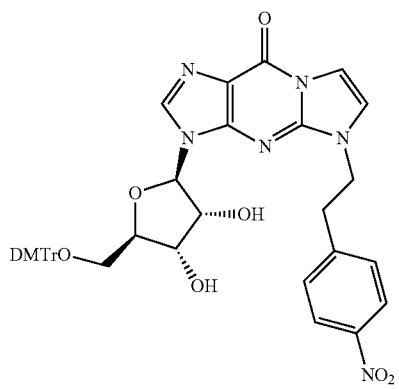

A solution containing 2C (2.5 g, 5.48 mmol) in pyridine (40 mL) was concentrated to a thick oil. The oil was azeotroped a second time with additional pyridine (40 mL). The resulting viscous oil was re-dissolved in pyridine (30 mL) under a nitrogen atmosphere and 4,4'-(chloro(phenyl)methylene)bis(methoxybenzene) (2.227 g, 6.57 mmol) was added in small portions. The reaction was stirred for 20 h, and then concentrated on the rotary evaporator. The resulting residue was diluted with DCM (100 mL) and washed with sat. aq. NaHCO$_3$ solution (25 mL) and sat. aq. NaCl solution, then dried (Na$_2$SO$_4$), filtered and concentrated. The crude product was dissolved in a small amount of DCM and charged to a 40 g ISCO silica gel column and purified using a Teledyne ISCO system, eluting over a 20 min gradient with 5%-100% EtOAc/DCM (DCM containing 0.25% TEA) to give 2D (1.95 g, 2.57 mmol, 46.9% yield), m/z (759, M+H). $^1$H NMR (400 MHz, DMSO-d$_6$) δ 8.13-8.06 (m, 3H), 7.68-7.62 (m, 1H), 7.45-7.39 (m, 3H), 7.35-7.29 (m, 2H), 7.21-7.12 (m, 7H), 6.72 (dd, J=16.5, 8.9 Hz, 4H), 5.92 (d, J=4.3 Hz, 1H), 5.55 (d, J=5.6 Hz, 1H), 5.23 (d, J=6.1 Hz, 1H), 4.68 (q, J=5.2 Hz, 1H), 4.40 (q, J=5.6 Hz, 1H), 4.33-4.14 (m, 2H), 4.10-4.04 (m, 1H), 3.69 (s, 3H), 3.68-3.66 (m, 3H), 3.32-3.26 (m, 1H), 3.22-3.13 (m, 3H).

Preparation of Intermediate 2E:

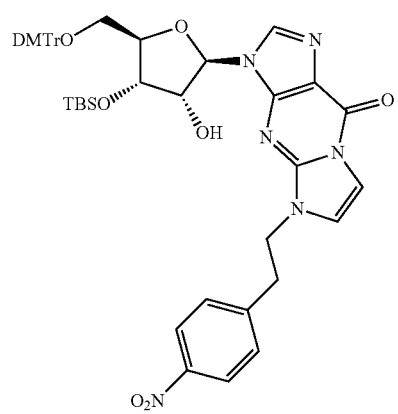

Intermediate 2D (3.75 g, 4.94 mmol) and imidazole (0.841 g, 12.36 mmol) were dissolved in DMF (25 mL) and TBS-Cl (0.782 g, 5.19 mmol) was added. The reaction was stirred under a nitrogen atmosphere for 18 h. The reaction mixture was then poured into a separatory funnel containing EtOAc/aq. 10% LiCl solution (200 mL/50 mL) and shaken. The aqueous layer was decanted and the organic layer was washed with additional aq. 10% LiCl solution (50 mL) and sat. aq. NaCl solution, then dried (Na$_2$SO$_4$), filtered and concentrated. The crude product was dissolved in a small amount of DCM and charged onto an ISCO 220 g silica gel column and purified using the Teledyne ISCO system, eluting over a 30 min gradient with 0%-50% EtOAc/DCM (0.25% TEA) to give slower eluting 2E (900 mg, 1.03 mmol, 21% yield). Retention Time: 1.18 min. (Column: ACQUITY UPLC® BEH C18 1.7 μm; Mobile Phase A: water with 0.05% TFA; Mobile Phase B: acetonitrile with 0.05% TFA; Gradient: 2% B to 98% B over 1 min, then a 0.5 min hold at 98% B; Flow: 0.8 mL/min; Detection: MS and UV (220 nm)). Observed mass 873.5 (M+H). $^1$H NMR (400 MHz, CHLOROFORM-d) δ 8.24-8.09 (m, 2H), 8.00-7.86 (m, 1H), 7.74-7.56 (m, 1H), 7.44 (d, J=7.0 Hz, 2H), 7.36-7.34 (m, 2H), 7.34-7.31 (m, 3H), 7.31-7.29 (m, 1H), 7.27-7.22 (m, 3H), 6.93-6.77 (m, 4H), 6.73-6.64 (m, 1H), 6.09-5.95 (m, 1H), 4.53-4.48 (m, 1H), 4.47-4.42 (m, 1H), 4.38-4.29 (m, 2H), 4.24-4.16 (m, 1H), 3.80 (d, J=0.8 Hz, 6H), 3.56-3.46 (m, 1H), 3.37-3.29 (m, 1H), 3.27-3.19 (m, 2H), 3.18-3.11 (m, 1H), 0.92 (s, 9H), 0.02 (s, 6H).

Preparation of Intermediate 2F:

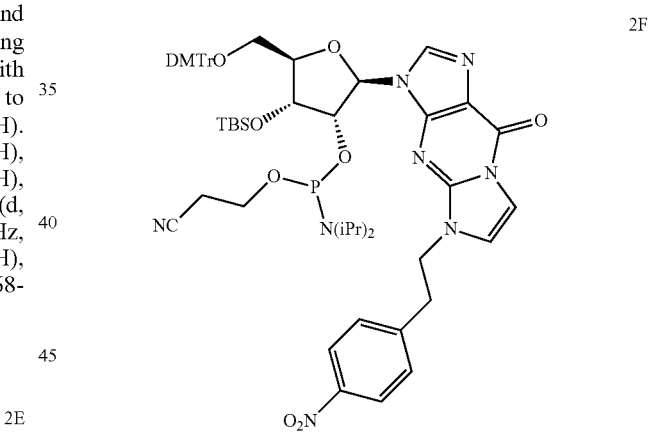

To a solution containing 2E (900 mg, 1.031 mmol) in DCM (10 mL) was added 1H-imidazole-4,5-dicarbonitrile (146 mg, 1.237 mmol) followed by the addition of 3-((bis(diisopropylamino)phosphanyl)oxy)propanenitrile (0.680 mL, 2.062 mmol). The mixture was stirred for 20 h and then diluted with additional DCM (50 mL) and quenched with aqueous 10% NaHCO$_3$ solution (25 mL). The organic layer was isolated, dried (Na$_2$SO$_4$), filtered and concentrated. The crude product was dissolved in a small amount of DCM and charged onto a 12 g ISCO silica gel column and purified using the Teledyne ISCO system, eluting over a 15 min gradient with 0%-100% EtOAc/DCM (0.25% TEA) to give 2F (1.1 g, 1.025 mmol, 99% yield). Retention Time: 1.15 min, (Column: ACQUITY UPLC® BEH C18 1.7 μm; Mobile Phase A: water with 0.05% TFA; Mobile Phase B: acetonitrile with 0.05% TFA; Gradient: 2% B to 98% B over 1 min, then a 0.5 min hold at 98% B; Flow: 0.8 mL/min; Detection: MS and UV (220 nm)).

Preparation of Intermediate 2G:

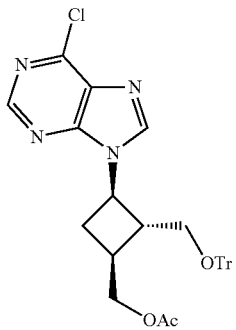

2G

To a 0° C. solution of Ph₃P (1.071 g, 4.08 mmol) in THF (20 mL)/toluene (4 mL) was added DIAD (0.700 ml, 3.60 mmol). The reaction was stirred at 0° C. for 30 min. To the reaction was added 6-chloro-9H-purine (0.557 g, 3.60 mmol) and 1G (1.0 g, 2.4 mmol). The reaction was stirred at 50° C. for 16 h and then concentrated in vacuo. The crude material was purified by flash chromatography over 40 g of silica gel (15 min gradient, with 0-100% ethyl acetate in hexanes) to give 2G (1.0 g, 1.8 mmol, 75% yield) as a white foam. [M+H]+=553.2.

Preparation of Intermediate 2H:

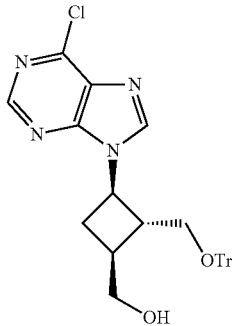

2H

To a 0° C. solution of 2G (1.74 g, 3.15 mmol) in THF (16 mL) was added methylmagnesium chloride (3 M in THF) (2.1 mL, 6.3 mmol). The mixture was warmed to room temperature and the reaction was stirred for 2 h. The reaction was then quenched with saturated aqueous ammonium chloride and stirred at room temperature for 10 min. The mixture was then partitioned between EtOAc and water, the organic layer separated, and the aqueous phase extracted with EtOAc. The combined organic layers were dried (sodium sulfate) and concentrated in vacuo. The crude material was purified by flash chromatography over 80 g of silica gel (15 minute gradient, with 0-100% EtOAcDCM) to afford 2H (1.16 g, 2.27 mmol, 72% yield) as a white solid. LCMS, [M+H]+=511.3.

Preparation of Intermediate 2I:

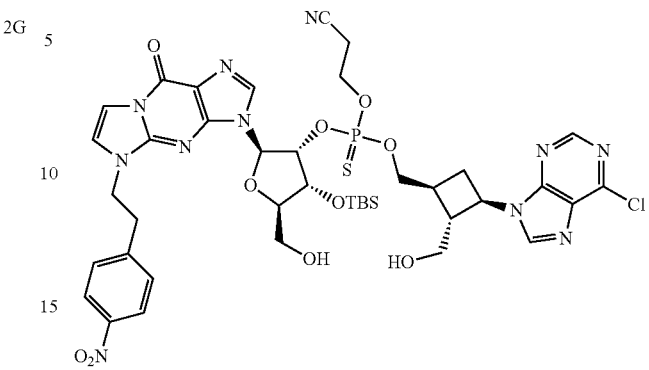

2I

A solution containing 1H-tetrazole (212 mg, 3.03 mmol) and 2H (310 mg, 0.607 mmol) in MeCN (3 mL) was azeotroped on the rotary evaporator (2×3 mL) and then re-suspended in MeCN (3 mL) and activated MS 4 Å (150 mg) was added and the mixture was left under a nitrogen atmosphere. In a separate vial was suspended 2F (846 mg, 0.789 mmol) in dry acetonitrile (4 mL) and this was azeotroped on the rotoary evaporator (3×1 mL) and then resuspended in acetonitrile (4 mL). This mixture was added to the above stirring solution of alcohol-tetrazole via syringe. The reaction was allowed to stir at room temperature overnight. The reaction mixture was then treated with (E)-N,N-dimethyl-N'-(3-thioxo-3H-1,2,4-dithiazol-5-yl)formimidamide (249 mg, 1.213 mmol) and stirred at room temperature overnight. The reaction mixture was then concentrated, dissolved in EtOAc, washed with sat. NaHCO₃, and then brine. The organic layer phase was dried with Na₂SO₄ and then concentrated and dried under vacuum. The crude material was then suspended in DCM (30 mL) and 2,2-dichloroacetic acid (2.444 mL, 4.25 mmol) followed by triethylsilane (0.678 mL, 4.25 mmol) were added. The reaction mixture was stirred at room temperature for 1 h. The reaction was then diluted with DCM and neutralized with aq. NaHCO₃. The organic phase was washed with brine, dried with Na₂SO₄ and concentrated in vacuo. The crude mixture was purified on C18, 120 g reverse phase ISCO gold column and eluted with solvent A: 95% water, 5% acetonitrile, 0.01 M ammonium acetate; Solvent B: 95% acetonitrile, 5% water, 0.01 M ammonium acetate hold at 20% B for 5 min, then 20-100% B over 20 min, product peak eluted at 70-80% gradient to afford 2I (340 mg, 0.350 mmol, 57.8% yield). m/z (970.3, M+H).

Preparation of Intermediate 2J:

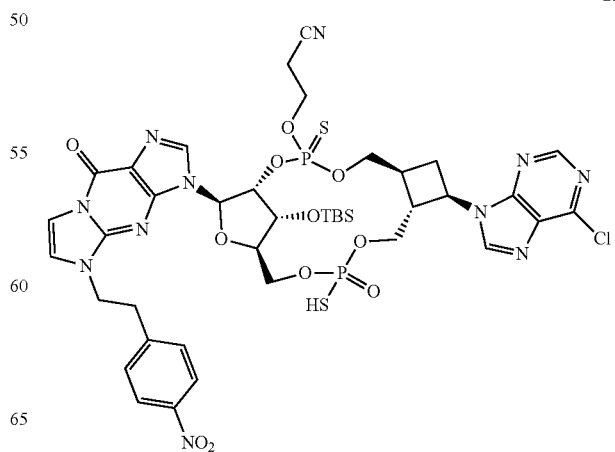

2J

Intermediate 2I (0.34 g, 0.350 mmol) was dissolved in dry pyridine (5 mL). The solution was azeotroped on the rotary evaporator. This azeotrope with pyridine was repeated (2×3 mL). The residue was then re-dissolved in dry pyridine (70.1 mL) under a nitrogen atmosphere and treated dropwise over 30 min with a solution of diphenyl phosphite (0.136 mL, 0.701 mmol) in 1 mL of pyridine. After 20 min, (E)-N,N-dimethyl-N'-(3-thioxo-3H-1,2,4-dithiazol-5-yl)formimid-amide (0.288 g, 1.401 mmol) was added and the reaction was stirred at room temperature overnight. The reaction mixture was then concentrated to dryness. The residue was suspended in EtOAc and washed with aq. NaHCO$_3$. The organic phase was collected and washed with brine, and then dried with Na$_2$SO$_4$, filtered and concentrated to dryness. The crude material was then azeotroped a few times with MeCN, suspended in MeCN and filtered. The filtrate was concentrated, suspended in MeOH and filtered again. The filtrate was then purified on a C18, 150 g reverse phase ISCO gold column and eluted with solvent A: 95% water, 5% acetonitrile, 0.01 M ammonium acetate; Solvent B: 95% acetonitrile, 5% water, 0.01 M ammonium acetate, hold at 10% B for 3 min, then 10-65% B over 15 min, then hold at 65% B for 2 min and 65%-100% B over 12 min, three overlapping product peaks eluted at 55-65% gradient to afford 2J (28%, 104 mg). m/z (1048.3, M+H).

Preparation of Intermediate 2K:

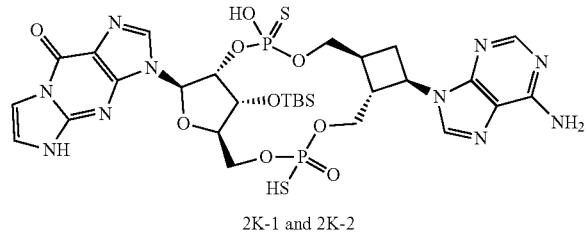 [SMILES: CC(C)(C)[Si](C)(C)O[C@H]1[C@H]2OP(O)(=S)OC[C@H]3C[C@@H](n4cnc5c(N)ncnc54)[C@@H]3COP(=O)(S)OC[C@H]1O[C@H]2n1cnc2c(=O)n3cc[nH]c3nc21]

2K-1 and 2K-2

To a vial containing 2J (83 mg, 0.079 mmol) was added 30% ammonium hydroxide (5 mL, 34.7 mmol) and the reaction mixture was stirred at 30° C. overnight. The reaction mixture was concentrated under a nitrogen stream and then azeotroped with toluene (3×3 mL) to remove water. The residue was then azeotroped with acetonitrile (3×3 mL), and then azeotroped with pyridine (3×3 mL). The crude product was treated with a mixture of pyridine (1.583 mL), DBU (0.119 mL, 0.792 mmol) and nitromethane (0.064 mL, 1.187 mmol) and heated at 30° C. overnight. An additional 200 uL of dry pyridine, DBU (0.060 mL, 0.396 mmol) and nitromethane (0.021 mL, 0.396 mmol) were added to the reaction mixture and it was stirred at 30° C. for an additional 4 h. The reaction mixture was diluted with MeCN and treated with acetic acid (0.091 mL, 1.583 mmol) and then concentrated. The crude material was purified on C18, ISCO 50 g reverse phase gold column and eluted with solvent A: 95% water, 5% acetonitrile, 0.01 M ammonium acetate; Solvent B: 95% acetonitrile, 5% water, 0.01 M ammonium acetate, 0-40% B over 15 min, then 40-100% B over 5 min to afford 2K-1 as a single diastereomer and 2K-2 as a mixture of two diastereomers.

2K-1:
(26 mg). LCMS: m/z 827.2 (M+H), retention time: 0.71 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm):

2K-2:
(14 mg). LCMS: m/z 827.2 (M+H), retention time: 0.65 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Example 2-1, 2-2, and 2-3

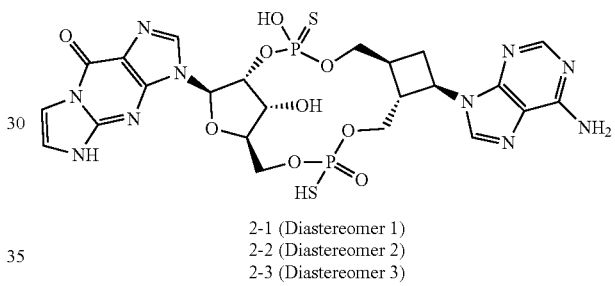

2-1 (Diastereomer 1)
2-2 (Diastereomer 2)
2-3 (Diastereomer 3)

To a solution of 2K-1 (25 mg, 0.030 mmol) in pyridine (1 mL) was added triethyl amine trihydrofluoride (0.074 mL, 0.454 mmol) and the reaction mixture was stirred at 37° C. overnight. The reaction mixture was then evaporated under a gentle stream of nitrogen and then azeotroped with MeCN. The crude material was purified on an ISCO 15.5 g reverse phase gold column and eluted with solvent A: 95% water, 5% acetonitrile, 0.01 M ammonium acetate; Solvent B: 95% acetonitrile, 5% water, 0.01 M ammonium acetate: Hold at 0% B for 1.5 min, 0-20% B over 6 min, hold at 20% B for 1.5 min and then 20-100% B over 7 min. to afford Example 2-1 (9.5 mg) as a single diastereomer: LCMS: m/z 713.0 (M+H), retention time: 0.42 min (Waters Acquity UPLC BEH C18 (2.1×50 mm), 1.7 micron; Solvent A=100% water with 0.05% TFA; Solvent B=100% acetonitrile with 0.05% TFA; Gradient=$^2$-98% B over 1 minute, then a 0.5-minute hold at 98% B; Flow rate: 0.8 mL/min; Detection: UV at 220 nm).

Intermediate 2K-2 was treated in a manner similar to 2K-1 to give a mixture of two diastereomer, Example 2-2 and Example 2-3. LCMS: m/z 713.0 (M+H), retention time: 0.41 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Alternatively, Example 2-1 may be prepared as described below.

Preparation of Intermediate 2L:

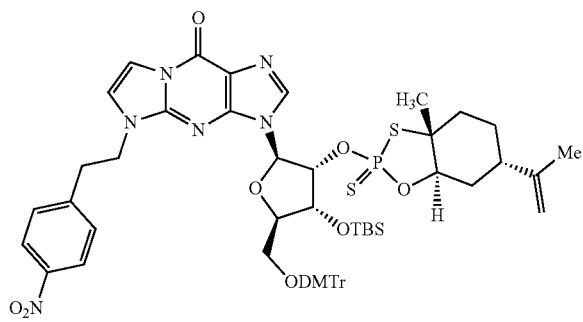

To a solution of Intermediate 2E (1.01 g, 1.16 mmol) and Reagent 4 (1.03 g, 2.31 mmol) in acetonitrile (15 mL) was added DBU (0.35 mL, 2.31 mmol). After 20 minutes, the reaction mixture was neutralized with acetic acid (0.21 g, 3.47 mmol), and then concentrated and the residue was purified by silica gel flash column chromatography (40 g, eluting with 0-100% EtOAc/DCM to give Intermediate 2L (1.20 g, 1.07 mmol, 93% yield). LCMS: m/z 1119.8 (M+H); Retention time: 1.32 min (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm)).

Preparation of Intermediate 2M:

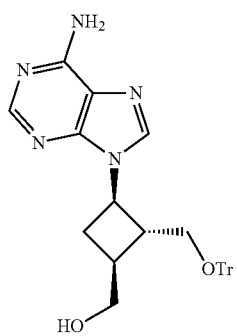

To a steel bomb was added Intermediate 2E (1.94 g, 3.51 mmol) and dioxane (10 mL). To the resulting colorless solution was added 30% aqueous ammonium hydroxide (20 mL, 154 mmol). The resulting cloudy reaction mixture was heated at 70° C. for 2 d.

The reaction mixture was then concentrated to dryness. The crude product was adsorbed onto Celite and was purified by silica gel chromatography using an 80 g column and eluting with 0-20% MeOH in DCM to afford Intermediate 2M (1.59 g, 3.23 mmol) as a white solid. LCMS: m/z 492.5 (M+H), $t_R$: 0.82 min. (Column: ACQUITY UPLC® BEH C18, 2.1×50 mm, 1.7 μm; Mobile Phase A: $H_2O$:ACN (95:5) with 10 mM $NH_4OAc$; Mobile Phase B: $H_2O$:ACN (5:95) with 10 mM $NH_4OAc$; Gradient: 5% B to 95% B in 1 min, then a 0.5 min hold at 95% B; Flow: 0.8 mL/min; Detection: MS and UV (220 nm)). $^1H$ NMR (499 MHz, CHLOROFORM-d) δ 8.32 (s, 1H), 7.72 (s, 1H), 7.42-7.33 (m, 6H), 7.31-7.18 (m, 9H), 5.61 (br s, 2H), 4.61 (q, J=8.6 Hz, 1H), 3.81-3.66 (m, 2H), 3.39 (dd, J=9.9, 5.5 Hz, 1H), 3.30 (dd, J=10.0, 6.5 Hz, 1H), 3.23 (br s, 1H), 3.08-2.98 (m, 1H), 2.63-2.48 (m, 2H), 2.36-2.25 (m, 1H).

Preparation of Intermediate 2N:

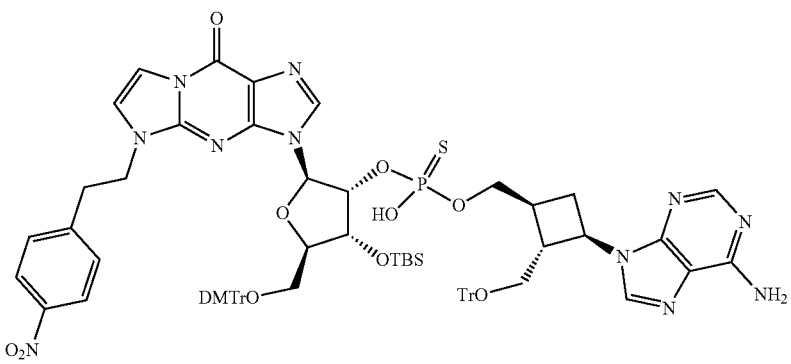

Intermediate 2M (0.791 g, 1.608 mmol) was azeotroped with ACN (5 mL). Then Intermediate 2L (1.2 g, 1.072 mmol) was added and the mixture was azeotroped again with ACN (5 mL). The resulting residue was dissolved in THF (20 mL) and DBU (0.65 mL, 4.3 mmol) was added. After stirring at room temperature for 20 min, acetic acid (0.248 mL, 4.29 mmol) was added, and then the mixture was concentrated. The residue was purified by silica gel chromatography (80 g, eluting with 0-10% MeOH/DCM in 35 min) to give Intermediate 2N (0.71 g, 0.49 mmol, 46% yield). LCMS: m/z 1442.5 (M+H); Retention time: 1.19 min (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm).

Preparation of Intermediate 2O:

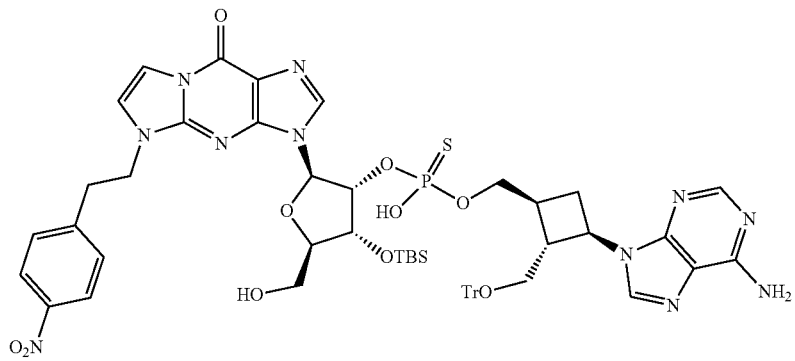

2O

To a solution of Intermediate 2N (710 mg, 0.49 mmol) in DCM (5 mL) was added triethylsilane (0.39 mL, 2.46 mmol) and 2,2-dichloroacetic acid (0.12 mL, 1.48 mmol). The reaction mixture was stirred at room temperature for 1 h. Pyridine (311 mg, 3.94 mmol) was then added and the reaction mixture was concentrated. The residue was purified by silica gel chromatography (40 g, eluting with 0-29% MeOH/DCM) to give Intermediate 2O (408 mg, 0.36 mmol, 73% yield). LCMS: m/z 1140.6 (M+H); Retention time: 1.03 min (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm).

Preparation of Intermediate 2P

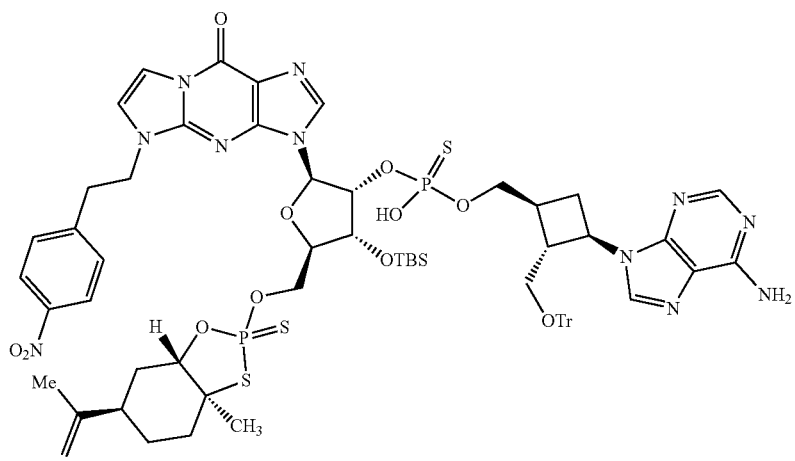

2P

Intermediate 2O (408 mg, 0.36 mmol) was azeotroped with ACN (5 mL). Then Reagent 3 (320 mg, 0.72 mmol) was added, followed by dry THF (10 mL) and DBU (0.22 mL, 1.43 mmol). The reaction was stirred at room temperature for seven minutes. The reaction was then treated with acetic acid (130 mg, 2.15 mmol), and was then concentrated. The residue was purified on an ISCO silica gel gold column (24 g, eluting with 0-20% MeOH/DCM) to give Intermediate 2O (0.5 g, 0.24 mmol, 66% yield). LCMS: m/z 1386.4 (M+H); Retention time: 1.18 min (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm).

Preparation of Intermediate 2Q:

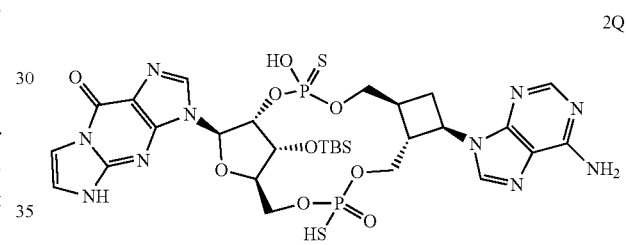

2Q

To a solution of Intermediate 2P (500 mg, 0.24 mmol) in DCM (5 mL) was added triethylsilane (0.45 mL, 2.8 mmol) and 2,2-dichloroacetic acid (0.20 mL, 2.36 mmol). After 30 minutes, the reaction mixture was added dropwise to a flask containing DBU (1.07 mL, 7.1 mmol) and THF (5 mL). The resulting mixture was stirred for an additional 10 min, and then concentrated. The residue was re-dissolved in ACN (1 mL) and stirred at room temperature overnight. The mixture was then stirred at 40° C. for 4 h. The reaction mixture was then concentrated and the residue was triturated with diethyl ether (10 mL×5). The resulting solid was dissolved in MeOH (10 mL), mixed with 5 g of celite, and then concentrated to dryness. The solid was purified on a C18, 100 g reverse phase ISCO gold column (eluting with solvent A: 95% water, 5% acetonitrile, 0.01 M ammonium acetate; Solvent B: 95% acetonitrile, 5% water, 0.01 M ammonium acetate; hold at 100% A for 10 min, then 0-35% B over 15 min, then hold at 35% B for 2 min and 35%-100% B over 12 min) to give Intermediate 2Q (132 mg, 67.7%). LCMS: m/z 827.1 (M+H); Retention time: 0.57 min. (Column: ACQUITY UPLC® BEH C18, 2.1×50 mm, 1.7 µm; Mobile Phase A: H$_2$O:ACN (95:5) with 10 mM NH$_4$OAc; Mobile Phase B: H$_2$O:ACN (5:95) with 10 mM NH$_4$OAc; Gradient: 5% B to 95% B in 1 min, then a 0.5 min hold at 95% B; Flow: 0.8 mL/min; Detection: MS and UV (220 nm))

Example 2-1

2-1

Intermediate 2Q (132 mg, 0.078 mmol) was dissolved in triethylamine trihydrofluoride (3 mL, 18.4 mmol) and stirred at 37° C. for 3 h. Then the mixture was cooled to room temperature, and triethylamine (5.1 mL, 36.6 mmol) was added and the mixture was stirred at room temperature for 10 min. Then isopropoxytrimethylsilane (8.0 g, 60.5 mmol) was added at room temperature. After stirring for 1 h, the reaction mixture was concentrated and the solid residue was purified via preparative LC/MS (Preparative LC/MS conditions: Column: Xselect RP Prep C18 OBD Column 5 µm, 10×250 mm; Mobile Phase A: water with 100 mM NH$_4$OAc; Mobile Phase B: MeOH; Gradient: 5% B-21.5% B 0-14 minutes, 21.5% B-95% B over 0.5 min, then a 0.5-minute hold at 95% B; Flow: 20 mL/min. Analytical LCMS conditions: Agilent 1290 HPLC/MS, column: Xselect CSH C18 Column 3.5 µm, 2.1×150 mm; Mobile Phase A: water with 20 mM NH$_4$OAc; Mobile Phase B: MeOH; Temperature: 50° C.; Gradient: 5% B-45% B over 15 min, 45% B-95% B over 2 min; Flow: 0.35 mL/min; Detection: MS and UV (260 nm)) to give Example 2-1 (34 mg). LCMS: m/z 713.2 (M+H), retention time: 6.42 min. $^1$H NMR (700 MHz, METHANOL-d$_4$) δ 8.39 (s, 1H), 8.20 (s, 1H), 8.15 (s, 1H), 7.59 (d, J=2.7 Hz, 1H), 7.17 (d, J=2.5 Hz, 1H), 6.13 (d, J=8.1 Hz, 1H), 5.56 (br d, J=3.9 Hz, 1H), 4.80-4.76 (m, 2H), 4.38-4.32 (m, 1H), 4.32-4.29 (m, 1H), 4.28-4.22 (m, 1H), 4.20 (dt, J=11.0, 5.7 Hz, 2H), 4.14-4.08 (m, 1H), 3.94-3.87 (m, 1H), 3.26-3.18 (m, 1H), 2.57-2.51 (m, 1H), 2.46 (br d, J=8.5 Hz, 1H), 2.37 (q, J=9.8 Hz, 1H).

Examples 3-1, 3-2, 3-3 and 3-4

(1R,6S,8R,9R,15R,17R,18R)-17-(6-amino-9H-purin-9-yl)-18-fluoro-8-{3H-imidazo[2,1-f]purin-3-yl}-3,12-disulfanyl-2,4,11,13,16-pentaoxa-3λ$^5$,12λ$^5$-diphosphatricyclo[13.3.0.0$^{6,9}$]octadecane-3,12dione

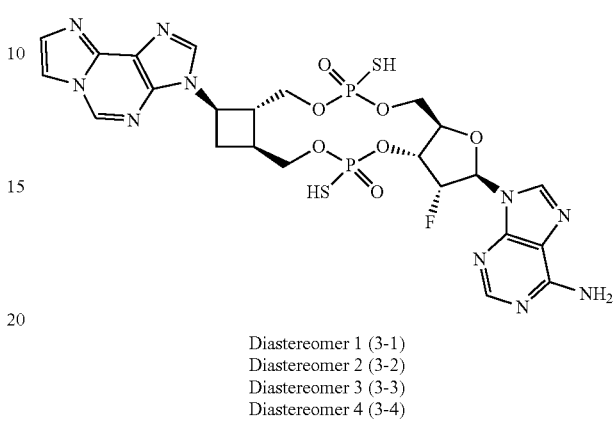

Diastereomer 1 (3-1)
Diastereomer 2 (3-2)
Diastereomer 3 (3-3)
Diastereomer 4 (3-4)

Preparation of Intermediate 3A:

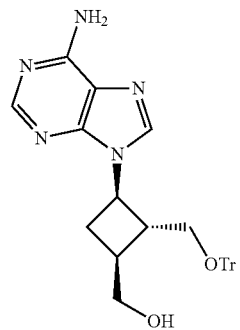

3A

A mixture of 2H (0.35 g, 0.685 mmol) and ammonium hydroxide (6.7 mL, 171 mmol) in dioxane (2 mL) was stirred at 50° C. for 16 h. The solvent was removed in vacuo. The resulting material was partitioned between DCM and water, and the organic layer was separated. The aqueous phase was extracted 2×10 mL with DCM, 2×10 mL with 2-Me-THF, and the combined organic layers were dried (MgSO$_4$) and concentrated in vacuo to 3A (0.337 g, 0.686 mmol, 100% yield) as a solid. [M+H]+=492.3

Preparation of Intermediate 3B:

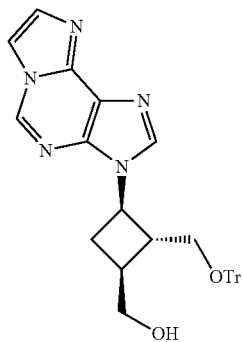

3B

A mixture of 3A (0.326 g, 0.663 mmol) and 2-bromoacetaldehyde (4.9 mL, 6.6 mmol) in pH 4.5 AcOH/NaOAc buffer (4 mL) was stirred at 80° C. for 2 h followed by room temperature for 16 h. The reaction was then stirred at 80° C. for 2 h and then the organic solvent was removed in vacuo. Solid ammonium carbonate was slowly added until the evolution of gas ceased. The aqueous layer was extracted 2×15 mL with EtOAc, and the combined organic layers were dried (sodium sulfate) and concentrated in vacuo. The crude material was purified by flash chromatography over 24 g of silica gel (15 min gradient, with 0-20% MeOH in DCM) to afford 3B (0.236 g, 0.46 mmol, 69% yield) as a white foam. LCMS, [M+H]+=516.4>

Preparation of Intermediate 3C and 3D:

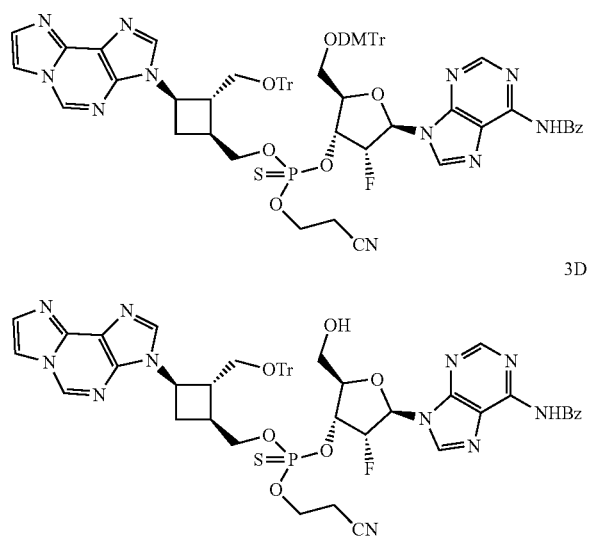

A mixture of 3B (0.236 g, 0.458 mmol) and 1H-tetrazole (0.038 g, 0.549 mmol) was azeotroped with 3 mL of dry ACN. The residue was then dissolved in 3 mL of dry ACN. A separate mixture of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Sigma-Aldrich, 0.601 g, 0.687 mmol) was azeotroped with 3 mL of dry ACN. This material was then dissolved in 1.5 mL of ACN and added dropwise to the stirred mixture of 3B from above at room temperature. The reaction was stirred at room temperature for 16 h. To the reaction was added (E)-N,N-dimethyl-N'-(3-thioxo-3H-1,2,4-dithiazol-5-yl)formimidamide (0.141 g, 0.687 mmol) and the reaction was stirred at room temperature for 2 h. The mixture was then partitioned between DCM and water, and the organic layer was separated. The aqueous phase was extracted with DCM, and the combined organic layers were dried (sodium sulfate) and concentrated in vacuo. The crude material was purified by flash chromatography over 40 g of silica gel (15 min gradient, with 0-20% MeOH in DCM) to afford 3C (0.245 g, 0.185 mmol, 40.5% yield) as an oil LCMS: [M+H]+=1322.6 and 3D (0.150 g, 0.147 mmol, 32.1% yield) as a solid.

Preparation of Intermediate 3E:

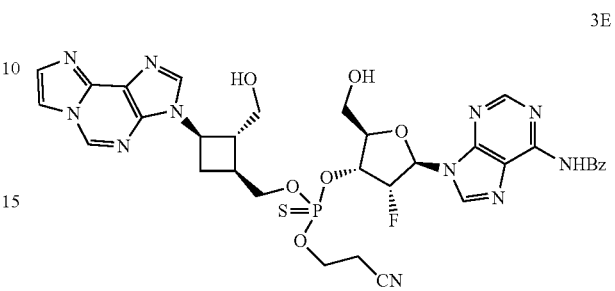

To a solution of 3C (0.245 g, 0.185 mmol) 3D (0.150 g, 0.147 mmol) and triethylsilane (0.296 ml, 1.853 mmol) in dichloromethane (2 mL) was added TFA (0.043 mL, 0.56 mmol) at room temperature. The reaction mixture was stirred at room temperature for 3 h. The reaction was quenched with 50% aqueous sodium bicarbonate. The organic layer was separated and the aqueous layer was extracted with 10 mL DCM, followed by 2×10 mL 2-MeTHF. The combined organic layers were dried (sodium sulfate) and concentrated in vacuo. The material was triturated with diethyl ether and the solid collected by vacuum filtration to give 3E (0.245 g, 0.315 mmol, 95% yield) as an off-white solid. LCMS, [M+H]+=778.3.

Preparation of Intermediate 3F:

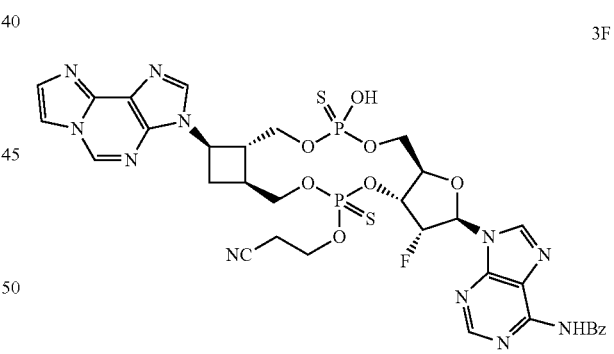

To a 0° C. solution of 3E (0.243 g, 0.312 mmol) in pyridine (11 mL) was added a solution of diphenyl phosphonate (0.121 mL, 0.625 mmol) in pyridine (1 mL) dropwise over a period of 1 h. The reaction was stirred at room temperature for 16 h. (E)-N,N-dimethyl-N'-(3-thioxo-3H-1,2,4-dithiazol-5-yl)formimidamide (0.160 g, 0.781 mmol) was then added and the reaction was stirred at room temperature for 3 h, then concentrated in vacuo. The crude material was purified by reverse phase ISCO over 50 g of C18 with 0-100%, 15 min gradient, (ACN/water/ammonium acetate 95/5/0.5) in (water/ACN/ammonium acetate 95/5/

0.5) to give mixture of four diasteromers of 3F (0.267 g, 0.312 mmol, 100% yield) as a solid. LCMS, [M+H]+=856.8.

Examples 3-1, 3-2, 3-3 and 3-4

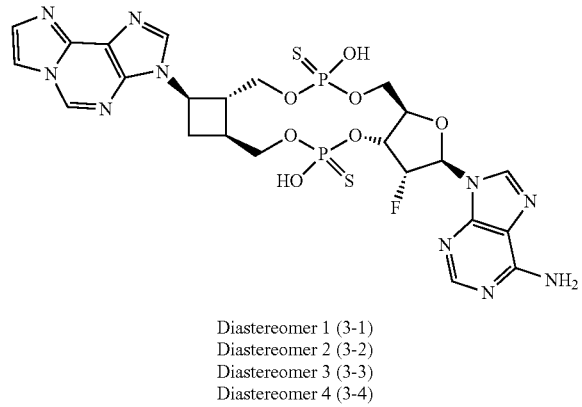

Diastereomer 1 (3-1)
Diastereomer 2 (3-2)
Diastereomer 3 (3-3)
Diastereomer 4 (3-4)

A mixture of 3F (four diastereomers) (0.267 g, 0.312 mmol) and ammonia (7 N in MeOH) (6.69 mL, 46.8 mmol) was stirred at room temperature for 1 h. The reaction was then heated to 50° C. for 3 h. The solvent was removed in vacuo and the resulting residue was purified by reverse phase ISCO chromatography over 50 g of C18 with a 0-100%, 15 min gradient, (ACN/water/ammonium acetate 95/5/0.5) in (water/ACN/ammonium acetate 95/5/0.5) to give a mixture of four diastereomers. The crude material was then purified via preparative LC/MS with the following conditions: Column: Agilent Bonus RP 21.2×100 mm, 5-μm particles; Mobile Phase A: water with 20 mM ammonium acetate; Mobile Phase B: acetonitrile; Gradient: 0% B hold 0-6 minute. 0%-25% B over 16 minutes, then a 4-minute hold at 100% B; Flow: 20 mL/min. to afford two individual diastereomers (3-1 and 3-2) and a mixture of two diastereomers (3-3 and 3-4).

Example 3-1

2.4 mg. Retention Time: 2.34 min. (Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm). LCMS, [M+H]+=698.9.

Example 3-2

2 mg. Retention time 2.47 min. (Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm). LCMS, [M+H]+=698.9.

Examples 4-1 and 4-2

(1R,6S,8R,9R,15R,17R,18R)-8-(6-amino-9H-purin-9-yl)-3,18-dihydroxy-17-{9-oxo-3H,4H,9H-imidazo[1,2-a]purin-3-yl}-12-sulfanyl-2,4,11,13,16-pentaoxa-3λ$^5$,12λ$^5$-diphosphatricyclo[13.2.1.0$^{6,9}$]octadecane-3,12-dione

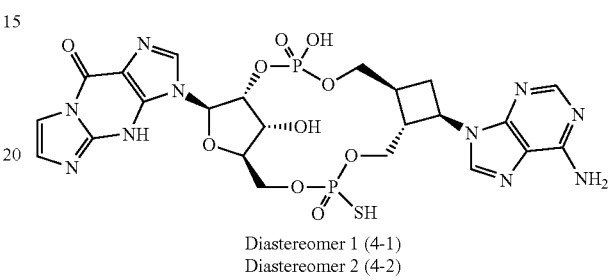

Diastereomer 1 (4-1)
Diastereomer 2 (4-2)

Preparation of Intermediate 4A:

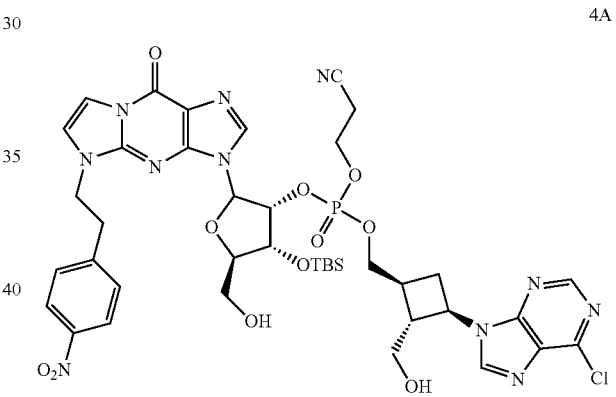

4A

A solution containing 1H-tetrazole (104 mg, 1.491 mmol) and 2H (152 mg, 0.298 mmol) in MeCN (3 mL) was azeotroped on the rotary evaporator (2×3 mL) and then re-suspended in MeCN (3 mL) and activated MS 4 Å (150 mg) were added and the reaction mixture was left under a nitrogen atmosphere. In a separate vial was taken 2F (320 mg, 0.298 mmol) and dry acetonitrile (4 mL) was added and this was azeotroped on the rotoary evaporator (3×1 mL) and then resuspended in acetonitrile (4 mL). This mixture was then added to the above stirring solution of alcohol-tetrazole via syringe. The reaction was allowed to stir at room temperature overnight. To the reaction mixture was added tert-butyl hydroperoxide (0.072 mL, 0.745 mmol) dropwise and it was stirred for an additional 30 min. The reaction mixture was then concentrated to dryness and then diluted with EtOAc. The resulting suspension was washed with sat. NaHCO$_3$, then brine and the organic phase was dried with Na$_2$SO$_4$, filtered and concentrated to dryness. The resulting crude material was suspended in DCM (30 mL) and dichloroacetic acid (1.201 mL, 2.087 mmol) followed by triethylsilane (0.476 mL, 2.98 mmol) were added. The resulting mixture was stirred at room temperature for 1 h. The reaction was then diluted with DCM and neutralized with aq. NaHCO₃. The organic phase was separated and washed with brine, dried over Na₂SO₄ and concentrated in vacuo. The crude material was purified on a C18, 50 g reverse phase ISCO gold column employing manufacturer recommended flow rates with the following conditions: Solvent A: 95% water, 5% acetonitrile, 0.01 M ammonium acetate; Solvent B: 95% acetonitrile, 5% water, 0.01 M ammonium acetate; Gradient: Gradient: Hold at 20% B for 2 min, 20-60% B over 6 min, hold at 60% B for 3 min, 60-100% B over 2 min and hold at 100% B for 3 min to give 4A (115 mg, 0.120 mmol, 40.4% yield): LCMS: m/z 954.2 (M+H), retention time: 0.93 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Preparation of Intermediate 4B:

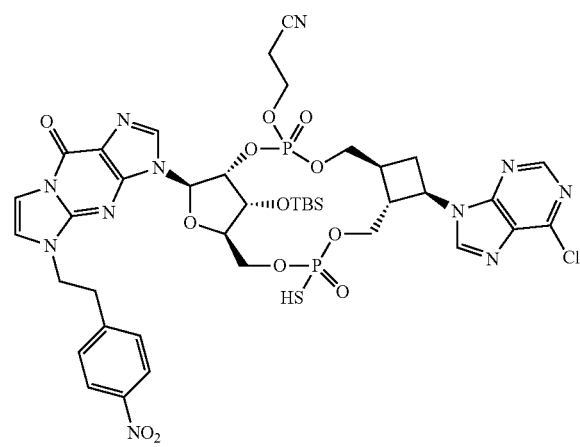

4B

A solution of 4A (0.088 g, 0.092 mmol) in dry pyridine (18.44 ml) was azeotroped on the rotary evaporator. The azeotrope with pyridine was repeated (2×3 mL). The residue was re-dissolved in dry pyridine (18.44 mL) under a nitrogen atmosphere and treated dropwise over 30 min with a solution of diphenyl phosphite (0.036 ml, 0.184 mmol) in 1 mL of pyridine. After 20 min (E)-N,N-dimethyl-N'-(3-thioxo-3H-1,2,4-dithiazol-5-yl)formimidamide (0.057 g, 0.277 mmol) was added and the reaction was stirred at room temperature overnight. The reaction mixture was then concentrated to dryness. The resulting residue was suspended in EtOAc and washed with aq. NaHCO₃. The organic phase was washed with brine and then dried over Na₂SO₄ and then concentrated. The crude material was azeotroped a few times with MeCN, suspended in MeCN and filtered. The filtrate was concentrated and then suspended in MeOH and filtered again. The filtrate was concentrated and the crude product was purified on a C18, 50 g reverse phase ISCO Gold column using Solvent A (95% water, 5% acetonitrile, 0.01 M ammonium acetate)/Solvent B (95% acetonitrile, 5% water, 0.01 M ammonium acetate) with the following gradient: hold at 10% B for 2 min, 10-40% B over 8 min, at 40% B for 6 min, 40-100% B over 3 min and hold at 100% B for 3 min, to afford 4B as a mixture of diastereomers: m/z 1032.2 (M+H), retention time: 0.90 and 0.95 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Preparation of Intermediates 4C and 4D:

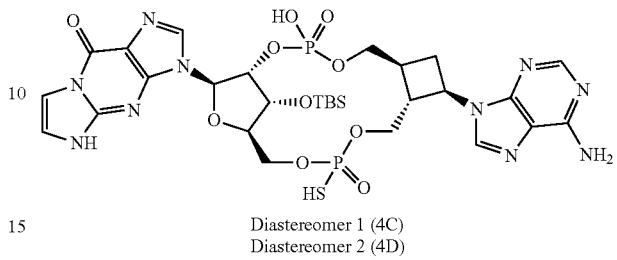

Diastereomer 1 (4C)
Diastereomer 2 (4D)

In a vial containing a mixture of diastereomers 4B was added 30% ammonium hydroxide (4 mL, 34.7 mmol) and the reaction was stirred at 40° C. for 2 h. The solvent was removed with a stream of nitrogen and then the residue was azeotroped with toluene (3×3 mL) to remove remaining water. This crude material was treated with a mixture of pyridine (1.240 mL), DBU (0.140 mL, 0.930 mmol) and nitromethane (0.050 mL, 0.930 mmol). The reaction mixture was heated at 30° C. overnight and then concentrated to dryness. The reaction mixture was then diluted with acetonitrile and acetic acid (0.160 mL, 2.79 mmol) was added. The mixture was then concentrated and azeotroped with acetonitrile several times. The crude product was purified on C18, 50 g reverse phase Gold ISCO column eluting with Solvent A (95% water, 5% acetonitrile, 0.01 M ammonium acetate)/Solvent B (95% acetonitrile, 5% water, 0.01 M ammonium acetate) using the following gradient: hold at 0% B for 6 min, 0-30% B over 8 min, at 30% B for 6 min, 30-100% B 3 min, to afford two separated diastereomers as 4C: LCMS: m/z 811.11 (M+H), retention time: 0.62 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm) and 4D: LCMS: m/z 811.1 (M+H), retention time: 0.67 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Examples 4-1 and 4-2

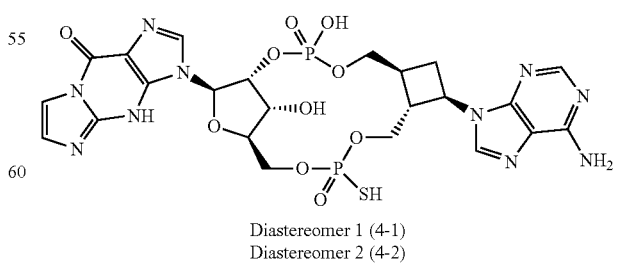

Diastereomer 1 (4-1)
Diastereomer 2 (4-2)

Intermediate 4C (11 mg, 0.014 mmol) was treated with triethylamine trihydrofluoride (200 µL, 1.228 mmol) and stirred at 40° C. for 2 h. The reaction mixture was then quenched with aq. NH₄OAc and purified on an ISCO 15.5 g reverse phase gold column and eluted with Solvent A: 95% water, 5% acetonitrile, 0.01 M ammonium acetate; Solvent B: 95% acetonitrile, 5% water, 0.01 M ammonium acetate using a 0-20% B gradient. The desired product eluted with solvent front. The fractions containing the desired material were concentrated and purified by preparative-HPLC (Xselect RP Prep C18 OBD Column, 5 μm, 19×150 mm, Mobile Phase A: 100 mM NH₄OAc (pH 6.5); Mobile Phase B: acetonitrile; Gradient: 0-70.5% B over 15 minutes, 70.5-95% B over 1 minute, then a 1-minute hold at 95% B; Flow: 20 mL/min. to afford Example 4-1: (3.3 mg, 33% yield) as a white solid. LCMS: m/z 697.1 (M+H), retention time: 0.51 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Intermediate 4D (14 mg, 0.017 mmol) was treated with triethylamine trihydrofluoride (250 μl, 1.535 mmol) and stirred at 40° C. for 2 h. The reaction mixture was quenched with aq. NH₄OAc and purified on a C18Aq, 50 g reverse phase ISCO Gold High performance column and eluted with Solvent A: 95% water, 5% acetonitrile, 0.01 M ammonium acetate/Solvent B: 95% acetonitrile, 5% water, 0.01 M ammonium acetate using the following gradient: hold 0% B for 2 min, 0-10% B over 6 min. to afford Example 4-2: (7.3 mg, 9.9 μmol, 58% yield) as a white solid. LCMS: m/z 697.1 (M+H), retention time: 0.37 min (Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm).

Examples 5-1, 5-2, 5-3 and 5-4

(1S,6S,8R,9R,15R,17R,18R)-8-(6-amino-9H-purin-9-yl)-18-hydroxy-17-{9-oxo-3H,5H,9H-imidazo[1,2-a]purin-3-yl}-3,12-disulfanyl-2,4,11,13,16-pentaoxa-3λ⁵,12λ⁵-diphosphatricyclo[13.3.0.0⁶,⁹]octadecane-3,12-dione

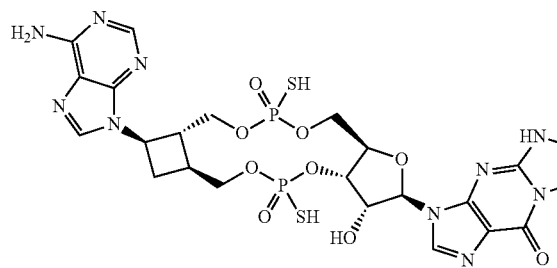

Diastereomer 1 (5-1)
Diastereomer 2 (5-2)
Diastereomer 3 (5-3)
Diastereomer 4 (5-4)

Preparation of Intermediate 5A:

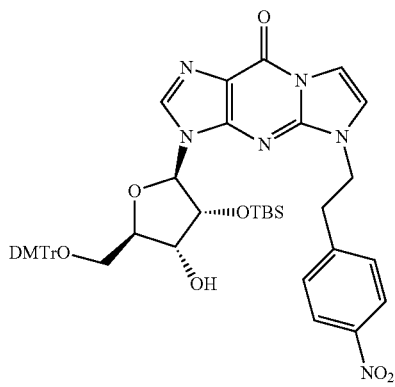

5A

To a solution of Intermediate 2D (3.75 g, 4.94 mmol) in DMF (25 mL) was added imidazole (0.84 g, 12.4 mmol), followed by the addition of TBS-Cl (0.78 g, 5.2 mmol). The reaction mixture was stirred at room temperature for 18 h, and it was then diluted with ethyl acetate (200 mL), washed with water (1×50 mL), aq. 10% LiCl solution (2×50 mL) and finally with sat. aq. NaCl solution (50 mL). The organic layer was dried (Na₂SO₄), filtered and concentrated. The crude product was dissolved in a small amount of DCM and charged to a 220 g ISCO silica gel column that had been equilibrated with DCM (w/0.25% TEA). The crude material was purified using a Teledyne ISCO system, eluting with 0%-50% ethyl acetate/DCM (w/0.25% TEA) to afford Intermediate 5A (950 mg, 1.0 mmol, 21% yield). Observed mass: 873.5 (M+H). ¹H NMR (400 MHz, DMSO-d₆) δ 8.36-8.32 (m, 1H), 8.17-8.13 (m, 2H), 8.06 (d, J=1.6 Hz, 1H), 7.67-7.60 (m, 2H), 7.50 (d, J=1.6 Hz, 1H), 7.17-7.05 (m, 5H), 7.05-6.97 (m, 4H), 6.70 (br d, J=8.9 Hz, 2H), 6.69-6.65 (m, 2H), 6.31 (d, J=2.7 Hz, 1H), 5.75-5.74 (m, 1H), 5.30 (d, J=7.0 Hz, 1H), 4.93-4.89 (m, 1H), 4.82-4.69 (m, 2H), 4.35 (br d, J=4.8 Hz, 1H), 4.22-4.17 (m, 1H), 3.70 (s, 3H), 3.69 (s, 3H), 3.32-3.24 (m, 2H), 3.00 (dd, J=10.8, 3.8 Hz, 1H), 0.81 (s, 9H), 0.06 (s, 3H), 0.01 (s, 3H).

Preparation of Intermediate 5B:

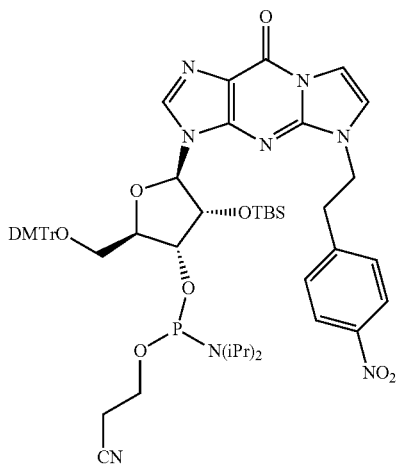

5B

To a solution of Intermediate 5A (950 mg, 1.0 mmol) in DCM (12 mL) was added 2-cyanoethyl N,N,N',N'-tetraisopropylphosphorodiamidite (0.717 mL, 2.176 mmol). After stirring at room temperature for 20 h, the reaction mixture was diluted with additional DCM (20 mL), washed with sat. aq. NaHCO₃ solution (10 mL), and then sat. aq. NaCl solution (10 mL). The organic layer was dried (Na₂SO₄), filtered and concentrated. The crude product was dissolved in a small amount of DCM and charged on a 40 g silica column that had been equilibrated with DCM (w/0.25% TEA) and purified using a Teledyne ISCO system, eluting with 0%-50% EtOAc/DCM (0.25% TEA) to afford Intermediate 5B (950 mg, 0.89 mmol, 81% yield) as a mixture of two diastereomers. Observed mass: 1073.3; Retention Time: 1.46 min, LCMS: (Column: ACQUITY UPLC® BEH C18, 2.1×50 mm, 1.7 μm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm)).

Preparation of Intermediate 5C:

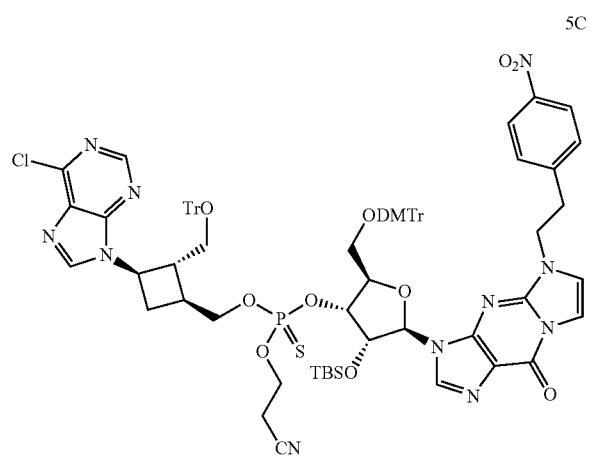

Intermediate 5B (630 mg, 0.59 mmol) was co-evaporated with ACN (2 mL) three times, and then 100 mg of molecular sieves (4 Å) were added, followed by ACN (2 mL). This solution was capped and set aside. In a separate flask, Intermediate 2H (250 mg, 0.50 mmol) and 1H-tetrazole (69 mg, 0.98 mmol) were co-evaporated with ACN (10 mL) two times. The resulting residue was again taken up in acetonitrile (10 mL) and concentrated to a volume of approximately 4 mL. The prepared solution of Intermediate 5B was added to the mixture of Intermediate 2H via cannula. The resulting mixture was sonicated and stirred for about 16 h, then (E)-N,N-dimethyl-N'-(3-thioxo-3H-1,2,4-dithiazol-5-yl)formimidamide (110 mg, 0.54 mmol) was added and stirring was continued for 30 min. The mixture was then concentrated, and then treated with MeOH. The resulting solids were removed by filtration, and the filtrate was concentrated and purified by silica gel chromatography (40 g, eluting with 0-100% EtOAc/hexanes) to give Intermediate 5C (574 mg, 0.38 mmol, 77% yield). Observed mass: 1514.7; Retention time 1.41 min. (Column: ACQUITY UPLC® BEH C18, 2.1×50 mm, 1.7 μm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm)).

Preparation of Intermediate 5D:

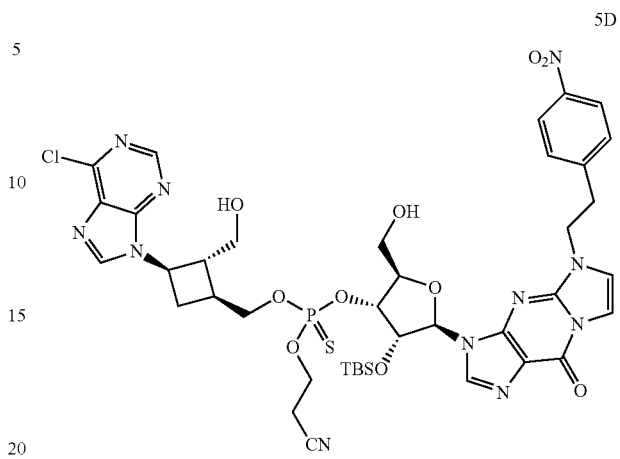

A solution of Intermediate 5C (574 mg, 0.38 mmol) in DCM (20 mL) was treated with triethylsilane (610 μl, 3.8 mmol) and 2,2-dichloroacetic acid (310 μl, 3.8 mmol). The mixture was stirred at room temperature for 3 h, and then was diluted with 20 mL of DCM and washed with aq. NaHCO₃. The aqueous layer was extracted with DCM (20 mL×2). The combined organic layers were dried over Na₂SO₄, filtered, concentrated and purified by silica gel chromatography (12 g, 0-10% MeOH/DCM) to give Intermediate 5D (160 mg, 0.16 mmol, 43% yield). Observed Mass: 970.3; Retention time: 0.94 min. (Column: ACQUITY UPLC® BEH C18, 2.1×50 mm, 1.7 μm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm))

Preparation of Intermediate 5E:

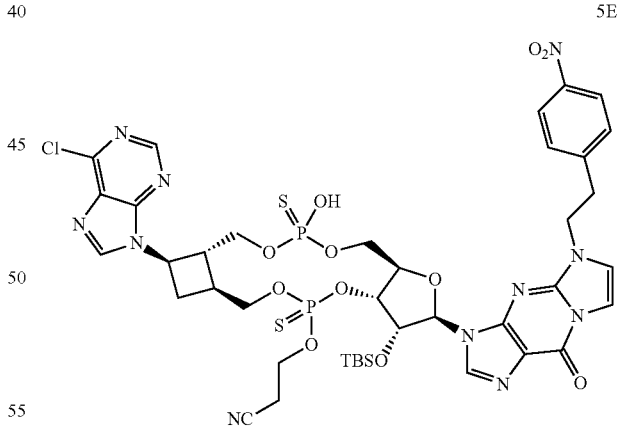

Intermediate 5D (160 mg, 0.16 mmol) was azeotroped with pyridine (2 mL), and then re-dissolved in pyridine (12 mL). To this pyridine solution under a nitrogen atmosphere, was added dropwise a solution of diphenyl phosphite (0.063 mL, 0.324 mmol) in pyridine (1 mL). After stirring for 20 min, (E)-N,N-dimethyl-N'-(3-thioxo-3H-1,2,4-dithiazol-5-yl)formimidamide (100 mg, 0.49 mmol) was added and the reaction was stirred at room temperature overnight. The reaction mixture was then concentrated to dryness. The residue was suspended in EtOAc (50 mL) and washed with aq. NaHCO₃ (30 mL). The organic phase was collected and washed with brine, dried over Na₂SO₄, filtered and then concentrated to dryness. The residue was treated with MeOH (10 mL) for 10 minutes and the resulting solids were removed by filtration. The filtrate was concentrated and then purified on a C18, 150 g reverse phase ISCO gold column (eluting with solvent A: 95% water, 5% acetonitrile, 0.01 M ammonium acetate; Solvent B: 95% acetonitrile, 5% water, 0.01 M ammonium acetate, hold at 10% B for 3 min, then 10-65% B over 15 min, then hold at 65% B for 2 min and 65%-100% B over 12 min) to afford 5E as a mixture of 4 diastereomers (99 mg, 0.094 mmol, 58% yield). Observed Mass: 1048.0; Retention time: 0.89-0.96 min. (Column: ACQUITY UPLC® BEH C18, 2.1×50 mm, 1.7 µm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm)).

Preparation of Intermediate 5F

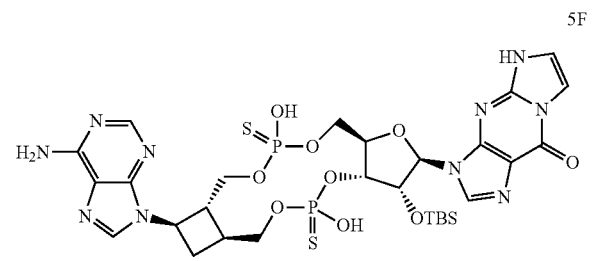 [SMILES: CC(C)(C)[Si](C)(C)O[C@@H]1[C@@H]2OP(O)(=S)OC[C@H]3C[C@@H](n4cnc5c(N)ncnc54)[C@@H]3COP(O)(=S)OC[C@H]2O[C@H]1n1cnc2c(=O)n3cc[nH]c3nc21]

5F

Intermediate 5E (99 mg, 0.094 mmol) in 2 mL of 28% ammonia hydroxide was heated to 40° C. for 4 h. The mixture was then concentrated under a stream of nitrogen. The residue was re-dissolved in 3 mL of pyridine and DBU (113 µl, 0.76 mmol) was added. The mixture was stirred at 40° C. for 8 h, and then concentrated. The residue was then triturated with 5 mL of diethyl ether three times, dissolved in 10 mL of MeOH and mixed with 2 g of celite and concentrated. The crude celite mixture was purified on a C18, 100 g reverse phase ISCO gold column (eluting with solvent A: 95% water, 5% acetonitrile, 0.01 M ammonium acetate; Solvent B: 95% acetonitrile, 5% water, 0.01 M ammonium acetate, hold at 100% A for 10 min, then 0-35% B over 15 min, then hold at 35% B for 2 min and 35%-100% B over 12 min) to give Intermediate 5F as a mixture of 4 diastereomers (58 mg, 0.070 mmol, 74% yield). Observed Mass: 827.0; Retention time: 0.51-0.52 min. (Column: ACQUITY UPLC® BEH C18, 2.1×50 mm, 1.7 µm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm))

Example 5-1, 5-2, 5-3 and 5-4

Intermediate 5F (58 mg, 0.070 mmol) was dissolved in 0.5 mL of triethylamine trihydrofluoride and stirred at 37° C. for 2 h. Then the reaction was quenched with 2 mL of 2M NH₄OAC and purified via preparative LC/MS to afford 4 individual diastereomers, Example 5-1, 5-2, 5-3 and 5-4. Preparative LC/MS conditions: Column: Xselect RP Prep C18 OBD Column, 19×150 mm, 5-µm particles; Mobile Phase A: water with 20 mM TEA; Mobile Phase B: acetonitrile:water (80:20) with 20 mM TEA; Gradient: 8% B-18% B 0-21 minutes, 18%-95% over 2 min, then a 2-minute hold at 95% B; Flow: 20 mL/min. Analytical LCMS conditions: Agilent 1290 HPLC/MS, column: Xselect CSH C18 Column, 3.5 µm, 3.0×150 mm; Mobile Phase A: water with 20 mM TEA; Mobile Phase B: acetonitrile:water (80:20) with 20 mM TEA. Temperature: 50° C.; Gradient: 5% B-35% B over 25 min, then 35% B-95% B over 2 min; Flow: 0.5 mL/min; Detection: MS and UV (220 nm).

Example 5-1

4.2 mg. Retention Time: 8.29 min. LCMS, [M+H]+=713.0.

Example 5-2

3.1 mg. Retention Time: 9.43 min. LCMS, [M+H]+=713.0.

Example 5-3

6.8 mg. Retention Time: 10.04 min. LCMS, [M+H]+=713.0.

Example 5-4

5.6 mg. Retention Time: 12.56 min. LCMS, [M+H]+=713.0.

Examples 6-1, 6-2, 6-3 and 6-4

(1S,6S,8R,9R,15R,17R,18R)-8-(6-amino-9H-purin-9-yl)-18-fluoro-17-{9-oxo-3H,4H,9H-imidazo[1,2-a]purin-3-yl}-3,12-disulfanyl-2,4,11,13,16-pentaoxa-3λ⁵,12λ⁵-diphosphatricyclo[13.2.1.0⁶,⁹]octadecane-3,12-dione

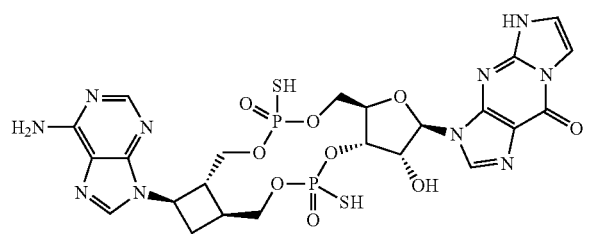

Diastereomer 1 (5-1)
Diastereomer 2 (5-2)
Diastereomer 3 (5-3)
Diastereomer 4 (5-4)

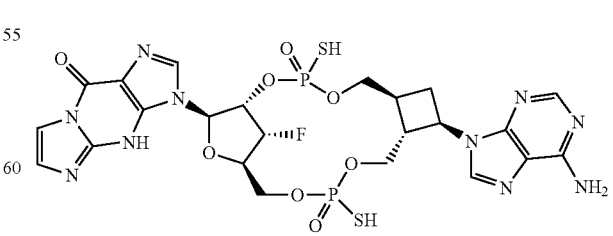

Diastereomer 1 (6-1)
Diastereomer 2 (6-2)
Diastereomer 3 (6-3)
Diastereomer 4 (6-4)

Preparation of Intermediate 6A:

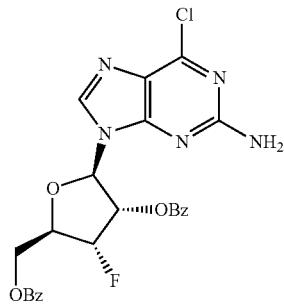

6A 6-chloro-7H-purin-2-amine (Oakwood, 3.4 g, 19.9 mmol) was dissolved in anhydrous acetonitrile (50 mL) and trimethylsilyl N-(trimethylsilyl)acetimidate (9.72 mL, 39.8 mmol) was added. The solution was refluxed for 2 h and was then allowed to cool to room temperature. A solution of ((2R,3R,4S)-5-acetoxy-4-(benzoyloxy)-3-fluorotetrahydrofuran-2-yl)methyl benzoate (Bioorg. Med. Chem Lett., 2003, 13, 817; 4.0 g, 9.94 mmol) in anhydrous acetonitrile (50 mL) was added, followed by trimethylsilyl trifluoromethanesulfonate (7.20 mL, 39.8 mmol). The resulting mixture was refluxed again for 4 h and then cooled to room temperature, diluted with EtOAc (200 mL), washed with saturated aqueous NaHCO$_3$, dried over MgSO$_4$, filtered, and concentrated in vacuo. The crude material was chromatographed on silica gel (40 g, EtOAc/DCM, 0-100%) to afford Intermediate 6A (3.99 g, 7.79 mmol, 78% yield). Observed mass: 512.2; $^1$H NMR (499 MHz, CHLOROFORM-d) δ 8.13-8.04 (m, 4H), 7.87 (s, 1H), 7.69-7.58 (m, 2H), 7.56-7.43 (m, 4H), 6.38-6.21 (m, 2H), 5.84-5.61 (m, 1H), 5.06 (s, 2H), 4.91 (dd, J=11.9, 4.4 Hz, 1H), 4.87-4.77 (m, 1H), 4.71-4.55 (m, 1H).

Preparation of Intermediate 6B:

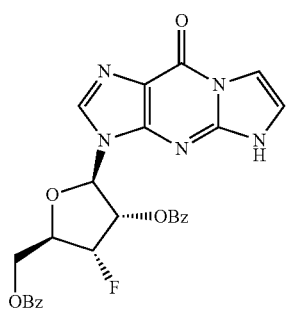

6B

To a solution of Intermediate 6A (3.2 g, 6.25 mmol) in EtOH (70 mL) was added NH$_4$OAc/AcOH buffer (4.5 pH, 150 mL) and 2-bromoacetaldehyde (14.4 mL, 18.8 mmol). The mixture was heated for 6 days at 37° C. Then most of the solvent was removed in vacuo and the reaction was diluted with 200 mL of EtOAc to form an emulsion. The resulting mixture was made basic with NaHCO$_3$ aq. The organic phase was separated and washed with water, then brine, dried over Na$_2$SO$_4$, filtered and concentrated to give an off-white solid which was washed with Et$_2$O (10 mL×2), then dried on vacuum to give crude product 6B. Observed mass: 518.2; $^1$H NMR (499 MHz, DMSO-d$_6$) δ 8.13 (s, 1H), 8.02 (dd, J=8.3, 1.2 Hz, 2H), 7.94 (dd, J=8.4, 1.3 Hz, 2H), 7.75-7.69 (m, 1H), 7.66-7.62 (m, 2H), 7.59-7.54 (m, 3H), 7.48-7.42 (m, 3H), 6.43 (d, J=5.0 Hz, 1H), 6.33-6.22 (m, 1H), 6.09-5.90 (m, 1H), 4.85-4.72 (m, 2H), 4.70-4.60 (m, 1H).

Preparation of Intermediate 6C:

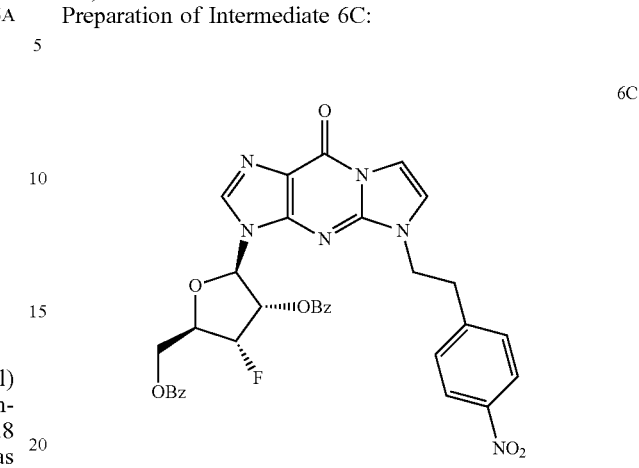

6C

To a solution of Intermediate 6B (3.5 g, 6.76 mmol), 2-(4-nitrophenyl)ethan-1-ol (1.7 g, 10.15 mmol) and triphenylphosphine (5.32 g, 20.30 mmol) in THF (30 mL) at 0° C. under nitrogen, was added diisopropyl (E)-diazene-1,2-dicarboxylate (1.97 ml, 10.15 mmol) dropwise. The reaction was allowed to slowly warm to room temperature and was then stirred for 60 min. The solvent was removed in vacuo. The resulting thick oil was triturated with diethyl ether (5 mL×4), then purified by silica gel chromatography (80 g, 0-60% EtOAC/hex) to give 6C (2.4 g, 3.60 mmol, 53% yield). Observed mass: 667.4; $^1$H NMR (499 MHz, METHANOL-d$_4$) δ 8.12-8.03 (m, 5H), 7.87 (dd, J=8.4, 1.3 Hz, 2H), 7.70-7.63 (m, 1H), 7.59 (d, J=2.7 Hz, 1H), 7.58-7.53 (m, 1H), 7.52-7.47 (m, 2H), 7.40 (d, J=8.7 Hz, 2H), 7.35 (t, J=7.9 Hz, 2H), 7.27 (d, J=2.6 Hz, 1H), 6.53 (dt, J=14.9, 5.2 Hz, 1H), 6.45 (d, J=4.9 Hz, 1H), 5.97-5.78 (m, 1H), 4.96-4.81 (m, 2H), 4.78-4.65 (m, 1H), 4.53-4.38 (m, 1H), 4.33 (dt, J=14.0, 6.9 Hz, 1H), 3.31-3.15 (m, 2H).

Preparation of Intermediate Q2D

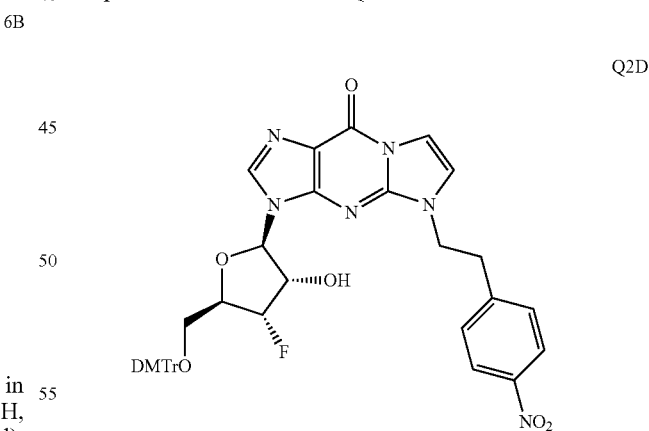

Q2D

A solution of Intermediate 6C (2.4 g, 3.60 mmol) in 20 mL of 7N NH$_3$/MeOH was stirred at room temperature for 5 h. The reaction mixture was then concentrated and the resulting solid was washed with MeOH (1 mL×3), then dried under vacuum. The solid was then azeotroped with pyridine (5 mL), then dissolved in 10 mL of pyridine, and 4,4'-(chloro(phenyl)methylene)bis(methoxybenzene) (1.220 g, 3.60 mmol) was added and the mixture was stirred at room temperature for 16 h. Then the reaction mixture was treated with 2 mL of MeOH and stirred at room temperature for 10 min. The mixture was then concentrated and the residue was dissolved in 50 mL of DCM, washed with aq. NaHCO₃, followed by brine and then concentrated. The crude material was purified on silica (40 g, 0-100% EtOAc/DCM (w/0.25% TEA)) to give Intermediate 6D (1.9 g, 2.5 mmol, 69% yield). Observed mass: 761.5; ¹H NMR (499 MHz, CHLOROFORM-d) δ 8.17 (d, J=8.7 Hz, 2H), 7.88 (s, 1H), 7.64 (d, J=2.7 Hz, 1H), 7.37-7.32 (m, 2H), 7.30 (br d, J=8.7 Hz, 2H), 7.28-7.19 (m, 7H), 6.80 (d, J=8.9 Hz, 4H), 6.67 (d, J=2.6 Hz, 1H), 5.99 (d, J=7.4 Hz, 1H), 5.15 (m, 1H), 4.99-4.80 (m, 1H), 4.65 (br d, J=5.1 Hz, 1H), 4.61-4.47 (m, 1H), 4.30 (t, J=7.0 Hz, 2H), 3.79 (s, 6H), 3.49 (dd, J=10.7, 3.5 Hz, 1H), 3.39 (dd, J=10.6, 3.5 Hz, 1H), 3.22 (td, J=6.9, 2.7 Hz, 2H).
Preparation of Intermediate 6E:

6E

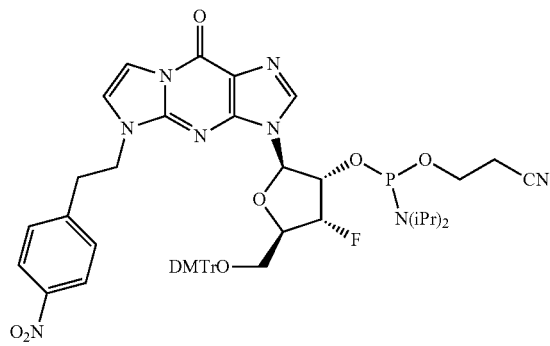

To a solution of 6D (0.5 g, 0.657 mmol) in DCM (5 mL) was added 1H-imidazole-4,5-dicarbonitrile (0.66 ml, 0.66 mmol) (1M in ACN), followed by the addition of 3-((bis(diisopropylamino)phosphanyl)oxy)propanenitrile (0.40 g, 1.31 mmol). The mixture was stirred at room temperature overnight and then diluted with DCM (30 mL) and washed with 10% NaHCO₃ aq. The aqueous layer was extracted with additional DCM (20 mL). The combined organic layers were dried (Na₂SO₄), filtered and concentrated. The crude product was purified on silica (40 g column, 0-100% EtOAc/DCM (w/0.25% TEA)) to give 6E as a pair of diastereomers (0.60 g, 0.624 mmol, 95% yield). Observed mass: 961.1. Retention time: 1.19 min and 1.25 min. (Column: ACQUITY UPLC® BEH C18, 2.1×50 mm, 1.7 µm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm)).
Preparation of Intermediate 6F

6F

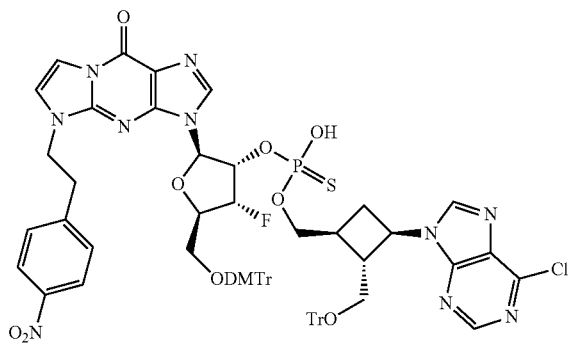

Intermediate 6E (635 mg, 0.66 mmol) was azeotroped with 2 mL of acetonitrile 3 times. Then 100 mg of 4 Å molecular sieves were added, followed by 2 mL of ACN. This solution was capped and set aside. In a separate flask, Intermediate 2H (270 mg, 0.53 mmol) and 5-(ethylthio)-1H-tetrazole (138 mg, 1.057 mmol) were co-evaporated with ACN (10 mL×2). The residue was again taken up in acetonitrile (10 mL) and concentrated to approximately 4 mL. The prepared solution of Intermediate 6E was added to the mixture of Intermediate 2H via cannula. The resulting mixture was sonicated and stirred for about 16 h, then (E)-N,N-dimethyl-N'-(3-thioxo-3H-1,2,4-dithiazol-5-yl)formimidamide (119 mg, 0.58 mmol) was added and stirring was continued for 30 min. The mixture was concentrated and then treated with MeOH. The solids were removed by filtration, and the filtrate was concentrated, then purified on silica (40 g, eluting with 0-100% EtOAc/hexanes (w/0.5% of TEA)) to give Intermediate 6F (600 mg, 0.40 mmol, 76% yield). Observed mass 1349.1; Retention time: 1.14 min. (Column: ACQUITY UPLC® BEH C18, 2.1×50 mm, 1.7 µm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm)).
Preparation of Intermediate 6G:

6G

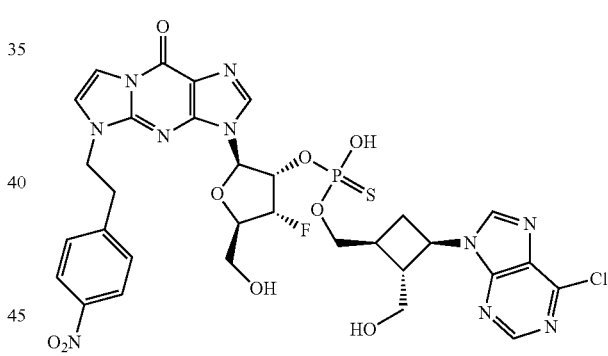

To a solution of Intermediate 6F (601 mg, 0.401 mmol) in 20 mL of DCM was added triethylsilane (710 µl, 4.5 mmol) and 2,2-dichloroacetic acid (370 µl, 4.5 mmol). The reaction mixture was stirred at room temperature for 3 h, then diluted with 20 mL of DCM and washed with aq. NaHCO₃. The aqueous layer was extracted with DCM (20 mL×2). The combined organic layers were dried over Na₂SO₄, filtered and concentrated. The crude material was purified on silica gel (12 g, 0-15% MeOH/DCM) to give Intermediate 6G (360 mg, 0.40 mmol, 100% yield). Observed mass: 805.2; Retention time: 0.80 min. (Column: ACQUITY UPLC® BEH C18, 2.1×50 mm, 1.7 µm; Mobile Phase A: H₂O:ACN (95:5) with 10 mM NH₄OAc; Mobile Phase B: H₂O:ACN (5:95) with 10 mM NH₄OAc; Gradient: 5% B to 95% B in 1 min, then a 0.5 min hold at 95% B; Flow: 0.8 mL/min; Detection: MS and UV (220 nm)).

Preparation of Intermediate 6H:

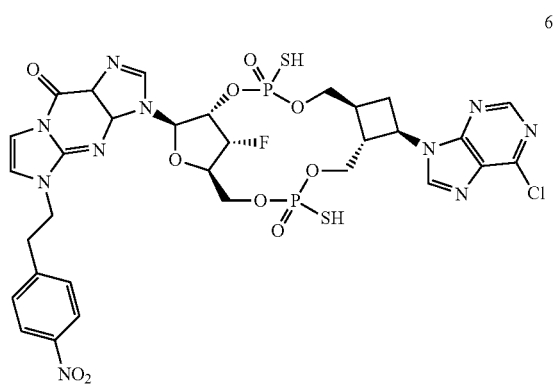

Intermediate 6G (360 mg, 0.45 mmol) was azeotroped with 2 mL of pyridine, and then re-dissolved in 12 mL of pyridine. To this solution, under a nitrogen atmosphere, was added dropwise a solution of diphenyl phosphite (0.17 mL, 0.89 mmol) in 2 mL of pyridine. After stirring for 20 min, (E)-N,N-dimethyl-N'-(3-thioxo-3H-1,2,4-dithiazol-5-yl)formimidamide (274 mg, 1.33 mmol) was added and the reaction was stirred at room temperature overnight. Then the reaction mixture was quenched with 0.1 mL of water and concentrated to dryness. The residue was then treated with 4 mL of MeOH for 10 min and the resulting solids were removed by filtration. The filtrate was concentrated and then purified on a C18, 150 g reverse phase ISCO gold column (eluting with solvent A: 95% water, 5% acetonitrile, 0.01 M ammonium acetate; Solvent B: 95% acetonitrile, 5% water, 0.01 M ammonium acetate, hold at 10% B for 5 min, then 10-65% B over 25 min, then hold at 65% B for 2 min and 65%-100% B over 12 min) to afford Intermediate 6H as a mixture of 4 diastereomers (120 mg, 0.136 mmol, 31% yield). Observed mass 883.1; Retention time: 0.48-0.54 min. (Column: ACQUITY UPLC® BEH C18, 2.1×50 mm, 1.7 µm; Mobile Phase A: H$_2$O:ACN (95:5) with 10 mM NH$_4$OAc; Mobile Phase B: H$_2$O:ACN (5:95) with 10 mM NH$_4$OAc; Gradient: 5% B to 95% B in 1 min, then a 0.5 min hold at 95% B; Flow: 0.8 mL/min; Detection: MS and UV (220 nm)).

Examples 6-1, 6-2, 6-3 and 6-4

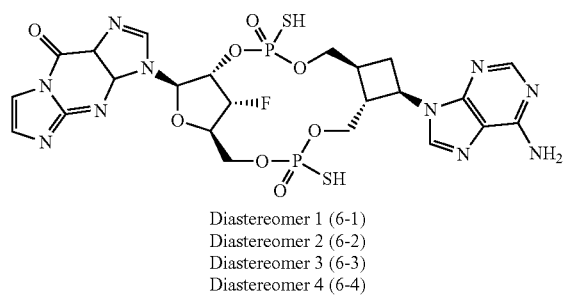

Diastereomer 1 (6-1)
Diastereomer 2 (6-2)
Diastereomer 3 (6-3)
Diastereomer 4 (6-4)

Intermediate 6H (120 mg, 0.136 mmol) in 2 mL of 30% ammonia hydroxide solution was heated at 50° C. for 3 h. Then, the reaction was concentrated and the residue was dissolved in 2 mL of ACN, and DBU (164 µl, 1.087 mmol) was added. The mixture was stirred at room temperature for 40 h and then was concentrated and triturated with diethyl ether (5 mL×3). The resulting solid was purified on a C18, 100 g reverse phase ISCO gold column (eluting with solvent A: 95% water, 5% acetonitrile, 0.01 M ammonium acetate; Solvent B: 95% acetonitrile, 5% water, 0.01 M ammonium acetate, hold at 100% A for 10 min, then 0-35% B over 15 min, then hold at 35% B for 2 min and 35%-100% B over 12 min) to give two fractions with the desired mass. Both fractions were further purified via preparative LC/MS. Fraction 1 gave 3 individual diastereomers (6-1, 6-2 and 6-3) and fraction 2 gave single diastereomer (6-4). Preparative LC/MS conditions: Column: Xselect RP Prep C18 OBD Column, 19×150 mm, 5-µm particles; Mobile Phase A: water with 20 mM NH$_4$OAc; Mobile Phase B: MeOH; Gradient: 10% B-22% B 0-15 minutes, 22% B-95% B over 0.5 min, then a hold at 95% B for 0.5 min; Flow: 20 mL/min. Analytical LCMS conditions: Agilent 1290 HPLC/MS, column: Xselect CSH C18 Column, 3.5 µm, 3.0×150 mm; Mobile Phase A: water with 20 mM NH$_4$OAc; Mobile Phase B: MeOH; Temperature: 50° C.; Gradient: 5% B-100% B over 15 min; Flow: 0.5 mL/min; Detection: MS and UV (220 nm).

Example 6

2.4 mg Retention Time: 10.26 min. LCMS, [M+H]+=715.2

Example 6-2

0.8 mg. Retention Time: 10.94 min. LCMS, [M+H]+=715.2

Example 6-3

1.6 mg. Retention Time: 11.88 min. LCMS, [M+H]+=715.2

Example 6-4

3.4 mg. Retention Time: 9.10 min. LCMS, [M+H]+=715.2

Alternatively, Example 6-2 may be prepared according to the procedures given below.

Example 6-2

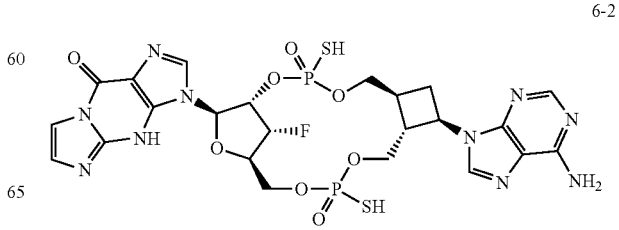

Preparation of Intermediate 6I:

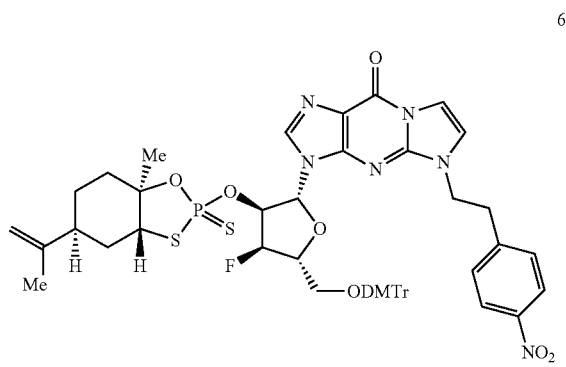

6I

To a solution of Intermediate 6D (500 mg, 0.66 mmol) and Reagent 4 (590 mg, 1.31 mmol) in acetonitrile (12 mL) was added DBU (0.20 mL, 1.31 mmol). The reaction mixture was stirred at room temperature for 20 minutes and then the reaction was quenched with acetic acid (120 mg, 1.97 mmol), and then concentrated. The residue was purified by silica gel chromatography (12 g, MeOH/DCM=0-10%) to give Intermediate 6I (600 mg, 0.59 mmol, 90% yield). LCMS: m/z 1007.8 (M+H); Retention time: 1.22 min, (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm).

Preparation of Intermediate 6J:

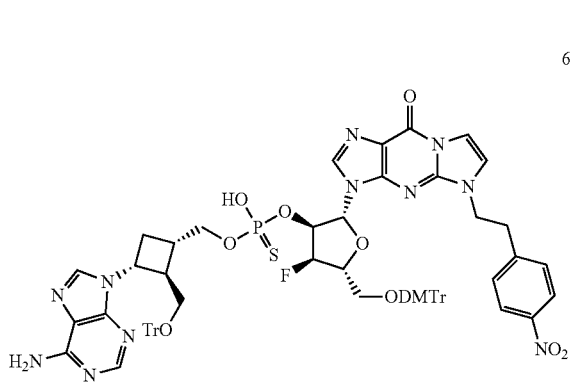

6J

Intermediate 2M (270 mg, 0.55 mmol) was azeotroped with ACN (2 mL×2).

Then Intermediate 6J (553 mg, 0.55 mmol) was added and the mixture was azeotroped with ACN (2 mL). To the mixture was then added THF (10 mL), followed by DBU (0.33 mL, 2.2 mmol) in one portion. The reaction mixture was stirred at room temperature for 30 min, and then was quenched with acetic acid (0.13 mL, 2.2 mmol) and concentrated. The resulting residue was purified by silica gel chromatography (12 g, MeOH/DCM=0-15%) to give Intermediate 6J (620 mg, 0.47 mmol, 85% yield). LCMS: m/z 1331.1 (M+H); Retention time: 1.05 min (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm).

Preparation of Intermediate 6K:

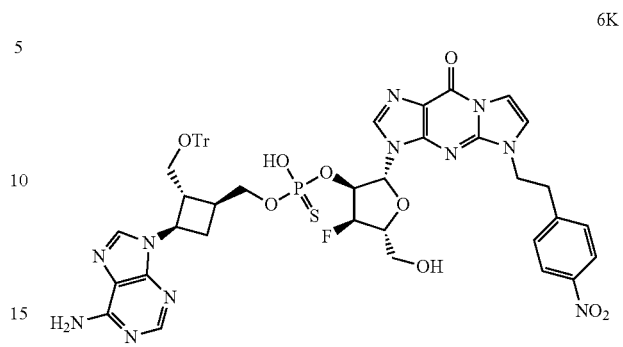

6K

A solution of Intermediate 6J (0.62 g, 0.466 mmol) in 10 mL of DCM was treated with triethylsilane (0.37 mL, 2.33 mmol), followed by 2,2-dichloroacetic acid (0.12 mL, 1.4 mmol). The reaction was stirred at 25° C. for 1 h. Upon completion, pyridine (0.18 g, 2.33 mmol) was added and the reaction mixture was concentrated. The resulting residue was purified on silica gel (12 g, 0-20% MeOH/DCM) to give Intermediate 6K (420 mg, 0.41 mmol, 88% yield). LCMS: m/z 1028.5 (M+H); Retention time: 0.80 min. (Column: ACQUITY UPLC® BEH C18, 2.1×50 mm, 1.7 μm; Mobile Phase A: H$_2$O:ACN (95:5) with 10 mM NH$_4$OAc; Mobile Phase B: H$_2$O:ACN (5:95) with 10 mM NH$_4$OAc; Gradient: 5% B to 95% B in 1 min, then a 0.5 min hold at 95% B; Flow: 0.8 mL/min; Detection: MS and UV (220 nm))

Preparation of Intermediate 6L:

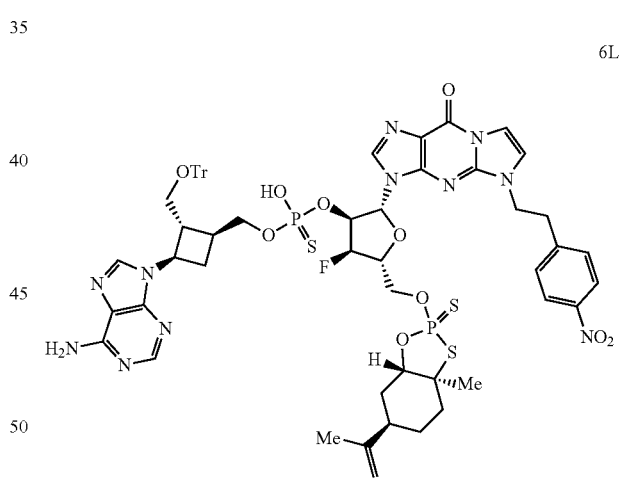

6L

To a solution of Intermediate 6K (422 mg, 0.41 mmol) and Reagent 3 (370 mg, 0.82 mmol) in THF (8 mL), was added DBU (0.37 mL, 2.46 mmol) with vigorous stirring. After 10 min, the reaction was quenched with acetic acid (150 mg, 2.46 mmol), and then concentrated. The residue was purified on an ISCO gold silica gel column (12 g, eluting with 0-15% MeOH/DCM) to give Intermediate 6L (460 mg, 0.36 mmol, 88% yield). LCMS: m/z 1274.9 (M+H), retention time: 1.03 min (Column conditions: Waters Acquity SDS; column: BEH C18 (2.1×50 mm), 1.7 micron; Solvent A=water w/0.05% TFA; Solvent B=acetonitrile w/0.05% TFA; Gradient=2-98% B over 1 minute, then a 0.5-minute hold at 98% B; Flow rate: 0.8 mL/min; Detection: UV at 220 nm)).

Example 6-2

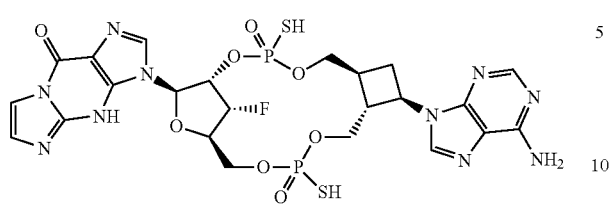

To a solution of Intermediate 6L (460 mg, 0.36 mmol) in 10 mL of DCM was added triethylsilane (0.69 mL, 4.3 mmol), followed by 2,2-dichloroacetic acid (0.30 mL, 3.6 mmol). The reaction mixture was stirred at room temperature for 40 min, and then, with vigorous stirring, the reaction mixture was added dropwise to a flask containing THF (10 mL) and DBU (1.63 mL, 10.8 mmol). The resulting mixture was stirred for an additional 5 min. The reaction mixture was then concentrated and the residue was re-dissolved in 0.5 mL of ACN and stirred for 16 h at 40° C. to completely remove the nitrophenethyl group. The reaction mixture was then concentrated and the residue was washed with diethyl ether (10 mL×3), and then re-dissolved in 10 mL of MeOH. To this solution, 3 g of celite was added and the resulting mixture was concentrated to dryness. The crude mixture was purified on a C18, 100 g reverse phase ISCO gold column (eluting with solvent A: 95% water, 5% acetonitrile, 0.01 M ammonium acetate; Solvent B: 95% acetonitrile, 5% water, 0.01 M ammonium acetate, hold at 100% A for 10 min, then 0-35% B over 15 min, then hold at 35% B for 2 min and 35%-100% B over 12 min) to give crude Example 6-2. LCMS: m/z 715.2 (M+H); Retention time: 0.26 min. (Column: ACQUITY UPLC® BEH C18, 2.1×50 mm, 1.7 μm; Mobile Phase A: H$_2$O:ACN (95:5) with 10 mM NH$_4$OAc; Mobile Phase B: H$_2$O:ACN (5:95) with 10 mM NH$_4$OAc; Gradient: 5% B to 95% B in 1 min, then a 0.5 min hold at 95% B; Flow: 0.8 mL/min; Detection: MS and UV (220 nm)) as a white solid and 17 mg of crude Example 7. LCMS: m/z 699.2 (M+H); Retention time: 0.19 min. (Column: ACQUITY UPLC® BEH C18, 2.1×50 mm, 1.7 μm; Mobile Phase A: H$_2$O:ACN (95:5) with 10 mM NH$_4$OAc; Mobile Phase B: H$_2$O:ACN (5:95) with 10 mM NH$_4$OAc; Gradient: 5% B to 95% B in 1 min, then a 0.5 min hold at 95% B; Flow: 0.8 mL/min; Detection: MS and UV (220 nm)) The crude Example 6-2 (167 mg) was further purified via preparative LC/MS [Preparative LC/MS conditions: Column: Agilent infinitylab Eclipse Plus C18 Column 5 μm, 21.2×250 mm; Mobile Phase A: water with 100 mM NH$_4$OAc; Mobile Phase B: ACN; Gradient: 5% B-17% B 0-11 minutes, 17% B-100% B over 1 min, then a 1-minute hold at 100% B; Flow: 25 mL/min. Analytical LCMS conditions: Agilent 1200 HPLC/MS, column: Agilent Eclipse Plus C18 Column 3.5 μm, 3×150 mm; Mobile Phase A: water with 20 mM NH$_4$OAc; Mobile Phase B: ACN; Temperature: 50° C.; Gradient: 5% B-100% B over 15 min; Flow: 0.5 mL/min; Detection: MS and UV (260 nm)] to give the final Example 6-2 (45 mg). LCMS, [M+H]+=715.0; $^1$H NMR (700 MHz, D$_2$O) δ 8.21 (s, 1H), 8.18 (s, 1H), 8.16 (s, 1H), 7.54 (d, J=2.54 Hz, 1H), 6.98 (d, J=2.54 Hz, 1H), 6.23 (d, J=7.78 Hz, 1H), 5.63 (m, 1H), 5.61 (m, 1H), 4.80 (m, 1H), 4.75 (m, 1H), 4.32 (m, 2H), 4.26 (t, J=7.41, 7.41 Hz, 2H), 4.06 (dt, J=10.28, 3.98, 3.98 Hz, 1H), 3.88 (dt, J=10.21, 4.99, 4.99 Hz, 1H), 3.01 (m, 1H), 2.64 (dt, J=11.33, 8.55, 8.55 Hz, 1H), 2.50 (m, 1H), 2.31 (m, 1H).

Example 7

3-[(1S,6S,8R,9R,15R,17R,18R)-8-(6-amino-9H-purin-9-yl)-18-fluoro-3,12-dihydroxy-12-oxo-3-sulfanylidene-2,4,11,13,16-pentaoxa-3λ$^5$,12λ$^5$-diphosphatricyclo[13.2.1.0$^{6,9}$]octadecan-17-yl]-3H,5H,9H-imidazo[1,2-a]purin-9-one

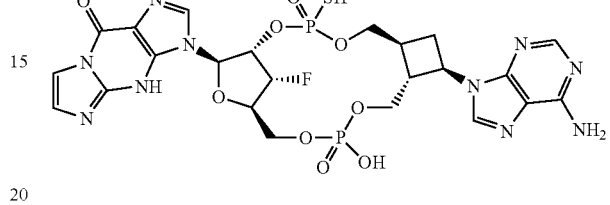

The crude Example 7 from above (17 mg) was further purified via preparative LC/MS [Preparative LC/MS conditions: Column: Agilent infinitylab Eclipse Plus C18 Column 5 μm, 21.2×250 mm; Mobile Phase A: water with 100 mM NH$_4$OAc; Mobile Phase B: ACN; Gradient: 0% B-13.5% B 0-13 minutes, 13.5% B-100% B over 1 min, then a 1-minute hold at 100% B; Flow: 25 mL/min. Analytical LCMS conditions: Agilent 1200 HPLC/MS, column: Agilent Eclipse Plus C18 Column 3.5 μm, 3×150 mm; Mobile Phase A: water with 20 mM NH$_4$OAc; Mobile Phase B: ACN; Temperature: 50° C.; Gradient: 5% B-100% B over 15 min; Flow: 0.5 mL/min; Detection: MS and UV (265 nm)] to give Example 7 (3.4 mg), LCMS, [M+H]+=699.0; $^1$H NMR (499 MHz, METHANOL-d$_4$) δ 8.48 (s, 1H), 8.21 (s, 1H), 8.07 (s, 1H), 7.62 (d, J=2.6 Hz, 1H), 7.22 (d, J=2.6 Hz, 1H), 6.12 (d, J=8.0 Hz, 1H), 6.08-5.94 (m, 1H), 5.70-5.40 (m, 1H), 4.82-4.75 (m, 1H), 4.61-4.44 (m, 2H), 4.33-4.25 (m, 1H), 4.16 (ddd, J=10.5, 6.7, 3.3 Hz, 1H), 4.09-3.95 (m, 3H), 3.70-3.64 (m, 1H), 3.57-3.51 (m, 1H), 3.50-3.44 (m, 1H), 3.26-3.18 (m, 1H).

Examples 8-1, 8-2, 8-3 and 8-4

(1S,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ$^5$,12λ$^5$-diphosphatricyclo[13.2.1.0$^{6,9}$]octadecane-3,12-dione

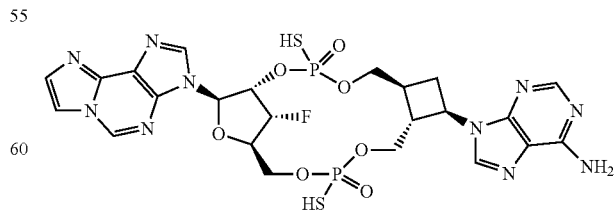

Diastereomer 1 (8-1)
Diastereomer 2 (8-2)
Diastereomer 3 (8-3)
Diastereomer 4 (8-4)

Preparation of Intermediate 8A:

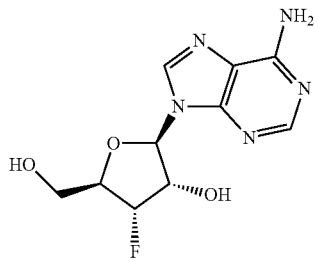

To a solution of ((2R,3R,4S,5R)-5-(6-benzamido-9H-purin-9-yl)-4-(benzoyloxy)-3-fluorotetrahydrofuran-2-yl) methyl benzoate [*Carbohydrate Research* 278, (1995), 71-89] (2.0 g, 3.44 mmol) in MeOH (4 mL) was added ammonia (7M in MeOH) (3.72 mL, 172 mmol). The reaction mixture was heated at 50° C. for 16 h, and then it was cooled to room temperature and concentrated under reduced pressure. The resulting residue was triturated with Et$_2$O, the solid was collected by filtration and dried to give Intermediate 8A (0.8 g, 86% yield) HPLC: Retention time=0.39 min (H$_2$O/ACN with 0.05% TFA, Waters Acquity HPLC BEH C18, 2.1×50 mm, 1.7-μm particles, gradient=2 min, wavelength=220 nm); MS (ES): m/z=270 [M+H]$^+$.

Preparation of Intermediate 8B:

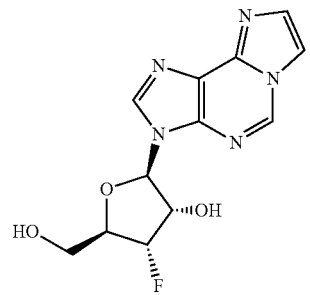

Intermediate 8A (3.5 g, 13.0 mmol) was dissolved in NaOAc/AcOH buffer (pH=4.5) (100 ml) and 50% 2-chloroacetaldehyde (30 mL) in water was added and the mixture was stirred at 35° C. overnight. The resulting mixture was concentrated and the residue was loaded onto celite and purified by silica gel column chromatography (80 g column, MeOH/DCM=5-20%) to give Intermediate 8B (3.21 g, 84%). HPLC: Retention time=0.40 min (H$_2$O/ACN with 0.05% TFA, Waters Acquity HPLC BEH C18, 2.1×50 mm, 1.7-μm particles, gradient=2 min, wavelength=220 nm); MS (ES): m/z=294 [M+H]$^+$.

Preparation of Intermediate 8C:

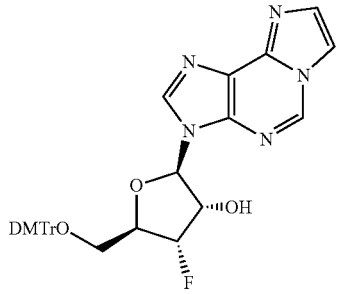

Intermediate 8B (3.2 g, 11.0 mmol) was azetroped with pyridine two times, and the resulting residue was dissolved in pyridine (100 mL). To this solution was added a catalytic amount of DMAP and 4,4'-(chloro(phenyl)methylene)bis(methoxybenzene) (4.1 g, 12.0 mmol). The mixture was stirred at room temperature overnight, and then MeOH (5 mL) was added, and stirring continued for 30 min. The reaction mixture was then concentrated to dryness. The residue was dissolved in DCM, washed with sat. aq. NaHCO$_3$, and the organic layer was concentrated. The residue was purified by silica gel column chromatography (80 g column, eluted with EtOAC/DCM 0-100% 25 min, then 0-10% MeOH/DCM, 25 min) to give Intermediate 8C (5.17 g, 79% yield).). HPLC: retention time=0.85 min (H$_2$O/ACN with 0.05% TFA, Waters Acquity HPLC BEH C18, 2.1×50 mm, 1.7-μm particles, gradient=2 min, wavelength=220 nm); MS (ES): m/z=596 [M+H]$^+$.

Preparation of Intermediate 8D:

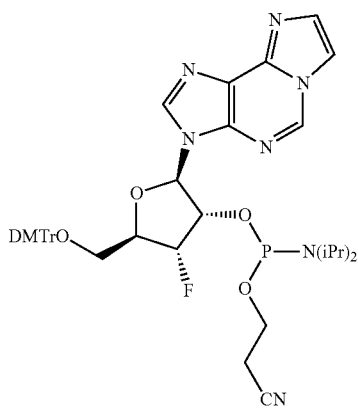

To a solution of Intermediate 8C (2.0 g, 3.36 mmol) in DCM (10 mL) was added 1.0 M 1H-imidazole-4,5-dicarbonitrile (2.35 mL, 2.35 mmol) in ACN, followed by 3-((bis(diisopropylamino)phosphanyl)oxy)propanenitrile (1.62 g, 5.37 mmol), and the reaction mixture was stirred at room temperature overnight. The reaction mixture was then diluted with DCM, washed with sat. NaHCO$_3$, dried with MgSO$_4$, filtered and concentrated. The residue was purified by silica gel column chromatography (column was pre-treated with 1% Et$_3$N in DCM) (40 g, EtOAc/Hexane=0-100%) to give Intermediate 8D (2.13 g, 80% yield). HPLC: retention time=1.16 and 1.22 min (H$_2$O/ACN with 10 mM NH$_4$OAc, Waters Acquity HPLC BEH C18, 2.1×50 mm, 1.7-μm particles, gradient=2 min, wavelength=220 nm); MS (ES): m/z=796 [M+H]+.

Preparation of Intermediate 8E:

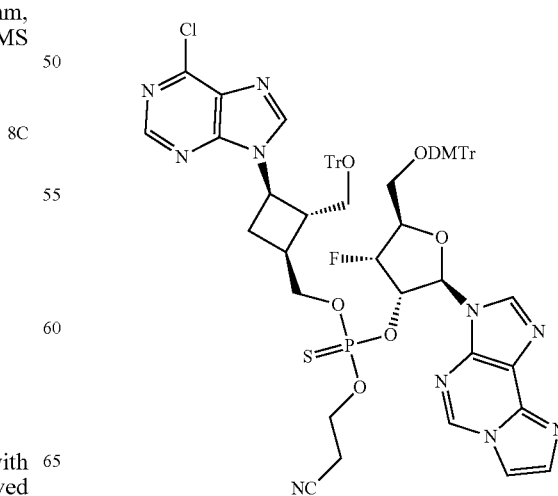

A solution of Intermediate 2H (250 mg, 0.489 mmol) and 1H-tetrazole (171 mg, 2.45 mmol) in MeCN (10 mL) was azeotroped three times, with the final azeotrope leaving about 6 mL of CH$_3$CN. The solution was dried by adding activated 4 Å (180 mg) molecular sieves and was left to stir under a N$_2$ atmosphere. In a separate flask, Intermediate 8D (580 mg, 0.73 mmol) was azeotroped with MeCN three times, with the final azeotrope leaving about 6 mL of CH$_3$CN. Activated 4 Å (180 mg) molecular sieves were then added. This solution was then transferred to the solution of Intermediate 2H by cannulae, and the flask was rinsed with dry MeCN (2×2 mL). The reaction was allowed to stirred at room temperature for 3 h, and then (E)-N,N-dimethyl-N'-(3-thioxo-3H-1,2,4-dithiazol-5-yl)formimidamide (201 mg, 0.978 mmol) was added and stirring was continued for 30 min. The reaction mixture was then allowed to sit overnight. The resulting mixture was then filtered and the filtrate was concentrated. The residue was dissolved in DCM, washed with sat. aq. NaHCO$_3$ and concentrated. The residue was then purified by flash silica gel chromatography (12 g, MeOH/DCM=0-10%) to give Intermediate 8E. HPLC: retention time=1.08 and 1.10 min (H$_2$O/ACN with 0.05% TFA, Waters Acquity HPLC BEH C18, 2.1×50 mm, 1.7-μm particles, gradient=2 min, wavelength=220 nm); MS (ES): m/z=1037 [M+H]$^+$.

Preparation of Intermediate 8F:

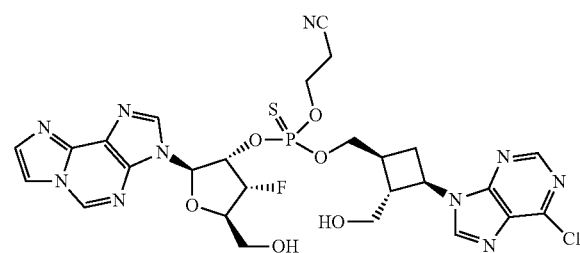

8F

To a solution of Intermediate 8E (770 mg, 0.62 mmol) in DCM (6 mL) was added MeOH (0.25 mL, 6.2 mmol) and 2,2-dichloroacetic acid (0.77 mL, 9.3 mmol) and the mixture was stirred at room temperature for 1.5 h. The reaction was then treated with pyridine (3 mL), concentrated and azeotroped with toluene two times. The resulting residue was loaded on celite and purified on a reverse phase C18 column (C18 100 g GOLD, H$_2$O/ACN=0-95% with 0.01 M NH$_4$OAc) to give 8F (170 mg, 39% yield). HPLC: retention time=0.62 min (H$_2$O/ACN with 0.05% TFA, Waters Acquity HPLC BEH C18, 2.1×50 mm, 1.7-μm particles, gradient=2 min, wavelength=220 nm); MS (ES): m/z=693.4 [M+H]$^+$.

Examples 8-1, 8-2, 8-3, and 8-4

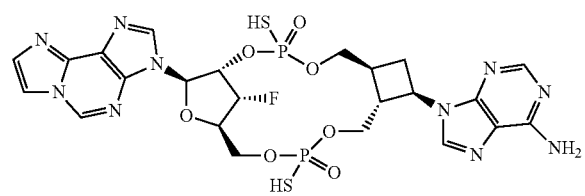 [SMILES: Nc1ncnc2c1ncn2[C@@H]1C[C@@H]2COP(=O)(S)O[C@@H]3[C@H](F)[C@@H](COP(=O)(S)OC[C@H]21)O[C@H]3n1cnc2c1ncn1ccnc21]

Intermediate 8F (170 mg, 0.25 mmol) was azeotroped with pyridine (15 mL), then dissolved in pyridine (50 mL) and concentrated to a volume of about 30 mL. The solution was cooled to 0° C. and a solution of diphenyl phosphonate (0.093 mL, 0.49 mmol) in pyridine (2 mL) was added very slowly over a period of 1.5 h. The mixture was stirred for 1 h after the addition was complete, and then (E)-N,N-dimethyl-N'-(3-thioxo-3H-1,2,4-dithiazol-5-yl)formimidamide (150 mg, 0.74 mmol) was added in one portion, and the mixture was stirred at room temperature overnight. The reaction mixture was then quenched with water (0.2 mL) and concentrated to dryness. The residue was dissolved in DCM/MeOH, dry loaded on celite, and purified on a C18 reverse phase column (50 G ISCO Gold, H$_2$O/ACN=0-70% with 0.01M NH$_4$OAc in 20 min) to give the cyclized intermediate. The intermediate was then treated with ammonium hydroxide (6 mL) and heated at 40° C. in a sealed 20 mL vial for 2 h, then concentrated. The crude material was purified via preparative LC/MS with the following conditions: Column: Agilent infinitylab Eclipse Plus C18 Column 21.2×250 mm, 5-μm particles; Mobile Phase A: water with 100-mM ammonium acetate; Mobile Phase B: MeOH; Gradient: 16-32% B over 20 minutes. 32%-95% B over 0.5 minute, then a 0.5 minute hold at 95% B; Flow: 20 mL/min. Fractions containing the desired products were concentrated to give four desired isomers.

Example 8-1

HPLC: Retention time=5.93 min (Agilent Eclipse Plus C18 Column 3.5 μm, 3×150 mm, 3.5 μm particles; Mobile Phase A: water with 20 mM ammonium acetate; Mobile Phase B: methanol. Gradient: 0% B to 50% B over 15 min, then 50% B to 95% B over 2 min; Flow: 0.5 mL/min; Detection: MS and UV (260 nm)) MS (ES): m/z=699 [M+H]$^+$.

Example 8-2

HPLC: Retention time=6.18 min (Agilent Eclipse Plus C18 Column 3.5 μm, 3×150 mm, 3.5 μm particles; Mobile Phase A: water with 20 mM ammonium acetate; Mobile Phase B: methanol. Gradient: 0% B to 50% B over 15 min, then 50% B to 95% B over 2 min; Flow: 0.5 mL/min; Detection: MS and UV (260 nm)) MS (ES): m/z=699 [M+H]$^+$.

Example 8-3

HPLC: Retention time=6.81 min (Agilent Eclipse Plus C18 Column 3.5 μm, 3×150 mm, 3.5 μm particles; Mobile Phase A: water with 20 mM ammonium acetate; Mobile Phase B: methanol. Gradient: 0% B to 50% B over 15 min, then 50% B to 95% B over 2 min; Flow: 0.5 mL/min; Detection: MS and UV (260 nm)) MS (ES): m/z=699 [M+H]$^+$.

Example 8-4

HPLC: Retention time=7.88 min (Agilent Eclipse Plus C18 Column 3.5 μm, 3×150 mm, 3.5 μm particles; Mobile Phase A: water with 20 mM ammonium acetate; Mobile Phase B: methanol. Gradient: 0% B to 50% B over 15 min, then 50% B to 95% B over 2 min; Flow: 0.5 mL/min; Detection: MS and UV (260 nm)) MS (ES): m/z=699 [M+H]$^+$.

Example 9

4-[(1R,6S,8R,9S,15R,17R,18R)-17-(6-amino-9H-purin-9-yl)-18-fluoro-3,12-dioxo-3,12-disulfanyl-2,4,11,13,16-pentaoxa-3λ⁵,12λ⁵-diphosphatricyclo[13.3.0.0⁶,⁹]octadecan-8-yl]pyridine-2-carboxamide Diastereomer 1

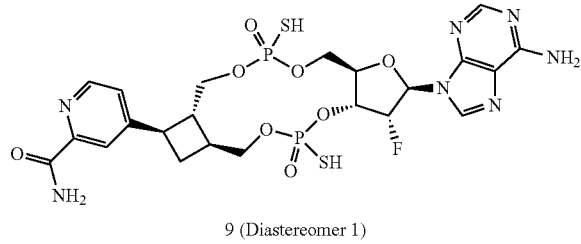 [SMILES: NC(=O)c1cc([C@@H]2C[C@@H]3COP(=O)(S)O[C@H]4[C@@H](F)[C@H](n5cnc6c(N)ncnc65)O[C@@H]4COP(=O)(S)OC[C@H]32)ccn1]

9 (Diastereomer 1)

Preparation of Intermediate 9A:

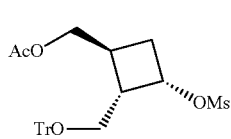

9A

Methanesulfonyl chloride (1.09 mL, 14.1 mmol) was added to a solution of Intermediate 1G (4.5 g, 10.8 mmol) and triethylamine (4.53 mL, 32.5 mmol) in DCM (20 mL) at 0° C. The mixture was stirred for 2 hours. The reaction mixture was then washed with saturated sodium bicarbonate, water, and brine, then dried over anhydrous sodium sulfate. It was then filtered and concentrated. The crude material was purified on an ISCO system (0-100% EtOAc/Hex, 40 g column, 30 min) to provided Intermediate 9A (5.42 g, 10.96 mmol, 100% yield). ¹H NMR (499 MHz, CHLOROFORM-d) δ 7.42-7.48 (m, 6H), 7.25-7.35 (m, 9H), 5.21 (dt, J=5.30, 7.00 Hz, 1H), 4.09-4.12 (m, 2H), 3.41 (dd, J=6.97, 9.60 Hz, 1H), 3.32 (dd, J=6.85, 9.60 Hz, 1H), 2.85 (s, 3H), 2.71-2.79 (m, 1H), 2.58 (td, J=5.96, 10.01 Hz, 1H), 2.41-2.50 (m, 1H), 2.25-2.32 (m, 1H), 2.06-2.07 (m, 3H). ¹³C NMR (126 MHz, CHLOROFORM-d) δ 171.0, 143.9, 128.7, 127.9, 127.1, 86.9, 74.3, 66.2, 61.2, 43.4, 38.1, 32.5, 31.3, 20.9.

Preparation of Intermediate 9B and 9C:

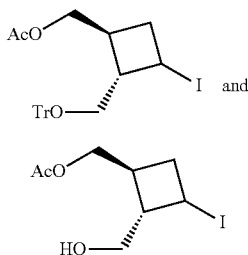

9B and

9C

To a solution of 9A (5.36 g, 10.8 mmol) in acetone (43 mL) was added sodium iodide (6.50 g, 43.0 mmol) and the resulting mixture was heated to reflux for one week under an argon atmosphere. The reaction mixture was then diluted with Et₂O (12 mL) and the resulting solids were filtered, and the filtrate was concentrated. The crude material was purified on an ISCO system (12 g column, 0-60% EtOAc/Hex, 30 min @ 20 mL/min) to provide Intermediate 9B (3.27 g, 6.21 mmol, 57% yield). LCMS, [M+H]⁺=549.08 and 9C (1 g, 3.52 mmol, 32.5% yield)

Preparation of Intermediate 9D:

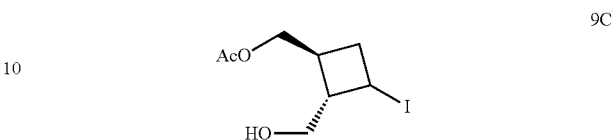

9C

To a solution of Intermediate 9B (3.4 g, 6.46 mmol) in DCM (30 mL) was added triethylsilane (10.32 mL, 64.6 mmol) and then 2,2-dichloroacetic acid (3.16 mL, 38.8 mmol). The mixture was stirred for 2 hours and then the solvent was removed. The residue was dissolved in MeOH and filtered. The crude product was purified on an ISCO system (80 g, 0-100% EtOAc/Hex, 40 min.) to provide 9D (1.28 g, 4.51 mmol, 70% yield).

Preparation of Intermediate 9E

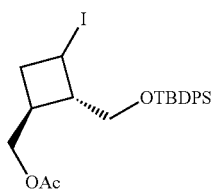

9E

To a solution of Intermediate 9D (1190 mg, 4.18 mmol) in pyridine (1.7 mL) was added imidazole (854 mg, 12.6 mmol) and then TBDPS-Cl (2.3 g, 8.4 mmol). The mixture was stirred for 2 hours at room temperature. The pyridine was removed and then the residue was treated with DCM (20 mL) and filtered. The filtrate was concentrated to dryness and then purified on an ISCO system (24 g, 0-50% EtOAc/Hex, 30 min) to provide a 9E (2.17 g, 4.15 mmol, 99% yield). ¹H NMR (499 MHz, CHLOROFORM-d) δ 7.65-7.71 (m, 4H), 7.40-7.48 (m, 6H), 7.28 (s, 1H), 4.37-4.43 (m, 1H), 4.06 (d, J=5.13 Hz, 2H), 3.68 (dd, J=3.16, 11.15 Hz, 1H), 3.55 (dd, J=3.22, 11.21 Hz, 1H), 2.66-2.75 (m, 3H), 2.28 (br dd, J=2.15, 9.42 Hz, 1H), 2.03-2.04 (m, 3H), 1.29 (br s, 1H), 1.07-1.13 (m, 9H).

Preparation of Intermediate 9F:

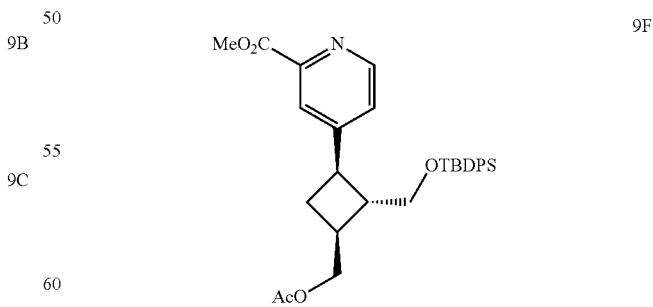

9F

Methyl 4-bromopicolinate (1.22 g, 5.63 mmol), Intermediate 9E (2.10 g, 4.02 mmol), tris (trimethylsilyl)silane (1.86 mL, 6.03 mmol), Ir(dF(CF₃)ppy)₂(dtbbpy)PF₆ (0.090 g, 0.080 mmol), and Na₂CO₃ (1.278 g, 12.06 mmol) were placed in a teflon screw cap vial with a stir bar. DME (35 mL) was added and the suspension was degassed with nitrogen for 5 minutes. To a separate vial was added nickel (II) chloride ethylene glycol dimethyl ether complex (0.088 g, 0.40 mmol) and 4,4'-di-tert-butyl-2,2'bipyridine (0.13 g, 0.48 mmol), which was evacuated and backfilled with nitrogen, followed by addition of 10 mL of DME. This solution was then degassed with nitrogen for 10 minutes. The resulting solution was added to the first vial and then it was further degassed with nitrogen for an additional 10 minutes. The resulting suspension was placed approximately 8 cm from a 34 W Blue LED, with the LED shining directly at the side of the vial. The reaction was then stirred for 15 hours. The reaction mixture was then filtered and poured into a mixture of ethyl acetate and water (100 mL) and DCM (100 mL). The water layer was extracted 2 times with DCM and then the combined organic layers were washed with brine, dried with $Na_2SO_4$, filtered and concentrated. The crude product was purified on an ISCO system (40 g column, 0-100% EtOAc/Hex, 30 min) to provide Intermediate 9F (1.53 g, 2.88 mmol, 71.6% yield). m/z 532.5 (M+H).

Preparation of Intermediate 9G:

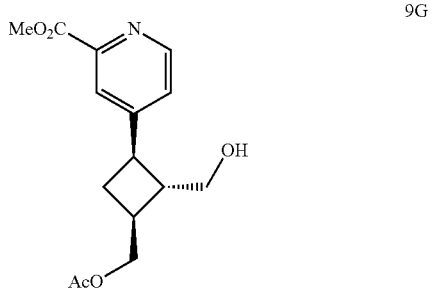 [SMILES: COC(=O)c1cc([C@@H]2C[C@H](COC(C)=O)[C@H]2CO)ccn1]

To Intermediate 9F (1530 mg, 2.88 mmol) was added triethylamine trihydrofluoride (3000 µl, 18.42 mmol) and the mixture was stirred at 37° C. under a nitrogen atmosphere for 2 hours. The reaction mixture was then diluted with $CH_3CN$ (6 mL) and quenched with $Et_3N$ (3850 µl, 27.6 mmol) and then isopropoxytrimethylsilane (9810 µl, 55.2 mmol). The mixture was stirred at room temperature for 10 min, and then concentrated in vacuo. The residue was purified by column chromatography using a 40 g ISCO column eluting with 0-60% ethyl acetate in hexane (20 min) and then 10% MeOH/DCM (10 min) to provide Intermediate 9G (700 mg, 2.39 mmol, 83% yield). $^1$H NMR (499 MHz, CHLOROFORM-d) δ 8.66 (d, J=5.01 Hz, 1H), 8.04 (s, 1H), 7.37 (dd, J=1.73, 4.95 Hz, 1H), 7.28 (s, 1H), 4.21 (dd, J=4.71, 11.27 Hz, 1H), 4.10 (dd, J=6.02, 11.38 Hz, 1H), 4.03 (s, 3H), 3.73-3.83 (m, 2H), 3.27-3.37 (m, 1H), 2.43-2.57 (m, 3H), 2.11 (s, 3H), 1.93 (dd, J=1.49, 9.95 Hz, 1H), 1.72 (t, J=5.07 Hz, 1H). m/z 294.3 (M+H).

Preparation of Intermediate 9H:

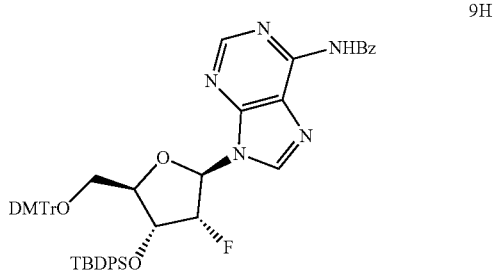

To a cooled (0° C.) solution of N-(9-((2R,3R,4R,5R)-5-((bis(4-methoxyphenyl)(phenyl)methoxy)methyl)-3-fluoro-4-hydroxytetrahydrofuran-2-yl)-9H-purin-6-yl)benzamide (Astatech, 500 mg, 0.740 mmol) and imidazole (151 mg, 2.20 mmol) in DMF (3.7 mL) was added tert-butyldiphenylchlorosilane (285 µl, 1.11 mmol) dropwise via syringe. The ice-water bath was then removed and the reaction was stirred at room temperature under a nitrogen atmosphere. After 22 hours, a second portion of imidazole (50.4 mg, 0.740 mmol) and tert-butyldiphenylchlorosilane (95 µl, 0.370 mmol) was added to the reaction. After 3 additional hours, a third portion of imidazole (50.4 mg, 0.740 mmol) and tert-butyldiphenylchlorosilane (95 µl, 0.370 mmol) was added to the reaction and the mixture was stirred for 24 hours. The reaction was then quenched with methanol (748 µL, 18.50 mmol), stirred at room temperature for 30 min, and then concentrated in vacuo. The remaining volatiles were removed under a stream of nitrogen. The residue was partitioned between EtOAc (20 mL) and water (20 mL), and the layers were separated. The aqueous phase was extracted with EtOAc (1×20 mL), and the combined organic layers were washed with water (4×10 mL), brine (10 mL), and dried ($Na_2SO_4$), filtered, and concentrated under reduced pressure. The crude Intermediate 9H was carried into the next step without further purification. LCMS, $[M+H]^+$=914.

Preparation of Intermediate 9I

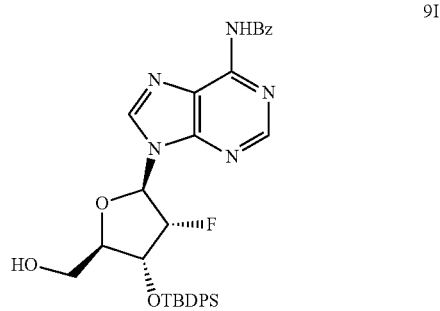

To a solution of Intermediate 9H (680 mg, 0.74 mmol) and triethylsilane (295 µL, 1.85 mmol) in $CH_2Cl_2$ (3.7 mL) was added trifluoroacetic acid (114 µL, 1.480 mmol) dropwise via syringe, resulting in a reddish color. The reaction was stirred at room temperature under a nitrogen atmosphere. After 1.5 hours, the reaction was treated with MeOH (4 mL) and stirred for 10 min. The mixture was then concentrated under reduced pressure and azeotroped twice with MeOH (4 mL). The crude product was dissolved in a small amount of $CH_2Cl_2$, adsorbed onto a plug of $SiO_2$, and purified by flash chromatography ($SiO_2$, 40 g column, 0-50% acetone/hexanes, 14.4 min gradient then a 14.4 min hold, 40 mL/min) to afford Intermediate 9I (384 mg, 85% yield) as a white solid. LCMS, $[M+H]^+$=612. $^1$H NMR (500 MHz, CHLOROFORM-d) δ 8.71 (s, 1H), 8.15 (s, 1H), 8.05-7.99 (m, 2H), 7.74-7.66 (m, 4H), 7.65-7.59 (m, 1H), 7.56-7.51 (m, 2H), 7.50-7.37 (m, 6H), 6.27 (dd, J=11.3, 6.8 Hz, 1H), 5.62 (ddd, J=51.8, 6.7, 4.8 Hz, 1H), 4.70-4.62 (m, 1H), 4.13 (br s, 1H), 3.68 (d, J=13.1 Hz, 1H), 3.10 (dd, J=13.1, 1.6 Hz, 1H), 1.17 (s, 9H).

Preparation of Intermediate 9J:

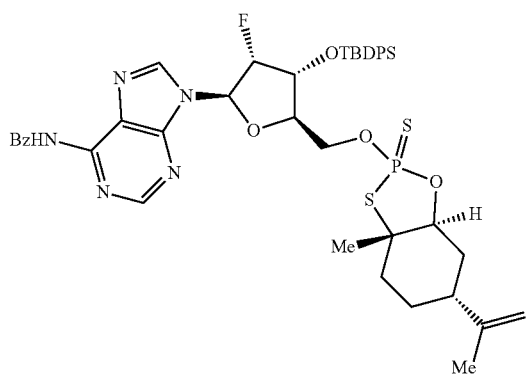

A mixture of Intermediate 9I (1.0 g, 1.64 mmol) and Reagent 3 (1.1 g, 2.45 mmol) in MeCN (15 mL) was cooled to an internal temperature of 0° C. DBU (0.4 mL, 2.45 mmol) was added in one portion and the mixture was stirred at 0° C. for 30 min. To the reaction mixture was added acetic acid (281 µL, 4.90 mmol) at 0° C., and then silica gel was added and the mixture was concentrated. The crude product was purified by ISCO silica gel chromatography (80 g, 0-10% gradient MeOH/DCM). Fractions containing the desired product were concentrated to a white foam which was co-evaporated with heptane (3×50 mL) to afford Intermediate 9J (1.22 g, 87% yield) as a white solid. LCMS, [M+H]$^+$=858.8: $^1$H NMR (499 MHz, CHLOROFORM-d) δ 8.95 (s, 1H), 8.69 (s, 1H), 8.07 (s, 1H), 7.99-8.04 (m, 2H), 7.69-7.74 (m, 4H), 7.61-7.66 (m, 1H), 7.38-7.57 (m, 9H), 7.28 (s, 2H), 6.32 (d, J=2.03 Hz, 1H), 6.28-6.38 (m, 1H), 4.95 (dd, J=2.09, 4.23 Hz, 1H), 4.85 (dd, J=2.15, 4.29 Hz, 1H), 4.81-4.98 (m, 1H), 4.62-4.71 (m, 2H), 4.58-4.61 (m, 1H), 4.43 (br s, 1H), 4.25-4.37 (m, 2H), 4.15 (ddd, J=4.23, 9.33, 11.59 Hz, 1H), 2.51 (br s, 1H), 2.20-2.26 (m, 1H), 1.99-2.06 (m, 5H), 1.81-1.91 (m, 3H), 1.65-1.75 (m, 5H), 1.23-1.32 (m, 1H), 1.16 (s, 9H).

Preparation of Intermediate 9K:

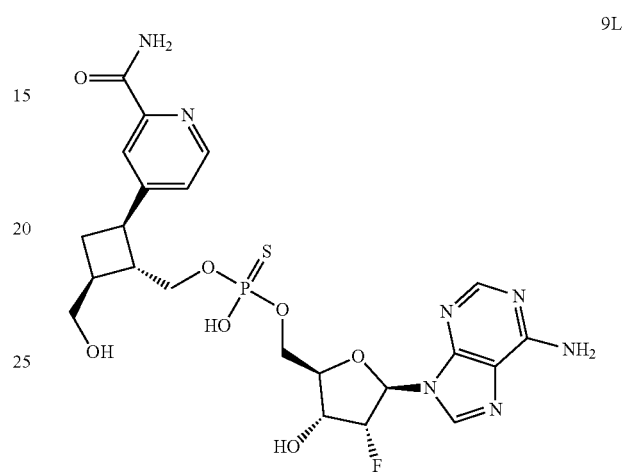

To a solution of Intermediate 9G (200 mg, 0.682 mmol) and Intermediate 9J (1170 mg, 1.364 mmol) in acetonitrile (14 mL) was added DBU (308 µl, 2.05 mmol) dropwise to give a pale yellow solution. After 10 min, the reaction mixture was diluted with DCM (5 mL) and treated with acetic acid (195 µL, 3.40 mmol). The resulting mixture was co-evaporated with silica gel and then purified by flash chromatography over 40 g of silica gel, eluting with 0-15% MeOH/DCM to afford Intermediate 9K (595 mg, 81% yield) as white solid. LCMS, [M+H]$^+$=983.08. $^{31}$P NMR (162 MHz, CHLOROFORM-d) δ 57.9 (s, 1P).

Preparation of Intermediate 9L:

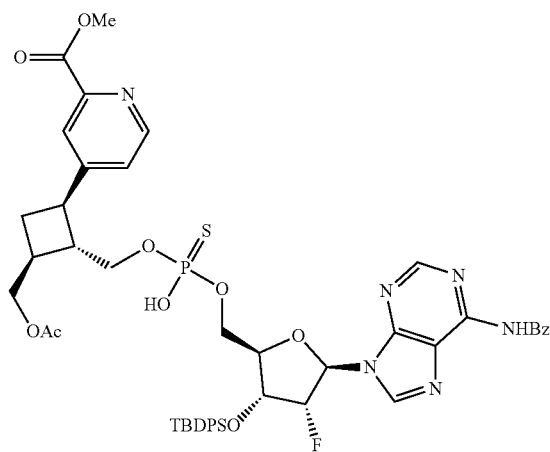

To Intermediate 9K, (600 mg, 0.61 mmol) was added ammonia in MeOH (8 mL, 56.0 mmol, 7N). The mixture was heated to 53° C. for 14 hours. The NH$_3$/MeOH was removed and then triethylamine trihydrofluoride (2.5 mL, 15.4 mmol) was added and the mixture was heated to 37° C. for 5 hrs. The reaction mixture was the diluted with CH$_3$CN (4 mL) and treated with Et$_3$N (1927 µl, 13.83 mmol) and isoprpoxytrimethylsilane (4910 µl, 27.7 mmol). The mixture was stirred at room temperature for 10 min. and then concentrated under reduced pressure. The crude product was dissolved in a small amount of MeOH, adsorbed onto a plug of Celite and then purified on an ISCO system (SiO$_2$, 50 g RediSep Rf Gold column, 0-35% water/acetonitrile containing 10 mM ammonium acetate, 5 min gradient, (0%) 0-35%, 30 min, 30 mL/min) to afford 9L (284 mg, 0.49 mmol, 80% yield). LCMS, [M+H]$^+$=584.5.

Example 9

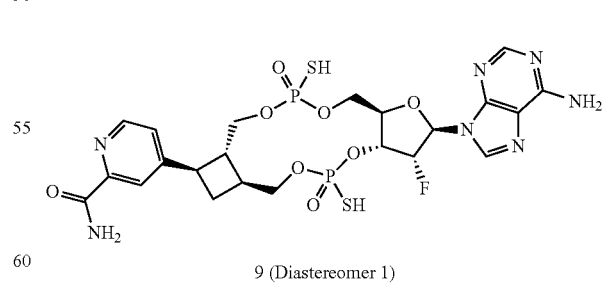

9 (Diastereomer 1)

To an anhydrous solution of 9L (183 mg, 0.314 mmol) in pyridine (30 mL) was added DBU (710 µl, 4.70 mmol). The mixture was stirred for 10 min and then Reagent 4 (210 mg, 0.470 mmol) in 2 mL of MeCN was added dropwise over 30 min. The mixture was then stirred for another 30 min. The pyridine was removed and the residue was washed with cold ether. The crude product was then purified by Preparative HPLC Chromatography: Instrument: Waters Autopure; Column:Xselect RP Prep C18 OBD Column, 5 μm, 10×250 mm; Flow rate: 25.0 mL/min; Mobile Phase: A: 0.1% FA in water; B: 0.1% FA in ACN (% A=100-% B): gradient 5-35% B over 10 min, 35-100% B over 1 min, to afford Example 9 (48 mg, 0.069 mmol, 21.98% yield). LCMS, $[M+H]^+$ =662.08. $^1$H NMR (499 MHz, DEUTERIUM OXIDE) δ 8.59 (d, J=5.60 Hz, 1H), 8.49 (s, 1H), 8.34 (s, 1H), 8.18 (s, 1H), 7.84 (d, J=5.64 Hz, 1H), 6.44-6.52 (m, 1H), 5.53-5.66 (m, 1H), 5.06-5.16 (m, 1H), 4.35-4.50 (m, 2H), 4.08-4.22 (m, 2H), 3.87-4.04 (m, 3H), 3.48 (q, J=9.18 Hz, 1H), 2.66-2.73 (m, 1H), 2.56-2.64 (m, 1H), 2.41-2.49 (m, 1H), 1.99-2.09 (m, 1H). $^{31}$P NMR (202 MHz, DEUTERIUM OXIDE) δ 55.25 (s, 1P), 55.12 (s, 1P), 55.10 (s, 1P), 55.07 (s, 1P).

Example 10

4-[(1R,6S,8R,9S,15R,17R,18R)-17-(6-amino-9H-purin-9-yl)-18-fluoro-3,12-dioxo-3,12-disulfanyl-2,4,11,13,16-pentaoxa-3λ$^5$,12λ$^5$-diphosphatricyclo[13.3.0.0$^{6,9}$]octadecan-8-yl]pyridine-2-carboxamide Diastereomer 2

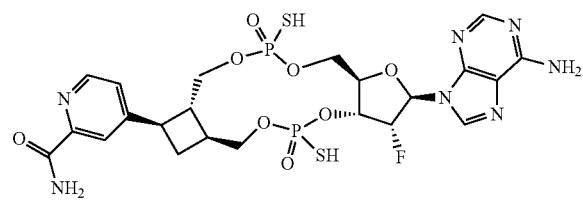

10 (Diastereomer 2)

Example 10 was prepared from 9L, according to procedures analogous to those outlined in Example 9 above using Reagent 3 in the final step. LCMS, $[M+H]^+$=662.3. $^1$H NMR (499 MHz, METHANOL-d$_4$) δ 8.61-8.66 (m, 1H), 8.46-8.54 (m, 1H), 8.21 (s, 1H), 7.99-8.05 (m, 1H), 7.46-7.55 (m, 1H), 6.30-6.42 (m, 1H), 5.48-5.66 (m, 1H), 5.18-5.30 (m, 1H), 4.50-4.59 (m, 1H), 4.39-4.48 (m, 1H), 4.23-4.32 (m, 2H), 3.92-4.10 (m, 2H), 3.52-3.63 (m, 2H), 2.55-2.72 (m, 2H), 2.35-2.53 (m, 2H). $^{31}$P NMR (202 MHz, METHANOL-d$_4$) δ 58.0 (s, 1P), 56.0 (s, 1P).

Example 11

4-[(1R,6S,8R,9S,15R,17R,18S)-17-(6-amino-9H-purin-9-yl)-18-fluoro-3,12-dioxo-3,12-disulfanyl-2,4,11,13,16-pentaoxa-3λ$^5$,12λ$^5$-diphosphatricyclo[13.3.0.0$^{6,9}$]octadecan-8-yl]pyridine-2-carboxamide

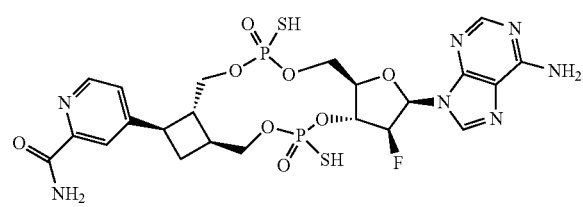 [SMILES: NC(=O)c1cc([C@@H]2C[C@@H]3COP(=O)(O)O[C@H]4[C@@H](F)[C@H](n5cnc6c(N)ncnc65)O[C@@H]4COP(=O)(O)OC[C@H]32)ccn1]

11 (Diastereomer 1)

Example 11, shown above, was prepared according to procedures analogous to those outlined in Example 9, starting from Intermediate 9G and N-(9-((2R,3S,4R,5R)-5-((bis(4-methoxyphenyl)(phenyl)methoxy)methyl)-3-fluoro-4-hydroxytetrahydrofuran-2-yl)-9H-purin-6-yl)benzamide (CAS 226415-08-3, BLDPHARM), using Reagent 3 for the first coupling step and Reagent 4 for the cyclization step. LCMS, $[M+H]^+$=662.1. $^1$H NMR (499 MHz, METHANOL-d$_4$) δ 8.56 (d, J=4.9 Hz, 1H), 8.43 (d, J=2.6 Hz, 1H), 8.33 (s, 1H), 8.08-8.03 (m, 1H), 7.71 (dd, J=5.0, 1.2 Hz, 1H), 6.70-6.55 (m, 1H), 5.70-5.69 (m, 1H), 5.58-5.40 (m, 1H), 5.25-5.05 (m, 1H), 4.50-4.35 (m, 2H), 4.21-4.09 (m, 3H), 4.06-3.95 (m, 2H), 3.37-3.35 (m, 1H), 3.31-3.29 (m, 1H), 2.94-2.85 (m, 1H), 2.62-2.53 (m, 1H). $^{31}$P NMR (202 MHz, METHANOL-d$_4$) δ 59.2 (s, 1P), 56.3 (s, 1P). $^{19}$F NMR (470 MHz, METHANOL-d$_4$) δ −197.97 (s, 1F).

Example 12

4-[(1R,6S,8R,9S,15R,17R,18R)-17-(6-amino-9H-purin-9-yl)-18-fluoro-3,12-dihydroxy-3,12-dioxo-2,4,11,13,16-pentaoxa-3λ$^5$,12λ$^5$-diphosphatricyclo[13.3.0.0$^{6,9}$]octadecan-8-yl]pyridine-2-carboxamide

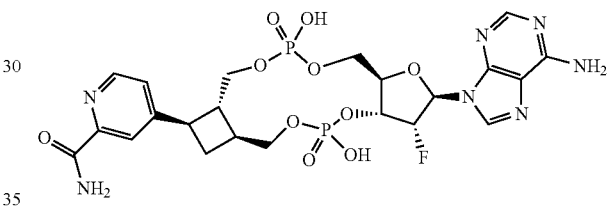

Preparation of Intermediate 12A:

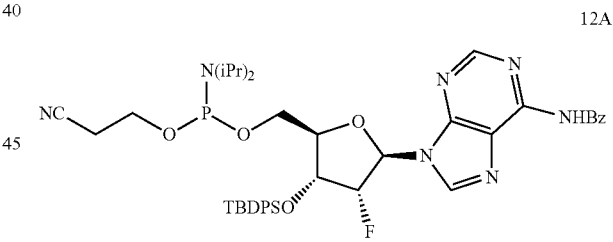

12A

To a solution of Intermediate 9I (725 mg, 1.19 mmol) in DCM (12 mL) was added a solution of 1H-imidazole-4,5-dicarbonitrile (0.95 mL, 0.95 mmol, 1M) in ACN. Then, a solution of 3-((bis(diisopropylamino)phosphanyl)oxy) propanenitrile (714 mg, 2.37 mmol) in DCM (1 mL) was added to the reaction mixture dropwise. The reaction mixture was stirred for 3 hours at room temperature and then quenched with MeOH (2 mL). The mixture was then diluted with saturated aq. sodium bicarbonate (50 mL) and diluted with DCM (50 mL). The organic layer was dried (Na$_2$SO$_4$), filtered and concentrated. The crude product was dissolved in a small amount of DCM, charged onto a 40 g ISCO silica gel column and purified using a Teledyne ISCO system, eluting over 10 minutes, 0-50% gradient; Solvent A: DCM with 0.25% TEA; Solvent B: EtOAc to give Intermediate 12A (820 mg, 1.02 mmol, 85% yield) as a mixture of diastereomers. LCMS, $[M+H]^+$=813.8.

Preparation of Intermediate 12B:

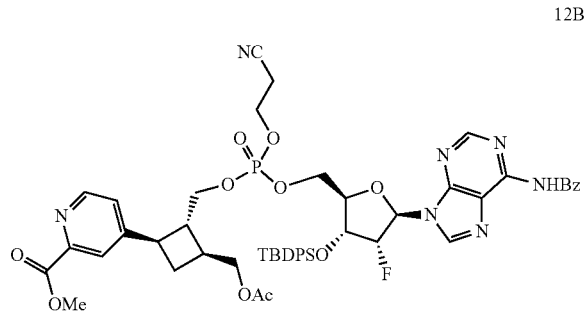

A mixture of Intermediate 9G (200 mg, 0.68 mmol) and 1H-tetrazole (143 mg, 2.05 mmol) in dry ACN (6 mL) was concentrated to dryness (repeated two times). Intermediate 12A (690 mg, 0.85 mmol) was dissolved in ACN (5 mL) and concentrated to dryness (repeated two times). Then, 3 Å molecular sieves (0.5 g) and acetonitrile (5 mL) were added to Intermediate 12A, and this solution was then added to Intermediate 9G in dry ACN (6 mL). The reaction mixture was stirred at room temperature for 90 minutes and then 2-butanone peroxide (0.55 mL, 2.7 mmol) was added. The reaction was stirred for 2 hours at room temperature. The reaction was then filtered through celite and concentrated under reduced pressure. The crude product was dissolved in a small amount of DCM, charged onto a 40 g ISCO silica gel column and purified using a Teledyne ISCO system, eluting over a 35 minute, 0-10% gradient; Solvent A: DCM; Solvent B: EtOAc to give Intermediate 12B (612 mg, 0.6 mmol, 88% yield). m/z 1020.8 (M+H).

Preparation of Intermediates 12C and 12D:

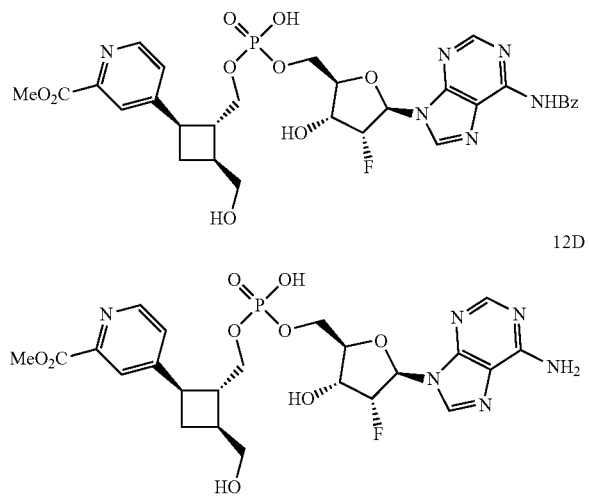

To a solution of Intermediate 12B (0.610 g, 0.60 mmol) in anhydrous MeOH (12 mL) was added potassium carbonate (0.250 g, 1.8 mmol). The resulting mixture was stirred at 0° C. under a nitrogen atmosphere overnight. The reaction mixture was then neutralized to pH=7 with acetic acid (0.14 mL, 2.4 mmol) and then the solvent was evaporated. To the crude material was added triethylamine trihydrofluoride (3 mL, 18 mmol) and the mixture was stirred at 37° C. under a nitrogen atmosphere for 4 hours. The reaction mixture was then diluted with ACN (4 mL) and treated with triethylamine (7.70 mL, 55.3 mmol) and isopropoxytrimethylsilane (4.79 mL, 27.0 mmol). The mixture was stirred at room temperature for 10 minutes and then concentrated in vacuo. The crude product was dissolved in a small amount of MeOH, adsorbed onto a plug of Celite purified by hydrophilic interaction liquid chromatography (SiO$_2$, 50 g RediSep Rf Gold column, 0-35% water/acetonitrile containing 10 mM ammonium acetate, 5 min gradient, (0%) 0-35%, 30 min, 30 mL/mim) to afford two products: Intermediate 12C (250 mg, 30.3% yield). m/z 687.6 (M+H) and Intermediate 12D (175 mg, 25% yield). m/z 583.6 (M+H). $^1$H NMR (499 MHz, METHANOL-d$_4$) δ 8.72 (br s, 2H), 8.57 (d, J=5.01 Hz, 1H), 8.45 (d, J=4.77 Hz, 1H), 8.09 (br d, J=6.91 Hz, 2H), 7.97 (s, 1H), 7.63-7.71 (m, 1H), 7.50-7.63 (m, 3H), 6.45 (br d, J=16.09 Hz, 1H), 5.52 (br s, 1H), 5.37-5.57 (m, 1H), 5.41 (br s, 1H), 4.57-4.78 (m, 1H), 4.19-4.32 (m, 2H), 4.10-4.19 (m, 1H), 3.93 (s, 3H), 3.69 (d, J=5.60 Hz, 1H), 3.46-3.63 (m, 2H), 3.34-3.39 (m, 1H), 3.19-3.32 (m, 1H), 2.31-2.53 (m, 3H), 2.04 (s, 1H), 1.83-2.00 (m, 3H).

Preparation of Intermediate 12E:

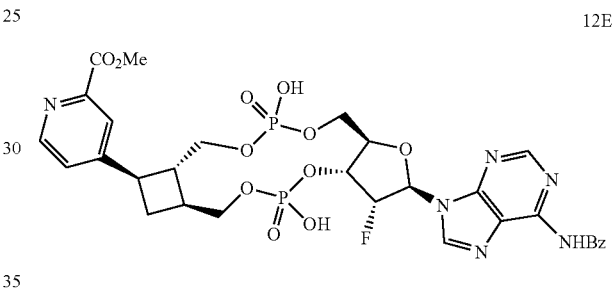

To a room temperature solution of Intermediate 12C (200 mg, 0.29 mmol) in pyridine (26 mL) was added a solution of diphenyl phosphonate (0.11 mL, 0.38 mmol) in DCM (1 mL) dropwise over 20 minutes. To this reaction mixture was added an iodine solution in THF/H$_2$O (305 mg, 0.04 M) and the mixture was stirred at room temperature for 20 min. The reaction mixture was then concentrated under reduced pressure. The resulting residue was purified on a reverse phase ISCO Gold 50 g C18 column (Mobile Phase A: 5:95 acetonitrile:water with 0.01M ammonium acetate; Mobile Phase B: 95:5 acetonitrile:water with 0.01M ammonium acetate; Gradient: 0% 7 min, 0-40% B gradient over 23 min) to afford Intermediate 12E (70 mg, 0.094 mmol, 32% yield) as white solid. LCMS, [M+H]$^+$=749.5.

Example 12

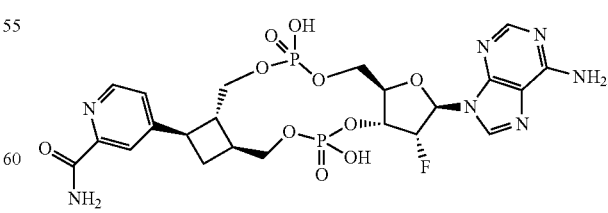

Intermediate 12E (70 mg, 0.094 mmol) was treated with ammonia (5 mL, 35.0 mmol, 7N) and the reaction mixture was stirred for 1.5 h at 55° C. The reaction mixture was then concentrated and the crude product was purified by Preparative HPLC (Chromatographic Conditions: Instrument: Waters Autopure; Column: Luna Omega Polar C18 Column, 5 μm, 21.2×250 mm; Flow rate: 20.0 mL/min; Mobile Phase: A: 100 mM NH$_4$OAc (pH:6.5) in H$_2$O; B: MeOH (% A=100-% B): gradient 0-31% B over 10.5 min, 31-95% B over 0.5 min, 95% B hold for 1 min and 95-0% B for 0.5 min) to afford Example 12 (32 mg, 0.05 mmol, 49% yield). LCMS, [M+H]$^+$=630.5. $^1$H NMR (499 MHz, METHANOL-d$_4$) δ 8.59 (s, 1H), 8.51 (d, J=5.01 Hz, 1H), 8.20 (s, 1H), 7.99 (s, 1H), 7.52 (br d, J=4.77 Hz, 1H), 6.37 (d, J=16.09 Hz, 1H), 5.51 (d, J=3.93 Hz, 1H), 5.41 (d, J=3.93 Hz, 1H), 5.37-5.55 (m, 1H), 4.92-5.03 (m, 1H), 4.49 (br d, J=11.92 Hz, 1H), 4.39 (br d, J=8.46 Hz, 1H), 4.19-4.31 (m, 1H), 4.06-4.17 (m, 1H), 3.87-4.01 (m, 2H), 3.34-3.47 (m, 1H), 2.62-2.75 (m, 2H), 2.38 (td, J=8.23, 10.25 Hz, 1H). $^{31}$P NMR (202 MHz, METHANOL-d$_4$) δ −0.12 (s, 1P), −0.78 (s, 1P).

Example 13

4-[(1R,6S,8R,9S,15R,17R,18R)-17-(6-amino-9H-purin-9-yl)-18-fluoro-12-hydroxy-3,12-dioxo-3-sulfanyl-2,4,11,13,16-pentaoxa-3λ$^5$,12λ$^5$-diphosphatricyclo[13.3.0.0$^{6,9}$]octadecan-8-yl]pyridine-2-carboxamide

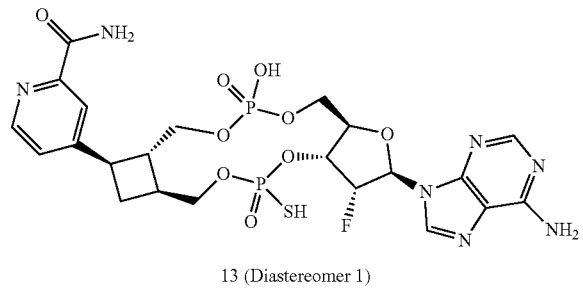 [SMILES: NC(=O)c1cc([C@@H]2C[C@@H]3COP(=O)(S)O[C@H]4[C@@H](F)[C@H](n5cnc6c(N)ncnc65)O[C@@H]4COP(=O)(O)OC[C@H]32)ccn1]

13 (Diastereomer 1)

To an anhydrous solution of Intermediate 12D (88 mg, 0.15 mmol)) in pyridine (15 mL) was added DBU (342 μl, 2.27 mmol). The mixture was stirred for 10 min and then Reagent 4 (110 mg, 0.24 mmol) in 2 mL of DCM was added dropwise over 30 min. The mixture was then stirred for another 30 min. at room temperature. The pyridine was removed under reduce pressure and the residue was washed with cold ether. The crude product was then heated with 4 mL of 7N NH$_3$ in MeOH at 55° C. for 5 hours. The solvent was evaporated and the crude material was purified by Preparative HPLC (Chromatographic Conditions: Instrument: Waters Autopure; Column: Zorbax Eclipse C18 plus Column, 5 μm, 21.2×250 mm; Flow rate: 20.0 mL/min; Mobile Phase: A: 100 mM NH$_4$OAc (pH:6.5); B: ACN (% A=100-% B): gradient 5-40% B over 14 min, 40-95% B over 0.5 min.) to afford Example 13 (47 mg, 43% yield). LCMS, [M+H]$^+$=646.45. $^1$H NMR (499 MHz, METHANOL-d$_4$) δ 8.62 (s, 1H), 8.51 (d, J=5.01 Hz, 1H), 8.21 (s, 1H), 7.97 (s, 1H), 7.53 (br d, J=4.89 Hz, 1H), 6.35-6.41 (m, 1H), 5.37-5.53 (m, 1H), 5.05-5.16 (m, 1H), 4.40-4.49 (m, 2H), 4.14-4.32 (m, 3H), 3.91-4.07 (m, 2H), 3.34-3.50 (m, 1H), 2.69 (br s, 2H), 2.32-2.43 (m, 1H), 1.94-1.98 (m, 1H). $^{31}$P NMR (202 MHz, METHANOL-d$_4$) δ 56.95 (s, 1P), −0.02 (s, 1P).

Example 14

4-[(1R,6S,8R,9S,15R,17R,18R)-17-(6-amino-9H-purin-9-yl)-18-fluoro-12-hydroxy-3,12-dioxo-3-sulfanyl-2,4,11,13,16-pentaoxa-3λ$^5$,12λ$^5$-diphosphatricyclo[13.3.0.0$^{6,9}$]octadecan-8-yl]pyridine-2-carboxamide

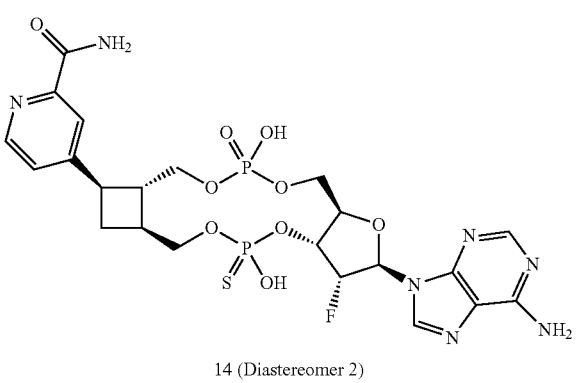 [SMILES: NC(=O)c1cc([C@@H]2C[C@@H]3COP(O)(=S)O[C@H]4[C@@H](F)[C@H](n5cnc6c(N)ncnc65)O[C@@H]4COP(=O)(O)OC[C@H]32)ccn1]

14 (Diastereomer 2)

Example 14, shown above, was prepared from Intermediate 12D, according to procedures analogous to those outlined in Example 13 above using Reagent 3 for the cyclization step. LCMS, [M+H]$^+$=646.45. $^1$H NMR (499 MHz, METHANOL-d$_4$) δ 8.64 (s, 1H), 8.52 (d, J=5.01 Hz, 1H), 8.23 (s, 1H), 8.00 (s, 1H), 7.52 (d, J=5.02 Hz, 1H), 6.34-6.43 (m, 1H), 5.42-5.59 (m, 1H), 5.25-5.37 (m, 1H), 4.39-4.49 (m, 1H), 4.25-4.37 (m, 2H), 4.05-4.14 (m, 1H), 3.98-4.04 (m, 1H), 3.92 (td, J=3.67, 11.03 Hz, 1H), 3.39-3.49 (m, 1H), 3.34-3.38 (m, 1H), 2.67-2.80 (m, 1H), 2.53-2.67 (m, 1H), 2.37 (td, J=8.11, 10.01 Hz, 1H), 1.72-1.89 (m, 1H). $^{31}$P NMR (202 MHz, METHANOL-d$_4$) δ 58.36 (s, 1P), −0.09 (s, 1P).

Examples 15-1 and 15-2

4-[(1S,7S,8R,10S,16R,17R)-17-(6-amino-9H-purin-9-yl)-4,13-dioxo-4,13-disulfanyl-3,5,12,14-tetraoxa-4λ$^5$,13λ$^5$-diphosphatricyclo[14.2.0.0$^{7,10}$]octadecan-8-yl]pyridine-2-carboxamide

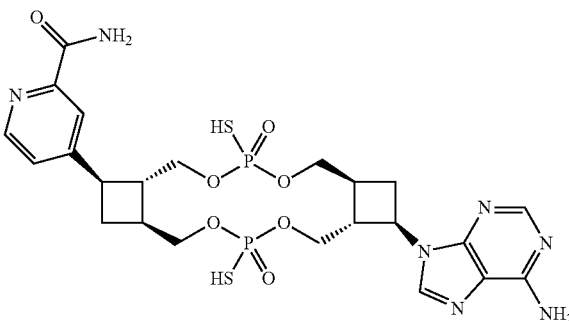

Diastereomer 1 (15-1)
Diastereomer 2 (15-2)

Preparation of Intermediate 15A:

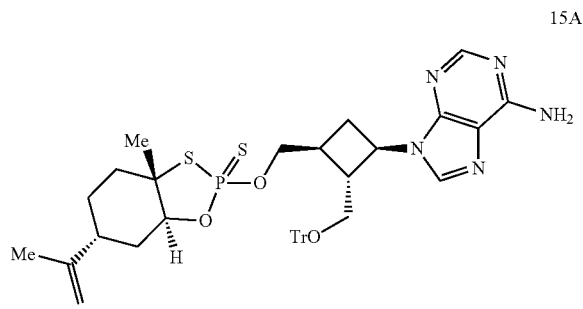

A suspension of Intermediate 2M (250 mg, 0.51 mmol) and Reagent 3 (295 mg, 0.661 mmol) in THF (5 mL) was cooled to an internal temperature of 0° C. DBU (0.1 mL, 0.66 mmol) was added dropwise, and the mixture was stirred at 0° C. for 10 min. To the reaction mixture was added acetic acid (116 µL, 2.0 mmol) at 0° C., and then silica gel was added and the mixture was concentrated. The crude product was purified by ISCO silica gel chromatography (24 g, 0-10% gradient MeOH/DCM). Fractions containing the desired product were concentrated to a white foam which was co-evaporated with heptane (3×50 mL) to afford 15A (320 mg, 85% yield). LCMS, [M+H]$^+$=738.6.

Preparation of Intermediate 15B:

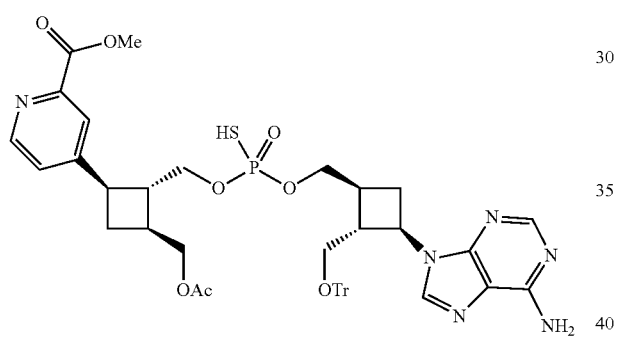

To a solution of Intermediate 9G (103 mg, 0.351 mmol) and Intermediate 15A (402 mg, 0.544 mmol) in acetonitrile (7 mL) was added DBU (159 µl, 1.05 mmol) dropwise to give a pale yellow solution. After 10 min, the reaction mixture was diluted with DCM (4 mL) and treated with acetic acid (100 µL, 1.76 mmol). The resulting mixture was co-evaporated with silica gel, and then purified by flash chromatography over 24 g of silica gel, eluting with 0-15% MeOH/DCM to afford Intermediate 15B (300 mg, 99% yield) as a white solid.

Preparation of Intermediate 15C:

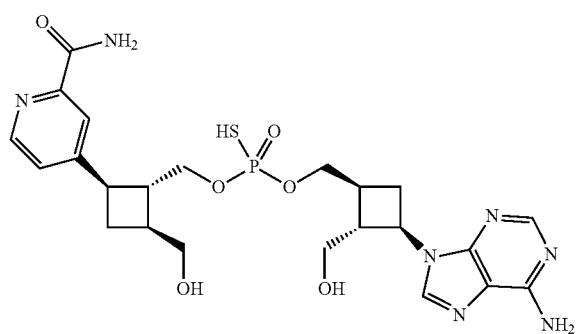

To Intermediate 15B (302 mg, 0.35 mmol) was added ammonia in MeOH (5 mL, 35.0 mmol, 7N). The mixture was heated to 55° C. for 3 hours and then stirred at room temperature for 14 hours. The NH$_3$/MeOH was removed under a stream of nitrogen. To the residue was added DCM (5 mL) and triethylsilane (0.56 ml, 3.5 mmol) and then 2,2-dichloroacetic acid (0.20 mL, 2.45 mmol) was added. The reaction mixture was stirred for 2 hours and then concentrated under reduced pressure. The crude product was dissolved in a small amount of MeOH, adsorbed onto a plug of Celite purified by hydrophilic interaction liquid chromatography (SiO$_2$, 50 g RediSep Rf Gold column, 0-40% water/acetonitrile containing 10 mM ammonium acetate, 5 min gradient, (0%) 0-35%, 30 min, 30 mL/min) to afford Intermediate 15C (72 mg, 0.13 mmol, 36% yield) LCMS, [M+H]$^+$=564.5. $^1$H NMR (499 MHz, METHANOL-d$_4$) δ 8.48 (d, J=5.40 Hz, 1H), 8.39 (s, 1H), 8.20 (s, 1H), 8.05 (s, 1H), 7.54 (d, J=4.65 Hz, 1H), 4.70-4.77 (m, 1H), 4.00-4.13 (m, 4H), 3.67-3.76 (m, 2H), 3.55-3.65 (m, 3H), 3.39-3.48 (m, 1H), 2.91-3.03 (m, 1H), 2.51-2.63 (m, 2H), 2.34-2.50 (m, 4H), 1.71-1.84 (m, 1H).

Examples 15-1 and 15-2

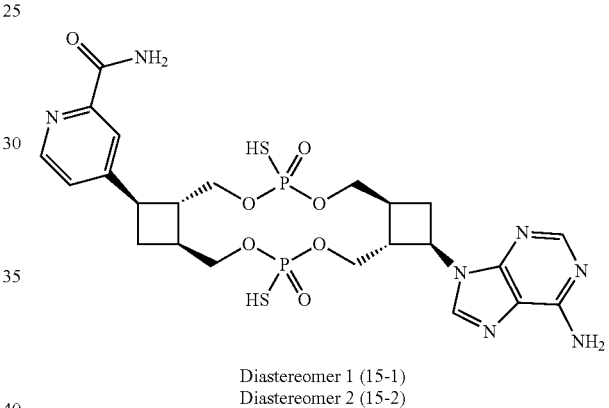

Diastereomer 1 (15-1)
Diastereomer 2 (15-2)

To an anhydrous solution of Intermediate 15C (68 mg, 0.12 mmol) in pyridine (12 mL) was added DBU (270 µl, 1.8 mmol). The mixture was stirred for 10 min and then Reagent 4 (210 mg, 0.47 mmol) in 2 mL of MeCN was added dropwise over 30 min. The mixture was then stirred for another 30 min. at room temperature. The pyridine was removed and the residue was washed with cold ether. The crude product was purified by Preparative HPLC (Chromatographic Conditions: Instrument: Waters Autopure; Column:Zorbax Eclipse C18 plus Column, 5 µm, 21.2×250 mm; Flow rate: 20.0 mL/min; Mobile Phase: A: 100 mM NH$_4$OAc (pH:6.5); B: ACN (% A=100-% B): gradient 5-50% B over 20 min, 50-95% B over 1 min, 95% B hold for 1 min) to afford Example 15-1 (14 mg, 0.02 mmol, 17% yield) and Example 15-2 (26 mg, 0.04 mmol, 30% yield).

Example 15-1 t$_R$: 7.53 min; M+1 obs=642.5 (Agilent 1290 HPLC/MS; Column: Eclipse C18 plus 1.8 um 2.1×150 mm Column; Flow rate: 0.3 mL/min; Mobile Phase: A: 20 mM NH$_4$OAc (pH 6.5); B: MeOH (% A=100-% B); Gradient: 5-100% B in 15 min)$^1$H NMR (499 MHz, METHANOL-d$_4$) δ 8.49 (d, J=5.01 Hz, 1H), 8.40 (s, 1H), 8.17 (s, 1H), 8.00 (s, 1H), 7.55-7.65 (m, 1H), 4.79-4.84 (m, 1H), 4.22 (ddd, J=3.93, 6.59, 10.46 Hz, 1H), 3.96-4.18 (m, 7H), 3.35-3.26 (m, 2H), 2.45-2.69 (m, 6H), 1.86-1.98 (m, 1H). ³¹P NMR (202 MHz, METHANOL-d₄) δ 56.94 (s, 2P).

Example 15-2

$t_R$: 7.98 min; M+1 obs=642.5; (Agilent 1290 HPLC/MS; Column: Eclipse C18 plus 1.8 um 2.1×150 mm Column; Flow rate: 0.3 mL/min; Mobile Phase: A: 20 mM NH₄OAc (pH 6.5); B: MeOH (% A=100-% B); Gradient: 5-100% B in 15 min); ¹H NMR (499 MHz, METHANOL-d₄) δ 8.47 (d, J=5.01 Hz, 1H), 8.40 (d, J=4.41 Hz, 1H), 8.17 (s, 1H), 7.99 (br s, 1H), 7.60 (br s, 1H), 4.76-4.82 (m, 1H), 4.15-4.25 (m, 3H), 3.98-4.15 (m, 4H), 3.87 (td, J=5.53, 10.76 Hz, 1H), 3.34-3.42 (m, 1H), 3.26-3.31 (m, 1H), 2.74-2.81 (m, 1H), 2.52-2.69 (m, 2H), 2.40-2.52 (m, 3H), 2.00-2.06 (m, 1H). ³¹P NMR (202 MHz, METHANOL-d₄) δ 57.11 (s, 2P).

The following Examples, shown in Table 2 below, were prepared according to procedures analogous to those outlined in Examples described above using the appropriate nucleoside monomers described as preparations or as obtained from commercial sources.

TABLE 2

| Example | Structure | Name | Mass [M + H]⁺ | Ret. Time (Min.) |
|---|---|---|---|---|
| 16 | 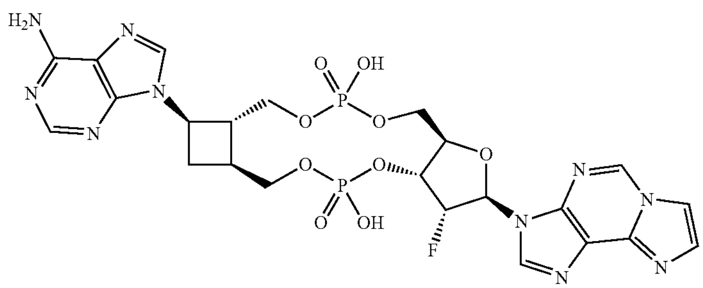 | (1R,6S,8R,9R,15R,17R,18R)-8-(6-amino-9H-purin-9-yl)-18-fluoro-3,12-dihydroxy-17-{3H-imidazo[2,1-f]purin-3-yl}-2,4,11,13,16-pentaoxa-3λ⁵,12λ⁵-diphosphatricyclo[13.3.0.0⁶,⁹]octadecane-3,12-dione | 667.2 | 5.99 |
| 17-1 | 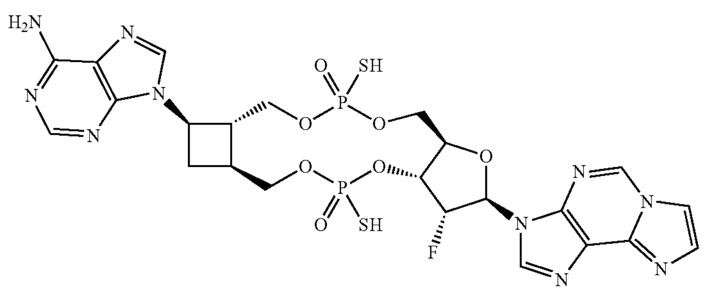 [SMILES: Nc1ncnc2c1ncn2[C@@H]1C[C@@H]2COP(=O)(O)O[C@H]3[C@@H](F)[C@H](n4cnc5c4ncn4ccnc54)O[C@@H]3COP(=O)(O)OC[C@H]21] | (1R,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 1 | 696.82 [M − H]⁻ | 2.53 |
| 17-2 | 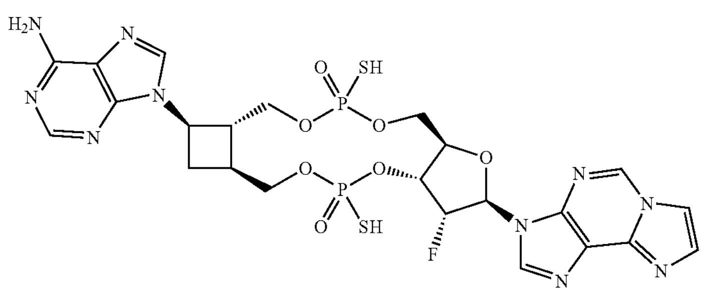 [SMILES: Nc1ncnc2c1ncn2[C@@H]1C[C@@H]2COP(=O)(S)O[C@H]3[C@@H](F)[C@H](n4cnc5c4ncn4ccnc54)O[C@@H]3COP(=O)(S)OC[C@H]21] | (1R,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 2 | 699.1 | 2.55 |
| 17-3 | 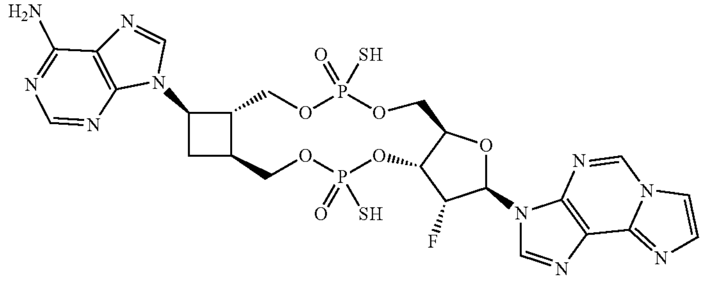 | (1R,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 3 | 696.96 [M − H]⁻ | 2.65 |

TABLE 2-continued

| Example | Name | Mass [M + H]+ | Ret. Time (Min.) |
|---|---|---|---|
| 18-1 | (1R,6S,8R,9R,15R,17R,18R)-8-(6-chloro-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 1 | 717.0 [M − H]⁻ | 2.29 |
| 18-2 | (1R,6S,8R,9R,15R,17R,18R)-8-(6-chloro-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 2 | 717.0 [M − H]⁻ | 2.34 |
| 18-3 | (1R,6S,8R,9R,15R,17R,18R)-8-(6-chloro-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 3 | 717.0 [M − H]⁻ | 2.37 |
| 18-4 | (1R,6S,8R,9R,15R,17R,18R)-8-(6-chloro-9H-purin-9-yl)-18-fluoro-17-{3H-imidazo[2,1-f]purin-3-yl}-3,12-disulfanyl-2,4,11,13,16-pentaoxa-3λ⁵,12λ⁵-diphosphatricyclo[13.3.0.0⁶,⁹]octadecane-3,12-dione Diastereomer 4 | 717.0 [M − H]⁻ | 2.49 |
| 19 | 4-[((1R,6S,8R,9S,15R,17R,18R)-18-fluoro-17-{3H-imidazo[2,1-f]purin-3-yl}-3,12-dioxo-3,12-disulfanyl-2,4,11,13,16-pentaoxa-3λ⁵,12λ⁵-diphosphatricyclo[13.3.0.0⁶,⁹]octadecan-8-yl]pyridine-2-carboxamide | 686.37 | 10.48 |

TABLE 2-continued

| Example | Structure | Name | Mass [M + H]+ | Ret. Time (Min.) |
|---|---|---|---|---|
| 20-1 | 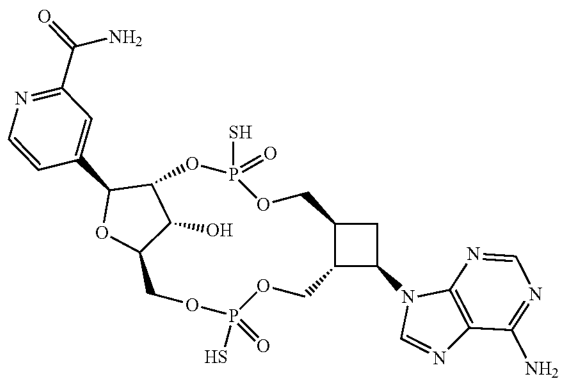 [SMILES: NC(=O)c1cc([C@@H]2O[C@@H]3COP(=O)(S)OC[C@@H]4[C@@H](COP(=O)(S)O[C@@H]2[C@@H]3O)C[C@H]4n2cnc3c(N)ncnc32)ccn1] | 4-[(1R,6S,8R,9R,15R,17S,18R)-8-(6-amino-9H-purin-9-yl)-18-hydroxy-3,12-dioxo-3,12-disulfanyl-2,4,11,13,16-pentaoxa-3λ$^5$,12λ$^5$-diphosphatricyclo[13.2.1.0$^{6,9}$]octadecan-17-yl]pyridine-2-carboxamide Diastereomer 1 | 660.0 | 0.39 |
| 20-2 | 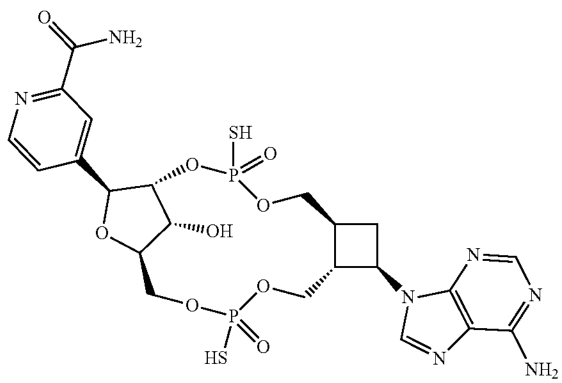 [SMILES: NC(=O)c1cc([C@@H]2O[C@@H]3COP(=O)(S)OC[C@@H]4[C@@H](COP(=O)(S)O[C@@H]2[C@@H]3O)C[C@H]4n2cnc3c(N)ncnc32)ccn1] | 4-[(1R,6S,8R,9R,15R,17S,18R)-8-(6-amino-9H-purin-9-yl)-18-hydroxy-3,12-dioxo-3,12-disulfanyl-2,4,11,13,16-pentaoxa-3λ$^5$,12λ$^5$-diphosphatricyclo[13.2.1.0$^{6,9}$]octadecan-17-yl]pyridine-2-carboxamide Diastereomer 2 | 660.0 | 0.39 |
| 20-3 | 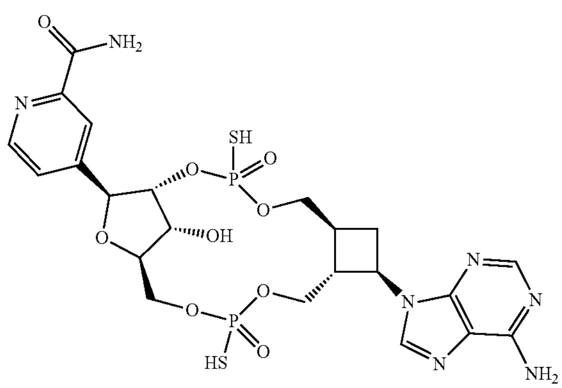 [SMILES: NC(=O)c1cc([C@@H]2O[C@@H]3COP(=O)(S)OC[C@@H]4[C@@H](COP(=O)(S)O[C@@H]2[C@@H]3O)C[C@H]4n2cnc3c(N)ncnc32)ccn1] | 4-[(1R,6S,8R,9R,15R,17S,18R)-8-(6-amino-9H-purin-9-yl)-18-hydroxy-3,12-dioxo-3,12-disulfanyl-2,4,11,13,16-pentaoxa-3λ$^5$,12λ$^5$-diphosphatricyclo[13.2.1.0$^{6,9}$]octadecan-17-yl]pyridine-2-carboxamide Diastereomer 3 | 660.0 | 0.39 |
| 20-4 | 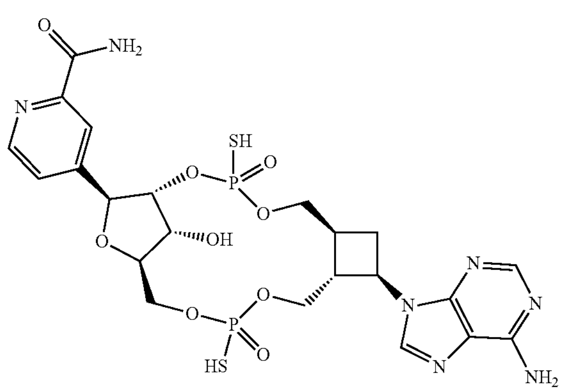 [SMILES: NC(=O)c1cc([C@@H]2O[C@@H]3COP(=O)(S)OC[C@@H]4[C@@H](COP(=O)(S)O[C@@H]2[C@@H]3O)C[C@H]4n2cnc3c(N)ncnc32)ccn1] | 4-[(1R,6S,8R,9R,15R,17S,18R)-8-(6-amino-9H-purin-9-yl)-18-hydroxy-3,12-dioxo-3,12-disulfanyl-2,4,11,13,16-pentaoxa-3λ$^5$,12λ$^5$-diphosphatricyclo[13.2.1.0$^{6,9}$]octadecan-17-yl]pyridine-2-carboxamide Diastereomer 4 | 660.0 | 0.41 |

Examples 21-1 and 21-2

(1R,6S,8R,9R,15R,17R,18R)-17-(6-amino-9H-purin-9-yl)-18-fluoro-8-{5-oxo-5H,8H,9H-[1,2,4]triazolo[4,3-a]purin-8-yl}-3,12-disulfanyl-2,4,11,13,16-pentaoxa-3λ⁵,12λ⁵-diphosphatricyclo[13.3.0.0⁶,⁹]octadecane-3,12-dione

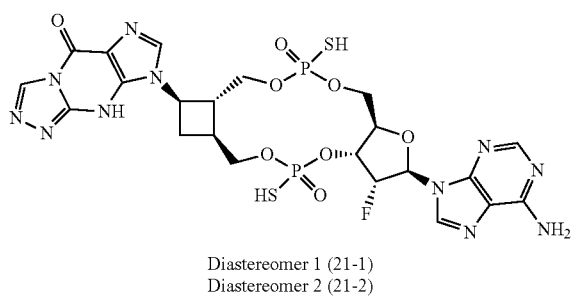 [SMILES: Nc1ncnc2c1ncn2[C@@H]1O[C@@H]2COP(=O)(S)OC[C@@H]3[C@@H](COP(=O)(S)O[C@H]2[C@H]1F)C[C@H]3n1cnc2c(=O)n3cnnc3[nH]c21]

Diastereomer 1 (21-1)
Diastereomer 2 (21-2)

Preparation of Intermediate 21A:

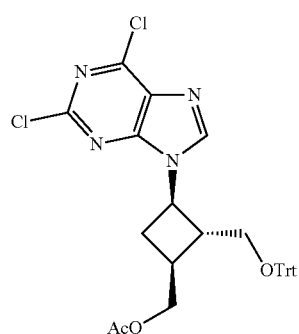

21A

To a solution of Intermediate 1G (479 mg, 1.15 mmol), 2,6-dichloro-9H-purine (326 mg, 1.73 mmol), and 2,6-dichloro-9H-purine (326 mg, 1.73 mmol) in THF (11.5 mL) was added DIAD (0.350 mL, 1.80 mmol) via syringe. The resulting mixture was stirred at 50° C. After 18 hours, the reaction was allowed to cool to room temperature and then concentrated in vacuo. The crude product was dissolved in a small amount of CH₂Cl₂, adsorbed onto a plug of SiO₂, and purified twice by flash chromatography (SiO₂, 40 g RediSep Rf Gold column, 0% to 100% EtOAc/hexanes then 0% to 20% MeOH/DCM) to afford Intermediate 21A (437 mg, 0.744 mmol, 65% yield) as a white foam. ¹H NMR (500 MHz, CHLOROFORM-d) δ 8.14 (s, 1H), 7.34-7.27 (m, 9H), 7.25-7.20 (m, 6H), 4.77 (apparent q, J=8.7 Hz, 1H), 4.16 (d, J=4.8 Hz, 2H), 3.34 (dd, J=10.1, 4.4 Hz, 1H), 3.26 (dd, J=10.1, 6.4 Hz, 1H), 2.96-2.87 (m, 1H), 2.74-2.64 (m, 1H), 2.48-2.38 (m, 2H), 2.05 (s, 3H). LCMS: retention time=1.16 min. [M+H]⁺=587. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 220 nm.

Preparation of Intermediate 21B:

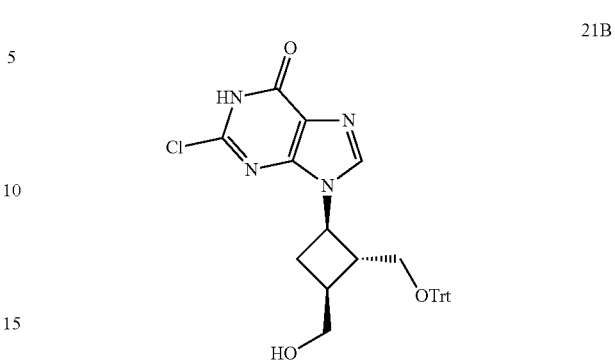

21B

Intermediate 21A (437 mg, 0.744 mmol) was dissolved in a small amount of 1,4-dioxane and added dropwise with stirring to a boiling solution of 1,4-dioxane (3 mL) and 1.0 M aqueous sodium hydroxide (3.00 mL, 3 mmol). After 30 min the reaction was allowed to cool to room temperature, diluted with water (10 mL) then quenched slowly with acetic acid to pH~7. The mixture was extracted with EtOAc (3×10 mL) and the combined organic layers were dried (Na₂SO₄), filtered and concentrated in vacuo. The crude product was purified by reversed phase-HPLC to afford Intermediate 21B (179 mg, 0.340 mmol, 46% yield). LCMS: retention time=0.91 min. [M+H]⁺=527. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 21C:

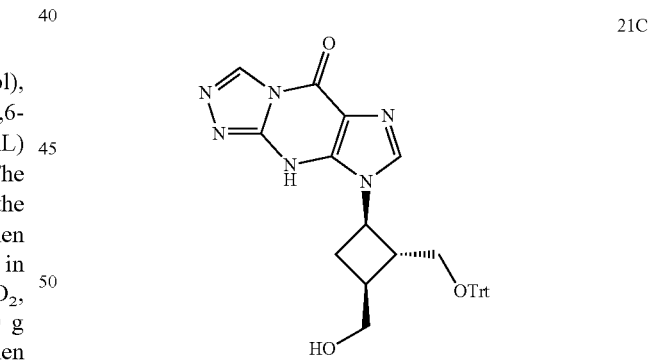

21C

A mixture of Intermediate 21B (179 mg, 0.340 mmol) and hydrazine hydrate (1 mL, 31.9 mmol) in pyridine (1.5 mL) was refluxed for 6 hours and evaporated to dryness. The residue was washed with 3% aqueous potassium carbonate and extracted with DCM. The combined organic layers were concentrated to afford a white solid that was carried into the next step without further purification. A suspension of the crude hydrazine intermediate (50 mg, ~0.096 mmol) in triethyl orthoformate (1 mL) was stirred at 60° C. for 4 hours. The reaction mixture was allowed to cool to room temperature then concentrated. The crude material (containing two regioisomeric products) was taken up in MeOH and purified by reversed phase-HPLC to afford Intermediate 21C (major regioisomer) (27 mg, 0.051 mmol, 53% yield over two steps). $^1$H NMR (500 MHz, METHANOL-$d_4$) δ 8.89 (s, 1H), 8.50 (s, 1H), 7.30-7.21 (m, 15H), 4.76 (apparent q, J=8.6 Hz, 1H), 3.75-3.68 (m, 4H), 2.98-2.88 (m, 1H), 2.65-2.58 (m, 1H), 2.44-2.36 (m, 1H), 2.30-2.21 (m, 1H). LCMS: retention time=0.85 min. [M+H]$^+$=533. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 21D:

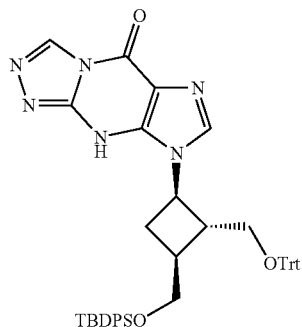

21D

To a solution of Intermediate 21C (125 mg, 0.235 mmol) in DMF (2 mL) was added imidazole (80 mg, 1.17 mmol) and tert-butyldiphenylchlorosilane (0.181 mL, 0.704 mmol). The resulting mixture was stirred at room temperature for 16 hours. The reaction was quenched with methanol (0.4 mL), then stirred at room temperature for 30 min. Volatiles were removed under a stream of nitrogen. The crude product was dissolved in a small amount of $CH_2Cl_2$, adsorbed onto a plug of $SiO_2$, and purified by flash chromatography ($SiO_2$, 40 g RediSep Rf Gold column, 0% MeOH/EtOAc to 100% MeOH/EtOAc) to afford Intermediate 21D (131 mg, 0.170 mmol, 72% yield) as a white solid. LCMS: retention time=1.23 min. [M+H]$^+$=771.7. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 21E:

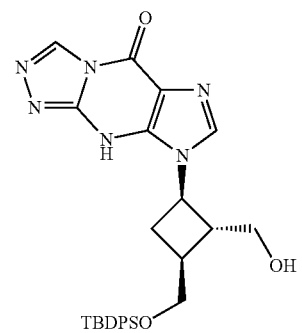

21E

To a solution of Intermediate 21D (107 mg, 0.139 mmol) and triethylsilane (0.0746 mL, 0.467 mmol) in $CH_2Cl_2$ (1.4 mL) was added trifluoroacetic acid (0.021 mL, 0.278 mmol) dropwise. The reaction was stirred at room temperature under nitrogen atmosphere for 2 hours. The reaction was diluted with MeOH (0.6 mL) and stirred for 10 min. The mixture was then concentrated in vacuo and azeotroped twice more with MeOH (2×3 mL). The crude product was dissolved in a small amount of DCM, adsorbed onto a plug of silica, and purified by flash chromatography ($SiO_2$, 40 g column, 0% MeOH/EtOAc to 100% MeOH/EtOAc) to afford Intermediate 21E (45 mg, 0.085 mmol, 61% yield). LCMS: retention time=0.98 min. [M+H]$^+$=529. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 21F:

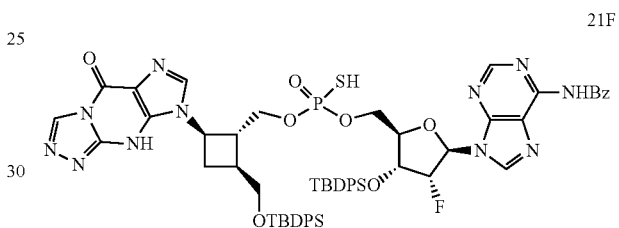

21F

To a solution containing Intermediate 21E and Intermediate 9J (73.0 mg, 0.085 mmol) (azeotroped together 3× with $CH_3CN$ and dried under high vacuum for 1 hour) in $CH_3CN$ (3 mL) was added DBU (0.0257 mL, 0.170 mmol) dropwise via syringe. The resulting mixture was stirred at room temperature under nitrogen atmosphere. After 18 hours, the reaction mixture was concentrated in vacuo. The crude was dissolved small amount DCM and purified by flash chromatography ($SiO_2$, 24 g RediSep Rf Gold column, 0% to 100% MeOH in DCM) to afford Intermediate 21F (77 mg, 0.063 mmol, 74% yield) as a white solid. LCMS: retention time=1.23 min. [M+H]$^+$=1218.5. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 21G:

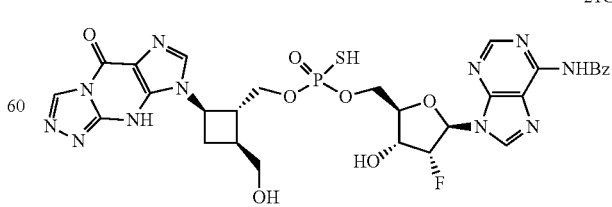

21G

A suspension of Intermediate 21F (77 mg, 0.063 mmol) in neat triethylamine trihydrofluoride (0.50 mL, 3.07 mmol)

was stirred at room temperature. After 22 hours, the reaction mixture was diluted with CH$_3$CN (1 mL) and quenched with triethylamine (0.86 mL, 6.14 mmol) (2 equiv, relative to Et$_3$N.3HF) and isopropoxytrimethylsilane (1.6 mL, 9.21 mmol) (3 equiv, relative to Et$_3$N.3HF). The mixture was stirred at room temperature for 30 min, then concentrated in vacuo. The crude product was purified by reversed phase HPLC (Sunfire C18, 5-micron, 19×150 mm, 18-90% acetonitrile/water containing 0.1% trifluoroacetic acid, 20 mL/min, 9 min gradient, monitored at 254 nm) to give Intermediate 21G (37 mg, 0.050 mmol, 79% yield). LCMS: retention time=0.53 min. [M+H]$^+$=742. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Example 21-1

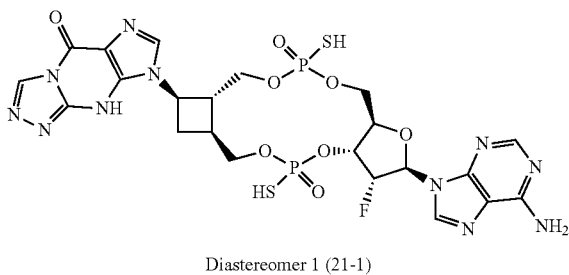 [SMILES: Nc1ncnc2c1ncn2[C@@H]1O[C@@H]2COP(=O)(S)OC[C@@H]3[C@@H](COP(=O)(S)O[C@H]2[C@H]1F)C[C@H]3n1cnc2c(=O)n3cnnc3[nH]c21]

Diastereomer 1 (21-1)

To a solution of Intermediate 21G (19 mg, 0.026 mmol) and DBU (0.058 mL, 0.384 mmol) in DMF (3 mL) was added a solution of Reagent 4 (17.2 mg, 0.038 mmol) in DMF (1 mL) dropwise via syringe over 10 min. The resulting mixture was stirred for 2 hours, then it was quenched with methanol (3 mL) and acetic acid (0.044 mL). Volatiles were then removed under a stream of nitrogen. The crude product was purified by reversed phase HPLC to give the cyclized product (7.1 mg, 8.66 µmol, 33% yield). LCMS: retention time=0.53 min. [M+H]$^+$=820. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm. A solution of the partially protected macrocycle (7.1 mg, 8.66 µmol) in MeOH (0.5 mL) and conc. NH$_4$OH (0.5 mL) was heated in a sealed pressure vessel at 35° C. overnight. The reaction vessel was cooled in an ice-water bath for 10 min before opening. The reaction mixture was transferred to a round bottom flask and concentrated in vacuo. The crude material was purified via preparative LC/MS with the following conditions: Column: Waters Xselect RP Prep C18 OBD Column, 19 mm×150 mm, 5 µm particles; Mobile Phase A: 100 mM NH$_4$OAc in water (pH 6.5); Mobile Phase B: MeOH; Gradient: 15-24% B over 25 minutes; Flow Rate: 20 mL/min. Fractions containing the desired product were combined and dried to afford Example 21-1 (2.9 mg). LCMS: retention time=15.7 min. [M+H]$^+$=716. Column: Waters XSelect CSH C18 3.0×150 mm 3.5 µm particles; Mobile Phase A: 20 mM NH$_4$OAc in water (pH 6.5) with 5% MeOH; Mobile Phase B: MeOH; Gradient: 0% B to 50% B over 15 min, then to 95% at 17 min and hold for 3 min at 95% B; Column Temperature: 45° C.; Flow: 0.5 mL/min; Detection: UV at 260 nm.

Preparation of Example 21-2

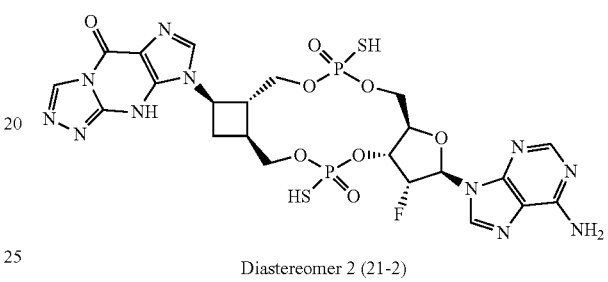

Diastereomer 2 (21-2)

To a solution of 21G (19 mg, 0.026 mmol) and DBU (0.058 mL, 0.384 mmol) in DMF (3 mL) was added a solution of Reagent 3 (17.2 mg, 0.038 mmol) in DMF (1 mL) dropwise via syringe over 10 min. The resulting mixture was stirred for 2 hours, then it was quenched with methanol (3 mL) and acetic acid (0.044 mL). Volatiles were then removed under a stream of nitrogen. The crude product was purified by reversed phase HPLC to give the cyclized product (7.3 mg, 8.91 µmol, 35% yield). LCMS: retention time=0.53 min. [M+H]$^+$=820. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm. A solution of the partially protected macrocycle (7.3 mg, 8.91 µmol) in MeOH (0.5 mL) and conc. NH$_4$OH (0.5 mL) was heated in a sealed pressure vessel at 35° C. overnight. The reaction vessel was cooled in an ice-water bath for 10 min before opening. The reaction mixture was transferred to a round bottom flask and concentrated in vacuo. The crude material was purified via preparative LC/MS with the following conditions: Column: Waters Xselect RP Prep C18 OBD Column, 19 mm×150 mm, 5 µm particles; Mobile Phase A: 100 mM NH$_4$OAc in water (pH 6.5); Mobile Phase B: MeOH; Gradient: 15-24% B over 25 minutes; Flow Rate: 20 mL/min. Fractions containing the desired product were combined and dried to afford Example 21-2 (3.9 mg). LCMS: retention time=17.5 min. [M+H]$^+$=716. Column: Waters XSelect CSH C18 3.0×150 mm 3.5 µm particles; Mobile Phase A: 20 mM NH$_4$OAc in water (pH 6.5) with 5% MeOH; Mobile Phase B: MeOH; Gradient: 0% B to 50% B over 15 min, then to 95% at 17 min and hold for 3 min at 95% B; Column Temperature: 45° C.; Flow: 0.5 mL/min; Detection: UV at 260 nm.

Examples 22-1, 22-2, 22-3, and 22-4

(1R,6S,8R,9R,15R,17R,18R)-17-(6-amino-9H-purin-9-yl)-18-fluoro-8-(6-oxo-6,9-dihydro-1H-purin-9-yl)-3,12-disulfanyl-2,4,11,13,16-pentaoxa-3λ⁵,12λ⁵-diphosphatricyclo[13.3.0.0⁶,⁹]octadecane-3,12-dione

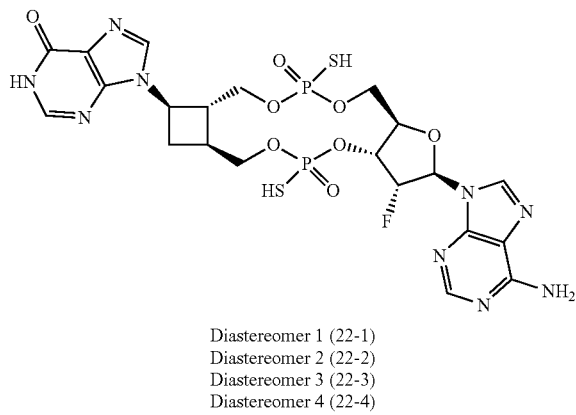 [SMILES: Nc1ncnc2c1ncn2[C@@H]1O[C@@H]2COP(=O)(S)OC[C@@H]3[C@@H](COP(=O)(S)O[C@H]2[C@H]1F)C[C@H]3n1cnc2c(=O)[nH]cnc21]

Diastereomer 1 (22-1)
Diastereomer 2 (22-2)
Diastereomer 3 (22-3)
Diastereomer 4 (22-4)

Preparation of Intermediate 22A:

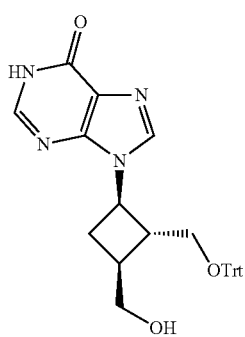

22A

To a solution of Intermediate 2G (0.6 g, 1.085 mmol) in dioxane (9 mL) was added sodium hydroxide (0.121 g, 3.04 mmol). The reaction was stirred for 16 h. LCMS analysis displays mostly starting material. An aqueous 1N solution of LiOH (3.25 mL, 3.25 mmol) was added to the reaction and the mixture was stirred at 60° C. for an additional 16 h. The reaction was concentrated in vacuo and treated with pH 4.5 phosphate buffer (~10 mL) and extracted with EtOAc, and the combined organic layers dried (MgSO₄) and concentrated in vacuo. The crude product was dissolved in a small amount of DCM and charged to a 40 g ISCO silica gel column and purified using a Teledyne ISCO system, eluting over a 15 min gradient with 1%-10% DCM/MeOH to give to afford Intermediate 22A (0.5 g, 1.015 mmol, 94% yield), m/z (493, M+H), as a solid. ¹H NMR (400 MHz, CHLOROFORM-d) δ 8.21-8.17 (m, 1H), 8.00-7.96 (m, 1H), 7.41-7.18 (m, 15H), 4.72-4.63 (m, 1H), 3.79-3.69 (m, 2H), 3.40-3.29 (m, 2H), 3.01-2.91 (m, 1H), 2.62-2.53 (m, 1H), 2.48-2.38 (m, 1H), 2.34-2.24 (m, 1H).

Preparation of Intermediate 22B:

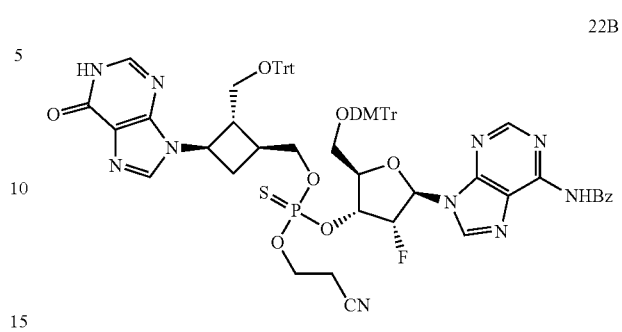

22B

A mixture containing Intermediate 22A (0.38 g, 0.771 mmol) and 1H-tetrazole (0.065 g, 0.926 mmol) in dry acetonitrile was concentrated to dryness on the rotary evaporator (2×5 mL) and then re-suspended in acetonitrile (5 mL) and left under a nitrogen atmosphere. In a separate round bottom flask, (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (Sigma-Aldrich, 0.845 g, 0.964 mmol) in acetonitrile (5 mL) was concentrated to dryness on the rotary evaporator. The azeotroph procedure was repeated with additional acetonitrile (5 mL) and then re-suspended in acetonitrile (2.5 mL) and this solution was dropwise to the stirred mixture of 22A at room temperature. The reaction was stirred at room temperature for 16 h. To the reaction was added (E)-N,N-dimethyl-N'-(3-thioxo-3H-1,2,4-dithiazol-5-yl)formimidamide (0.190 g, 0.926 mmol) and the reaction stirred at room temperature for 2 h. The solvent was removed in vacuo. The residue was dissolved in minimal amount of MeOH and charged to a reverse phase ISCO 50 g of C18 Redisep Rf, High Performance Gold column and purified on a Teledyne ISCO system using gradient 0-100% (ACN/water/ammonium acetate 95/5/0.5) in (water/ACN/ammonium acetate 95/5/0.5) over 15 min gradient to give Intermediate 22B (0.604 g, 0.465 mmol, 100% yield), m.z (1300, M+H), as a white foam following concentration in vacuo by azeotroping with 3×10 mL acetonitrile Preparation of Intermediate 22C:

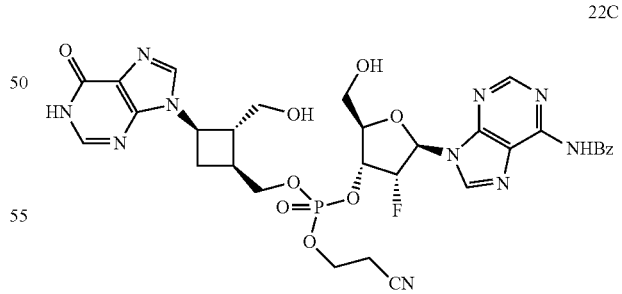

22C

To a solution of Intermediate 22B (1.0 g, 0.770 mmol) and triethylsilane (0.615 ml, 3.85 mmol) in dichloromethane (15 mL) was added TFA (0.178 ml, 2.309 mmol) at room temperature. The reaction mixture was stirred at room temperature for 1 h. Water was added (5 mL) followed by the addition of saturated aqueous NaHCO₃ solution (~5 mL). The mixture was transferred to a separatory funnel and extracted with DCM (2×10 mL) and Me-THF (2×10 mL).

The extracts were combined, dried (MgSO₄), filtered and concentrated. The concentrate was suspended in diethyl ether (~20 mL) and stirred for 1 h. The fine powder that had formed was collected by vacuum filtration and washed with mixture of hexanes and diethyl ether (1/1). The material was partitioned between hexanes and methanol. The methanol layer was isolated and concentrated in vacuo to give Intermediate 22C (0.49 g, 0.649 mmol, 84% yield), m/z (755, M+H), as a pale-yellow solid.

Preparation of Intermediate 22D:

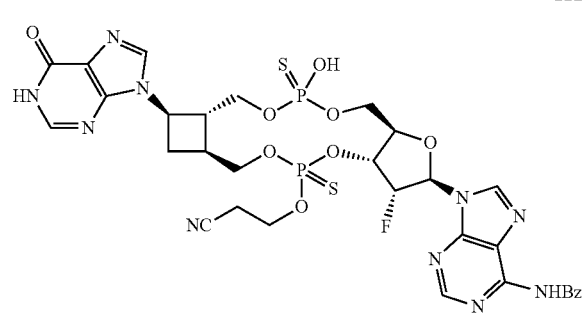

22D

To a 0° C. solution of Intermediate 22C (0.44 g, 0.583 mmol) in pyridine (21.20 ml) was added a solution of diphenyl phosphonate (0.135 ml, 0.700 mmol) in Pyridine (2.120 ml) dropwise over a period of 1 h. The reaction was stirred at room temperature for 16 h. Solid (E)-N,N-dimethyl-N'-(3-thioxo-3H-1,2,4-dithiazol-5-yl)formimidamide (0.180 g, 0.875 mmol) was added and the reaction stirred for an additional 3 h at room temperature. The reaction was concentrated in vacuo. The residue was dissolved in minimal amount of MeOH and charged to a reverse phase ISCO 50 g of C18 Redisep Rf, High Performance Gold column and purified on a Teledyne ISCO system using gradient 0-100% (ACN/water/ammonium acetate 95/5/0.5) in (water/ACN/ammonium acetate 95/5/0.5) over 15 min gradient to give Intermediate 22D (0.081 g, 0.097 mmol, 16.68% yield), m/z (833, M+H) as a mixture of diasteromers.

Examples 22-1, 22-2, 22-3, and 22-4

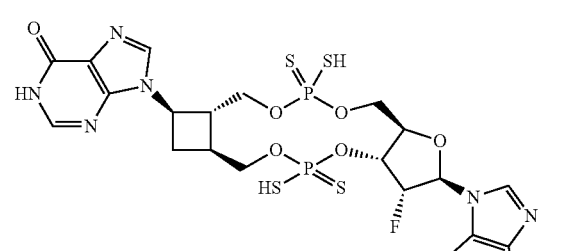

A mixture of Intermediate 22D (0.081 g, 0.097 mmol) and ammonia (7N in MeOH) (6.95 mL, 48.6 mmol) was stirred at room temperature for 1 h and heated in a sealed vial at 50° C. for 3 h. The solvent removed in vacuo. The residue was dissolved in minimum amount of MeOH and charged to a ISCO 50 g of C18 Redisep Rf, High Performance Gold column that had been equilibrated with mobile Phase A: 5:95 acetonitrile: water with 0.01 M ammonium acetate; Mobile Phase B: 95:5 acetonitrile: water with 0.01 M ammonium acetate and purified using a Teledyne ISCO system with Gradient: 0% B for 2 column volumes to 100% B over 20 columns to give crude mixture of products. The individual diasteromers were isolated via preparative LC/MS with the following conditions: Column: Agilent Bonus RP 21.2×100 mm, 5-μm particles; Mobile Phase A: water with 20-mM ammonium acetate; Mobile Phase B: acetonitrile; Gradient: 0% B hold 0-6 minute. 0%-25% B over 16 minutes, then a 4-minute hold at 100% B; Flow: 20 mL/min. Fractions containing the desired product were combined and dried via centrifugal evaporation. Analytical LC/MS was used to determine the final purity. Injection conditions: Column: Agilent Bonus RP, 2.1 mm×50 mm, 1.8 μm particles; Mobile Phase A: water with 20 mM ammonium acetate; Mobile Phase B: acetonitrile. Temperature: 50° C.; Gradient: 0% B hold 1 min, then 0% B to 100% B over 4 min, then a 0.75 min hold at 100% B; Flow: 1 mL/min; Detection: MS and UV (220 nm).

Example 22-1

The yield of the product was 3.5 mg, retention time: 2.0 min; Observed Mass: m/z (676.0, M+H)

Example 22-2

The yield of the product was 3.0 mg, retention time: 2.05 min; Observed Mass: m/z (676.0, M+H)

Example 22-3

The yield of the product was 3.5 mg, retention time: 2.14 min; Observed Mass: m/z (676.0, M+H)

Example 22-4

The yield of the product was 3.1 mg, retention time: 2.29 min; Observed Mass: m/z (676.0, M+H)

Example 23

(1R,6S,8R,9R,15R,17R,18R)-17-(6-amino-9H-purin-9-yl)-18-fluoro-8-{8-oxo-4H,5H,8H-[1,2,3,4]tetrazolo[1,5-a]purin-5-yl}-3,12-disulfanyl-2,4,11,13,16-pentaoxa-3λ⁵,12λ⁵-diphosphatricyclo[13.3.0.0⁶,⁹]octadecane-3,12-dione (23)

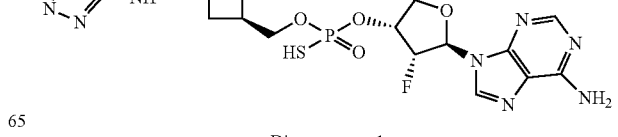

Diastereomer 1

Preparation of Intermediate 23A:

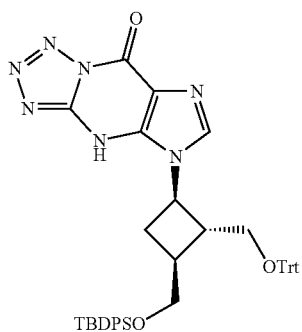

To a solution of Intermediate 21B (31.3 mg, 0.059 mmol) in DMF (0.60 mL) was added sodium azide (4.63 mg, 0.071 mmol). The resulting mixture was stirred at 70° C. for 3 hours. Imidazole (12.1 mg, 178 µmol) and tert-butyldiphenylchlorosilane (22.9 µL, 89 µmol) were then added, and the reaction was stirred at room temperature. After 16 hours, additional imidazole (24.2 mg, 356 µmol) and tert-butyldiphenylchlorosilane (46 µL, 178 µmol) were added. At 23 hours, the reaction was quenched with methanol (0.11 mL), then stirred at room temperature for 30 min. Volatiles were removed under a stream of nitrogen. The crude product was dissolved in a small amount of $CH_2Cl_2$, adsorbed onto a plug of $SiO_2$, and purified by flash chromatography ($SiO_2$, 4 g RediSep Rf Gold column, 0% MeOH/EtOAc to 10% MeOH/EtOAc, 10 min gradient then 5 min hold, 10% MeOH/EtOAc to 100% MeOH/EtOAc, 5 min gradient then 5 min hold, 18 mL/min) to 23A (33.3 mg) contaminated with imidazole. $^1$H NMR (500 MHz, METHANOL-$d_4$) δ 8.08 (s, 1H), 7.65-7.57 (m, 4H), 7.45-7.29 (m, 6H), 7.22-7.10 (m, 15H), 4.78 (td, J=9.3, 8.1 Hz, 1H), 3.78-3.69 (m, 2H), 3.43 (dd, J=9.6, 4.7 Hz, 1H), 3.16 (t, J=8.9 Hz, 1H), 2.99-2.91 (m, 1H), 2.55-2.46 (m, 1H), 2.20 (q, J=10.0 Hz, 1H), 2.16-2.05 (m, 1H), 0.99 (s, 9H). LCMS: RT=1.24 min. [M+H]$^+$=772. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 254 nm.

Preparation of Intermediate 23B:

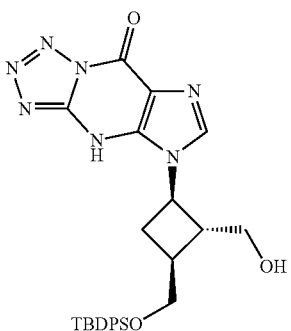

To a solution of partially purified 23A (33.3 mg) and triethylsilane (29 µL, 178 µmol) in $CH_2Cl_2$ (0.6 mL) was added trifluoroacetic acid (9 µL, 119 µmol). The reaction was stirred at room temperature under nitrogen atmosphere. After 3 hours, additional triethylsilane (57 µL, 356 µmol) and trifluoroacetic acid (18 µL, 238 µmol) were added. At 5 hours, the reaction was diluted with MeOH (0.6 mL) and stirred for 10 min. The mixture was then concentrated in vacuo and azeotroped twice more with MeOH (2×1 mL). The residue was dissolved in methanol (800 µL), then sodium methoxide (0.5 M in MeOH) (200 µL, 100 µmol) was added dropwise via syringe (to cleave the TFA ester that formed during the deprotection). The resulting mixture was stirred at room temperature for 30 min, then it was quenched with acetic acid (12 µL, 200 µmol) and concentrated in vacuo. The crude product was dissolved in a small amount of EtOAc (+MeOH), adsorbed onto a plug of silica, and purified by flash chromatography ($SiO_2$, 4 g column, 0% MeOH/EtOAc to 100% MeOH/EtOAc, 20 min gradient, 18 mL/min) to afford 23B (35.1 mg) contaminated with imidazole from the previous step. $^1$H NMR (400 MHz, METHANOL-$d_4$) δ 8.02 (s, 1H), 7.73-7.66 (m, 4H), 7.50-7.37 (m, 6H), 4.67 (q, J=8.6 Hz, 1H), 3.87-3.77 (m, 2H), 3.77-3.66 (m, 2H), 2.94-2.83 (m, 1H), 2.65-2.53 (m, 1H), 2.46-2.35 (m, 1H), 2.35-2.23 (m, 1H), 1.08 (s, 9H). LCMS: RT=0.98 min. [M+H]$^+$=530. Column: Waters BEH C18 2.1×50 mm 1.7 µm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 220 nm.

Preparation of Intermediate 23C:

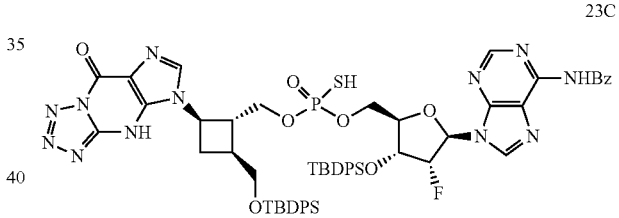

To a solution containing partially purified 23B (35.1 mg) and Intermediate 9J (54.4 mg, 63.4 µmol) (azeotroped together 3× with $CH_3CN$ and dried under high vacuum for 30 min) in $CH_3CN$ (0.6 mL) was added DBU (10 µL, 63.4 µmol) dropwise via syringe. The resulting mixture was stirred at room temperature under nitrogen atmosphere. Reaction did not proceed until excess DBU (40 µL, 254 µmol) and Intermediate 9J (109 mg, 127 µmol) were added. After product formation was observed by LCMS, the reaction was quenched by adding MeOH (2 mL). The mixture was then concentrated in vacuo. The crude product was dissolved in a small amount of MeOH, adsorbed onto a plug of Celite, and purified by reversed phase MPLC (C18, 15.5 g RediSep Rf Gold column, 5-95% acetonitrile/water containing 10 mM ammonium acetate, 8.6 min gradient, 30 mL/min) to afford 23C (10 mg) contaminated with adenosine monothiophosphate. LCMS: RT=1.06 min. [M+H]$^+$=1219. Column: Waters BEH C18 2.1×50 mm 1.7 µm particles; Mobile Phase A: 5:95 acetonitrile: water with 10 mM ammonium acetate; Mobile Phase B: 95:5 acetonitrile: water with 10 mM ammonium acetate; Temperature: 50° C.; Gradient: 5% B to 95% B over 1 min, then a 0.5 min hold at 95% B; Flow: 0.8 mL/min; Detection: UV at 220 nm.

Preparation of Intermediate 23D:

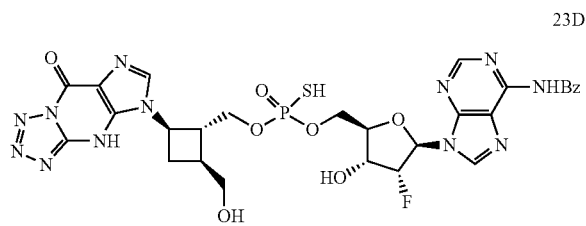

A suspension of partially purified 23C (10 mg) in neat triethylamine trihydrofluoride (0.50 mL, 3.07 mmol) was stirred at room temperature. After 22 hours, the reaction mixture was diluted with CH₃CN (0.86 mL) and quenched with triethylamine (0.86 mL, 6.14 mmol) (2 equiv, relative to Et₃N.3HF) and isopropoxytrimethylsilane (1.6 mL, 9.21 mmol) (3 equiv, relative to Et₃N.3HF). The mixture was stirred at room temperature for 30 min, then concentrated in vacuo. The crude product was dissolved in a small amount of 10% acetonitrile/water containing 10 mM ammonium acetate, adsorbed onto a plug of Celite, and purified by reversed phase MPLC (C18, 15.5 g RediSep Rf Gold column, 14% acetonitrile/water containing 10 mM ammonium acetate, isocratic, 30 mL/min) to afford 23D (5.6 mg) contaminated with adenosine monothiophosphate from the previous step. LCMS: RT=0.50 min. [M+H]⁺=743. Column: Waters BEH C18 2.1×50 mm 1.7 μm particles; Mobile Phase A: water with 0.05% trifluoroacetic acid; Mobile Phase B: acetonitrile with 0.05% trifluoroacetic acid; Temperature: 50° C.; Gradient: 2% B to 98% B over 1 min, then a 0.5 min hold at 98% B; Flow: 0.8 mL/min; Detection: UV at 220 nm.

Preparation of Example 23

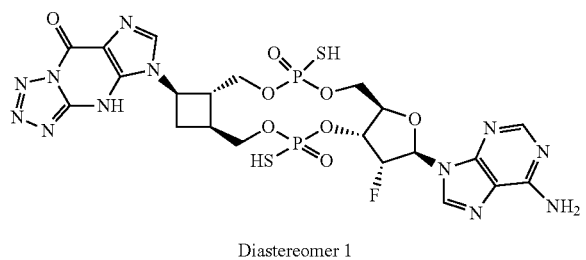

Diastereomer 1

To a slightly cloudy solution of partially purified 23D (2.4 mg) (azeotroped 3× with CH₃CN) and DBU (7 μL, 0.048 mmol) in DMF (0.24 mL) was added a solution of Reagent 3 (2.2 mg, 4.85 μmol) in DMF (80 μL) dropwise via syringe over 15 min. The resulting mixture was stirred at room temperature. After 30 min a second portion of Reagent 3 (2.2 mg, 4.85 μmol) in DMF (80 μl) was added dropwise via syringe. At 60 min the reaction was quenched with methanol (0.40 mL) and acetic acid (6 μL). Volatiles were then removed under a stream of nitrogen to afford the crude cyclized product as an 85:15 mixture of diastereomers. This material was carried into the next step without further purification. LCMS: RT=13.7 min (major isomer), 14.2 min (minor isomer). [M+H]⁺=821. Column: Waters XSelect CSH C18 3.0×150 mm 3.5 μm particles; Mobile Phase A: 10 mM TEAA in water (pH 6.5); Mobile Phase B: 80:20 acetonitrile/10 mM TEAA in water (pH 6.5); Gradient: 5% B to 50% B over 15 min; Column Temperature: 25° C.; Flow: 0.5 mL/min; Detection: UV at 285 nm. A suspension of crude macrocycle in ammonia (7 N) in MeOH (1.0 mL, 7.0 mmol) was stirred at room temperature. After 24 hours, the reaction was concentrated in vacuo. The crude product was purified by reversed phase HPLC (XSelect CSH C18 OBD, 5-micron, 19×150 mm, Solvent A: 100 mM ammonium acetate (pH 6.5), Solvent B: pure acetonitrile, 15-24% B, 20 mL/min, 25 min gradient, monitored at 260 nm). The product (major isomer, retention time=10.7 min) was isolated and lyophilized to dryness to afford Example 23 (1.6 mg) as a white solid. LCMS: RT=14.6 min. [M+H]⁺=717. Column: Waters XSelect CSH C18 3.0×150 mm 3.5 μm particles; Mobile Phase A: 20 mM NH₄OAc in water (pH 6.5); Mobile Phase B: 20 mM NH₄OAc in acetonitrile; Gradient: 0% B to 13% B over 25 min; Column Temperature: 55° C.; Flow: 0.5 mL/min; Detection: UV at 260 nm.

Evaluation of Biological Activity

Evaluation of Biological Activity

STING THP1 Reporter Assay Protocol

THP1-Dual™ cells were derived from the human THP-1 monocyte cell line by stable integration of two inducible reporter constructs. To this end, THP1-Dual™ cells allow the simultaneous study of the NF-Bd pathway, by monitoring the activity of SEAP, and the IRF pathway by assessing the activity of a secreted luciferase (Lucia). Both reporter proteins are readily measurable in the cell culture supernatant when using QUANTI-Blue™, a SEAP detection reagent, and QUANTI-Luc™, a luciferase detection reagent.

THP1-Dual™ cells induce the activation of NF-κB in response to STING agonists. They also trigger the IRF pathway upon stimulation with STING agonists, such as cGAMP. Here, the THP-1-Dual cells were used to assess STING binders for function on the cellular level.

Serial dilutions of compounds in DMSO were added to low volume 384 well plates at 100 nl/well using an ECHO acoustic dispenser (Labcyte, model 550) to achieve final starting concentration of 100 μM in cell suspension. THP-1 Dual™ STING reporter cells (Invivogen, Dual cells cat #THPD-nfis) were added to the plates with compounds at 15,000 cells in 10 μL per well in RPMI media (Gibco, cat #11875) containing 10% human plasma in a low volume 384-well black wall clear bottom tissue culture plate (Corning, cat #3542) for SEAP assay and low volume solid white plate (Corning, cat #3826) for luciferase assay. One column of the plate was reserved for treatment with cGAMP at 100 μM for 100% activation calculation and one column for no treatment (DMSO only) for baseline activation. Plates were then incubated in 37 OC incubator at 5% CO₂ for 20 hours.

In the SEAP assay, 5 μl of 2× QuantiBlue (Invivogen, cat # Rep-qb2) is added to 384 well black plates seeded with THP1 cells and incubated at 37° C. for 2 hours. Plates were read on the Envision (Perkin Elmer) at 620 nm wavelength (OD620). In the luciferase assay, 5 μl of Quantiluc (Invivogen, Rep-qlc2) is added to white 384 well plates seeded with THP1 cells and read at 5 minutes on the Envision (Perkin Elmer) using a luminescence protocol (RLU). For both cell lines, 100% activation was determined by value (RLU) of THP-1 Dual STING cells stimulated with 100 μM cGAMP (Invivogen, cat # TLRL-NACGA23-5).

STING HTRF Binding Assays

A time resolved FRET-based competition binding assay was used to assess test article binding to STING WT and STING AQ. His-tagged STING cytoplasmic domain (WT or AQ) at a concentration of 20 nM was incubated with 2.5 nM Tb-labeled anti-His antibody, test compound, and fluorescein-labeled cGAMP analog probe (BioLog cat. no. C195) at a concentration of 200 nM (STING WT) or 40 nM (STING AQ) in PBS containing 0.005% Tween-20 and 0.1% BSA for one hour. Fluorescence at 495 nm and 520 nm was measured using an EnVision microplate reader to quantify FRET between Tb-labeled anti-His antibody and fluorescein-labeled probe. Background was defined as the signal obtained in the absence of STING protein, and background subtracted FRET ratios were normalized to the maximum signal obtained in the absence of test compound. These values were converted to a percent inhibition. Percent inhibition was determined for test compounds at 11 concentrations. The $IC_{50}$, defined as the concentration of competing test compound needed to reduce specific binding of the probe by 50%, was calculated using the 4 parameter logistic equation to fit the data

```
STING WT: His-TVMV-S-hSTING(155-341)-H232R
                                   (SEQ ID NO: 1)
MGSSHHHHHHSSGETVRFQGHMSVAHGLAWSYYIGYLRLILPELQARIRT

YNQHYNNLLRGAVSQRLYILLPLDCGVPDNLSMADPNIRFLDKLPQQTGD

RAGIKDRVYSNSIYELLENGQRAGTCVLEYATPLTLFAMSQYSQAGFSRE

DRLEQAKLFCRTLEDILADAPESQNNCRLIAYQEPADDSSFSLSQEVLRH

LRQEEKEEV

STING AQ: His-TVMV-S-hSTING(155-341)-G230A-R293Q
                                   (SEQ ID NO: 2)
MGSSHHHHHHSSGETVRFQGHMSVAHGLAWSYYIGYLRLILPELQARIRT

YNQHYNNLLRGAVSQRLYILLPLDCGVPDNLSMADPNIRFLDKLPQQTAD

RAGIKDRVYSNSIVELLENGQRAGTCVLEYATPLQTLFAMSQYSQAGFSR

EDRLEQAKLFCQTLEDILADAPESQNNCRLIAYQEPADDSSFSLSQEVLR

HLRQEEKEEV
```

| | THP1 Reporter Assays $EC_{50}$ (μM) | | HTRF Binding Assays $IC_{50}$ (μM) | |
|---|---|---|---|---|
| Example # | IRF3 | NFkB | WT | AQ |
| Example 1-1 | 41.00 | 54.65 | 0.19 | 0.01 |
| Example 1-2 | 31.33 | 53.95 | 0.90 | 0.04 |
| Example 1-3 | >100 | >100 | 0.84 | 0.02 |
| Example 1-4 | 0.39 | 1.21 | 0.01 | 0.002 |
| Example 2-1 | 3.07 | 7.15 | 0.06 | 0.002 |
| Example 3-1 | 93.06 | >100 | 1.38 | 0.09 |
| Example 3-2 | 26.59 | 42.65 | 1.49 | 0.03 |
| Example 4-1 | >100 | >100 | 11.10 | 0.10 |
| Example 5-1 | >100 | >100 | >100 | >100 |
| Example 5-2 | >100 | >100 | >100 | 11.84 |
| Example 5-3 | >100 | >100 | >100 | 5.73 |
| Example 5-4 | >100 | >100 | 34.51 | 0.11 |
| Example 6-1 | >100 | >100 | 6.31 | 0.18 |
| Example 6-2 | 3.18 | 6.99 | 0.13 | 0.01 |
| Example 6-3 | >100 | >100 | 9.24 | 0.22 |
| Example 6-4 | >100 | >100 | 19.38 | 0.63 |
| Example 7 | 3.01 | 11.50 | 0.12 | 0.002 |
| Example 8-1 | >100 | >100 | 11.14 | 3.41 |
| Example 8-2 | >100 | >100 | 3.43 | 0.51 |
| Example 8-3 | >100 | >100 | 0.89 | 0.30 |
| Example 8-4 | 26.10 | 32.39 | 0.35 | 0.08 |
| Example 9 | 18.45 | 23.52 | 1.41 | 0.02 |
| Example 10 | >100 | >100 | 40.87 | 2.30 |
| Example 11 | >100 | >100 | 52.51 | 10.14 |
| Example 12 | >100 | >100 | 31.20 | 0.35 |
| Example 13 | 54.61 | 90.02 | 4.78 | 0.10 |
| Example 14 | >100 | >100 | >100 | 7.78 |
| Example 15-1 | >100 | >100 | >100 | >100 |
| Example 15-2 | >100 | >100 | >100 | 73.46 |
| Example 16 | 23.88 | 72.75 | 4.66 | 0.02 |
| Example 17-1 | >100 | >100 | >100 | 3.55 |
| Example 17-2 | >100 | >100 | 39.05 | 0.46 |
| Example 17-3 | 73.70 | 89.58 | 5.22 | 0.11 |
| Example 18-1 | >100 | >100 | >100 | 26.44 |
| Example 18-2 | >100 | >100 | >100 | 35.69 |
| Example 18-3 | >100 | >100 | >100 | 2.81 |
| Example 18-4 | >100 | >100 | 24.46 | 2.18 |
| Example 19 | 0.97 | 2.38 | 0.01 | 0.01 |
| Example 20-1 | >100 | >100 | >100 | >100 |
| Example 20-2 | >100 | >100 | >100 | >100 |
| Example 20-3 | 5.23 | 7.64 | 0.01 | 0.01 |
| Example 20-4 | >100 | >100 | >100 | 35.67 |
| Example 21-1 | 5.36 | 25.0 | 0.150 | 0.004 |
| Example 21-2 | >100 | >100 | 6.97 | 0.20 |
| Example 22-1 | >100 | >100 | 5.68 | 0.10 |
| Example 22-2 | >100 | >100 | 0.44 | 0.02 |
| Example 22-3 | >100 | >100 | 2.71 | 0.04 |
| Example 22-4 | 12.98 | 91.67 | 0.12 | 0.01 |
| Example 23 | >100 | 92.18 | 4.96 | 0.07 |

We claim:
1. A compound of formula I

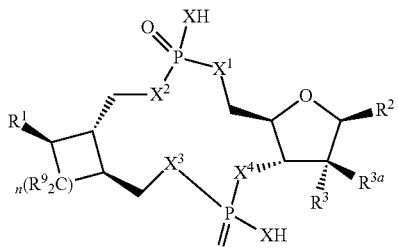
(I)

wherein
X is independently O or S;
$X^1$, $X^2$, $X^3$ and $X^4$ are each independently O or NH;
$R^1$ and $R^2$ are independently

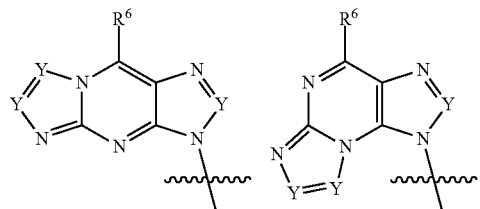

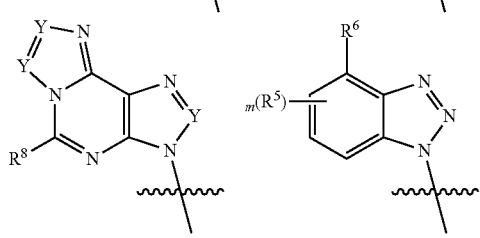

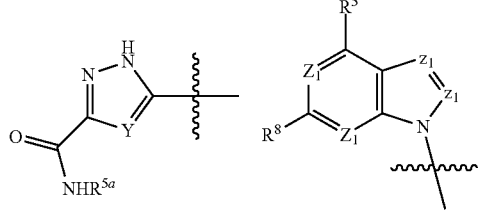

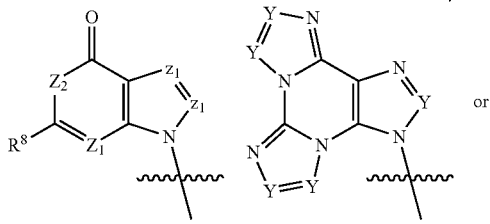

or

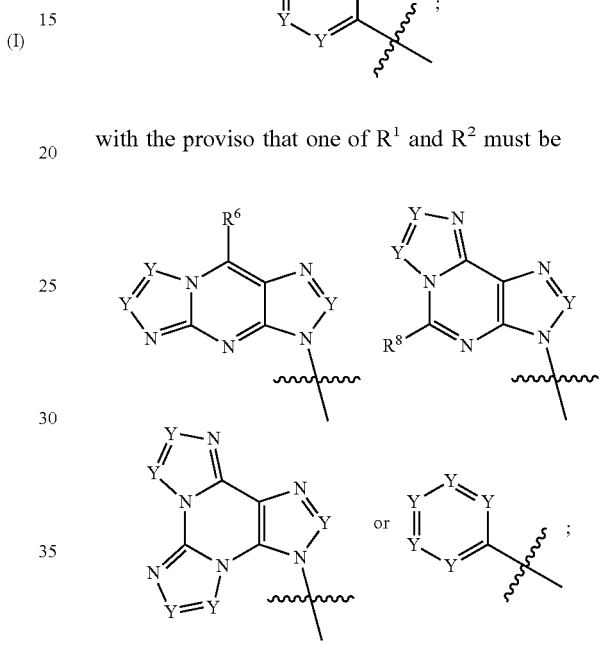

with the proviso that one of $R^1$ and $R^2$ must be $Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O) $R^{a1}$, —OC(O)$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O) $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
or two $R^5$ groups may be taken together to form a 5-6 membered carbocyclic or heterocyclic group;

or $R^5$ and $R^6$ may be taken together to form a 5-6 membered carbocyclic or heterocyclic group;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

2. The compound according to claim 1 of formula I

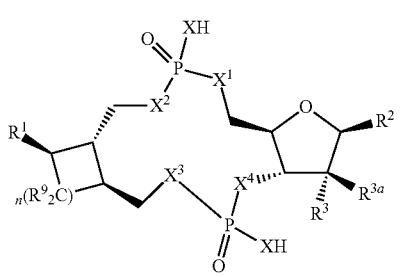

(I)

wherein

X is S;

$X^1$, $X^2$, $X^3$ and $X^4$ are each independently O or NH;

$R^1$ and $R^2$ are independently

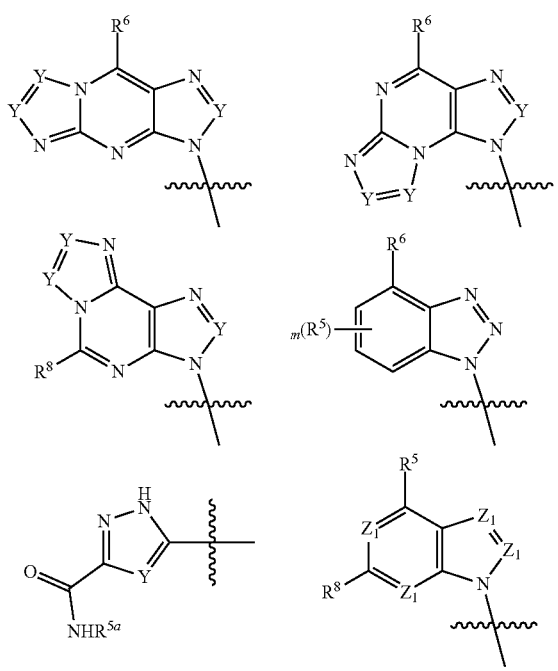

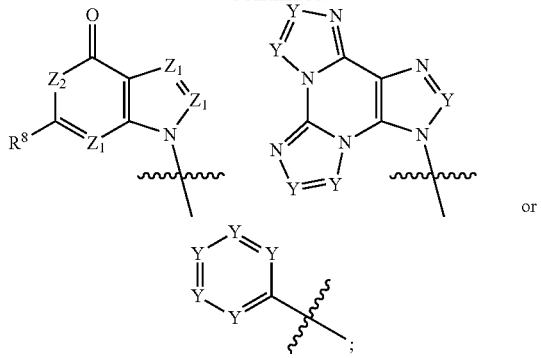

or with the proviso that one of $R^1$ and $R^2$ must be

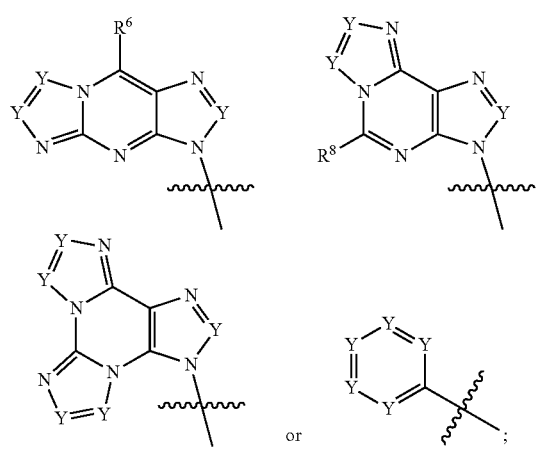

or

;

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

3. The compound according to claim 1 of formula I

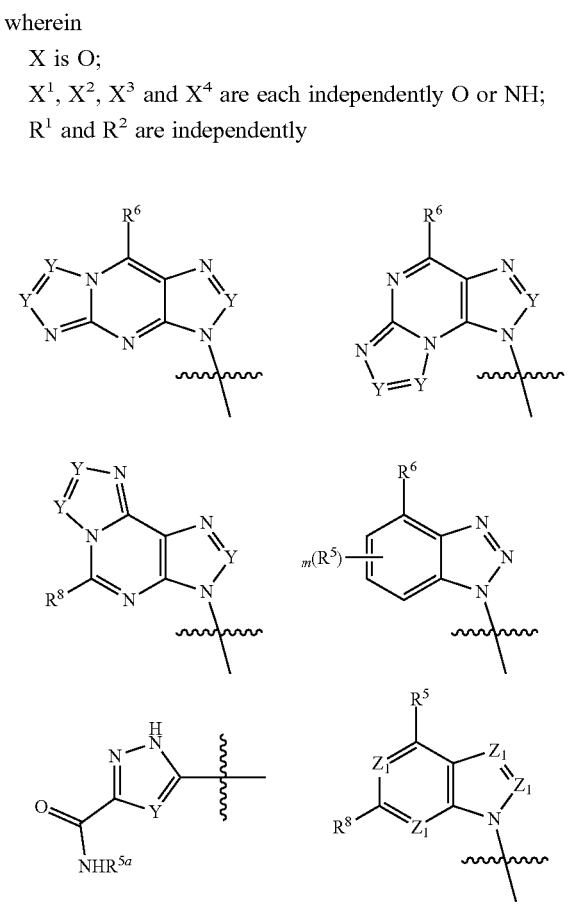

wherein

X is O;

$X^1$, $X^2$, $X^3$ and $X^4$ are each independently O or NH;

$R^1$ and $R^2$ are independently

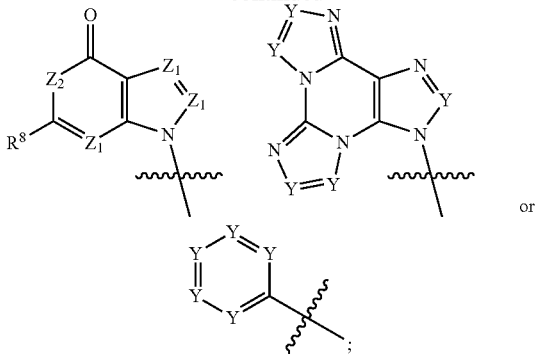

with the proviso that one of $R^1$ and $R^2$ must be $Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2$ $R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

4. The compound according to claim 1 of the formula

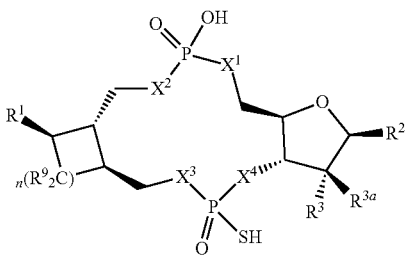

wherein
$X^1$, $X^2$, $X^3$ and $X^4$ are each independently O or NH;
$R^1$ and $R^2$ are independently

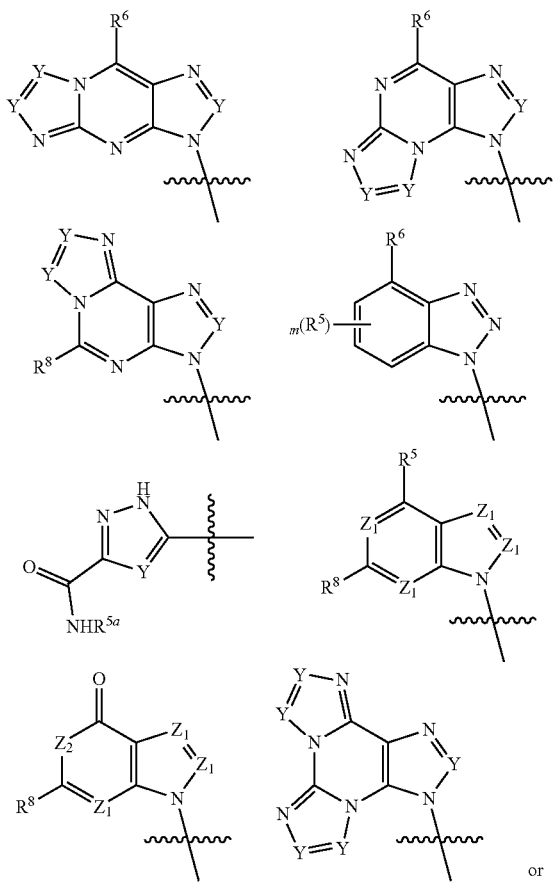

or

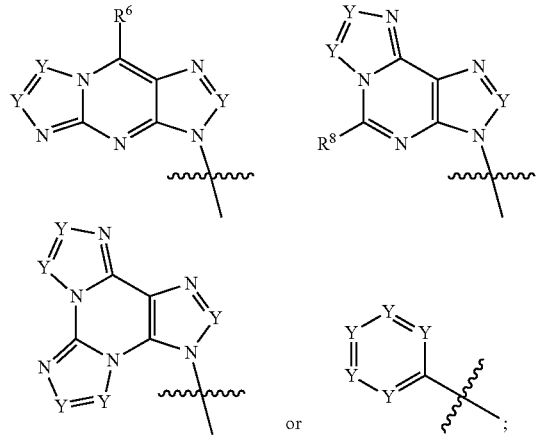

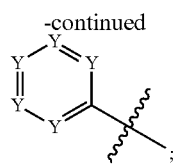

with the proviso that one of $R^1$ and $R^2$ must be $Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

5. The compound according to claim 1 of the formula

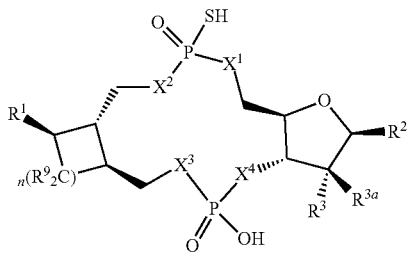

wherein
$X^1$, $X^2$, $X^3$ and $X^4$ are each independently O or NH;
$R^1$ and $R^2$ are independently

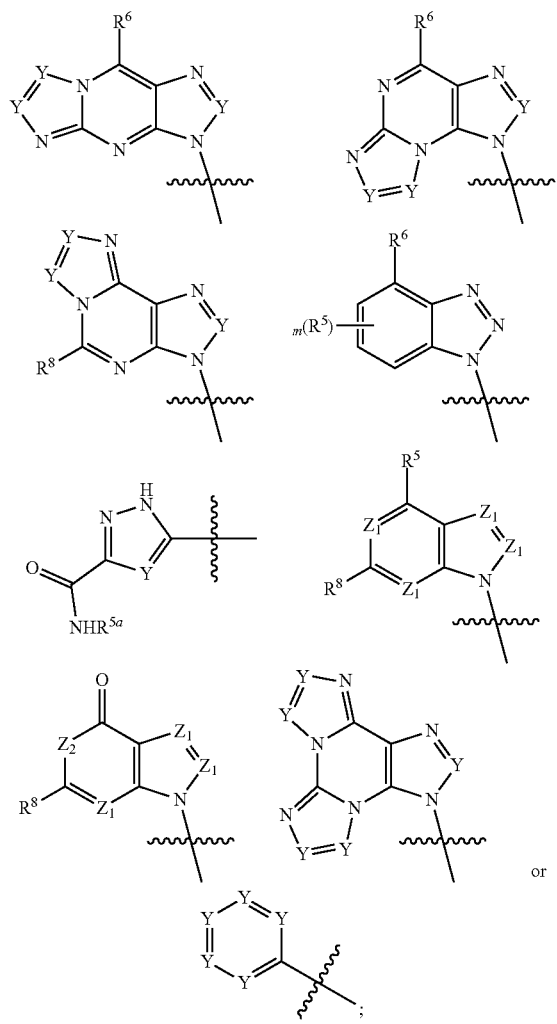

with the proviso that one of $R^1$ and $R^2$ must be

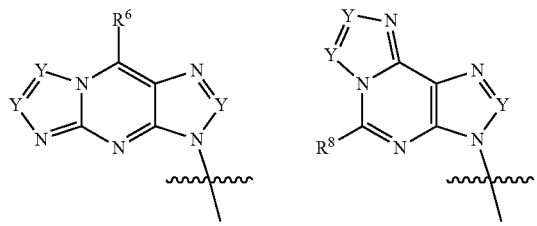

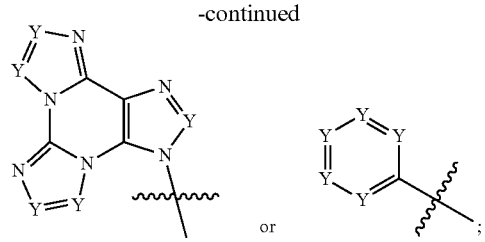

or ;

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2$$R^{a1}$ or S(O)$_2$$NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

6. The compound according to claim 1 of the formula

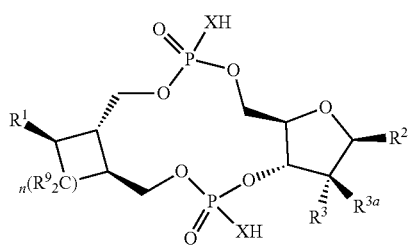

wherein
X is independently O or S;
$R^1$ and $R^2$ are independently

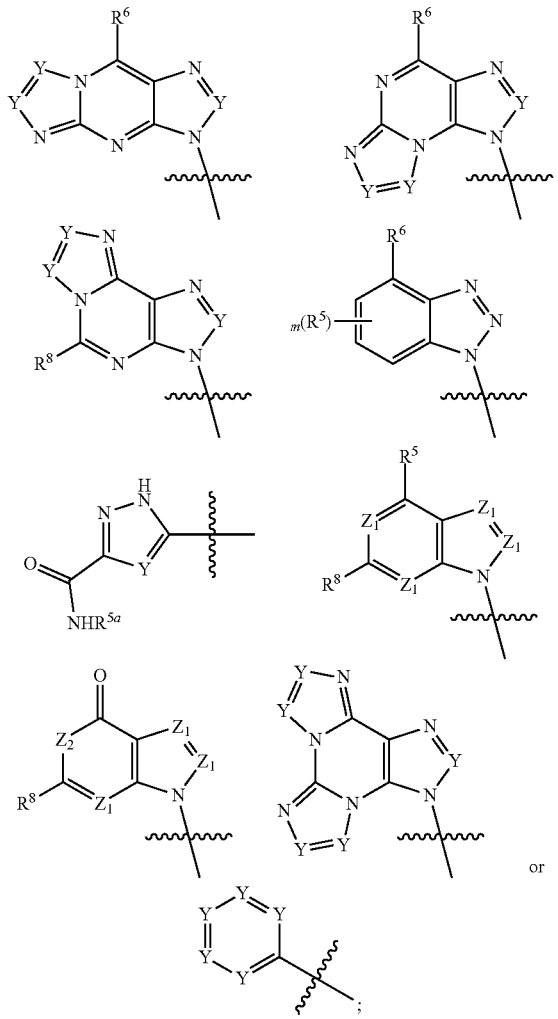

with the proviso that one of $R^1$ and $R^2$ must be

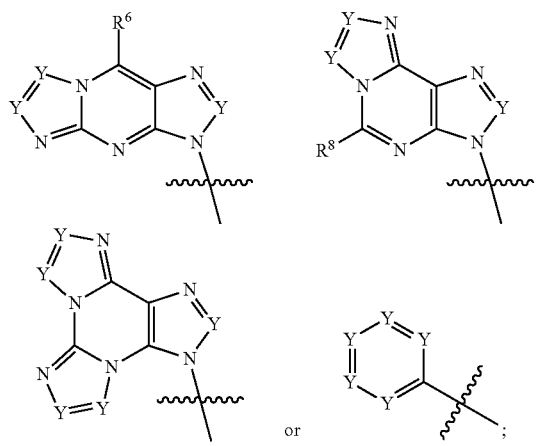

$Z_1$ is N or $CR^a$;
$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

7. The compound according to claim 1 of the formula

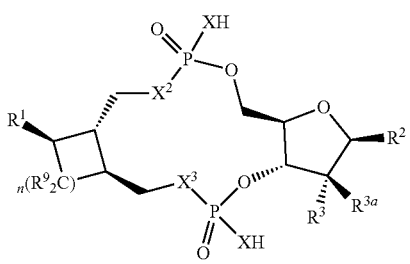

wherein
X is S;
$R^1$ and $R^2$ are independently

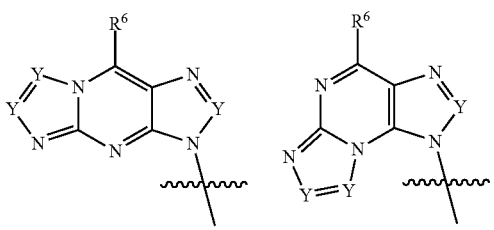

-continued

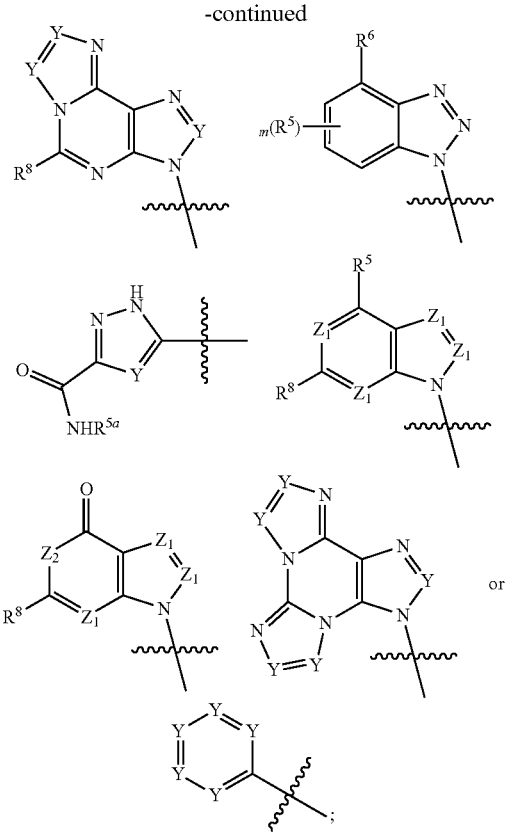

with the proviso that one of $R^1$ and $R^2$ must be

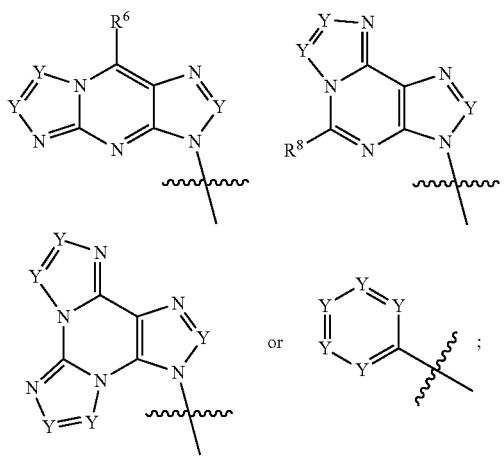

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2$$R^{a1}$ or S(O)$_2$$NR^{a1}R^{a1}$;

$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$$R^{a1}$, —$NR^{a1}$S(O)$_2$$NR^{a1}R^{a1}$, —S(O)$R^{a1}$, —S(O)$NR^{a1}R^{a1}$, —S(O)$_2$$R^{a1}$ or S(O)$_2$$NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

8. The compound according to claim 1 of the formula

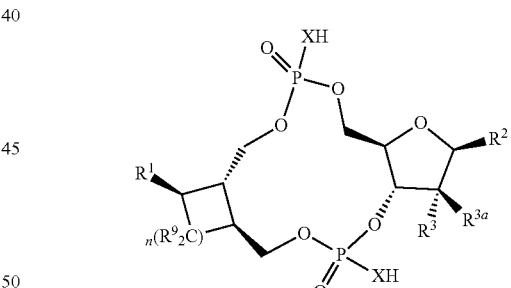

wherein
X is O;
$R^1$ and $R^2$ are independently

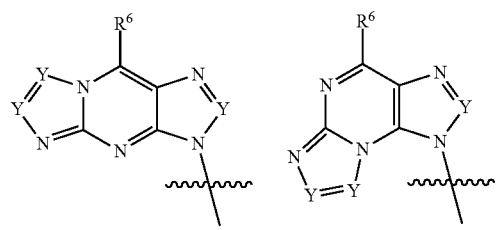

-continued

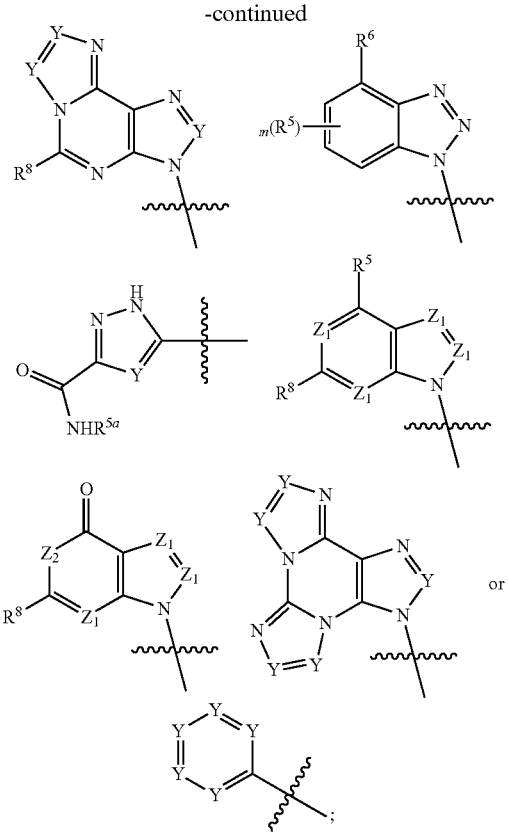

with the proviso that one of $R^1$ and $R^2$ must be

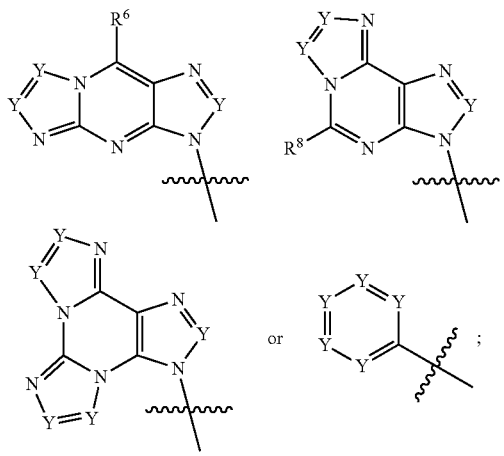

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;
$R^3$ is H, $CH_3$, halogen, $-NR^{a1}R^{a1}$ or $OR^{a1}$;
$R^{3a}$ is H, $CH_3$, halogen, $-NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

9. The compound according to claim 1 of the formula

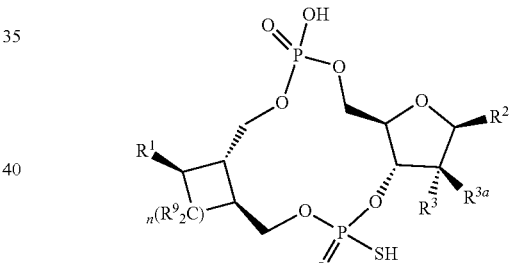

wherein
$R^1$ and $R^2$ are independently

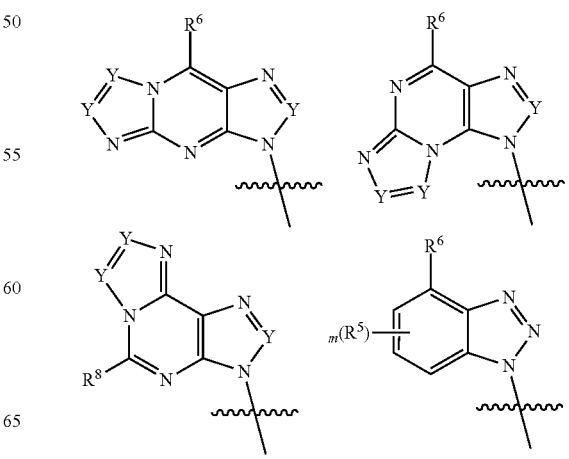

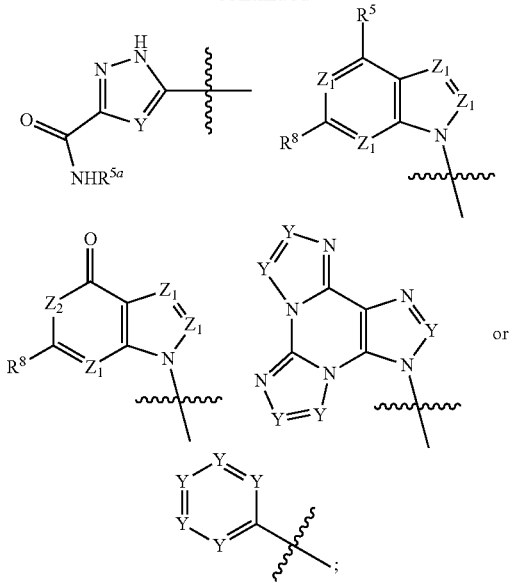

with the proviso that one of $R^1$ and $R^2$ must be

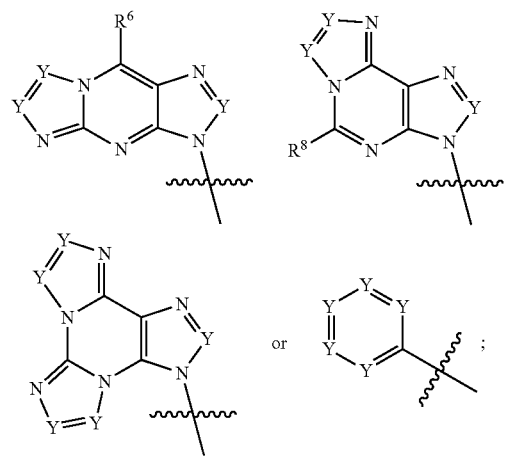

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

10. The compound according to claim 1 of the formula

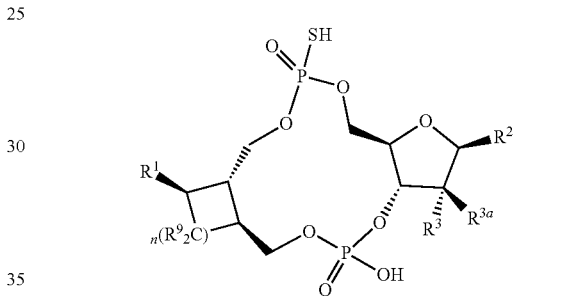

wherein
$R^1$ and $R^2$ are independently

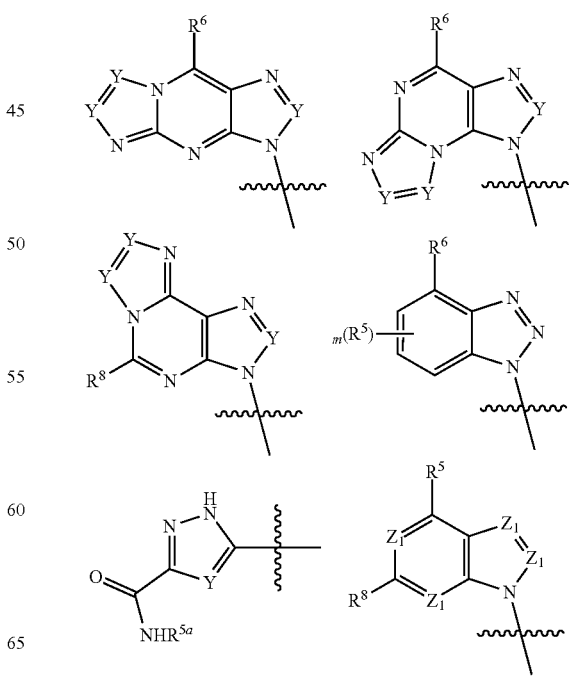

-continued

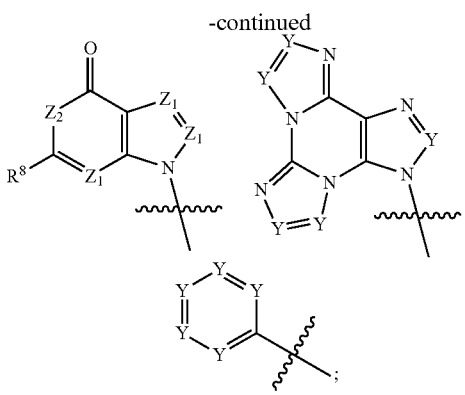

with the proviso that one of $R^1$ and $R^2$ must be

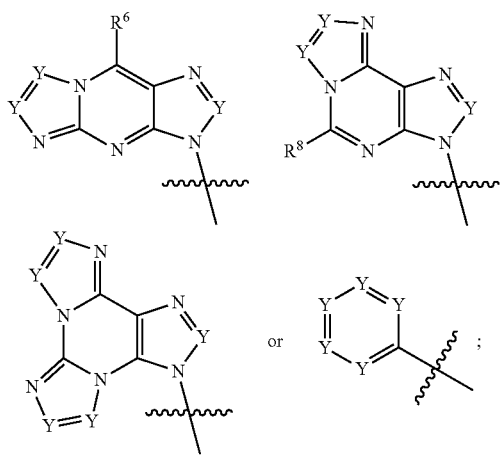

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a C=$CH_2$ substituent;

$R^5$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;

$R^8$ is H, halogen, $C_{1-3}$ alkyl, CN, $NO_2$, OH, $OR^{a1}$, $SR^{a1}$, —C(O)$NR^{a1}R^{a1}$, —COO$R^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}$COO$R^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

11. The compound according to claim 1 of the formula

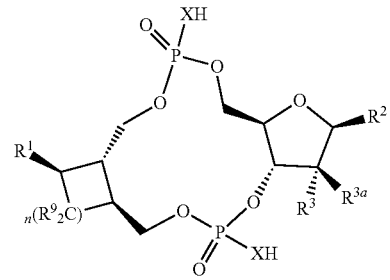

wherein

X is independently O or S;

$R^1$ and $R^2$ are independently

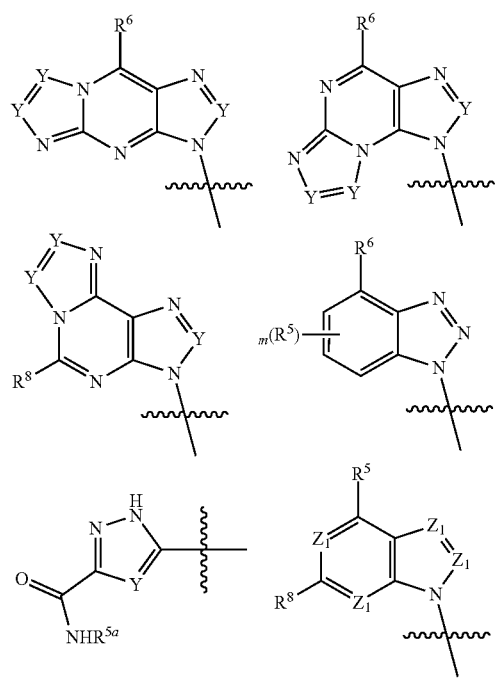

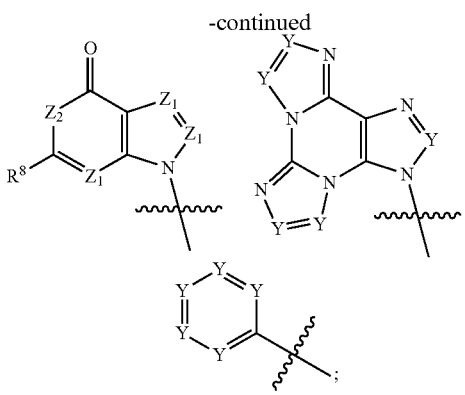

with the proviso that one of $R^1$ and $R^2$ must be

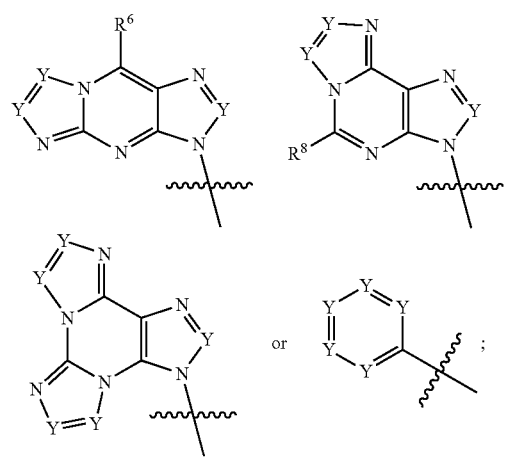

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is F;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;

$R^9$ is H, halogen or methyl;
Y is $CR^a$ or N;
m is 0, 1, 2 or 3;
n is 0 or 1;
or a pharmaceutically acceptable salt, tautomer or stereoisomer thereof.

12. The compound according to claim 1 of the formula

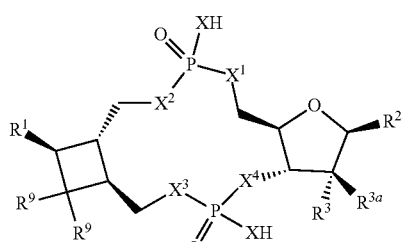

wherein
X is independently O or S;
$X^1$, $X^2$, $X^3$ and $X^4$ are each independently O or NH;
$R^1$ and $R^2$ are independently

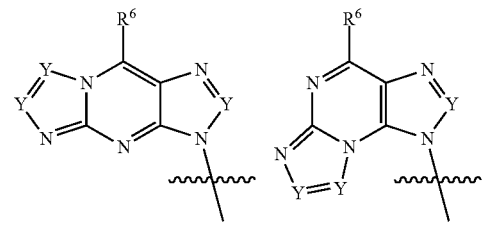

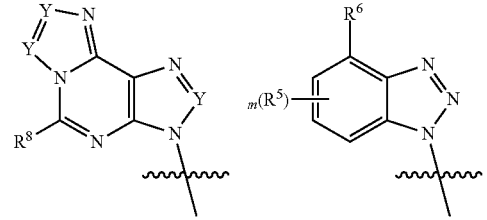

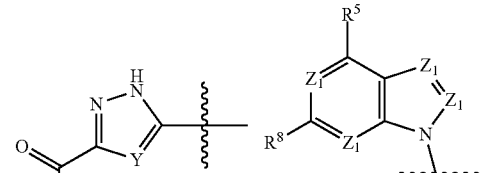

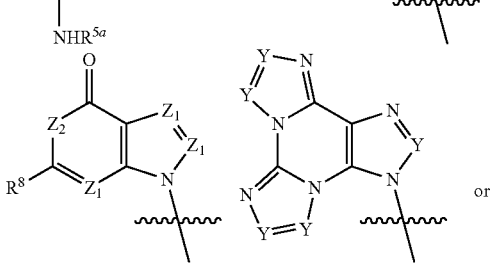

-continued

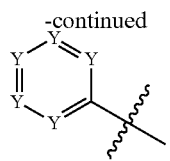

with the proviso that one of $R^1$ and $R^2$ must be

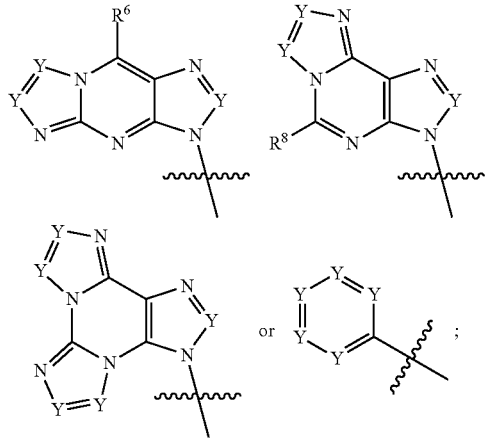

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

13. The compound according to claim 1 of the formula

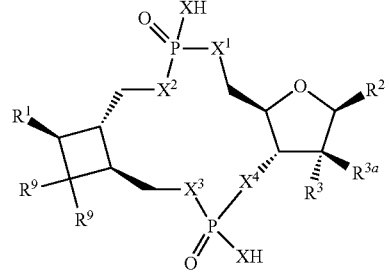

wherein
X is S;
$X^1$, $X^2$, $X^3$ and $X^4$ are each independently O or NH;
$R^1$ and $R^2$ are independently

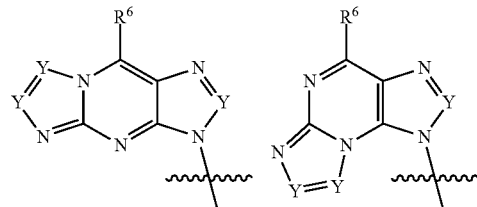

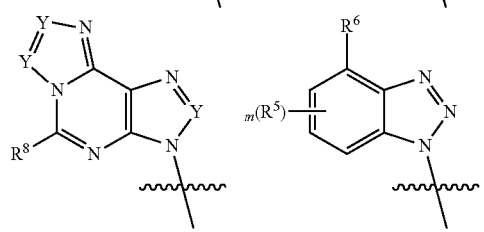

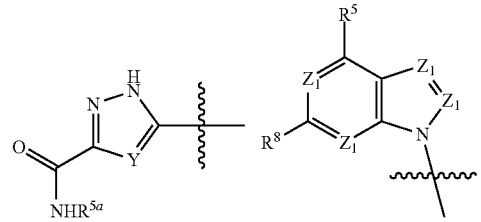

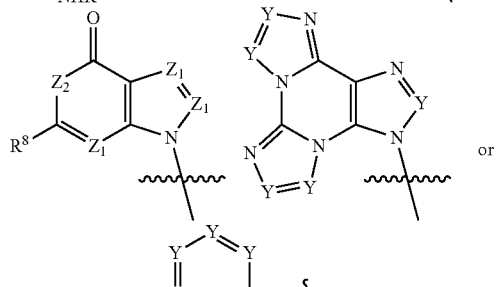

with the proviso that one of $R^1$ and $R^2$ must be

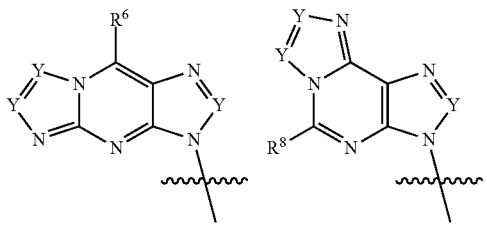

-continued

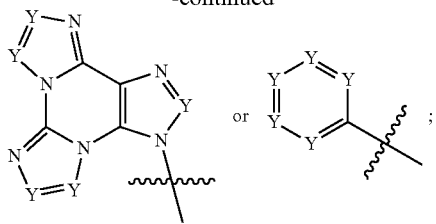 or 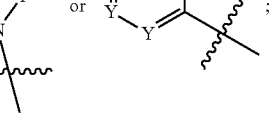 ;

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O)$NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

14. The compound according to claim 1 of the formula

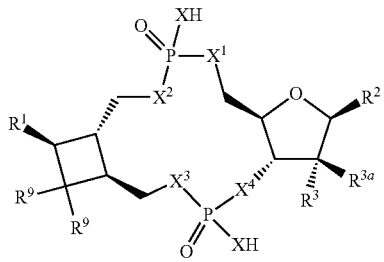

wherein
X is O;
$X^1$, $X^2$, $X^3$ and $X^4$ are each independently O or NH;

$R^1$ and $R^2$ are independently

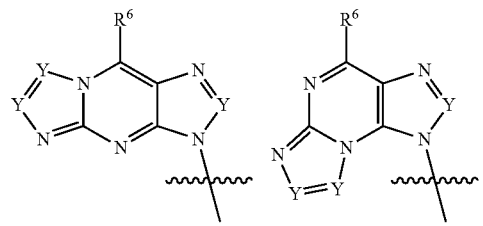

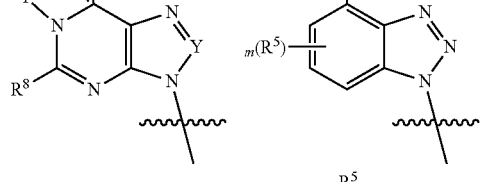

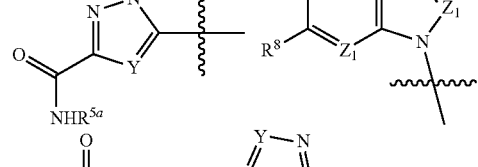

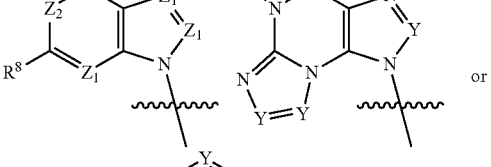

with the proviso that one of $R^1$ and $R^2$ must be

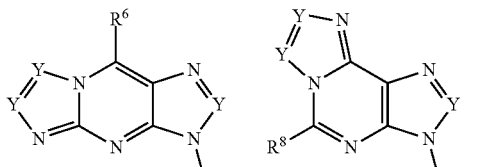

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O) $R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;

$R^{3a}$ is H, $CH_3$, halogen, —$NR^{a1}R^{a1}$ or $OR^{a1}$; or $R^3$ and $R^{3a}$ may be taken together to form a 3-4 membered carbocycle; or $R^3$ and $R^{3a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

15. The compound according to claim 1 of the formula

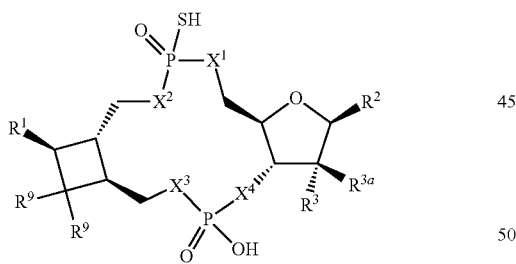

wherein $X^1$, $X^2$, $X^3$ and $X^4$ are each independently O or NH;

$R^1$ and $R^2$ are each independently

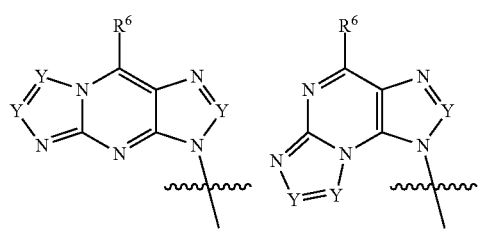

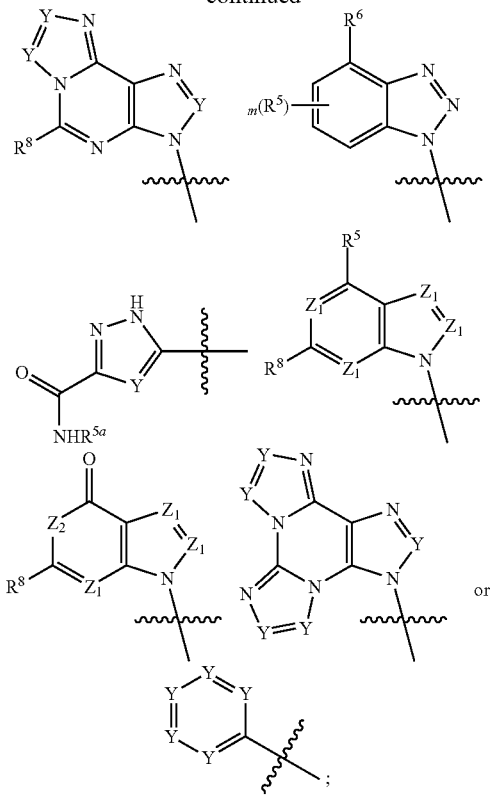

-continued

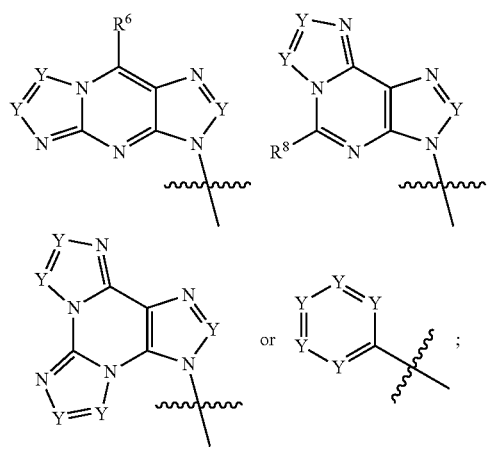

with the proviso that one of $R^1$ and $R^2$ must be $Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

16. The compound according to claim 1 of the formula

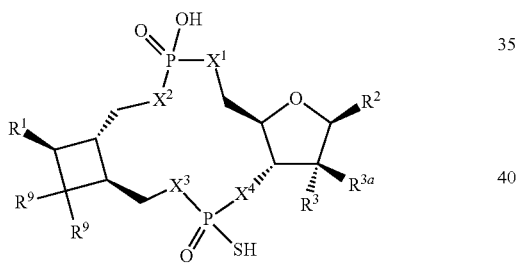

wherein
$X^1$, $X^2$, $X^3$ and $X^4$ are each independently O or NH;
$R^1$ and $R^2$ are each independently

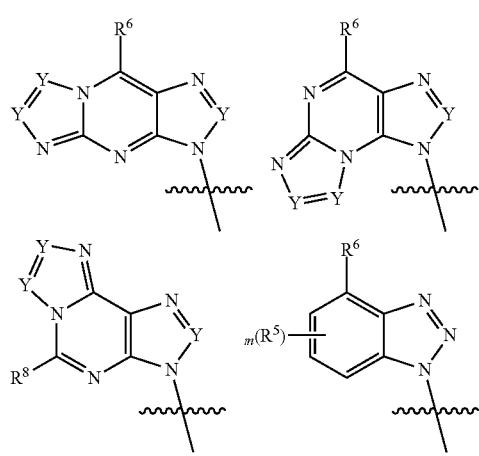

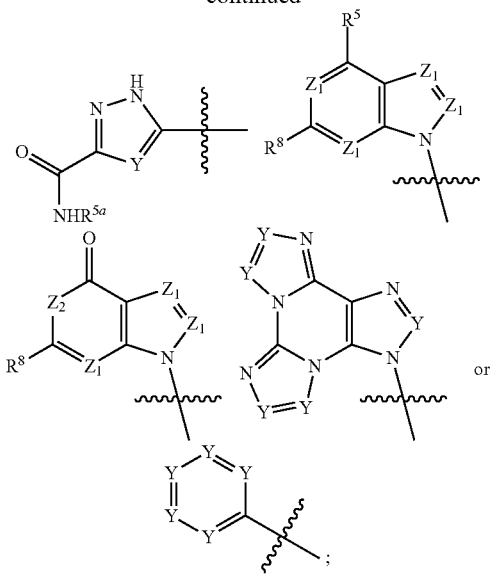

with the proviso that one of $R^1$ and $R^2$ must be

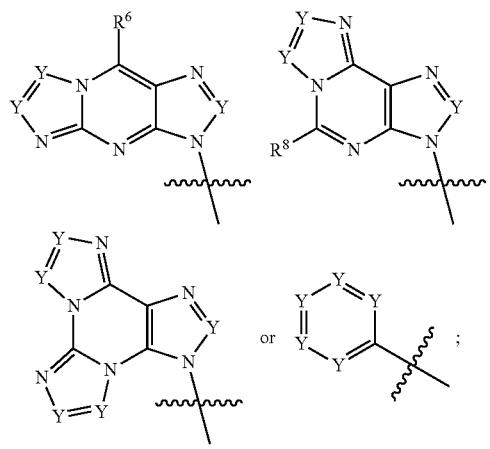

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C=CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

17. The compound according to claim 1 of the formula

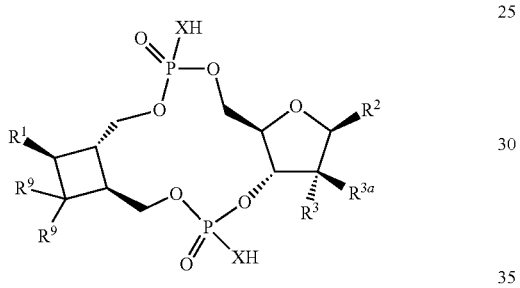

wherein

X is independently O or S;

R$^1$ and R$^2$ are each independently

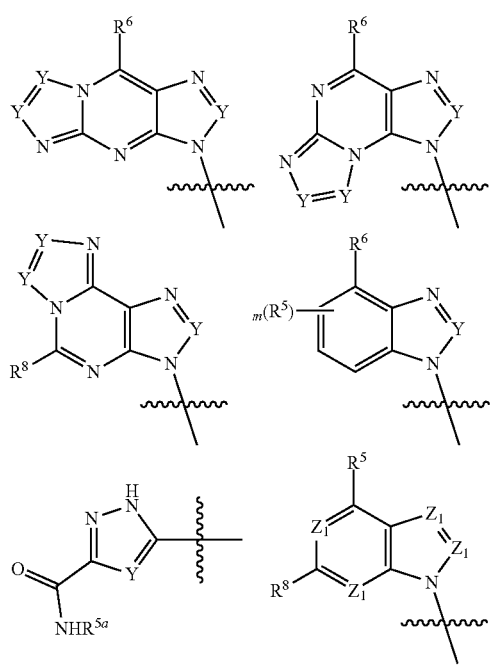

with the proviso that one of R$^1$ and R$^2$ must be

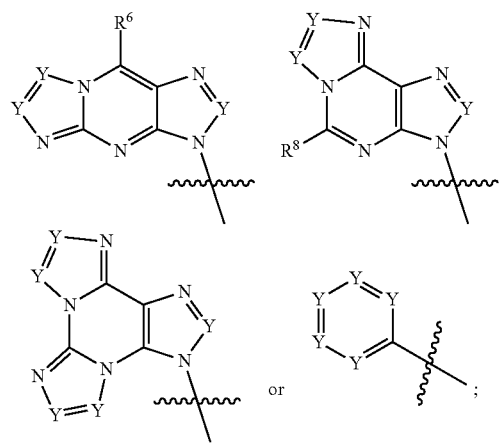

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^3$ is H, CH$_3$, halogen, —NR$^{a1}$R$^{a1}$ or OR$^{a1}$;

R$^{3a}$ is H, CH$_3$, halogen, —NR$^{a1}$R$^{a1}$ or OR$^{a1}$; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$ R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

18. The compound according to claim 1 of the formula

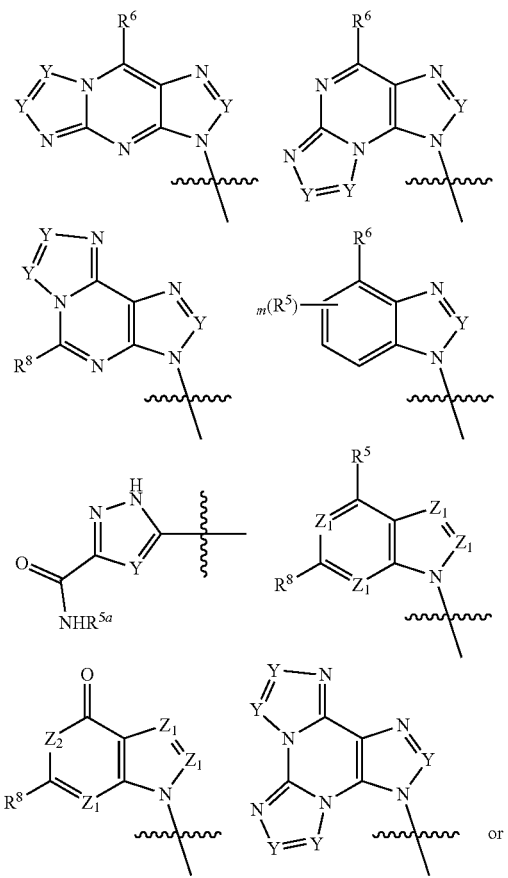

wherein

X is S;

R$^1$ and R$^2$ are each independently

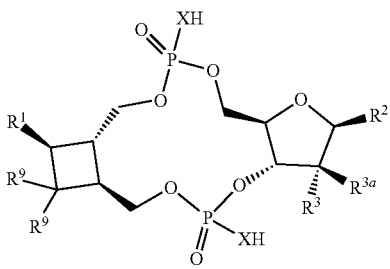

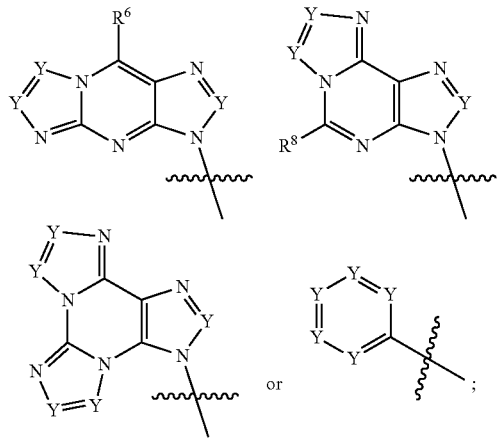

-continued

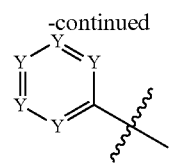

with the proviso that one of R$^1$ and R$^2$ must be

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^3$ is H, CH$_3$, halogen, —NR$^{a1}$R$^{a1}$ or OR$^{a1}$;

R$^{3a}$ is H, CH$_3$, halogen, —NR$^{a1}$R$^{a1}$ or OR$^{a1}$; or

R$^3$ and R$^{3a}$ may be taken together to form a 3-4 membered carbocycle; or

R$^3$ and R$^{3a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

19. The compound according to claim 1 of the formula

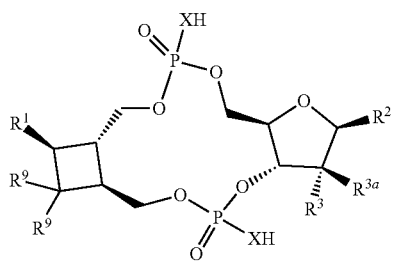

wherein
X is O;
$R^1$ and $R^2$ are each independently

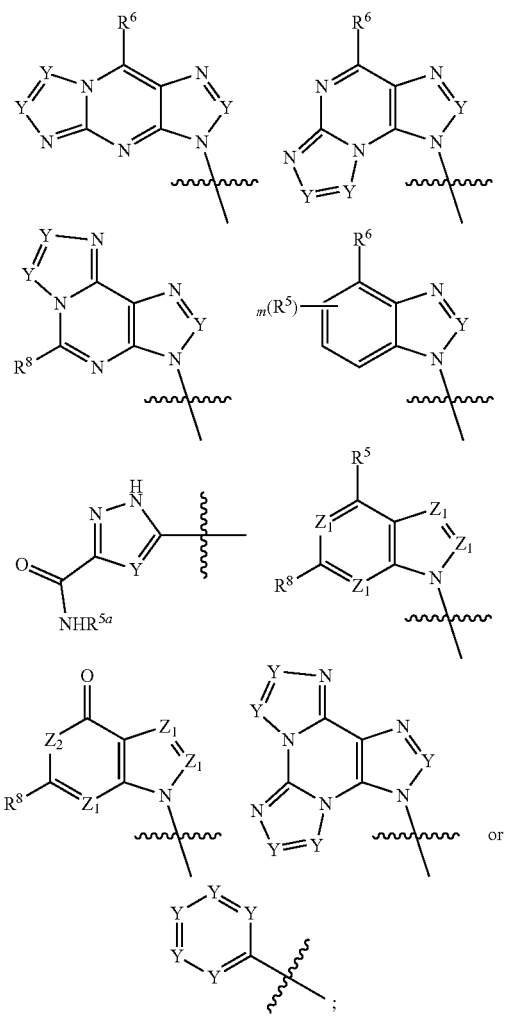

with the proviso that one of $R^1$ and $R^2$ must be

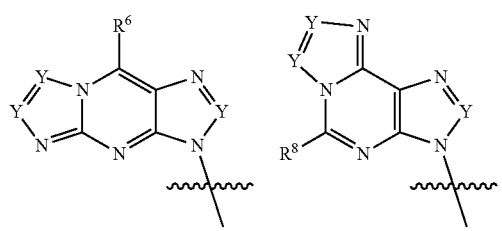

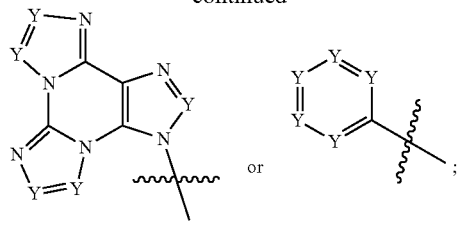

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;
$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}S(O)_2R^{a1}$, —$NR^{a1}S(O)_2NR^{a1}R^{a1}$, —S(O)$R^{a1}$, —S(O)$NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

20. The compound according to claim 1 of the formula

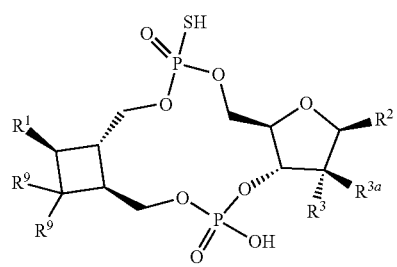

309 wherein
R¹ and R² are each independently

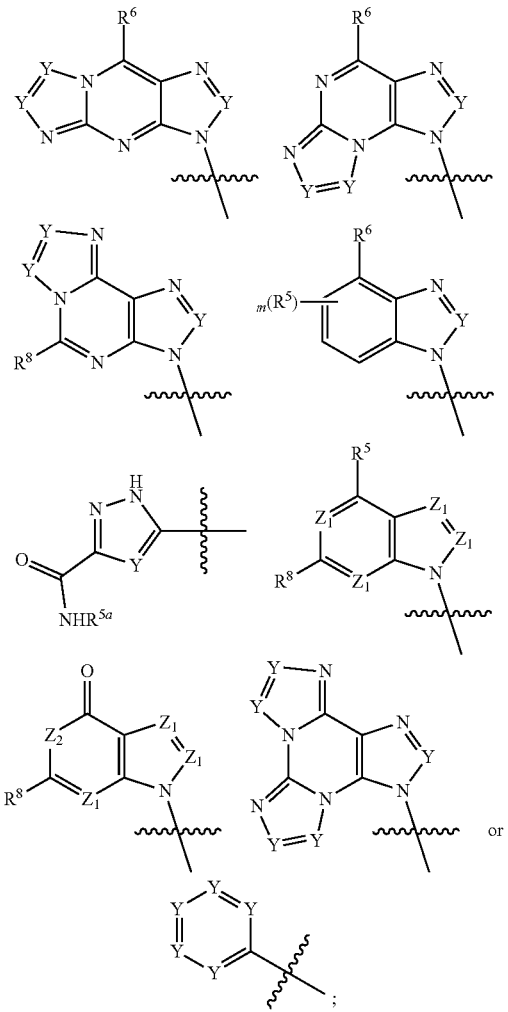

with the proviso that one of R¹ and R² must be

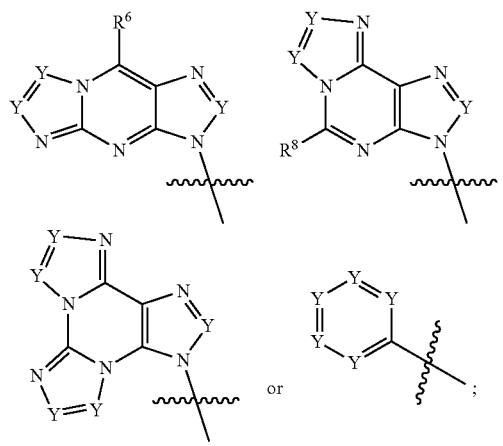

$Z_1$ is N or $CR^a$;
$Z_2$ is $NR^b$;

310

$R^a$ is H, halogen, $C_{1-6}$ alkyl substituted with 0-6 $R^5$, $C_{3-6}$ cycloalkyl substituted with 0-6 $R^5$, CN, NO$_2$, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;

$R^{a1}$ is H, $C_{1-3}$ alkyl or $C_{3-6}$ cycloalkyl;

$R^3$ is H, CH$_3$, halogen, —NR$^{a1}$R$^{a1}$ or OR$^{a1}$;

$R^{3a}$ is H, CH$_3$, halogen, —NR$^{a1}$R$^{a1}$ or OR$^{a1}$; or $R^3$ and $R^{3a}$ may be taken together to form a 3-4 membered carbocycle; or $R^3$ and $R^{3a}$ may be taken together to form a C=CH$_2$ substituent;

$R^5$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^{5a}$ is H or $C_{1-3}$ alkyl;

$R^6$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^8$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

$R^9$ is H, halogen or methyl;

Y is $CR^a$ or N;

m is 0, 1, 2 or 3;

or a pharmaceutically acceptable salt, tautomer or stereoisomer thereof.

21. The compound according to claim 1 of the formula

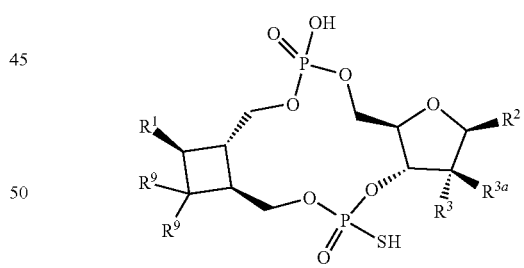

wherein
R¹ and R² are each independently

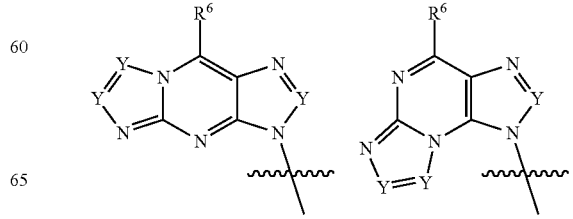

311

-continued

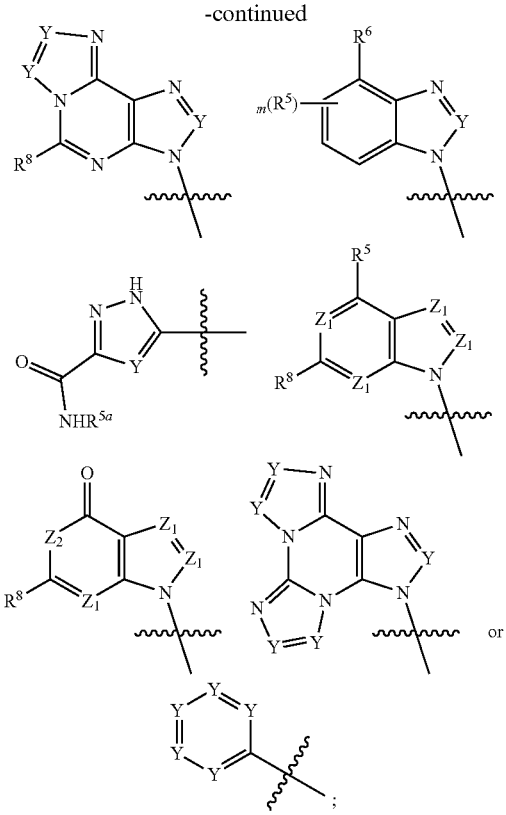

with the proviso that one of $R^1$ and $R^2$ must be

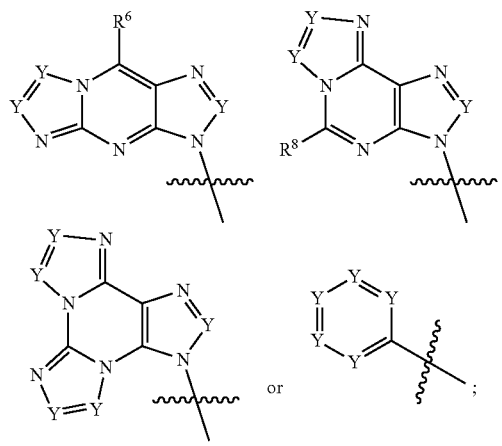

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)$ $R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2$ $R^{a1}$, —$NR^{a1}S(O)_2NR^{a1}R^{a1}$, —$S(O)R^{a1}$, —$S(O)$ $NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;
$R^3$ is H, $CH_3$, halogen, —$NR^{a1}R^{a1}$ or $OR^{a1}$;

312

$R^{3a}$ is H, $CH_3$, halogen, —$NR^{a1}R^{a1}$ or $OR^{a1}$; or
$R^3$ and $R^{3a}$ may be taken together to form a 3-4 membered carbocycle; or
$R^3$ and $R^{3a}$ may be taken together to form a $C\!=\!CH_2$ substituent;
$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2$ $R^{a1}$, —$NR^{a1}S(O)_2NR^{a1}R^{a1}$, —$S(O)R^{a1}$, —$S(O)$ $NR^{a1}R^{a1}$, —$S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2$ $R^{a1}$, —$NR^{a1}S(O)_2NR^{a1}R^{a1}$, —$S(O)R^{a1}$, —$S(O)$ $NR^{a1}R^{a1}$, —$S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2$ $R^{a1}$, —$NR^{a1}S(O)_2NR^{a1}R^{a1}$, —$S(O)R^{a1}$, —$S(O)$ $NR^{a1}R^{a1}$, —$S(O)_2R^{a1}$ or $S(O)_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

22. The compound according to claim 1 of the formula

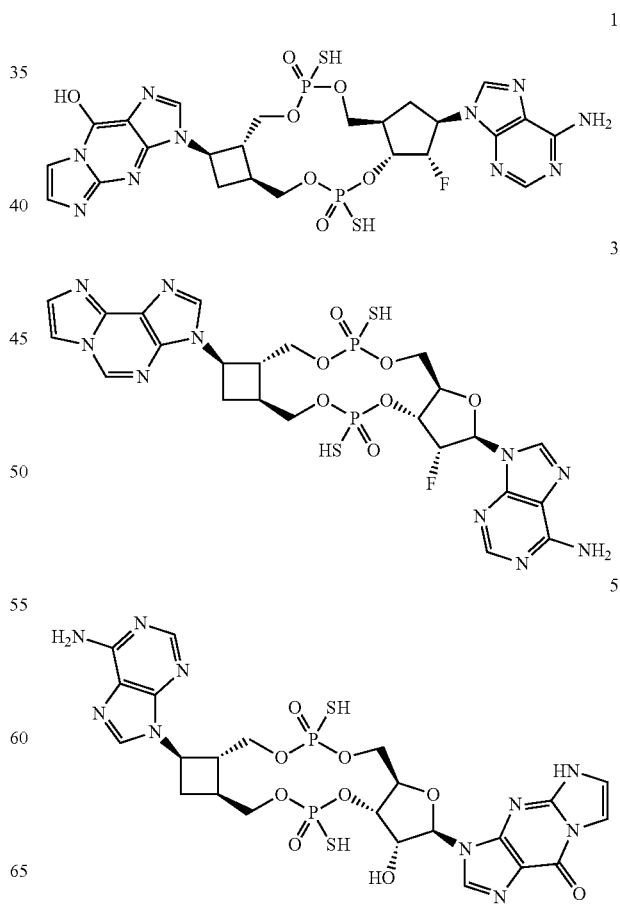

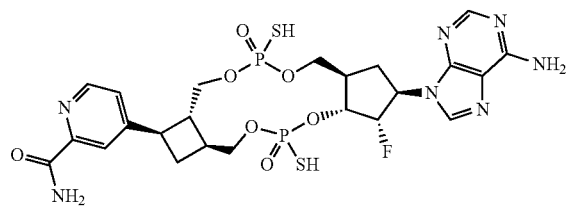
9
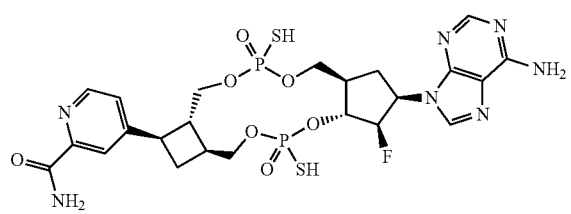
11
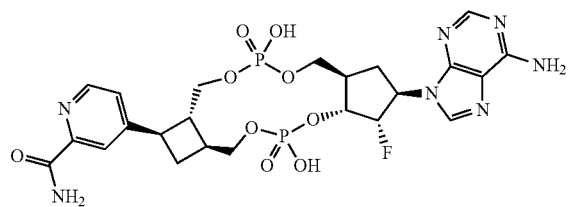
12
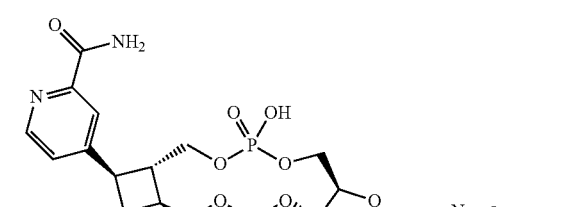
13
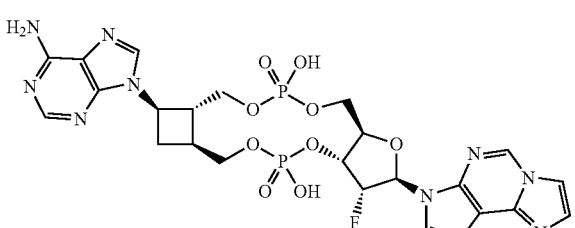
16
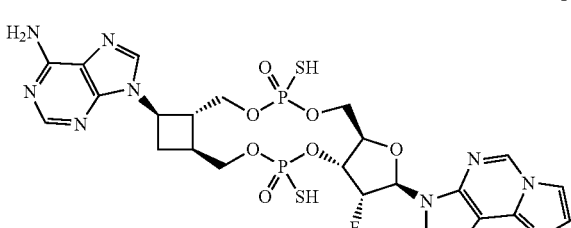
17
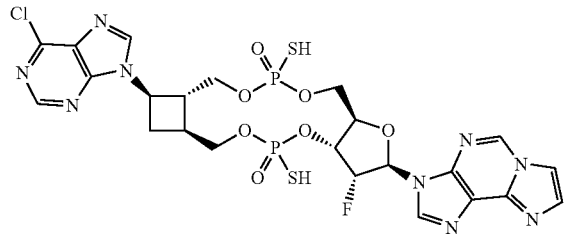
18
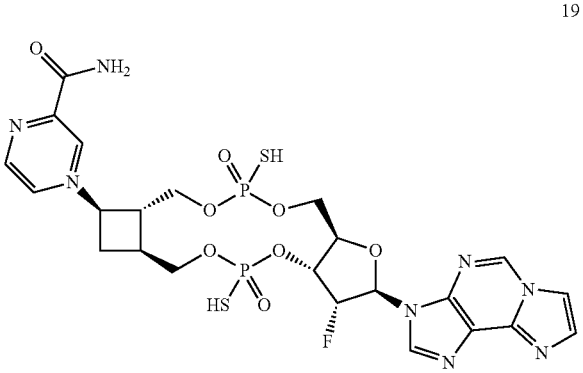
19
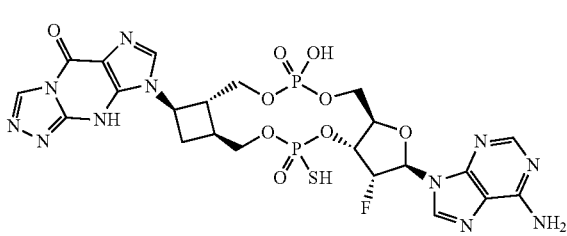
21
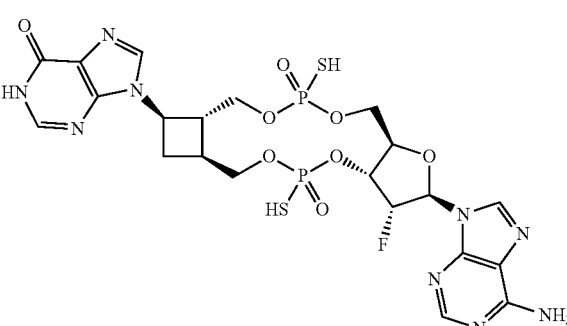
22
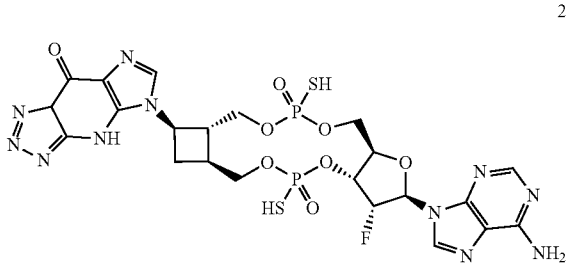
23
or a tautomer or stereoisomer thereof.

23. A pharmaceutically acceptable salt of a compound according to claim 1 of the formula
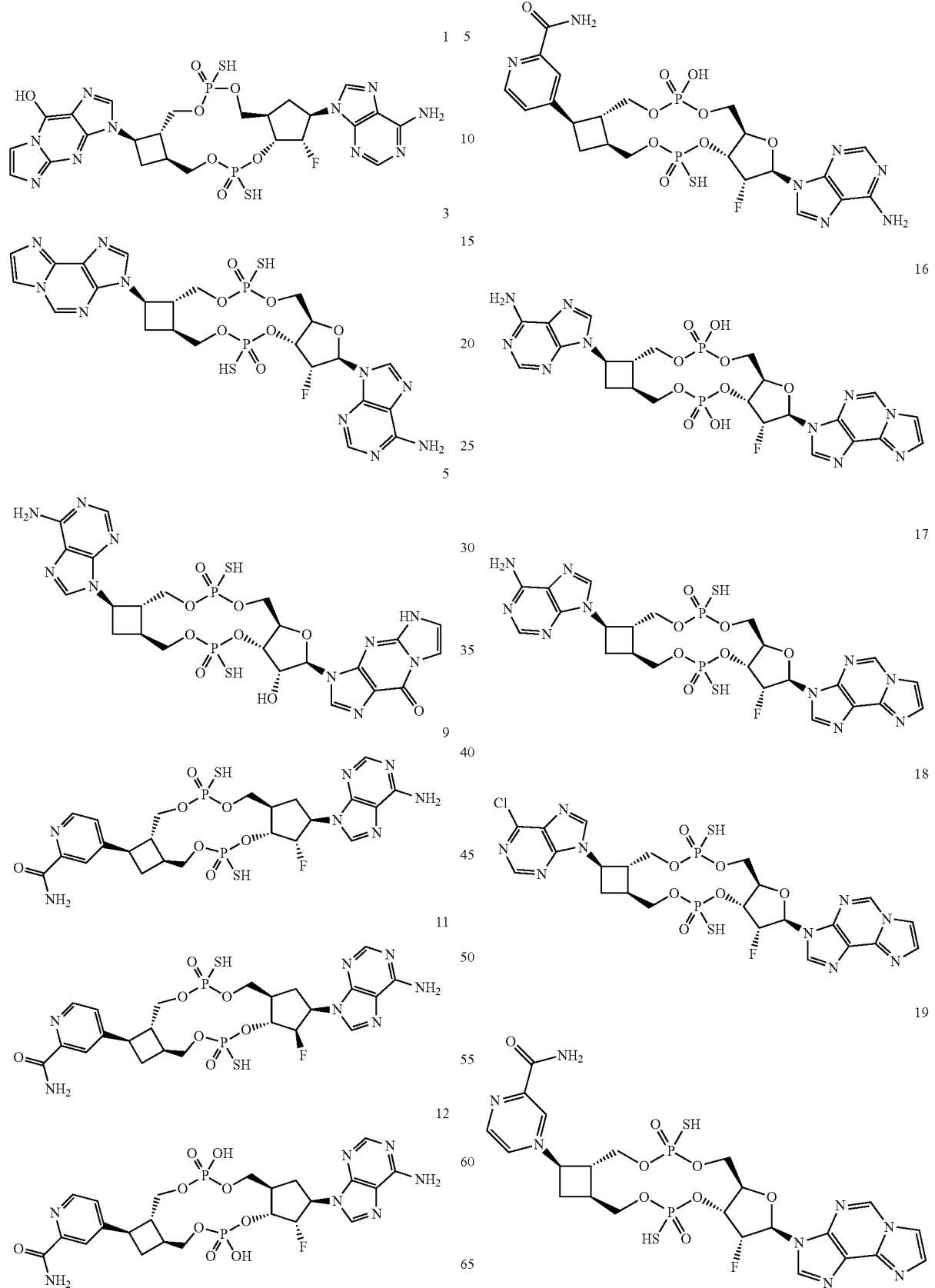

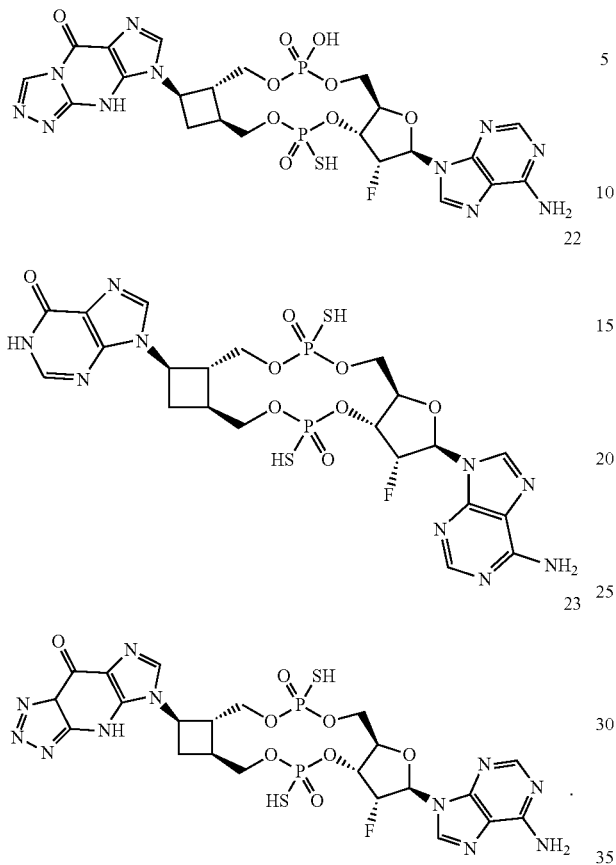

24. A compound of formula II

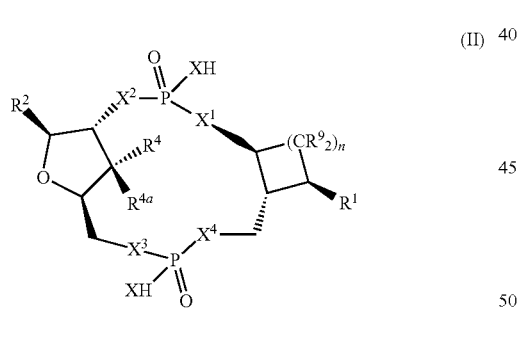
(II)

wherein
X is independently O or S;
$X^1$, $X^2$, $X^3$ and $X^4$ are each independently O or NH;
$R^1$ and $R^2$ are each independently

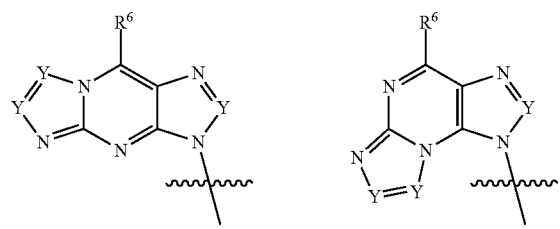

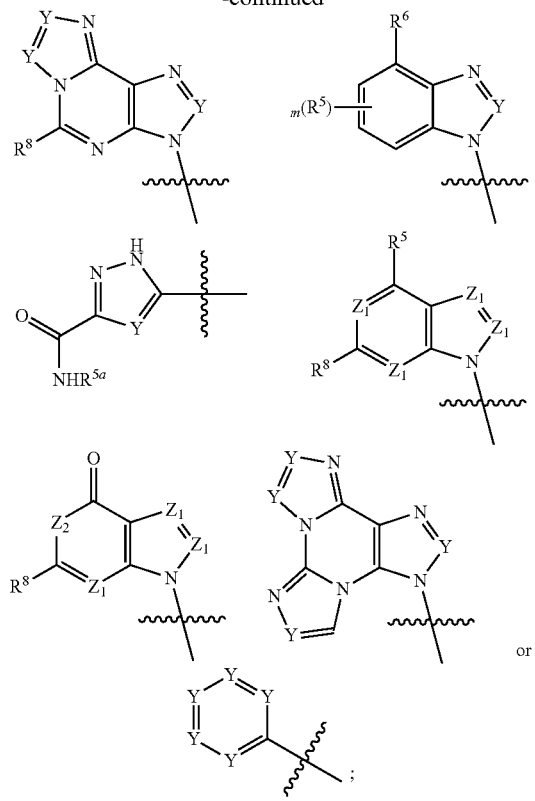

with the proviso that one of $R^1$ and $R^2$ must be

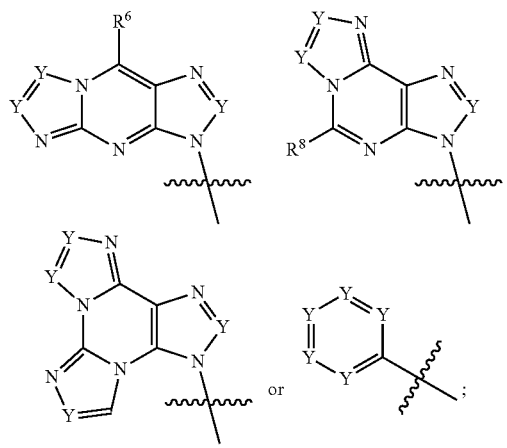

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;
$R^{a1}$ is H, $C_{1-3}$ alkyl or $C_{3-6}$ cycloalkyl;

319

R$^4$ is H, CH$_3$, halogen, —NR$^{a1}$R$^{a1}$ or OR$^{a1}$;
R$^{4a}$ is H, CH$_3$, halogen, —NR$^{a1}$R$^{a1}$ or OR$^{a1}$; or
R$^4$ and R$^{4a}$ may be taken together to form a 3-4 membered carbocycle; or
R$^4$ and R$^{4a}$ may be taken together to form a C═CH$_2$ substituent;
R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
or two R$^5$ groups may be taken together to form a 5-6 membered carbocyclic or heterocyclic group;
or R$^5$ and R$^6$ may be taken together to form a 5-6 membered carbocyclic or heterocyclic group;
R$^{5a}$ is H or C$_{1-3}$ alkyl;
R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^9$ is H, halogen or methyl;
Y is CR$^a$ or N;
m is 0, 1, 2 or 3;
n is 0 or 1;
or a pharmaceutically acceptable salt, tautomer or stereoisomer thereof.

25. The compound according to claim 24 of formula II

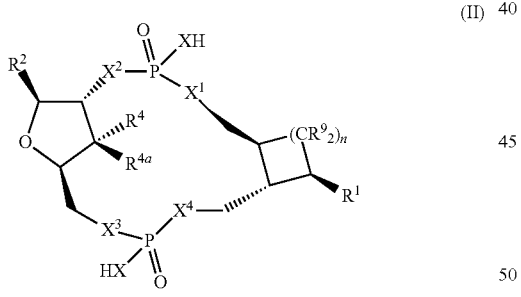
(II)

wherein
X is S;
X$^1$, X$^2$, X$^3$ and X$^4$ are each independently O or NH;
R$^1$ and R$^2$ are each independently

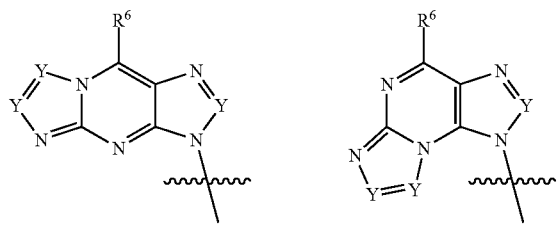

-continued

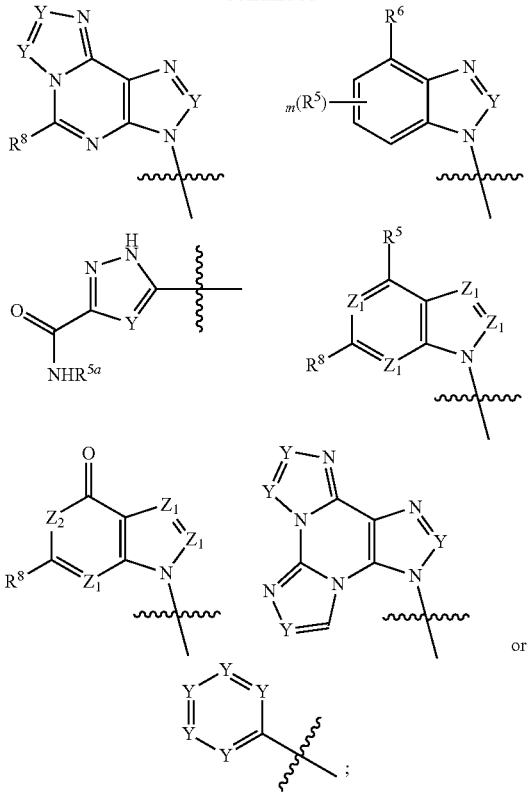

with the proviso that one of R$^1$ and R$^2$ must be

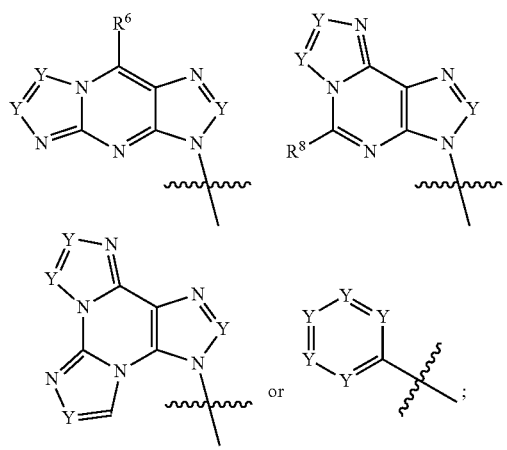

Z$_1$ is N or CR$^a$;
Z$_2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;
R$^{a1}$ is H, C$_{1-3}$ alkyl or C$_{3-6}$ cycloalkyl;

$R^4$ is H, $CH_3$, halogen, $-NR^{a1}R^{a1}$ or $OR^{a1}$;

$R^{4a}$ is H, $CH_3$, halogen, $-NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

26. The compound according to claim 24 of formula II

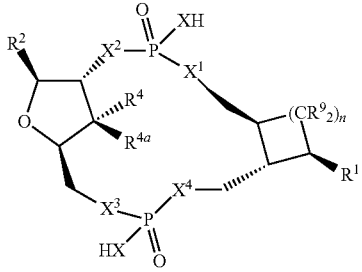

(II)

wherein

X is O;

$X^1$, $X^2$, $X^3$ and $X^4$ are each independently O or NH;

$R^1$ and $R^2$ are each independently

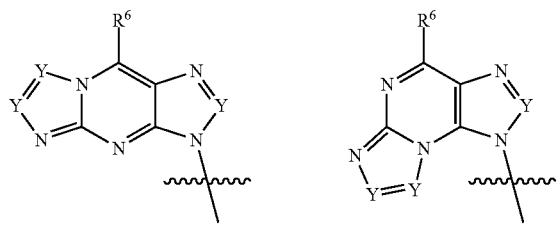

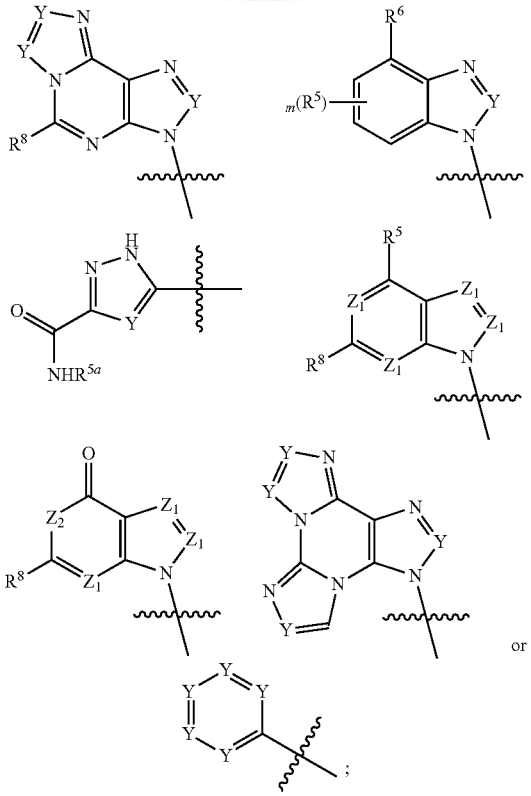

-continued with the proviso that one of $R^1$ and $R^2$ must be

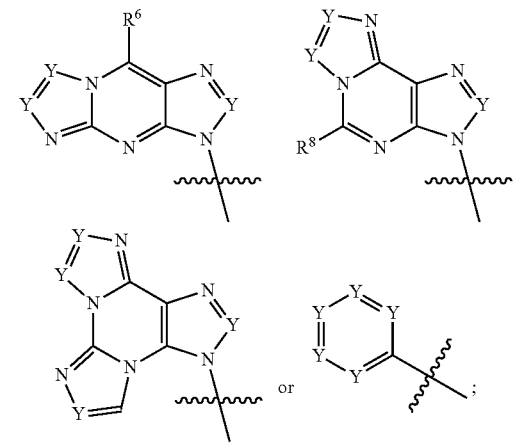

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;

$R^{a1}$ is H, $C_{1-3}$ alkyl or $C_{3-6}$ cycloalkyl;

R⁴ is H, CH₃, halogen, —NR^{a1}R^{a1} or OR^{a1};
R^{4a} is H, CH₃, halogen, —NR^{a1}R^{a1} or OR^{a1}; or
R⁴ and R^{4a} may be taken together to form a 3-4 membered carbocycle; or
R⁴ and R^{4a} may be taken together to form a C=CH₂ substituent;
R⁵ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R^{5a} is H or C₁₋₃ alkyl;
R⁶ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R⁸ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R⁹ is H, halogen or methyl;
Y is CR^{a} or N;
m is 0, 1, 2 or 3;
n is 0 or 1;
or a pharmaceutically acceptable salt, tautomer or stereoisomer thereof.

27. The compound according to claim 24 of the formula

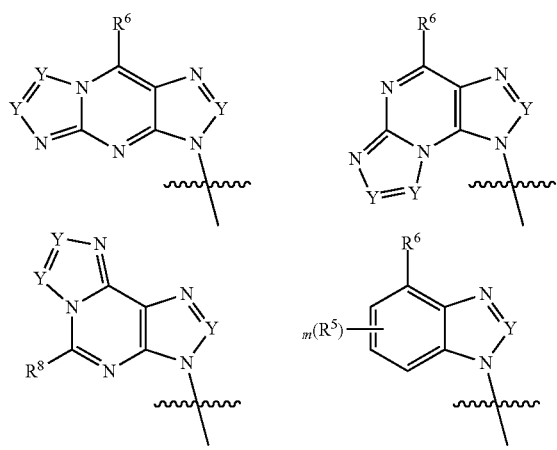

wherein
X¹, X², X³ and X⁴ are each independently O or NH;
R¹ and R² are each independently

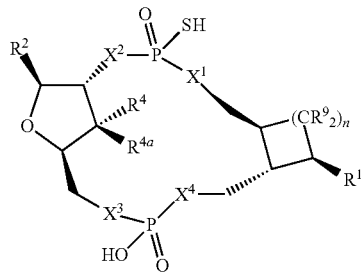

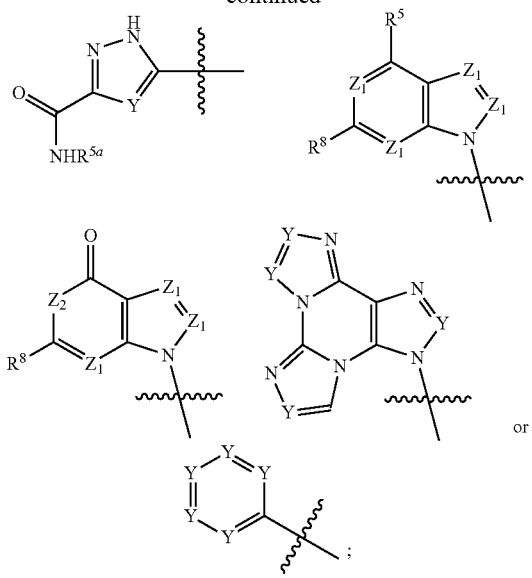

with the proviso that one of R¹ and R² must be

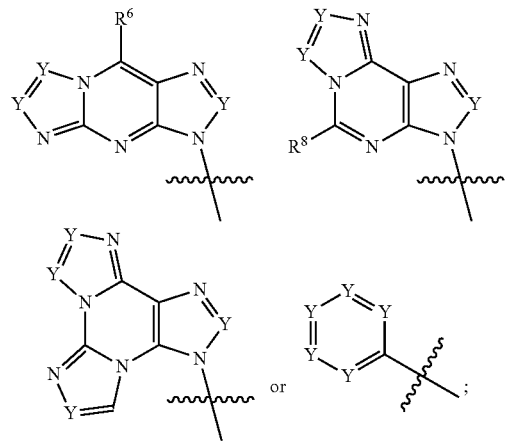

Z₁ is N or CR^{a};
Z₂ is NR^{b};
R^{a} is H, halogen, C₁₋₆ alkyl substituted with 0-6 R⁵, C₃₋₆ cycloalkyl substituted with 0-6 R⁵, CN, NO₂, OH, OR^{a1}, SR^{a1}, —C(O)NR^{a1}R^{a1}, —COOR^{a1}, —OC(O)R^{a1}, —OC(O)NR^{a1}R^{a1}, —NR^{a1}R^{a1}, —NR^{a1}C(O)R^{a1}, —NR^{a1}COOR^{a1}, —NR^{a1}C(O)NR^{a1}R^{a1}, —NR^{a1}S(O)₂R^{a1}, —NR^{a1}S(O)₂NR^{a1}R^{a1}, —S(O)R^{a1}, —S(O)NR^{a1}R^{a1}, —S(O)₂R^{a1} or S(O)₂NR^{a1}R^{a1};
R^{b} is H, C₁₋₆ alkyl substituted with 0-6 R⁵, C₃₋₆ cycloalkyl substituted with 0-6 R⁵, —C(O)R^{a1}, —C(O)NR^{a1}R^{a1}, —S(O)₂R^{a1} or S(O)₂NR^{a1}R^{a1};
R^{a1} is H, C₁₋₃ alkyl or C₃₋₆ cycloalkyl;
R⁴ is H, CH₃, halogen, —NR^{a1}R^{a1} or OR^{a1};
R^{4a} is H, CH₃, halogen, —NR^{a1}R^{a1} or OR^{a1}; or
R⁴ and R^{4a} may be taken together to form a 3-4 membered carbocycle; or
R⁴ and R^{4a} may be taken together to form a C=CH₂ substituent;
R⁵ is H, halogen, C₁₋₃ alkyl, CN, NO₂, OH, OR^{a1}, SR^{a1}, —C(O)NR^{a1}R^{a1}, —COOR^{a1}, —OC(O)R^{a1}, —OC(O)

$NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

28. The compound according to claim 24 of the formula

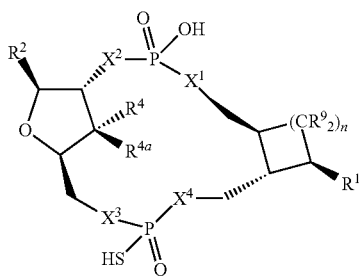

wherein $X^1$, $X^2$, $X^3$ and $X^4$ are each independently O or NH;

$R^1$ and $R^2$ are each independently

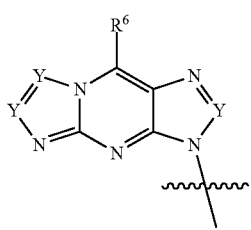 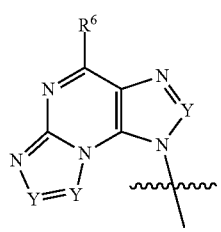

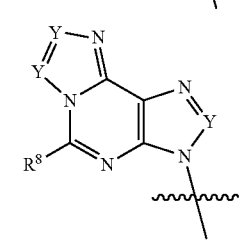

with the proviso that one of $R^1$ and $R^2$ must be

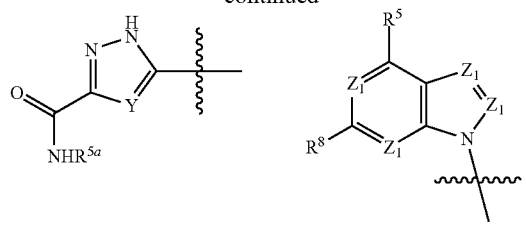

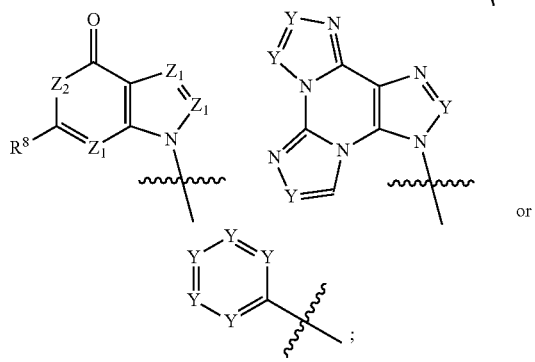

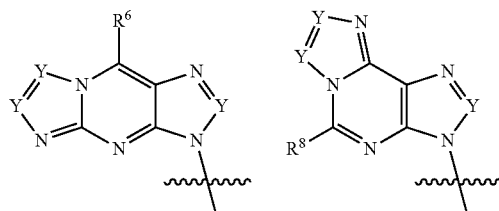

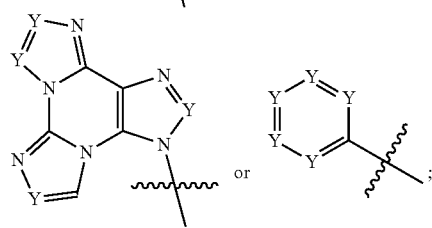

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C{=}CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

29. The compound according to claim 24 of the formula

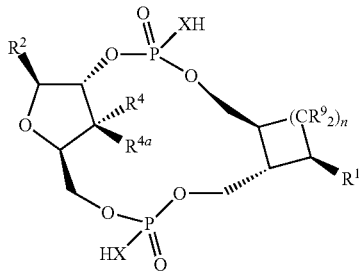

wherein

X is independently O or S;

$R^1$ and $R^2$ are each independently

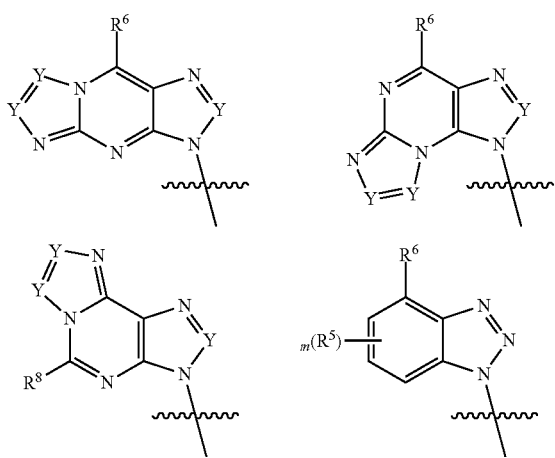

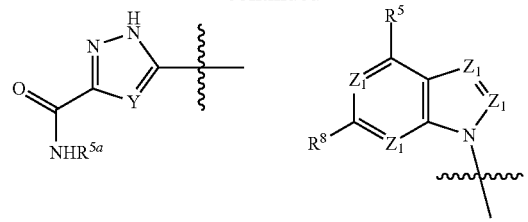

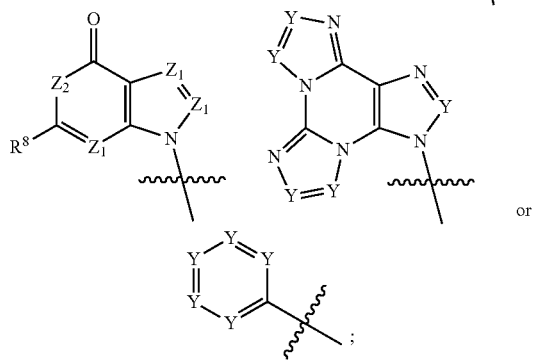

with the proviso that one of $R^1$ and $R^2$ must be

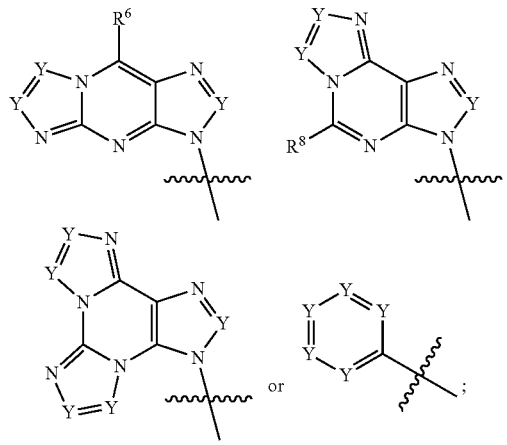

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, Cl-3 alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

30. The compound according to claim 24 of the formula

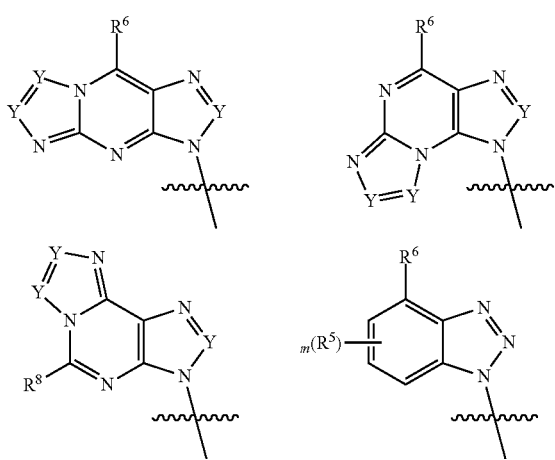

wherein

X is S;

$R^1$ and $R^2$ are each independently

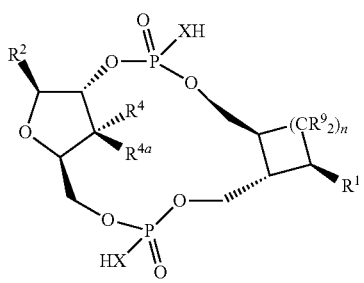

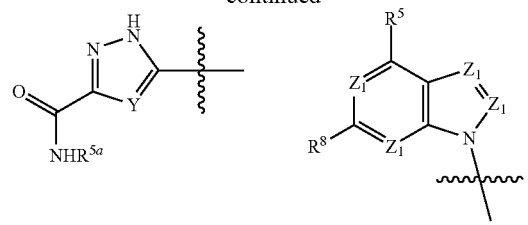

with the proviso that one of $R^1$ and $R^2$ must be

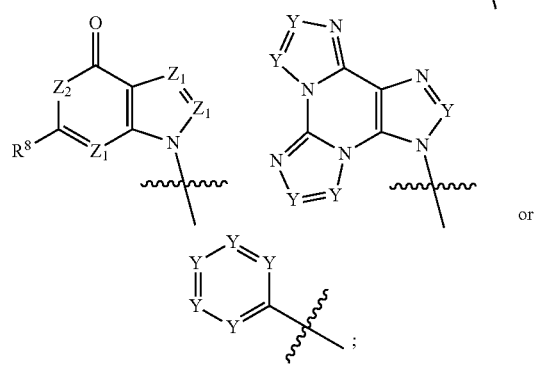

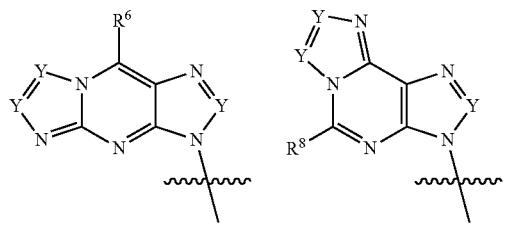

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ $NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

n is 0 or 1;

or a pharmaceutically acceptable salt, tautomer or stereoisomer thereof.

31. The compound according to claim 24 of the formula

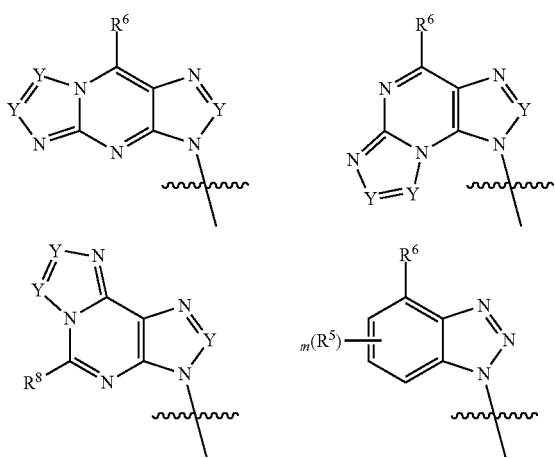

wherein

X is O;

$R^1$ and $R^2$ are each independently

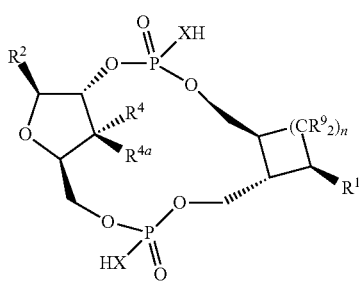

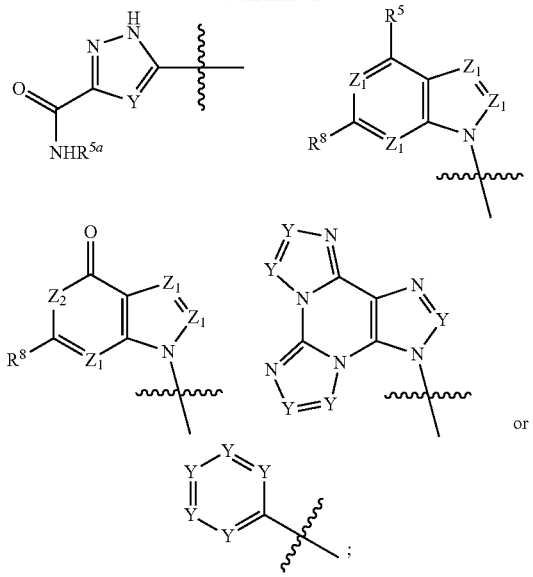

with the proviso that one of $R^1$ and $R^2$ must be

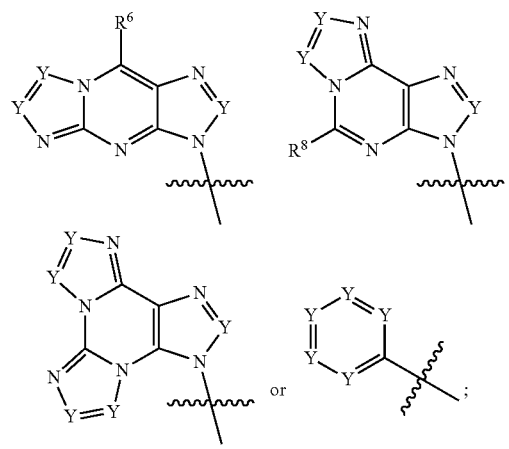

$Z_1$ is N or $CR^a$;

$Z_2$ is $NR^b$;

$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)$ NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

n is 0 or 1;

or a pharmaceutically acceptable salt, tautomer or stereoisomer thereof.

32. The compound according to claim 24 of the formula

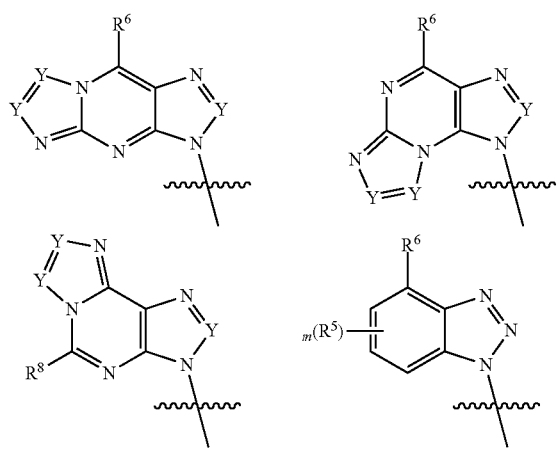

wherein

X is independently O or S;

X$^1$, X$^2$, X$^3$ and X$^4$ are each independently O or NH;

R$^1$ and R$^2$ are each independently

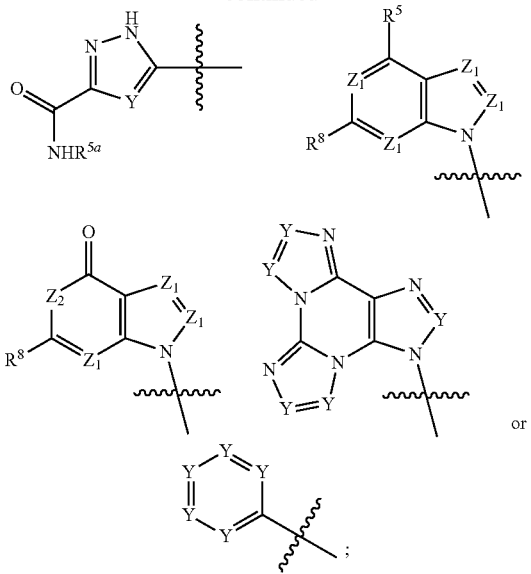

with the proviso that one of R$^1$ and R$^2$ must be

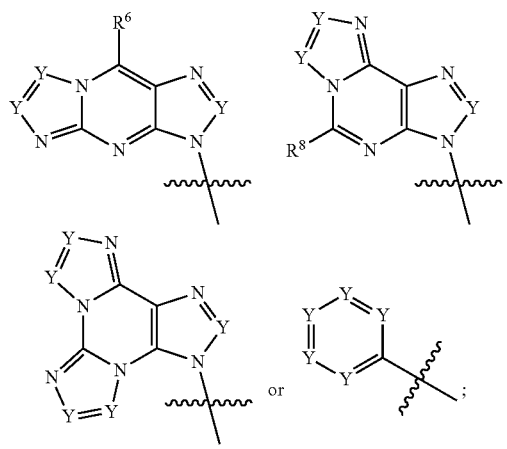

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^4$ is H, CH$_3$, halogen, —NR$^{a1}$R$^{a1}$ or OR$^{a1}$;

R$^{4a}$ is H, CH$_3$, halogen, —NR$^{a1}$R$^{a1}$ or OR$^{a1}$; or

R$^4$ and R$^{4a}$ may be taken together to form a 3-4 membered carbocycle; or

R$^4$ and R$^{4a}$ may be taken together to form a C═CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)

NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

33. The compound according to claim 24 of the formula

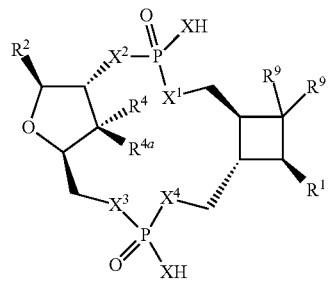

wherein

X is S;

X$^1$, X$^2$, X$^3$ and X$^4$ are each independently O or NH;

R$^1$ and R$^2$ are each independently

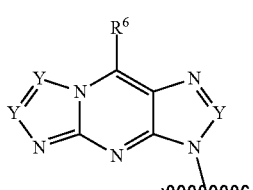
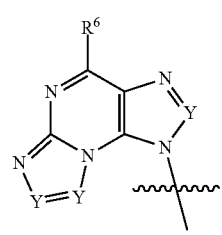
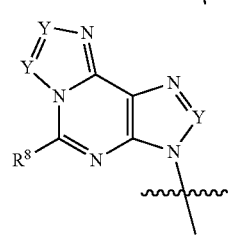

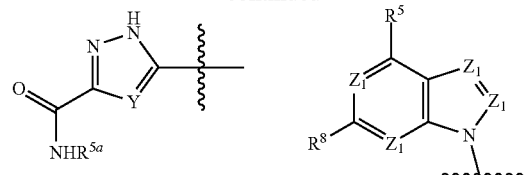
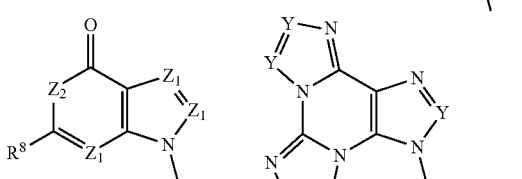
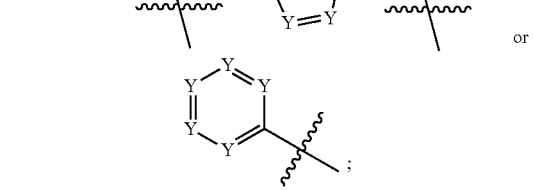

with the proviso that one of R$^1$ and R$^2$ must be

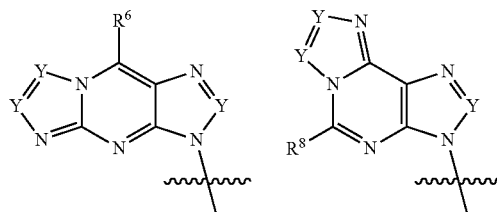
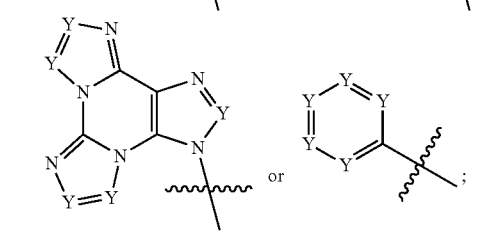

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^4$ is H, CH$_3$, halogen, —NR$^{a1}$R$^{a1}$ or OR$^{a1}$;

R$^{4a}$ is H, CH$_3$, halogen, —NR$^{a1}$R$^{a1}$ or OR$^{a1}$; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)

NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

34. The compound according to claim 24 of the formula

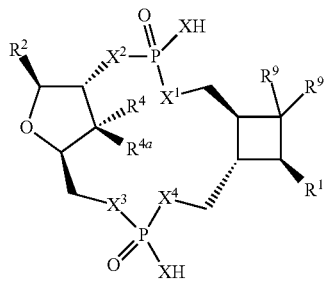

wherein

X is O;

X$^1$, X$^2$, X$^3$ and X$^4$ are each independently O or NH;

R$^1$ and R$^2$ are each independently

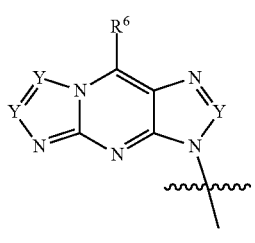 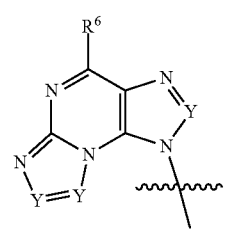

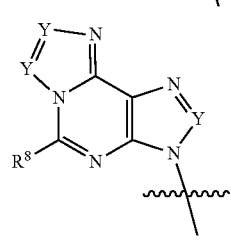

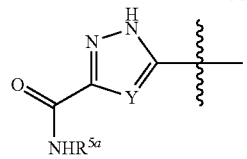 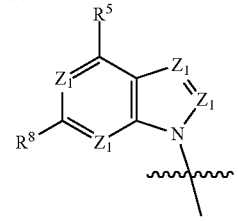

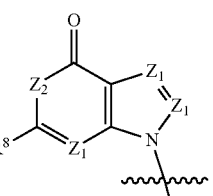 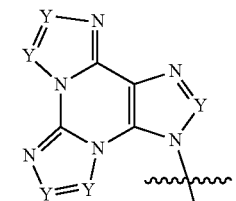

or

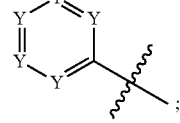

;

with the proviso that one of R$^1$ and R$^2$ must be

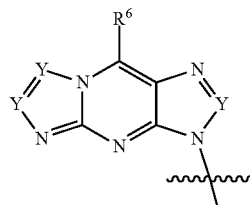 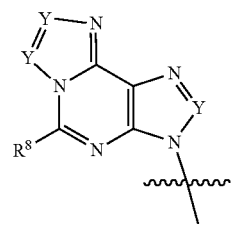

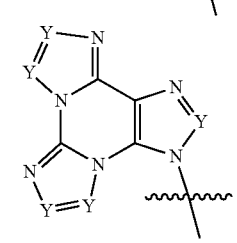

or 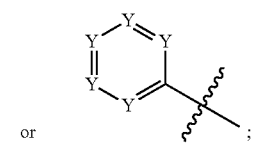 ;

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^4$ is H, CH$_3$, halogen, —NR$^{a1}$R$^{a1}$ or OR$^{a1}$;

R$^{4a}$ is H, CH$_3$, halogen, —NR$^{a1}$R$^{a1}$ or OR$^{a1}$; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)

NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;
Y is CR$^a$ or N;
m is 0, 1, 2 or 3;
or a pharmaceutically acceptable salt, tautomer or stereoisomer thereof.

35. The compound according to claim 24 of the formula

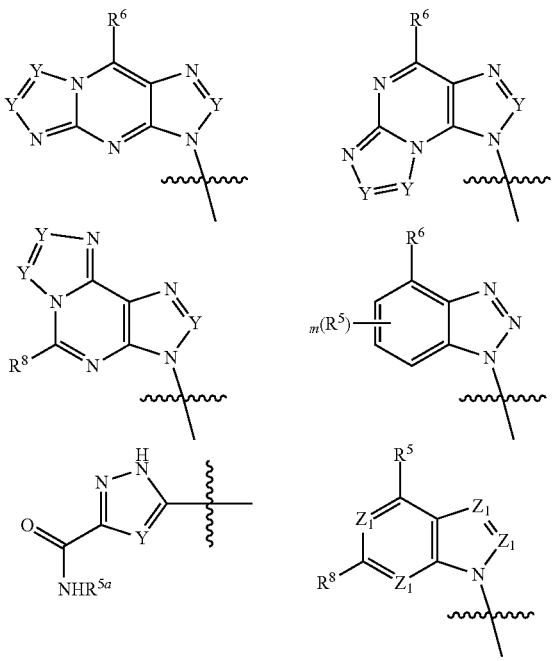

wherein
X$^1$, X$^2$, X$^3$ and X$^4$ are each independently O or NH;
R$^1$ and R$^2$ are each independently

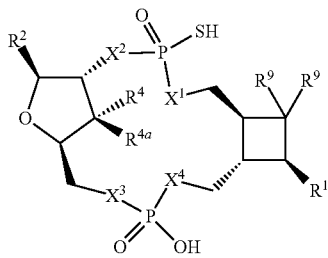

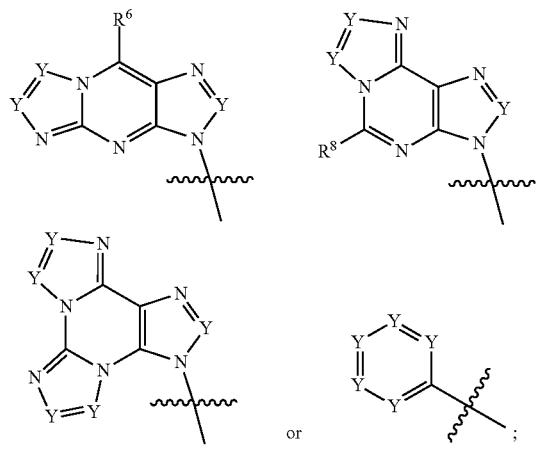

with the proviso that one of R$^1$ and R$^2$ must be

Z$_1$ is N or CR$^a$;
Z$_2$ is NR$^b$;
R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;
R$^4$ is H, CH$_3$, halogen, —NR$^{a1}$R$^{a1}$ or OR$^{a1}$;
R$^{4a}$ is H, CH$_3$, halogen, —NR$^{a1}$R$^{a1}$ or OR$^{a1}$; or
R$^4$ and R$^{4a}$ may be taken together to form a 3-4 membered carbocycle; or
R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;
R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$ R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

36. The compound according to claim 24 of the formula

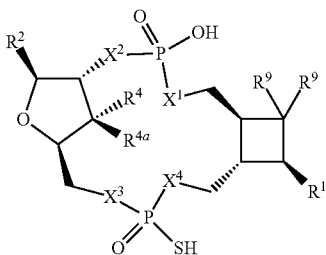

wherein

X$^1$, X$^2$, X$^3$ and X$^4$ are each independently O or NH;

R$^1$ and R$^2$ are each independently

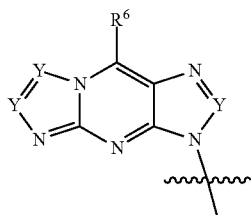
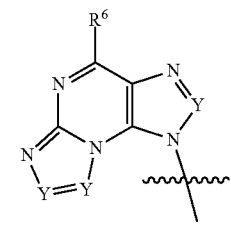
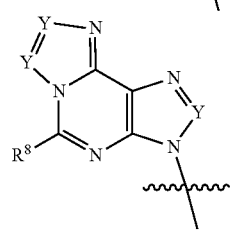
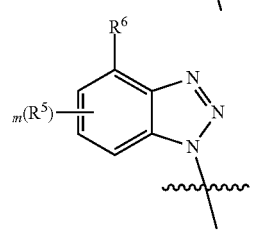
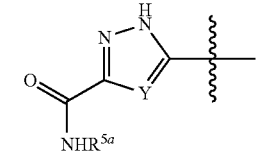
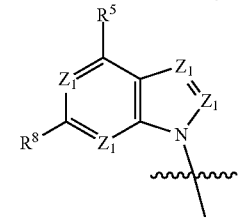
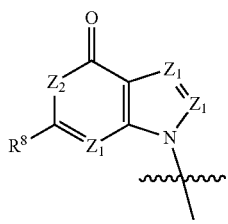
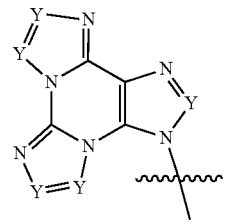

or

-continued

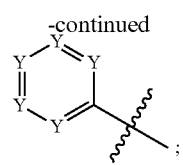

with the proviso that one of R$^1$ and R$^2$ must be

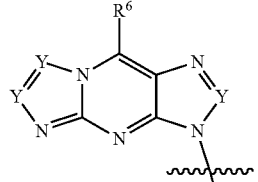
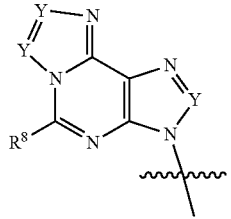
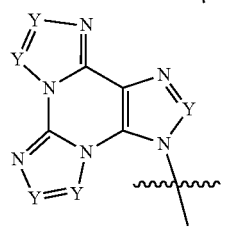
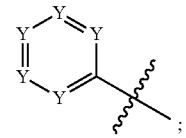

or

;

Z$_1$ is N or CR$^a$;

Z$_2$ is NR$^b$;

R$^a$ is H, halogen, C$_{1-6}$ alkyl substituted with 0-6 R$^5$, C$_{3-6}$ cycloalkyl substituted with 0-6 R$^5$, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^b$ is H, C$_{1-6}$ alkyl substituted with 0-6 R$^5$, C$_{3-6}$ cycloalkyl substituted with 0-6 R$^5$, —C(O)R$^{a1}$, —C(O)NR$^{a1}$R$^{a1}$, —S(O)$_2$R$^{a1}$ or S(O)$_2$NR$^{a1}$R$^{a1}$;

R$^{a1}$ is H, C$_{1-3}$ alkyl or C$_{3-6}$ cycloalkyl;

R$^4$ is H, CH$_3$, halogen, —NR$^{a1}$R$^{a1}$ or OR$^{a1}$;

R$^{4a}$ is H, CH$_3$, halogen, —NR$^{a1}$R$^{a1}$ or OR$^{a1}$; or

R$^4$ and R$^{4a}$ may be taken together to form a 3-4 membered carbocycle; or

R$^4$ and R$^{4a}$ may be taken together to form a C=CH$_2$ substituent;

R$^5$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^{5a}$ is H or C$_{1-3}$ alkyl;

R$^6$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^8$ is H, halogen, C$_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;

R$^9$ is H, halogen or methyl;

Y is CR$^a$ or N;

m is 0, 1, 2 or 3;

or a pharmaceutically acceptable salt, tautomer or stereoisomer thereof.

37. The compound according to claim 24 of the formula

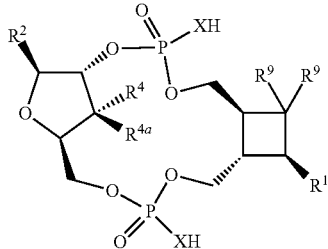

wherein

X is independently O or S;

R¹ and R² are each independently

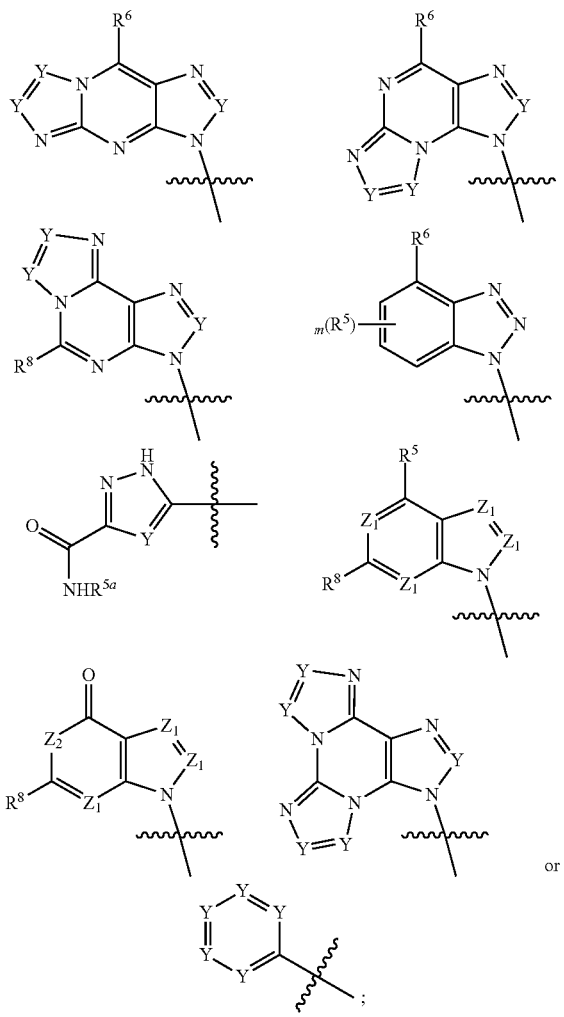

with the proviso that one of R¹ and R² must be

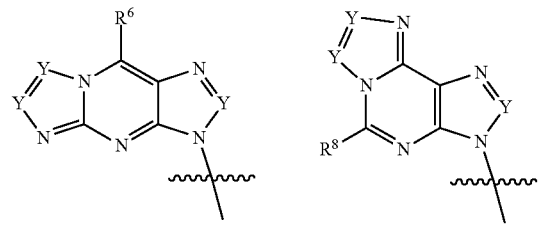

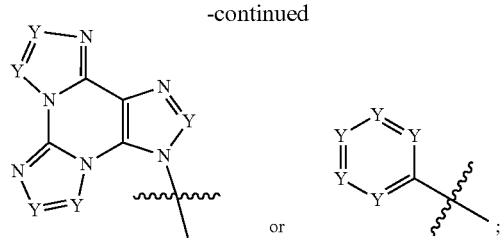

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^b$ is H, $C_{1-6}$ alkyl substituted with 0-6 $R^5$, $C_{3-6}$ cycloalkyl substituted with 0-6 $R^5$, —$C(O)R^{a1}$, —$C(O)NR^{a1}R^{a1}$, —$S(O)_2R^{a1}$ or $S(O)_2NR^{a1}R^{a1}$;

$R^{a1}$ is H, $C_{1-3}$ alkyl or $C_{3-6}$ cycloalkyl;

$R^4$ is H, $CH_3$, halogen, —$NR^{a1}R^{a1}$ or $OR^{a1}$;

$R^{4a}$ is H, $CH_3$, halogen, —$NR^{a1}R^{a1}$ or $OR^{a1}$; or $R^4$ and $R^{4a}$ may be taken together to form a 3-4 membered carbocycle; or $R^4$ and $R^{4a}$ may be taken together to form a $C=CH_2$ substituent;

$R^5$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^{5a}$ is H or $C_{1-3}$ alkyl;

$R^6$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^8$ is H, halogen, $C_{1-3}$ alkyl, CN, $NO_2$, OH, $OR^{a1}$, $SR^{a1}$, —$C(O)NR^{a1}R^{a1}$, —$COOR^{a1}$, —$OC(O)R^{a1}$, —$OC(O)NR^{a1}R^{a1}$, —$NR^{a1}R^{a1}$, —$NR^{a1}C(O)R^{a1}$, —$NR^{a1}COOR^{a1}$, —$NR^{a1}C(O)NR^{a1}R^{a1}$, —$NR^{a1}S(O)_2R^{a1}$, —$NR^{a1}S(O)_2NR^{a1}R^{a1}$, —$S(O)R^{a1}$, —$S(O)NR^{a1}R^{a1}$, —$S(O)_2R^{a1}$ or $S(O)_2NR^{a1}R^{a1}$;

$R^9$ is H, halogen or methyl;

Y is $CR^a$ or N;

m is 0, 1, 2 or 3;

or a pharmaceutically acceptable salt, tautomer or stereoisomer thereof.

38. The compound according to claim 24 of the formula

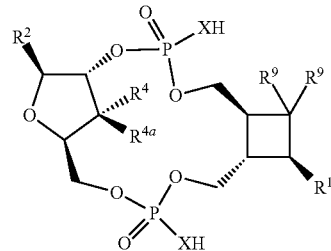

wherein
X is S;
R¹ and R² are each independently

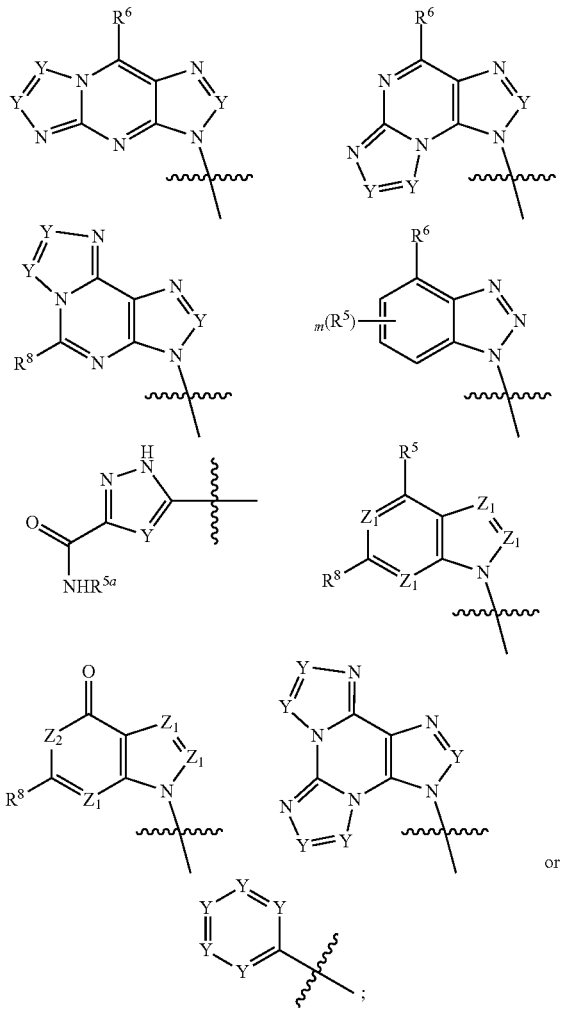

with the proviso that one of R¹ and R² must be

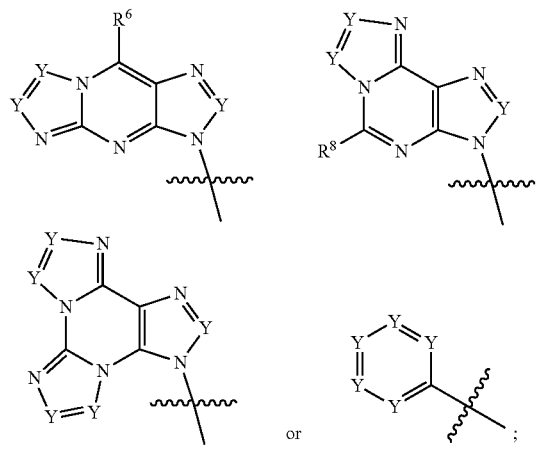

Z₁ is N or CR$^a$;
Z₂ is NR$^b$;

R$^a$ is H, halogen, C$_{1-6}$ alkyl substituted with 0-6 R⁵, C$_{3-6}$ cycloalkyl substituted with 0-6 R⁵, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R$^b$ is H, C$_{1-6}$ alkyl substituted with 0-6 R⁵, C$_{3-6}$ cycloalkyl substituted with 0-6 R⁵, —C(O)R$^{a1}$, —C(O)NR$^{a1}$R$^{a1}$, —S(O)₂R$^{a1}$ or S(O)₂NR$^{a1}$R$^{a1}$;

R$^{a1}$ is H, C$_{1-3}$ alkyl or C$_{3-6}$ cycloalkyl;

R⁴ is H, CH₃, halogen, —NR$^{a1}$R$^{a1}$ or OR$^{a1}$;

R$^{4a}$ is H, CH₃, halogen, —NR$^{a1}$R$^{a1}$ or OR$^{a1}$; or

R⁴ and R$^{4a}$ may be taken together to form a 3-4 membered carbocycle; or

R⁴ and R$^{4a}$ may be taken together to form a C=CH₂ substituent;

R⁵ is H, halogen, C$_{1-3}$ alkyl, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R$^{5a}$ is H or C$_{1-3}$ alkyl;

R⁶ is H, halogen, C$_{1-3}$ alkyl, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R⁸ is H, halogen, C$_{1-3}$ alkyl, CN, NO₂, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)₂R$^{a1}$, —NR$^{a1}$S(O)₂NR$^{a1}$R$^{a1}$, —S(O)R$^{a1}$, —S(O)NR$^{a1}$R$^{a1}$, —S(O)₂R$^{a1}$ or S(O)₂NR$^{a1}$R$^{a1}$;

R⁹ is H, halogen or methyl;

Y is CR$^a$ or N;

m is 0, 1, 2 or 3;

or a pharmaceutically acceptable salt, tautomer or stereoisomer thereof.

39. The compound according to claim 24 of the formula

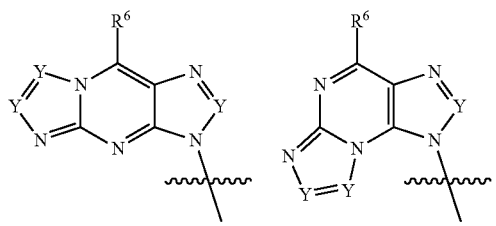

wherein
X is O;
R¹ and R² are each independently

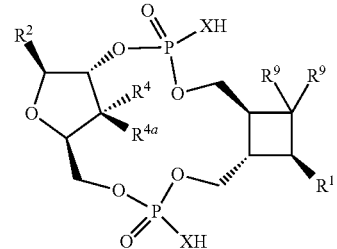

-continued

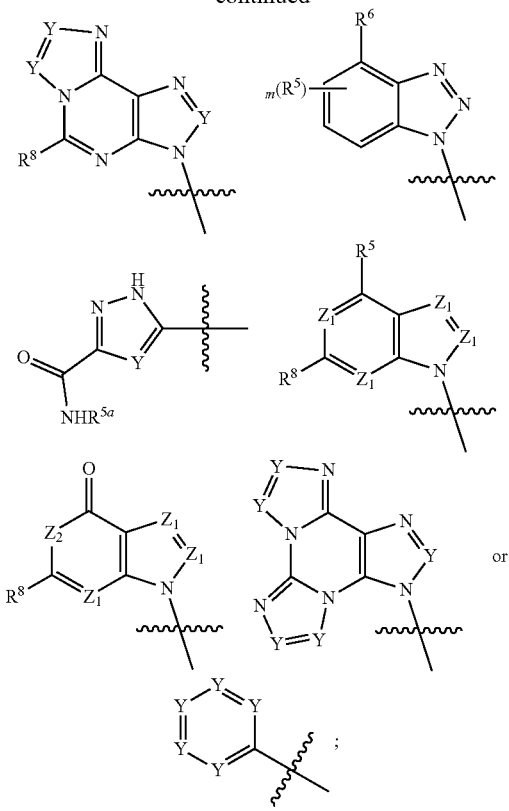

with the proviso that one of $R^1$ and $R^2$ must be

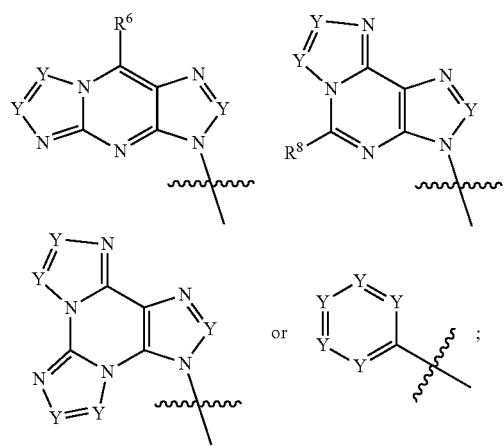

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, NO$_2$, OH, $OR^{a1}$, $SR^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^b$ is H, $C_{1-6}$ alkyl substituted with 0-6 $R^5$, $C_{3-6}$ cycloalkyl substituted with 0-6 $R^5$, —C(O)R$^{a1}$, —C(O)NR$^{a1}$R$^{a1}$, —S(O)$_2$R$^{a1}$ or S(O)$_2$NR$^{a1}$R$^{a1}$;
$R^{a1}$ is H, $C_{1-3}$ alkyl or $C_{3-6}$ cycloalkyl;

$R^4$ is H, CH$_3$, halogen, —NR$^{a1}$R$^{a1}$ or OR$^{a1}$;
$R^{4a}$ is H, CH$_3$, halogen, —NR$^{a1}$R$^{a1}$ or OR$^{a1}$; or
$R^4$ and $R^{4a}$ may be taken together to form a 3-4 membered carbocycle; or
$R^4$ and $R^{4a}$ may be taken together to form a C=CH$_2$ substituent;
$R^5$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^{5a}$ is H or $C_{1-3}$ alkyl;
$R^6$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^8$ is H, halogen, $C_{1-3}$ alkyl, CN, NO$_2$, OH, OR$^{a1}$, SR$^{a1}$, —C(O)NR$^{a1}$R$^{a1}$, —COOR$^{a1}$, —OC(O)R$^{a1}$, —OC(O)NR$^{a1}$R$^{a1}$, —NR$^{a1}$R$^{a1}$, —NR$^{a1}$C(O)R$^{a1}$, —NR$^{a1}$COOR$^{a1}$, —NR$^{a1}$C(O)NR$^{a1}$R$^{a1}$, —NR$^{a1}$S(O)$_2$R$^{a1}$, —NR$^{a1}$S(O)$_2$NR$^{a1}$R$^{a1}$, —S(O)R$^{a1}$, —S(O)NR$^{a1}$R$^{a1}$, —S(O)$_2$R$^{a1}$ or S(O)$_2$NR$^{a1}$R$^{a1}$;
$R^9$ is H, halogen or methyl;
Y is $CR^a$ or N;
m is 0, 1, 2 or 3;
or a pharmaceutically acceptable salt, tautomer or stereoisomer thereof.

40. The compound according to claim 24 of the formula

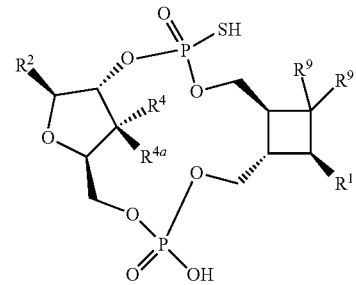

wherein
$R^1$ and $R^2$ are each independently

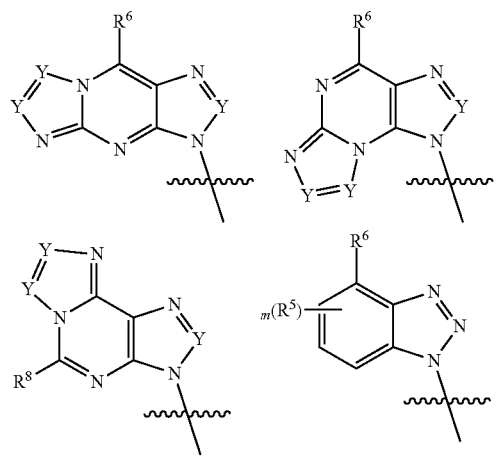

-continued

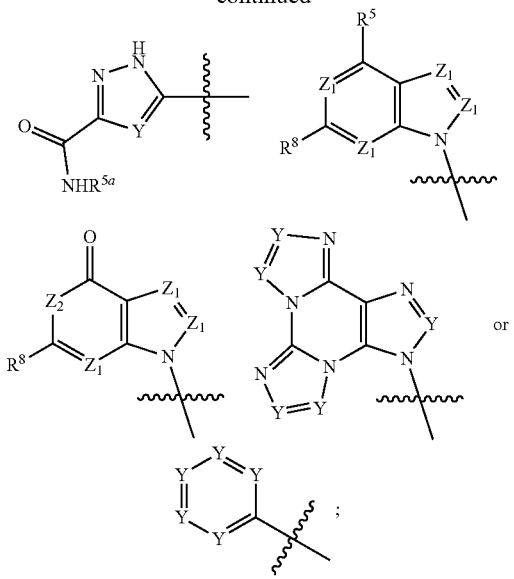

with the proviso that one of $R^1$ and $R^2$ must be

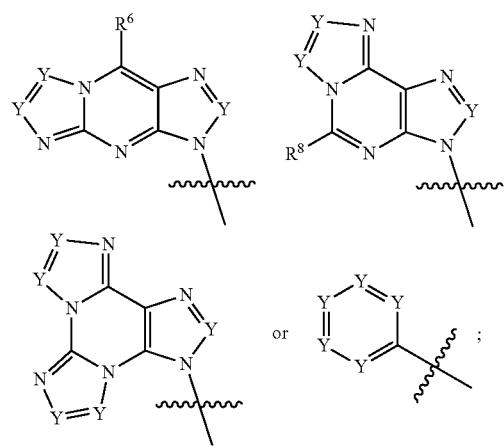

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, —C(O)$NR^{a1}R^{a1}$, —$COOR^{a1}$, —OC(O)$R^{a1}$, —OC(O)$NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^b$ is H, $C_{1-6}$ alkyl substituted with 0-6 $R^5$, $C_{3-6}$ cycloalkyl substituted with 0-6 $R^5$, —C(O)$R^{a1}$, —C(O)$NR^{a1}R^{a1}$, —S(O)$_2R^{a1}$ or S(O)$_2NR^{a1}R^{a1}$;
$R^{a1}$ is H, $C_{1-3}$ alkyl or $C_{3-6}$ cycloalkyl;
$R^4$ is H, $CH_3$, halogen, —$NR^{a1}R^{a1}$ or $OR^{a1}$;
$R^{4a}$ is H, $CH_3$, halogen, —$NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a C=$CH_2$ substituent;
$R^5$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^8$ is H, halogen, $C_{1-3}$ alkyl, CN, $NO_2$, OH, $OR^{a1}$, $SR^{a1}$, —C(O)$NR^{a1}R^{a1}$, —$COOR^{a1}$, —OC(O)$R^{a1}$, —OC(O) $NR^{a1}R^{a1}$, —$NR^{a1}R^{a1}$, —$NR^{a1}$C(O)$R^{a1}$, —$NR^{a1}COOR^{a1}$, —$NR^{a1}$C(O)$NR^{a1}R^{a1}$, —$NR^{a1}$S(O)$_2$ $R^{a1}$, —$NR^{a1}$S(O)$_2NR^{a1}R^{a1}$, —S(O)$R^{a1}$, —S(O) $NR^{a1}R^{a1}$, —S(O)$_2R^{a1}$ or S(O)$_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

41. The compound according to claim 24 of the formula

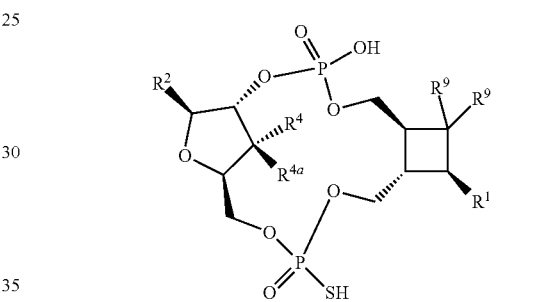

wherein
$R^1$ and $R^2$ are each independently

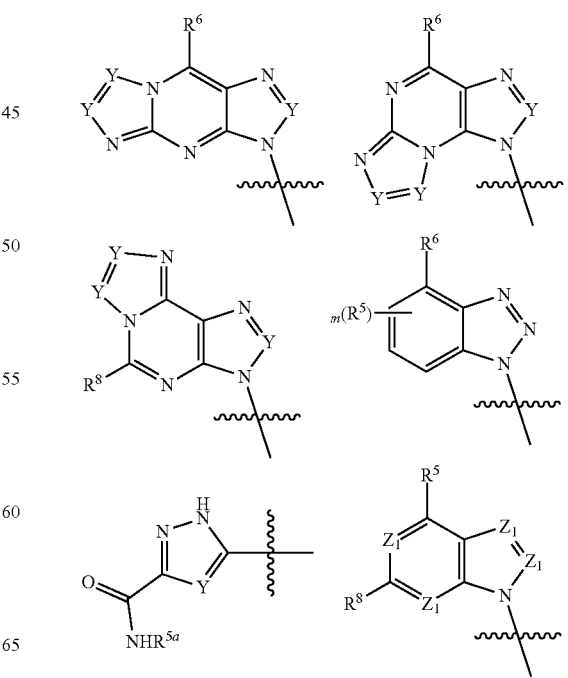

-continued

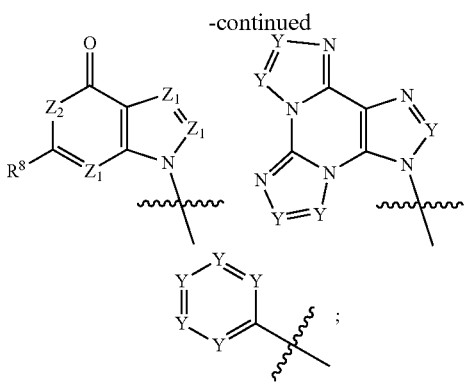

with the proviso that one of $R^1$ and $R^2$ must be

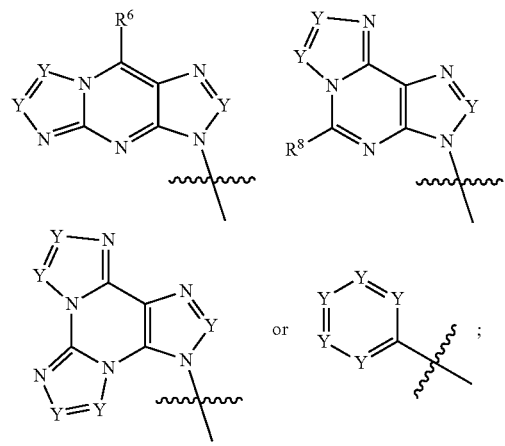

$Z_1$ is N or $CR^a$;
$Z_2$ is $NR^b$;
$R^a$ is H, halogen, $C_{1-6}$ alkyl substituted with 0-6 $R^5$, $C_{3-6}$ cycloalkyl substituted with 0-6 $R^5$, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^b$ is H, $C_{1-6}$ alkyl substituted with 0-6 $R^5$, $C_{3-6}$ cycloalkyl substituted with 0-6 $R^5$, $-C(O)R^{a1}$, $-C(O)NR^{a1}R^{a1}$, $-S(O)_2R^{a1}$ or $S(O)_2NR^{a1}R^{a1}$;
$R^{a1}$ is H, $C_{1-3}$ alkyl or $C_{3-6}$ cycloalkyl;
$R^4$ is H, $CH_3$, halogen, $-NR^{a1}R^{a1}$ or $OR^{a1}$;
$R^{4a}$ is H, $CH_3$, halogen, $-NR^{a1}R^{a1}$ or $OR^{a1}$; or
$R^4$ and $R^{4a}$ may be taken together to form a 3-4 membered carbocycle; or
$R^4$ and $R^{4a}$ may be taken together to form a $C=CH_2$ substituent;
$R^5$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^{5a}$ is H or $C_{1-3}$ alkyl;
$R^6$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^8$ is H, halogen, $C_{1-3}$ alkyl, CN, $NO_2$, OH, $OR^{a1}$, $SR^{a1}$, $-C(O)NR^{a1}R^{a1}$, $-COOR^{a1}$, $-OC(O)R^{a1}$, $-OC(O)NR^{a1}R^{a1}$, $-NR^{a1}R^{a1}$, $-NR^{a1}C(O)R^{a1}$, $-NR^{a1}COOR^{a1}$, $-NR^{a1}C(O)NR^{a1}R^{a1}$, $-NR^{a1}S(O)_2$ $R^{a1}$, $-NR^{a1}S(O)_2NR^{a1}R^{a1}$, $-S(O)R^{a1}$, $-S(O)NR^{a1}R^{a1}$, $-S(O)_2R^{a1}$ or $S(O)_2NR^{a1}R^{a1}$;
$R^9$ is H, halogen or methyl;
Y is $CR^a$ or N;
m is 0, 1, 2 or 3;
or a pharmaceutically acceptable salt, tautomer or stereoisomer thereof.

42. The compound according to claim 24 of the formula

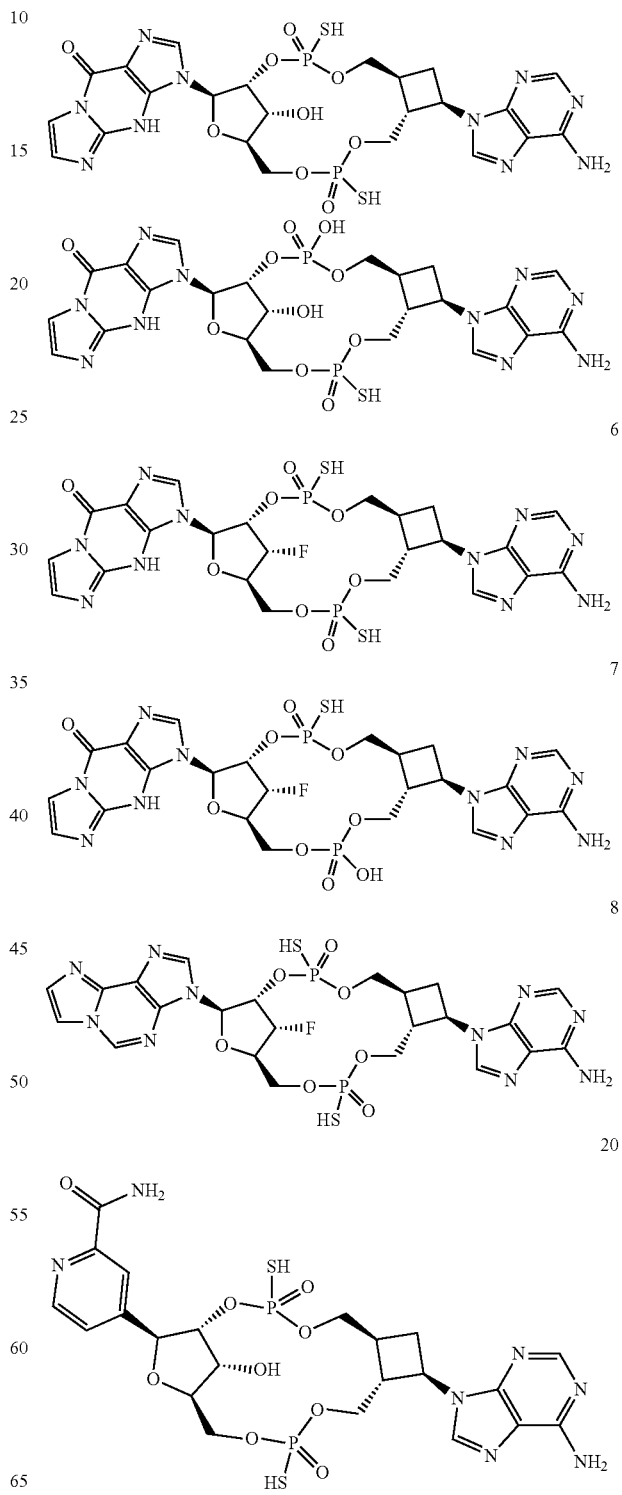

or a tautomer or stereoisomer thereof.

43. A pharmaceutically acceptable salt of a compound according to claim 24 of the formula
44. A compound of the formula
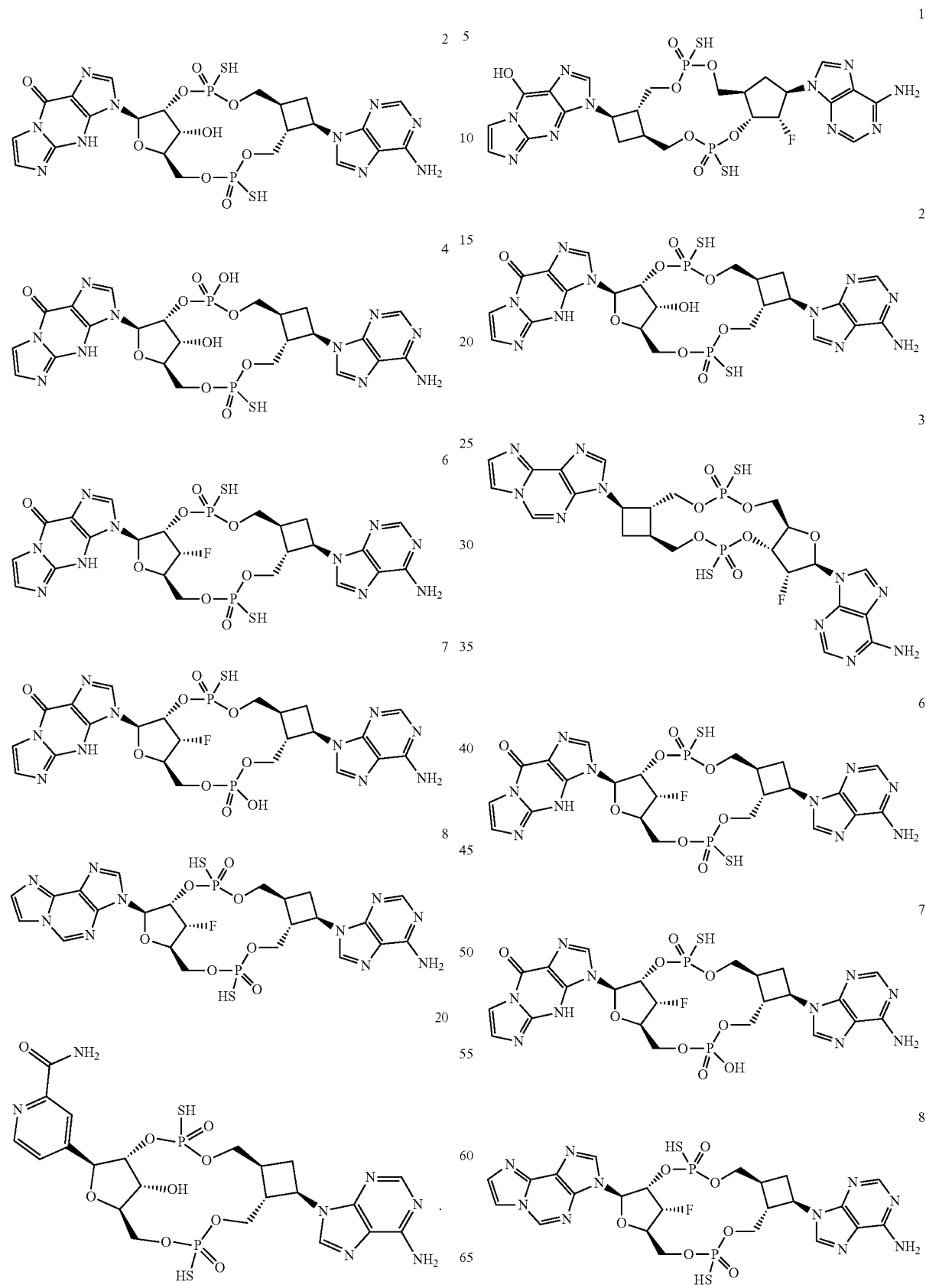

9
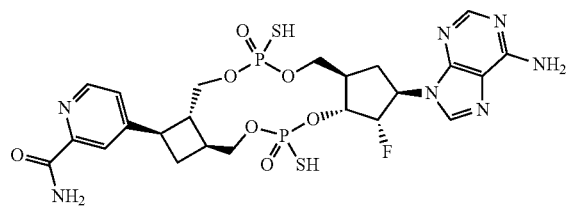
13
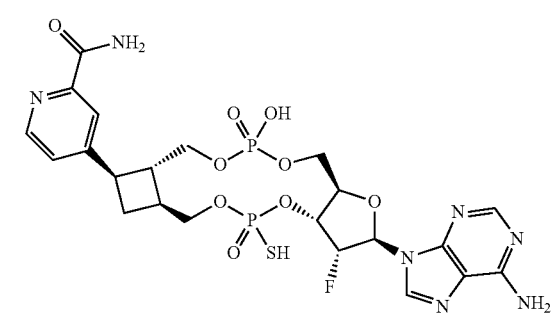
16
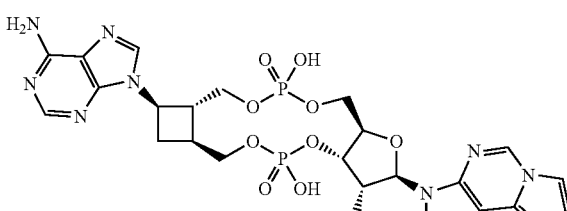
17
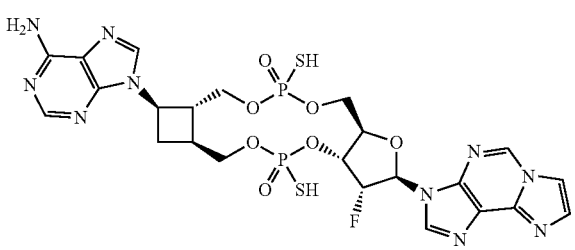
19
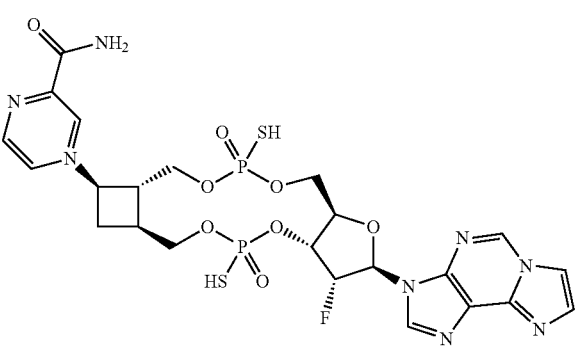
20
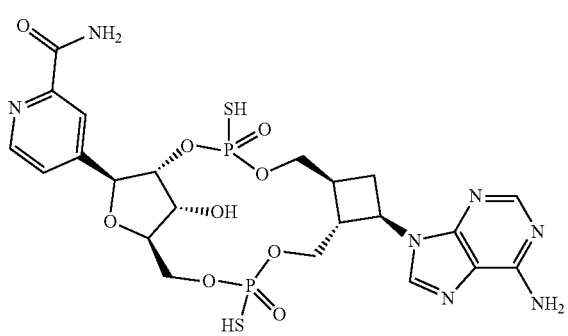
21
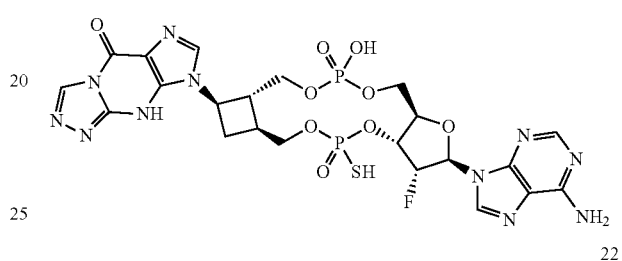
22
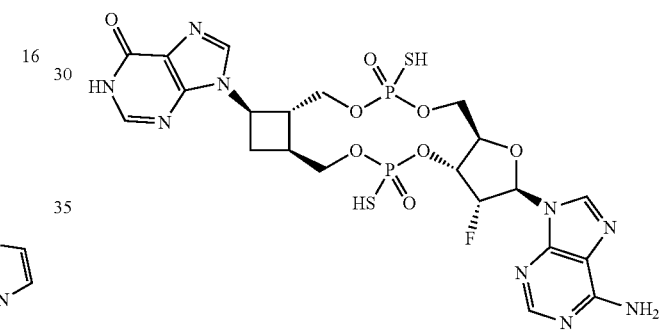
23
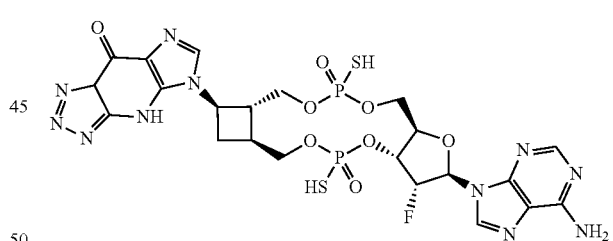
or a tautomer or stereoisomer thereof.
45. A pharmaceutically acceptable salt of a compound of the formula
1
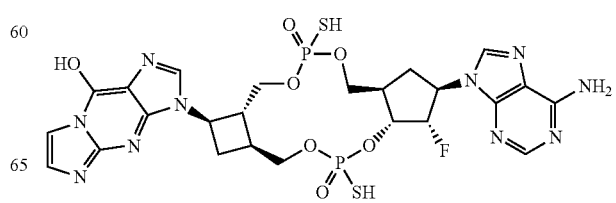

2
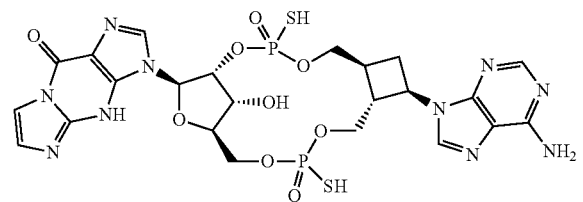
3
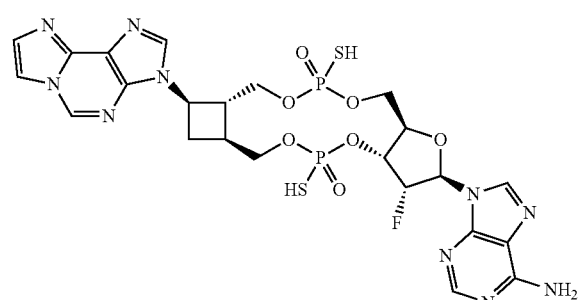
6
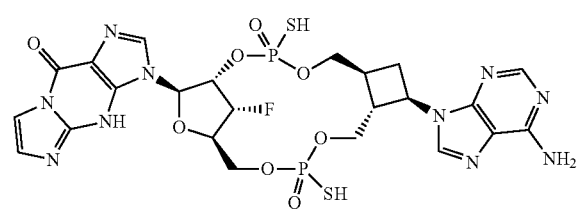
7
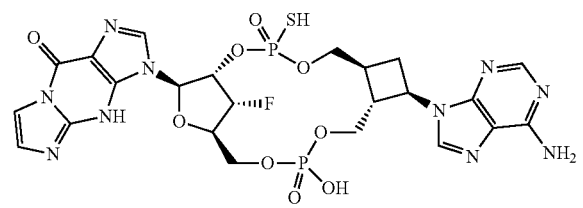
8
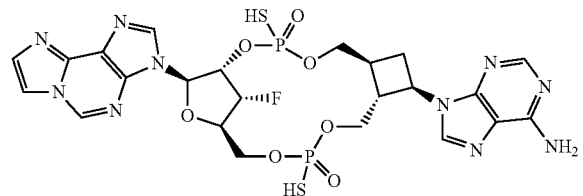
9
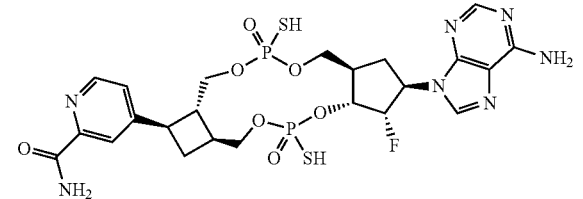
13
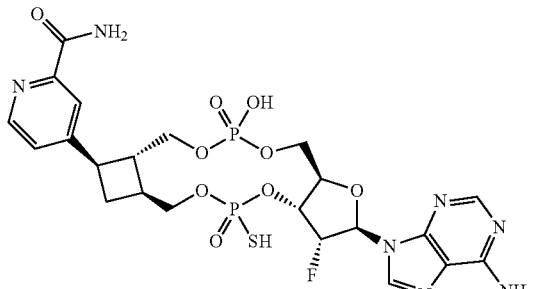
16
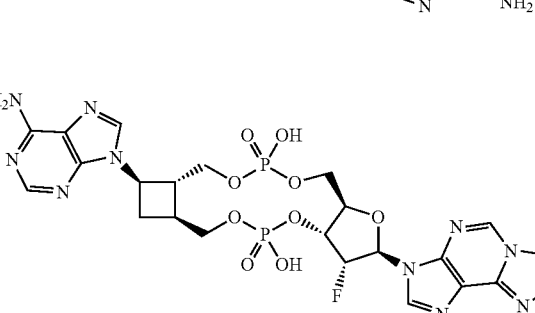
17
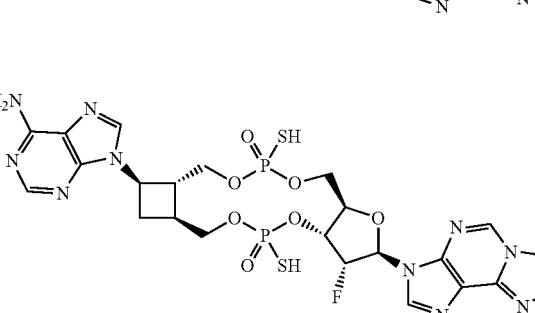
19
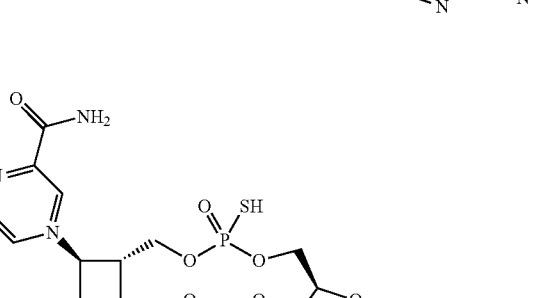
20
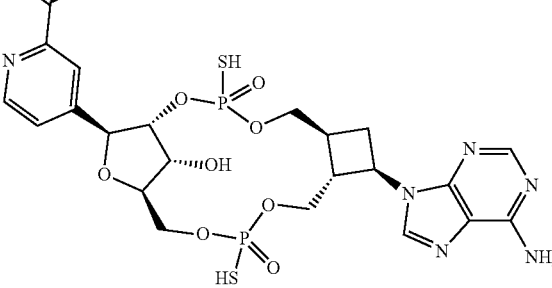

21
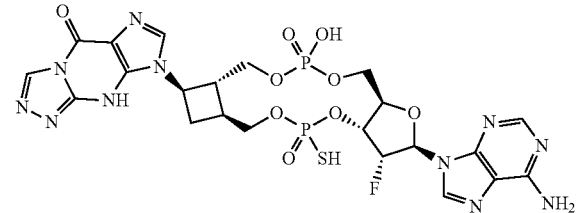
22
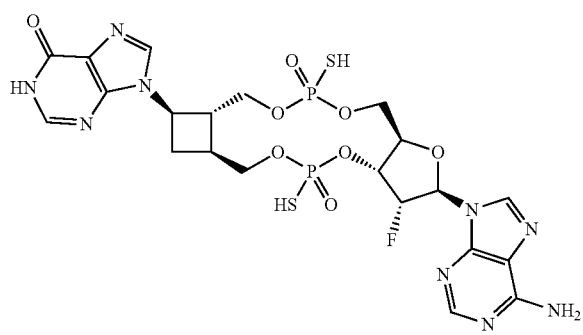
23
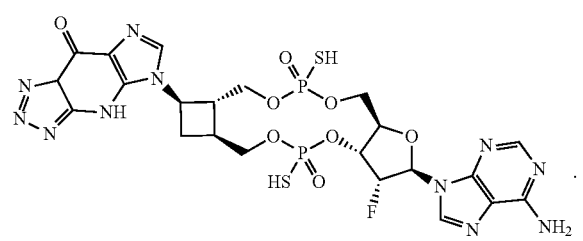
46. A compound of the formula
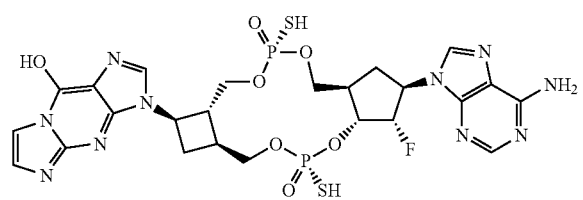
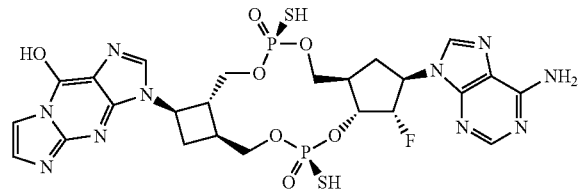
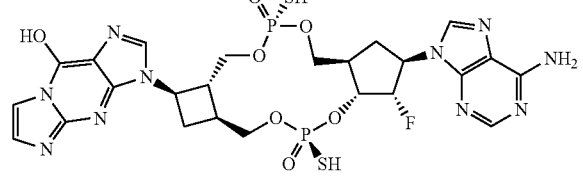
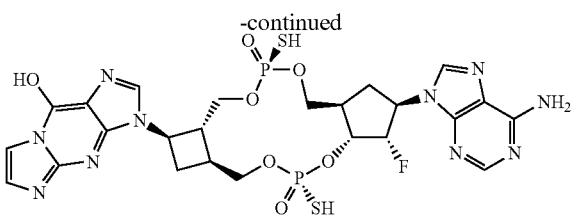
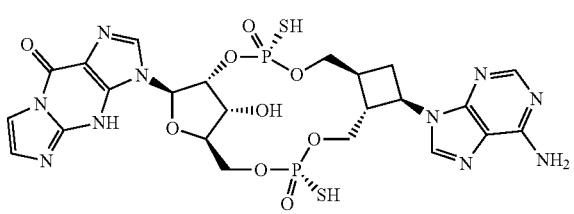
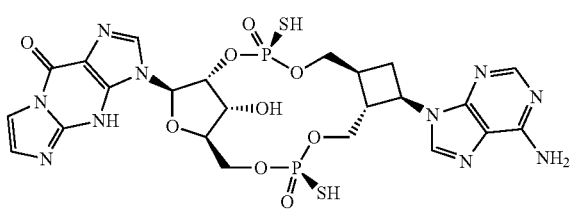
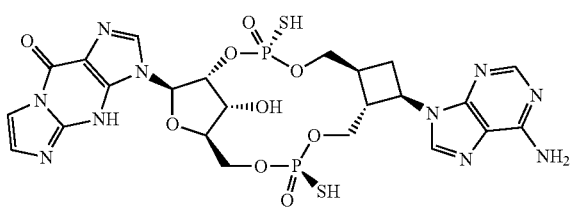
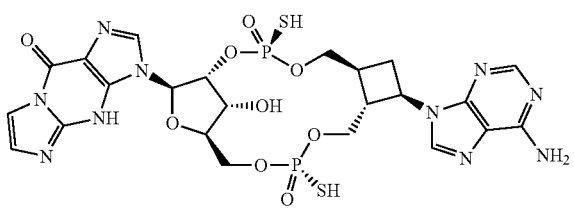
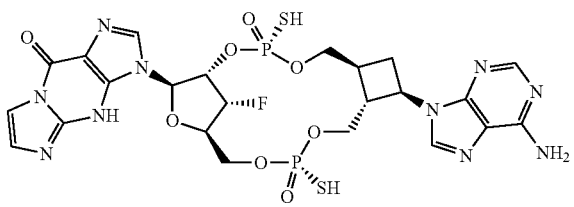
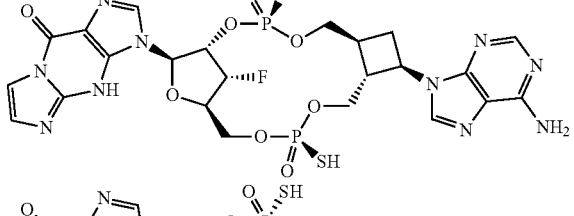
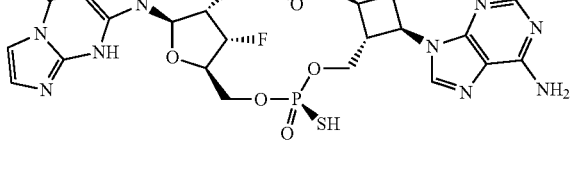

361
-continued
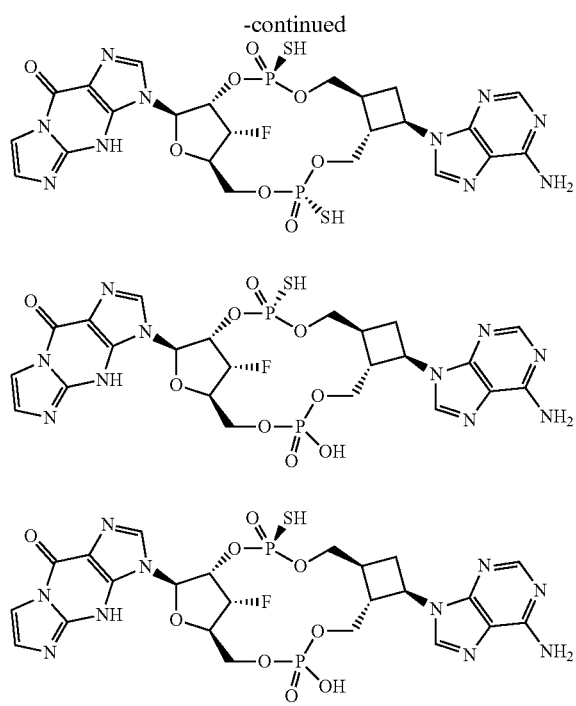
362
-continued
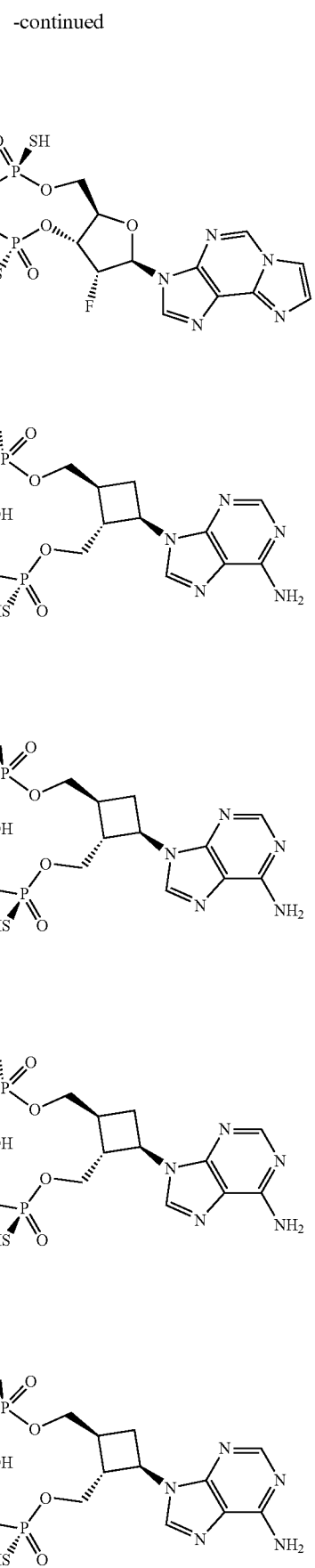

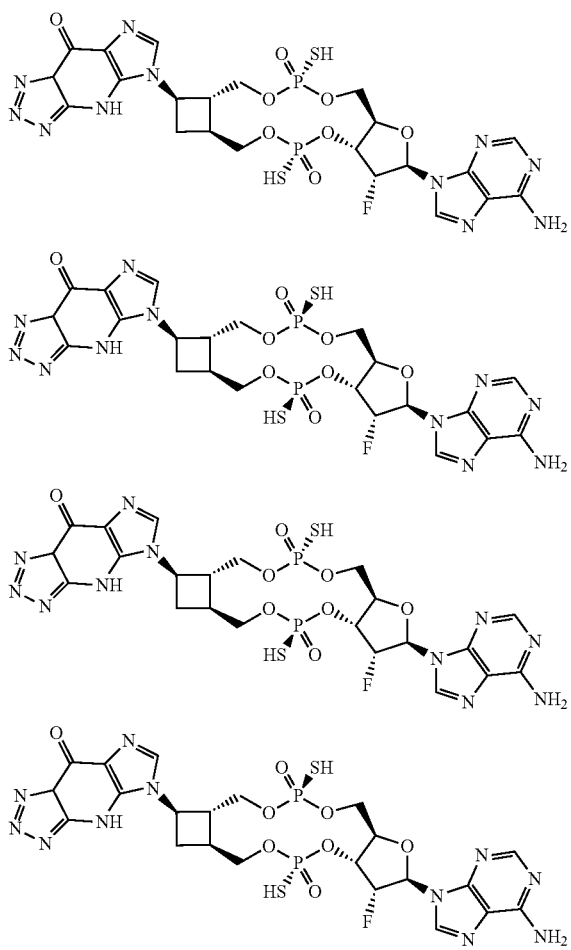
or a tautomer or stereoisomer thereof.
47. A pharmaceutically acceptable salt of a compound of the formula
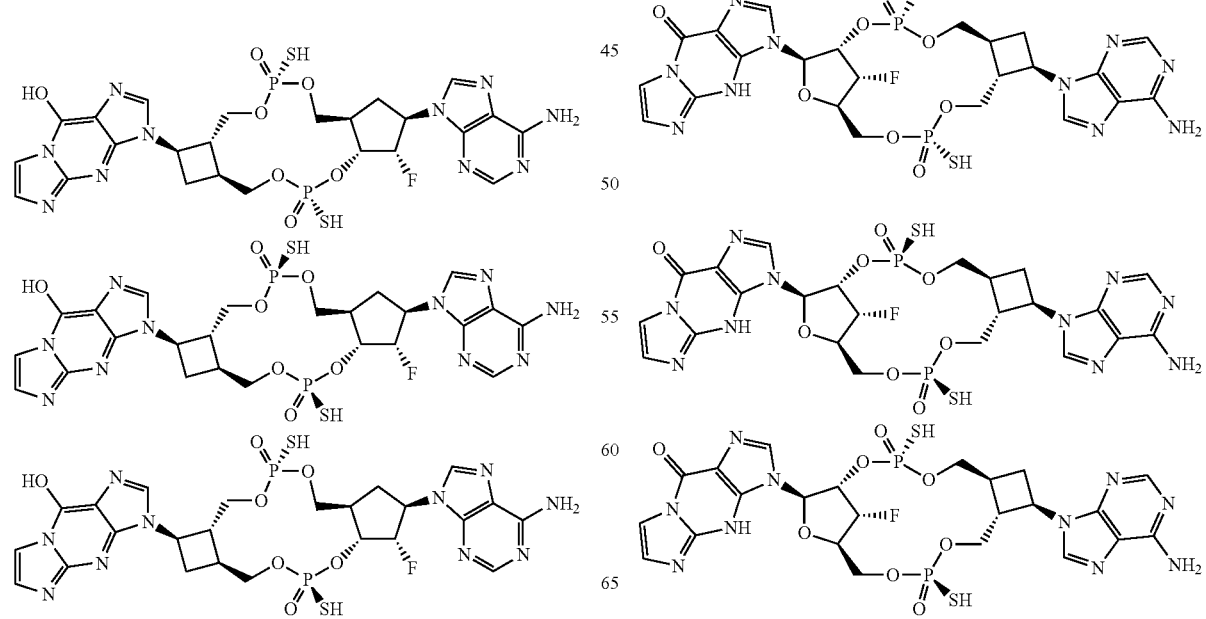
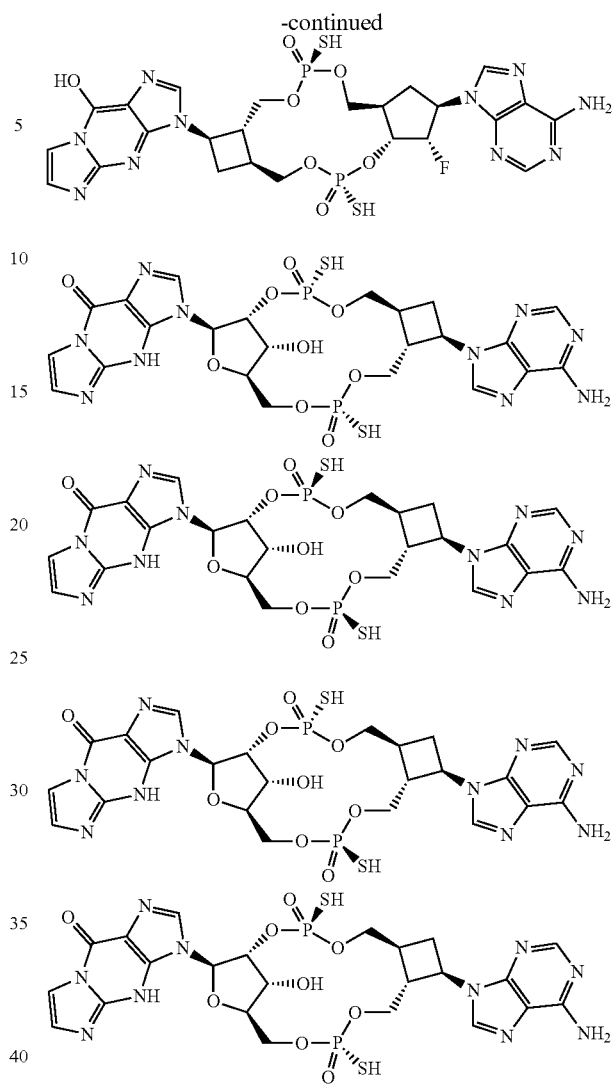

365
-continued
366
-continued
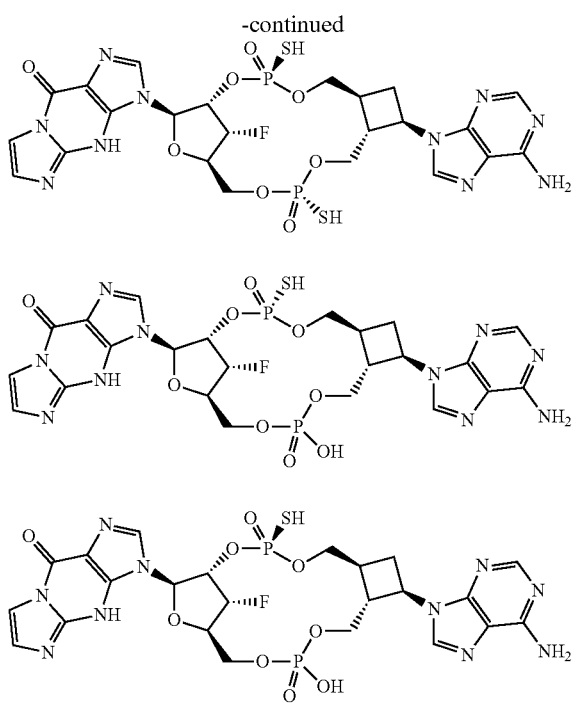
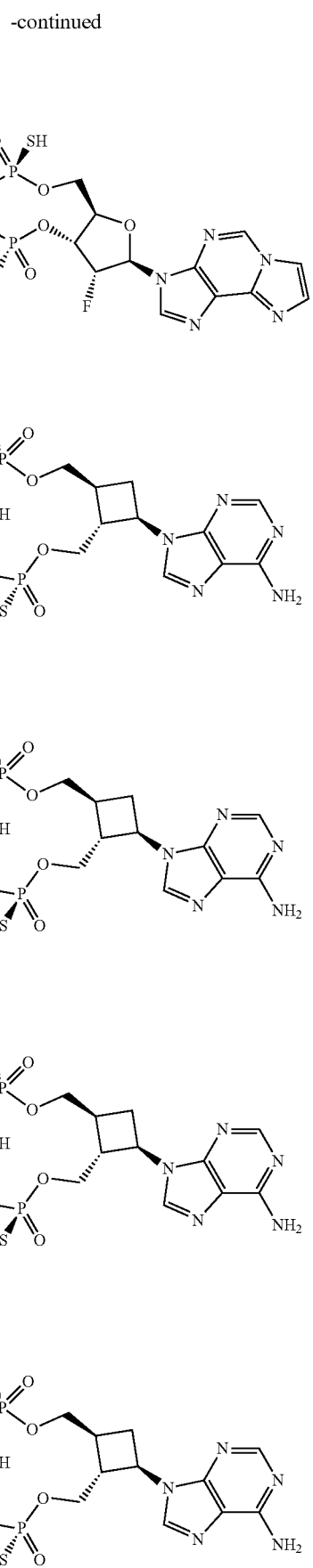

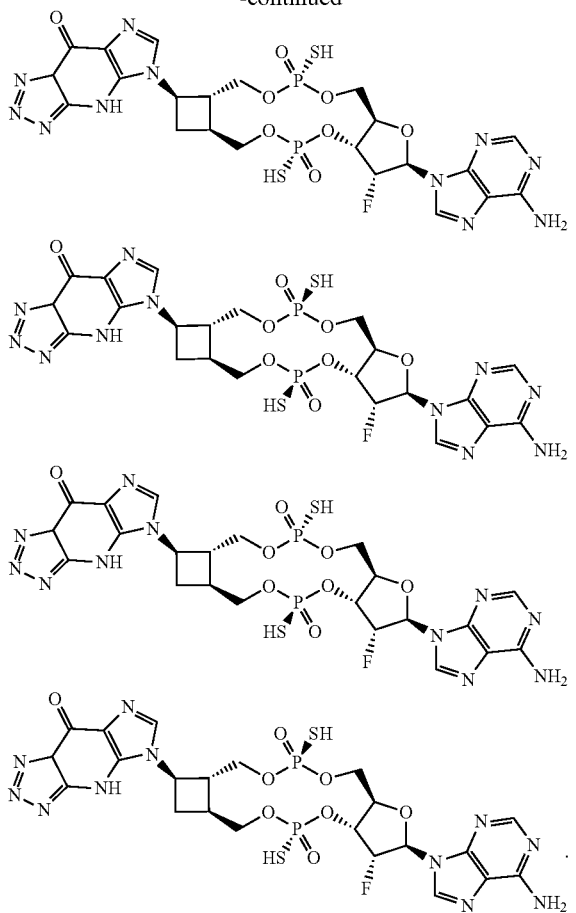

48. The compound which is
(1R,6S,8R,9R,15R,17R,18R)-17-(6-amino-9H-purin-9-yl)-18-fluoro-8-{9-hydroxy-3H-imidazo[1,2-a]purin-3-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione, (1R,6S,8R,9R,15R,17R,18R)-8-(6-amino-9H-purin-9-yl)-8-hydroxy-17-{9-oxo-3H,4H,9H-imidazo[1,2-a]purin-3-yl}-3,12-disulfanyl-2,4,11,13,16-pentaoxa-3$\lambda^5$,12$\lambda^5$-diphosphatricyclo[13.2.1.0$^{6,9}$]octadecane-3,12-dione, (1R,6S,8R,9R,15R,17R,18R)-17-(6-amino-9H-purin-9-yl)-18-fluoro-8-{3H-imidazo[2,1-f]purin-3-yl}-3,12-disulfanyl-2,4,11,13,16-pentaoxa-3$\lambda^5$,12$\lambda^5$-diphosphatricyclo[13.3.0.0$^{6,9}$]octadecane-3,12dione, (1R,6S,8R,9R,15R,17R,18R)-8-(6-amino-9H-purin-9-yl)-3,18-dihydroxy-17-{9-oxo-3H,4H,9H-imidazo[1,2-a]purin-3-yl}-12-sulfanyl-2,4,11,13,16-pentaoxa-3$\lambda^5$,12$\lambda^5$-diphosphatricyclo[13.2.1.0$^{6,9}$]octadecane-3,12-dione, (1S,6S,8R,9R,15R,17R,18R)-8-(6-amino-9H-purin-9-yl)-18-hydroxy-17-{9-oxo-3H,5H,9H-imidazo[1,2-a]purin-3-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione, (1S,6S,8R,9R,15R,17R,18R)-8-(6-amino-9H-purin-9-yl)-18-fluoro-17-{9-oxo-3H,4H,9H-imidazo[1,2-a]purin-3-yl}-3,12-disulfanyl-2,4,11,13,16-pentaoxa-3$\lambda^5$,12$\lambda^5$-diphosphatricyclo[13.2.1.0$^{6,9}$]octadecane-3,12-dione, (1S,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3$\lambda^5$,12$\lambda^5$-diphosphatricyclo[13.2.1.0$^{6,9}$]octadecane-3,12-dione, (1S,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3$\lambda^5$,12$\lambda^5$-diphosphatricyclo[13.2.1.0$^{6,9}$]octadecane-3,12-dione, 4-[(1R,6S,8R,9S,15R,17R,18R)-17-(6-amino-9H-purin-9-yl)-18-fluoro-3,12-dioxo-3,12-disulfanyl-2,4,11,13,16-pentaoxa-3$\lambda^5$,12$\lambda^5$-diphosphatricyclo[13.3.0.0$^{6,9}$]octadecan-8-yl]pyridine-2-carboxamide, 4-[(1R,6S,8R,9S,15R,17R,18S)-17-(6-amino-9H-purin-9-yl)-18-fluoro-3,12-dioxo-3,12-disulfanyl-2,4,11,13,16-pentaoxa-3$\lambda^5$,12$\lambda^5$-diphosphatricyclo[13.3.0.0$^{6,9}$]octadecan-8-yl]pyridine-2-carboxamide, 4-[(1R,6S,8R,9S,15R,17R,18R)-17-(6-amino-9H-purin-9-yl)-18-fluoro-3,12-dihydroxy-3,12-dioxo-2,4,11,13,16-pentaoxa-3$\lambda^5$,12$\lambda^5$-diphosphatricyclo[13.3.0.0$^{6,9}$]octadecan-8-yl]pyridine-2-carboxamide, 4-[(1R,6S,8R,9S,15R,17R,18R)-17-(6-amino-9H-purin-9-yl)-18-fluoro-12-hydroxy-3,12-dioxo-3-sulfanyl-2,4,11,13,16-pentaoxa-3$\lambda^5$,12$\lambda^5$-diphosphatricyclo[13.3.0.0$^{6,9}$]octadecan-8-yl]pyridine-2-carboxamide, 4-[(1S,7S,8R,10S,16R,17R)-17-(6-amino-9H-purin-9-yl)-4,13-dioxo-4,13-disulfanyl-3,5,12,14-tetraoxa-4$\lambda^5$,13$\lambda^5$-diphosphatricyclo[14.2.0.0$^{7,10}$]octadecan-8-yl]pyridine-2-carboxamide, (1R,6S,8R,9R,15R,17R,18R)-8-(6-amino-9H-purin-9-yl)-18-fluoro-3,12-dihydroxy-17-{3H-imidazo[2,1-f]purin-3-yl}-2,4,11,13,16-pentaoxa-3$\lambda^5$,12$\lambda^5$-diphosphatricyclo[13.3.0.0$^{6,9}$]octadecane-3,12-dione, (1R,6S,8R,9R,15R,17R,18R)-8-(6-amino-9H-purin-9-yl)-18-fluoro-17-{3H-imidazo[2,1-f]purin-3-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione, (1R,6S,8R,9R,15R,17R,18R)-8-(6-chloro-9H-purin-9-yl)-18-fluoro-17-{3H-imidazo[2,1-f]purin-3-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione, 4-[(1R,6S,8R,9S,15R,17R,18R)-18-fluoro-17-{3H-imidazo[2,1-f]purin-3-yl}-3,12-dioxo-3,12-disulfanyl-2,4,11,13,16-pentaoxa-3$\lambda^5$,12$\lambda^5$-diphosphatricyclo[13.3.0.0$^{6,9}$]octadecan-8-yl]pyridine-2-carboxamide, 4-[(1R,6S,8R,9R,15R,17S,18R)-8-(6-amino-9H-purin-9-yl)-18-hydroxy-3,12-dioxo-3,12-disulfanyl-2,4,11,13,16-pentaoxa-3$\lambda^5$,12$\lambda^5$-diphosphatricyclo[13.2.1.0$^{6,9}$]octadecan-17-yl]pyridine-2-carboxamide, (1R,6S,8R,9R,15R,17R,18R)-17-(6-amino-9H-purin-9-yl)-18-fluoro-8-{5-oxo-5H,8H,9H-[1,2,4]triazolo[4,3-a]purin-8-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione, (1R,6S,8R,9R,15R,17R,18R)-17-(6-amino-9H-purin-9-yl)-18-fluoro-8-(6-oxo-6,9-dihydro-1H-purin-9-yl)-3,12-disulfanyl-2,4,11,13,16-pentaoxa-3$\lambda^5$,12$\lambda^5$-diphosphatricyclo[13.3.0.0$^{6,9}$]octadecane-3,12-dione, (1R,6S,8R,9R,15R,17R,18R)-17-(6-amino-9H-purin-9-yl)-18-fluoro-8-{8-oxo-4H,5H,8H-[1,2,3,4]tetrazolo[1,5-a]purin-5-yl}-3,12-disulfanyl-2,4,11,13,16-pentaoxa-3$\lambda^5$,12$\lambda^5$-diphosphatricyclo[13.3.0.0$^{6,9}$]octadecane-3,12-dione or a pharmaceutically acceptable salt, tautomer or stereoisomer thereof.

49. A pharmaceutical composition comprising a compound according to claim 1 or a pharmaceutically acceptable salt thereof and one or more pharmaceutically acceptable carriers, diluents or excipients.

50. A pharmaceutical composition comprising a compound according to claim 24 or a pharmaceutically acceptable salt thereof and one or more pharmaceutically acceptable carriers, diluents or excipients.

51. A combination pharmaceutical product comprising a compound according to claim 1 or a pharmaceutically acceptable salt thereof together with one or more other therapeutically active agents.

52. A combination pharmaceutical product comprising a compound according to claim 24 or a pharmaceutically acceptable salt thereof together with one or more other therapeutically active agents.

53. A compound according to claim 1 or a pharmaceutically acceptable salt thereof for use in therapy.

54. A compound according to claim 24 or a pharmaceutically acceptable salt thereof for use in therapy.

55. A compound or a pharmaceutically acceptable salt thereof for use according to claim 1, wherein the disease or condition is cancer.

56. A compound or a pharmaceutically acceptable salt thereof for use according to claim 24, wherein the disease or condition is cancer.

57. A method of treating diseases and conditions in which the modulation of STING is indicated in a subject in need thereof, wherein the disease is cancer, which comprises administering a therapeutically effective amount of compound according to claim 1 or a pharmaceutically acceptable salt thereof.

58. A method of treating diseases and conditions in which the modulation of STING is indicated in a subject in need thereof, wherein the disease is cancer, which comprises administering a therapeutically effective amount of compound according to claim 24 or a pharmaceutically acceptable salt thereof.

59. A method of treating cancer comprising administering a therapeutically effective amount of one or more compounds according to claim 1 or a pharmaceutically acceptable salt thereof.

60. A method of treating cancer comprising administering a therapeutically effective amount of one or more compounds according to claim 24 or a pharmaceutically acceptable salt thereof.

61. The method of claim 59 wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers.

62. The method of claim 60 wherein the cancer is small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers.

63. The method of claim 61 wherein the cancer is small cell lung cancer, non-small cell lung cancer, colorectal cancer, melanoma, renal cell carcinoma, head and neck cancer, Hodgkin's lymphoma or bladder cancer.

64. The method of claim 62 wherein the cancer is small cell lung cancer, non-small cell lung cancer, colorectal cancer, melanoma, renal cell carcinoma, head and neck cancer, Hodgkin's lymphoma or bladder cancer.

65. A method for treating cancer in a subject in need thereof, comprising administering an effective amount of a compound, according to claim 1, or a pharmaceutically acceptable salt thereof,
  in combination with the administration of a therapeutically effective amount of one or more immuno-oncology agents.

66. A method for treating cancer in a subject in need thereof, comprising administering an effective amount of a compound, according to claim 24, or a pharmaceutically acceptable salt thereof,
  in combination with the administration of a therapeutically effective amount of one or more immuno-oncology agents.

67. A method for treating cancer in a subject in need thereof, comprising administering an effective amount of a compound, according to claim 44, or a pharmaceutically acceptable salt thereof,
  in combination with the administration of a therapeutically effective amount of one or more immuno-oncology agents.

68. The method of claim 65 wherein the immuno-oncology agent is ipilimumab.

69. The method of claim 66 wherein the immuno-oncology agent is ipilimumab.

70. The method of claim 68, wherein the immune-oncology agent is a PD-L1 antagonist.

* * * * *